United States Patent
Bosch Tubert et al.

(10) Patent No.: US 11,033,638 B2
(45) Date of Patent: Jun. 15, 2021

(54) SINGLE-VECTOR GENE CONSTRUCT COMPRISING INSULIN AND GLUCOKINASE GENES

(71) Applicant: Universitt Autònoma de Barcelona, Barcelona (ES)

(72) Inventors: Fatima Bosch Tubert, Cerdanyola del Valles (ES); Miguel Garcia Martinez, Cerdanyola del Valles (ES); Veronica Jiménez Cenzano, Cerdanyola del Valles (ES); Virginia Haurigot Mendonça, Cerdanyola del Valles (ES)

(73) Assignee: UNIVERSITÄT AUTONOMA DE BARCELONA, Barcelona (ES)

( * ) Notice: Subject to any disclaimer, the term of this patent is extended or adjusted under 35 U.S.C. 154(b) by 0 days.

(21) Appl. No.: 15/541,679

(22) PCT Filed: Jan. 7, 2016

(86) PCT No.: PCT/EP2016/050147
§ 371 (c)(1),
(2) Date: Jul. 5, 2017

(87) PCT Pub. No.: WO2016/110518
PCT Pub. Date: Jul. 14, 2016

(65) Prior Publication Data
US 2018/0000967 A1 Jan. 4, 2018

(30) Foreign Application Priority Data
Jan. 7, 2015 (EP) .................................... 15150376

(51) Int. Cl.
| | | |
|---|---|---|
| A61K 48/00 | (2006.01) | |
| C12N 15/63 | (2006.01) | |
| C12N 15/86 | (2006.01) | |
| A61K 38/28 | (2006.01) | |
| A61K 38/45 | (2006.01) | |
| C07K 14/62 | (2006.01) | |
| C12N 9/12 | (2006.01) | |
| A01K 67/00 | (2006.01) | |

(52) U.S. Cl.
CPC ............ *A61K 48/005* (2013.01); *A61K 38/28* (2013.01); *A61K 38/45* (2013.01); *C07K 14/62* (2013.01); *C12N 9/1205* (2013.01); *C12N 15/86* (2013.01); *C12Y 207/01002* (2013.01); *C12N 2710/16143* (2013.01); *C12N 2750/14143* (2013.01); *C12N 2830/60* (2013.01)

(58) Field of Classification Search
CPC .................. A61K 48/005; C12N 15/86; C12Y 207/01002; C07K 14/62
See application file for complete search history.

(56) References Cited

U.S. PATENT DOCUMENTS

| 5,139,941 A | 8/1992 | Muzyczka et al. |
|---|---|---|
| 5,436,146 A | 7/1995 | Shenk et al. |
| 5,446,143 A | 8/1995 | Simpson et al. |
| 5,464,758 A | 11/1995 | Gossen et al. |
| 5,478,745 A | 12/1995 | Samulski et al. |
| 5,741,683 A | 4/1998 | Zhou et al. |
| 5,858,351 A | 1/1999 | Podsakoff et al. |
| 5,891,717 A | 4/1999 | Newgard |
| 6,001,650 A | 12/1999 | Colosi |
| 6,057,152 A | 5/2000 | Samulski et al. |
| 6,136,597 A | 10/2000 | Hope et al. |
| 6,156,303 A | 12/2000 | Russell et al. |
| 6,165,782 A | 12/2000 | Naldini et al. |
| 6,204,059 B1 | 3/2001 | Samulski et al. |
| 6,207,455 B1 | 3/2001 | Chang |
| 6,211,163 B1 | 4/2001 | Podsakoff et al. |
| 6,218,181 B1 | 4/2001 | Verma et al. |
| 6,258,595 B1 | 7/2001 | Gao et al. |
| 6,268,213 B1 | 7/2001 | Samulski et al. |
| 6,277,633 B1 | 8/2001 | Olsen |
| 6,323,031 B1 | 11/2001 | Cichutek |

(Continued)

FOREIGN PATENT DOCUMENTS

| EP | 2394667 A1 | 12/2011 |
|---|---|---|
| EP | 2492347 A1 | 8/2012 |

(Continued)

OTHER PUBLICATIONS

Li et al. A small regulatory elemnt from chromosome 19 enhances liver-specific gene expression. Gene Therapy 16:43-51, 2009.*

(Continued)

*Primary Examiner* — Quang Nguyen
(74) *Attorney, Agent, or Firm* — Sterne, Kessler, Goldstein & Fox P.L.L.C.

(57) ABSTRACT

The invention relates to a viral expression construct and related viral vector and composition and to their use wherein the construct and vector comprise elements a) and b): a) a nucleotide sequence encoding an insulin operably linked to a first promoter, b) a nucleotide sequence encoding a glucokinase operably linked to a second promoter and the viral expression construct and related viral vector comprise at least one of elements c), d) and e): c) the first and the second promoters are positioned in reverse orientation within the expression construct, d) the first and the second promoters are positioned in reverse orientation within the expression construct and are located adjacent to each other and e) the first promoter is a CMV promoter, preferably a mini CMV promoter.

Figure 4:
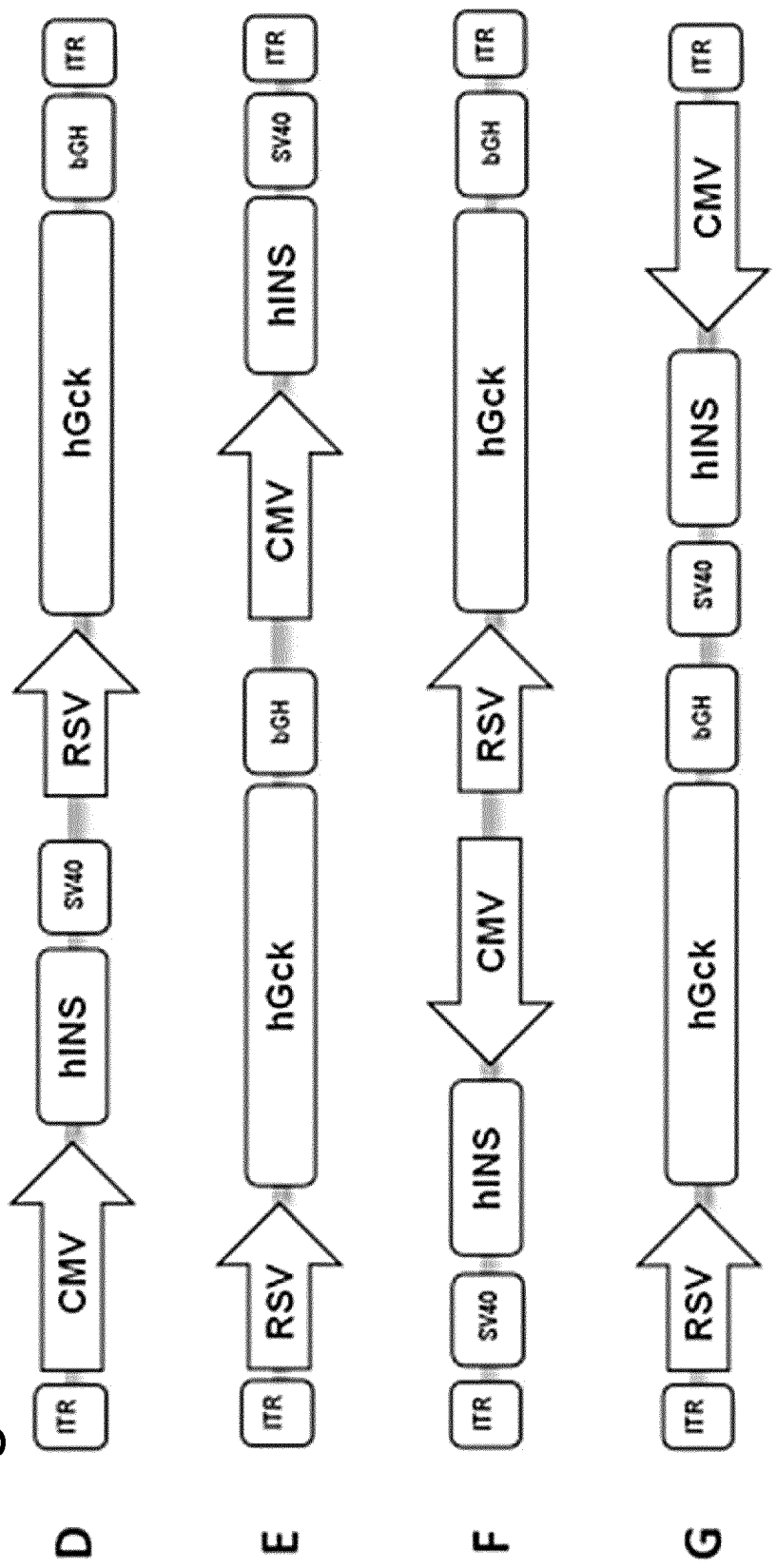

5 Claims, 13 Drawing Sheets
Specification includes a Sequence Listing.

(56) References Cited

U.S. PATENT DOCUMENTS

| | | | |
|---|---|---|---|
| 6,325,998 B1 | 12/2001 | Podsakoff et al. | |
| 6,358,732 B1 | 3/2002 | Sedlacek et al. | |
| 6,391,858 B2 | 5/2002 | Podsakoff et al. | |
| 6,432,705 B1 | 8/2002 | Yee et al. | |
| 6,491,907 B1 | 12/2002 | Rabinowitz et al. | |
| 6,531,456 B1 | 3/2003 | Kurtzman et al. | |
| 6,596,535 B1 | 7/2003 | Carter | |
| 6,642,051 B1 | 11/2003 | Lynch et al. | |
| 6,660,514 B1 | 12/2003 | Zolotukhin et al. | |
| 6,893,867 B1 | 5/2005 | Webster | |
| 6,951,753 B2 | 10/2005 | Shenk et al. | |
| 7,056,202 B2 | 6/2006 | Pein | |
| 7,056,502 B2 | 6/2006 | Hildinger et al. | |
| 7,091,029 B2 | 8/2006 | Hwang | |
| 7,094,604 B2 | 8/2006 | Snyder et al. | |
| 7,125,717 B2 | 10/2006 | Carter | |
| 7,172,893 B2 | 2/2007 | Rabinowitz et al. | |
| 7,198,951 B2 | 4/2007 | Gao et al. | |
| 7,201,898 B2 | 4/2007 | Monahan et al. | |
| 7,220,577 B2 | 5/2007 | Zolotukhin | |
| 7,229,823 B2 | 6/2007 | Samulski et al. | |
| 7,235,393 B2 | 6/2007 | Gao et al. | |
| 7,238,674 B2 | 7/2007 | Podsakoff et al. | |
| 7,250,406 B2 | 7/2007 | Tang et al. | |
| 7,282,199 B2 | 10/2007 | Gao et al. | |
| 7,319,002 B2 | 1/2008 | Wilson et al. | |
| 7,425,443 B2 | 9/2008 | Alam et al. | |
| 7,439,065 B2 | 10/2008 | Ferrari et al. | |
| 7,456,683 B2 | 11/2008 | Takano et al. | |
| 7,790,449 B2 | 9/2010 | Gao et al. | |
| 8,556,842 B2 | 10/2013 | Bridges et al. | |
| 8,865,881 B2 | 10/2014 | Balazs et al. | |
| 9,309,534 B2* | 4/2016 | Bosch Tubert et al. | |
| 9,365,829 B2* | 6/2016 | Simpson | C12N 5/067 |
| 9,527,904 B2 | 12/2016 | Balazs et al. | |
| 9,732,329 B2 | 8/2017 | Simpson et al. | |
| 10,426,845 B2 | 10/2019 | Nathwani et al. | |
| 2002/0065239 A1 | 5/2002 | Caplan et al. | |
| 2003/0138772 A1 | 7/2003 | Gao et al. | |
| 2003/0148506 A1 | 8/2003 | Kotin et al. | |
| 2003/0219409 A1* | 11/2003 | Coffin et al. | |
| 2004/0055023 A1 | 3/2004 | Bosch Tubert et al. | |
| 2005/0187154 A1 | 8/2005 | Kahn et al. | |
| 2008/0075740 A1 | 3/2008 | Gao et al. | |
| 2010/0216709 A1 | 8/2010 | Scheule et al. | |
| 2010/0240029 A1 | 9/2010 | Guarente et al. | |
| 2011/0166210 A1* | 7/2011 | Felber et al. | |
| 2012/0040401 A1* | 2/2012 | Ellis | C07K 16/00 435/69.6 |
| 2014/0194352 A1 | 7/2014 | Ling et al. | |

FOREIGN PATENT DOCUMENTS

| | | | |
|---|---|---|---|
| EP | 2692868 A1 | 2/2014 | |
| EP | 3101125 A1 | 12/2016 | |
| WO | 1998009524 A1 | 3/1998 | |
| WO | 1998011244 A2 | 3/1998 | |
| WO | WO-199832869 A1 | 7/1998 | |
| WO | 1999061601 A2 | 12/1999 | |
| WO | 2000028004 A1 | 5/2000 | |
| WO | 2000028061 A2 | 5/2000 | |
| WO | 2010010887 A1 | 1/2001 | |
| WO | 2001083692 A2 | 11/2001 | |
| WO | 2001094605 A2 | 12/2001 | |
| WO | 2002024234 A2 | 3/2002 | |
| WO | 2002049423 A1 | 6/2002 | |
| WO | WO-200249423 A1 | 6/2002 | |
| WO | 2003042397 A3 | 5/2003 | |
| WO | 2003052051 A2 | 6/2003 | |
| WO | 2003052052 A2 | 6/2003 | |
| WO | 2005033321 A3 | 4/2005 | |
| WO | WO-2006110689 A2 | 10/2006 | |
| WO | WO-2008027084 A2 | 3/2008 | |
| WO | 2008071959 A1 | 6/2008 | |
| WO | WO-2009151172 A1* | 12/2009 | C12N 9/0091 |
| WO | WO 2009151172 A1 | 12/2009 | |
| WO | WO-2011004051 A1 | 1/2011 | |
| WO | WO2011/154520 A1 | 12/2011 | |
| WO | 2012/007458 A1 | 1/2012 | |
| WO | 2012007458 A1 | 1/2012 | |
| WO | 2013033452 A2 | 3/2013 | |
| WO | 2014020149 A1 | 2/2014 | |
| WO | WO-2014020149 A1 | 2/2014 | |
| WO | 2015044292 A1 | 4/2015 | |
| WO | 2015060722 A1 | 4/2015 | |
| WO | 2015173308 A1 | 5/2015 | |
| WO | WO2015173308 A1 | 11/2015 | |
| WO | 2016041588 A1 | 3/2016 | |
| WO | 2016087678 A1 | 6/2016 | |
| WO | 2016110518 A1 | 7/2016 | |
| WO | WO2016193431 A1 | 12/2016 | |
| WO | WO2018/060097 A1 | 4/2018 | |
| WO | WO-2018060097 A1 | 4/2018 | |

OTHER PUBLICATIONS

Zarrin et al. Comparison of CMV, RSV, SV40 viral and Vlambda1 cellular promoters in B and T lymphoid and non-lymphoid cell lines. Biochimica et Biophysica Acta 1446:135-139, (Year: 1999).*

Boulos et al. Assessment of CMV, RSV and SYN1 promoters and the woodchuck post-transcriptional regulatory element in adenovirus vectors for transgene expression in cortical neuronal cultures. Brain Research 1102:27-38, (Year: 2006).*

Liu et al. Promoter effects of adeno-associated viral vector for transgene expression in the cochlea in vivo. Experimental and Molecular Medicine 39:170-175, (Year: 2007).*

Tian J et al. Independent and high-level dual-gene expression in adult stem-progenitor cells from a single lentiviral vector. Gene Therapy 16:874-884, (Year: 2009).*

Fagoe ND et al. A compact dual promoter adeno-assoicated viral vector for efficient delivery of two genes to dorsal root ganglion neurons. Gene Therapy 21:242-252, (Year: 2014).*

Callejas, D., et al., "Treatment of Diabetes and Long-Term Survival After Insulin and Glucokinase Gene Therapy," Diabetes, vol. 62, No. 5, pp. 1718-1729 (May 1, 2013).

Tae Keun Oh, et al., "Gene Therapy for Diabetes Mellitus in Rats by Intramuscular Injection of Lentivirus Containing Insulin Gene," Diabetes Research and Clinical Practice, vol. 71, No. 3, pp. 233-240 (Mar. 1, 2006).

Kamata, K., et al., "Structural Basis for Allosteric Regulation of the Monomeric Allosteric Enzyme Human Glucokinase," Structure, vol. 12, pp. 429-438 (Mar. 2004).

Smith, G. David., et al., "The Structure of T6 Human Insulin at 1.0 A Resolution," Acta Crystallographica Section D, Biological Crystallography, Research Papers, D59, pp. 474-482 (2003).

Monahan P et al, AAV vectors: is clinical success on the horizon?, Gene Therapy, vol. 7, pp. 24-30, Jan. 17, 2000.

Chao et al, Several log increase in therapeutic transgene delivery by distinct adeno-associated viral serotype vectors. Molecular Therapy vol. 2(6):619-623, 2000.

Ahi et al, Adenoviral Vector Immunity: Its implications and circumvention strategies. Curr. Gene Ther. vol. 11(4), pp. 307-320, 08.2011.

Azzoni AR, The impact of polyadenylation signals on plasmid nuclease-resistance and transgene expression. J Gene Med, vol. 9(5), pp. 392-402, 2007.

Ai-Dossari Mohammad et al, Evaluation of viral and mammalian promoters for driving transgene expression in mouse liver. Biochemical and Biophysical Research Communications vol. 339(2), pp. 673-678, Jan. 13, 2006.

Alexopoulou et al, The CMV earlyenhancer/chicken beta actin (CAG) promoter can be used to drive transgene expressionduring the differentiation of murine embryonic stem cells into vascular progenitors. Bmc Cell Biol. vol. 9(2), pp., Jan. 11, 2008.

Bish L, et aL, Adeno-Associated Virus (AAV) Serotype 9 Provides Global Cardiac Gene Transfer Superior to AAV1, AAV6, AAV7, and AAV8 in the Mouse and Rat. Hum. Gene Ther. vol. 19(12), pp. 1359-1368, 2008.

(56) References Cited

OTHER PUBLICATIONS

Boshart M, et al., Cell, 1985, A very strong enhancer is located upstream of an immediate early gene of human aytomegalovirus, vol. 41, pp. 521-530, Jun. 1, 1985.
Boulos et al, Assessment of CMV, RSV and SYN1 promoters and the woodchuck post-transcriptional regulatory element in adenovirus vectors for transgene expression in cortical neuronal cultures. Brain Research vol. 1102, pp. 27-38, 2006.
Callejas et al, Gene Therapy for Type I Diabetes by Engineering Skeletal Muscle to Express Insulin and Glucokinase (GK): Preclinical studies in Diabetic Dogs. Poster presentation, 2007.
Callejas et al, Gene Therapy for Type I Diabetes by Engineering Skeletal Muscle to Express Insulin and Glucokinase (GK): Preclinical studies in Diabetic Dogs. Poster presentation, 2008.
Carter and Samulski, Adeno-associated viral vectors as gene delivery vehicles. Int. J. Mol. Med. vol. 6, pp. 17-27, 2000.
Chiorini et al., Cloning and characterization of adeno-associated virus type 5., J . of Virology, vol. 73(2), pp. 1309-1319, Feb. 1, 1999.
Croyle M, et al., Development of Novel Formulations That Enhance Adenoviral-Mediated Gene Expression in the Lung in Vitro and in Vivo. Mol. Ther. vol. 4, pp. 22-28, 2001.
Donello J, et al., Woodchuck hepatitis virus contains a tripartite posttranscriptional regulatory element, J. Virol. 1998, vol. 72(6), pp. 5085-5092 ,Jun. 1998.
F-L Zhang et al, Celastrol enhances AAV1-mediated gene expression in mice adipose tissues. Gene Therapy vol. 18 (2), pp. 128-134, Jan. 2, 2011.
Gao et al, Clades of Adeno-associated viruses are widely disseminated in human tissues. J. Virol. vol. 78, pp. 3381-6388, 2004.
Gao et al, Novel adeno-associated viruses from rhesus monkeys as vectors for human gene therapy. PNAS vol. 99, pp. 11854-11859, 2002.
Jimenez et al, in vivo genetic engineering of murine pancreatic beta cells mediated by single-stranded adeno-associated viral vectors of serotypes 6, 8 and 9. Diabetologia ; Clinical and Experimental, Diabetes and Metabolism, Springer, Berlin, DE, vol. 54(5), pp. 1075-1086, Nov. 2, 2011.
Kapturczak et al., Transduction of Human and Mouse Pancreatic Islet Cells Using a Bicistronic Recombinant Adeno-associated Viral Vector. Molecular Therapy vol. 5(2), pp. 154-160, Feb. 2002.
Kitajima et al, Persistent liver expression of murine apoA-I using vectors based on adeno-associated viral vectors serotypes 5 and 1. Atherosclerosis vol. 186, pp. 65-73, 2006.
Larose M, et al., Essential cis-Acting Elements in Rat Uncoupling Protein Gene Are in an Enhancer Containing a complex Retinoic Acid Response Domain. J. Biol. Chem. 1996; 271(49):31533-31542, 1996.
Lebherz C, et al.,Novel Aav serotypes for improved ocular gene transfer. J. Gene Med. vol. 10, pp. 375-382, 2008.
Lee et al, Optimizing regulatable gene expression using adenoviral vectors. Experimental Physiology vol. 90, pp. 33-37, 2004.
Li et al, a small regulatory element from chromosome 19 enhances liver-specific gene expression. Gene Therapy 16, pp. 43-51, 2009.
Liu et al, Promoter effects of adeno-associated viral vector for transgene expression in the cochlea in vivo. Experimental and Molecular Medicine vol. 39, pp. 170-75, 2007.
Lock et al, Characterization of a recombinant adeno-associated virus type 2 Reference Standard Material. Hum. Gene Ther. vol. 21, pp. 1273-1285, 2010.
Loiler et al, Localized gene expression following administration of adeno-associated viral vectors via pancreatic lucts. Mot Ther. vol. 12, pp. 519-527, 2005.
Moris et al, Two novel adeno-associated viruses from cynomolgus monkey: pseudotyping characterization of capsid protein. Virology vol. 330, pp. 375-383, 2004.
Nakai H, et al., Unrestricted Hepatocyte Transduction with Adeno-Associated VirusSerotype 8 Vectors in Mice. J. Virol. vol. 79, pp. 214-224, 2005.

Okada T et al, Scalable purification of adeno-associated virus serotype 1 (AAV1) and AAV8 vectors, using dual ion-exchange adsorptive membranes., Hum. Gene Ther., vol. 20, pp. :1013-1021, Aug. 5, 2009.
Otaegui et al, Prevention of obesity and insulin resistance by glucokinase expression in skeletal muscle of transgenic mice. The FASEB Journal express article. Online 10.1096M.03-0081fje,18. 09.2003.
Pacak C, et al.,Recombinant Adeno-Associated Virus Serotype 9 Leads to Preferential Cardiac Transduction in Vivo. Circ. Res. vol. 99:e3-e9, 2006.
Qiao C et al, Liver-specific microRNA-122 target sequences incorporated in AAV vectors efficiently inhibits transgene expression in the liver, Gene Therapy vol. 18(4), pp. 403-410, Jan. 4, 2011.
Rabinowitz J et al, Cross-Packaging of a Single Adeno-Associated Virus (AAV) Type 2 Vector Genome into Multiple AAV Serotypes Enables Transduction with Broad Specificity, vol. 76(2), pp. 791-801, Jan. 2002.
Rehman et al, Efficient gene delivery to human and rodent islets with doublestranded (ds) AAV-based vectors. Gene Therapy, vol. 12(17), pp. 1313-23, 2005.
Smith T.J, Insulin-like growth factor-I regulation of immune function: a potential therapeutic target in autoimmune Diseases? Pharmacol. Rev. vol. 62, pp. 199-236, 2010.
Taymans J, et al., Comparative analysis of adeno-associated viral vector serotypes 1, 2, 5, 7, and 8 in mouse brain. Hum. Gene Ther. vol. 18, pp. 195-206, 2007.
Tian et al, Independent and high-level dual-gene expression in adult stem-progenitor cells from a single lentiviral vector. Gene Therapy vol. 16, pp. 874-884, 2009.
Urabe et al, a novel dicistronic AAV vector using a short Ires segment derived from hepatitis C virus genome. Gene vol. 200, pp. 157-62, 1997.
Vila GBP et al, 237: AAV8-mediated Sirt1 overexpression in the liver prevents high-carbohydrate diet induced NAFLD. Diabetologia, 49th Annual Meeting of the European Association for the Study of Diabetes, Springer, Berlin, DE; Barcelona, Spain, vol. 56, Suppl. 1, p. S105, 27.09.2013.
Wang et al, Improved neuronal transgene expression from an AAV-2 vector with a hybrid Cmv enhancer/PDGF-βpromoter, J Gene Med., vol. 7, pp. 945-955, Mar. 9, 2005.
Mao et al, Gene therapy vectors based on adeno-associated virus type 1. J. Virology vol. 73:3994, 1999.
Yan et al, Inverted Terminal Repeat Sequences are Important for Intermolecular Recombination and Circularization of Adeno-Associated Virus Genomes. Journal of Virology, vol. 79, pp. 364-379, 2005.
Zarrin et al, Comparison of CMV, RSV, SV40 viral and Vlambda1 cellular promoters in B and T lymphoid and non-lymphoid cell lines. Biochimica and Physica Acta vol. 1446, pp. 135-139, 1999.
Zincarelli et al, Analysis of AAV serotypes 1-9 mediated gene expression and tropism in mice after systemic Injection. Mol Ther vol. 16(6), pp. 1073-80, 2008.
Zufferey R, et al.,Woodchuck hepatitis virus post transcriptional regulatory element enhances expression of transgenes delivered by retroviral vectors. J. Virol. vol. 73, pp. 2886-2892, 1999.
Chlorini et al, Cloning of adeno-associated virus type 4 (AAV4) and generation of recombinant AAV4 particles. J. Vir. vol. 71, pp. 6823-33, 1998.
Mann et al, Gene therapy for type 1 diabetes by engineering skeletal muscle to express insulin and glucokinase (GK):Pre-clinical studies in diabetic. Diabetes (online), pp. A125-A126, 01.06.2008.
Dressman D., AAV-Mediated Gene Transfer to Models of Muscular Dystrophy: Insights into Assembly of Multi-Subunit Membrane Proteins. University of Pittsburgh, Graduate Faculty of the School of Medicine, Dept. Of Biochemistry and Molecular Genetics in partial fulfillment of the requirements for the degree of Doctor of Philosophy. 183 pp.,1997.
Mas et al., Reversal of type 1 diabetes by engineering a glucose sensor in skeletal muscle. Diabetes vol. 55(6), pp. 1546-53, Jun. 2006.

(56) References Cited

OTHER PUBLICATIONS

Jimenez-Chillaron et al., Increased glucose disposal induced by adenovirus-mediated transfer of glucokinase to skeletal muscle in vivo. Faseb J vol. 13, pp. 2153-2160, 1999.
Otaegui et al., Glucose-regulated glucose uptake by transplanted muscle cells expressing glucokinase counteracts liabetic hyperglycemia. Hum Gene Ther vol. 13, pp. 2125-2133, 2002.
Tae Keun Oh et al, Gene therapy for diabetes mellitus in rats by intramuscular injection of lentivirus containing insulin gene. Diabetes Research and Clinical Practice vol. 71(3), pp. 233-40 Jan. 3, 2006.
Lukashev et al. Viral Vectors for Gene Therapy: Current State and Clinical Perspectives. Biochemistry (Mosc) vol. 31(7), pp. 700-708, 2016.
Mas, A., et al., "Reversal of type 1 diabetes by engineering a glucose sensor in skeletal muscle," *Diabetes* 55(6):1546-53, American Diabetes Association Inc., United States (2006).
Otaegui, P.J., et al., "Glucose-regulated glucose uptake by transplanted muscle cells expressing glucokinase counteracts diabetic hyperglycemia," *Hum Gene Ther* 13(18):2125-2133, Mary Ann Liebert Inc., United States (2002).
Fagoe, N.D., et al., "A compact dural promoter adeno-associated viral vector for efficient delivery of two genes to dorsal root ganglion neurons," *Gene Ther.* 21:242-252, Nature Publishing Group, United Kingdom (2014).
American Diabetes Association, "Diagnosis and Classification of Diabetes Mellitus," *Diabetes Care* 33(Suppl 1):S62-69, American Diabetes Association, United States (2010).
Bergerot, I., et al., "Effects of insulin like growth factor-1 and insulin on effector T cells generating autoimmunie diabetes," *Diabetes Metab.* 22(4):235-239, Elsevier Masson, France (1996).
Daya, S., et al., "Gene therapy using adeno-associated virus vectors," *Clinical Microbiology Reviews* 21(4):583-593, American Society of Microbiology, United States (2008).
Gros, L., et al., "Insulin Production By Engineered Muscle Cells," *Human Gene Therapy* 10(7):1207-1217, Mary Ann Liebert, Inc., United States (1999).
Gros L., et al., "Regulated Production of Mature Insulin by Non-beta Cells," *Human Gene Therapy* 8(18):2249-2259, Mary Ann Liebert Inc., United States (1997).
Hafenrichter, D.G., et al., "Quantitative evaluation of liver-specific promoters from retroviral vectors after in vivo transduction of hepatocytes," *Blood* 84:3394-3404, American Society of Hematology, United States (1994).
Haurigot, V., et al., "Future Directions: Gene Therapy For Diabetes," Part 13, Ch. 70, in *Textbook of Diabetes*, 5th Edition, Holt, R., et al., eds., pp. 1029-1037, Wiley-Blackwell, United States (2017).
Jaen, M.L., et al., "Long-Term Efficacy And Safety Of Insulin And Glucokinase Gene Therapy For Diabetes: 8-Year Follow-Up In Dogs," *Molecular Therapy—Methods & Clinical Development* 6:1-7, Elsevier, Netherlands (2017).
Kapturczak, M., et al., "Transduction of human and mouse pancreatic islet cells using a bicistronic recombinant adeno-associated viral vector," *Molecular Therapy* 5(2):154-160, Cell Press, United States (2002).
Lee, H.C., et al., "Remission in models of type 1 diabetes by gene therapy using a single-chain insulin analogue," *Nature* 408:483-488, Nature Publishing Group, United Kingdon (2000).
Mann, C.J., et al., "Gene therapy for type 1 diabetes by expressing insulin and glucokinase (GK) in skeletal muscle; pre-clinical studies in diabetic dogs," Molecular Therapy /6(Supplement_1):5367, Cell Press, United States (2008).
Mann, C.J., et al., "Molecular Signature of the Immune and Tissue Response to Non-Coding Plasmid Dna in Skeletal Muscle After Electrotransfer," Gene Therapy /9(12):1177-1186, Macmillan Publishers Limited, United States (2012).
Mann, C.J., et al., "Skeletal Muscle Metabolism in the Pathology and Treatment of Type 1 Diabetes," Current Pharmaceutical Design 16(8):1002-1020, Bentham Science Publishers Ltd., Netherlands (2010).
Mann, C.J., et al., "Gene therapy for type 1 diabetes by engineering skeletal muscle to express insulin and glucokinase (GK): Preclinical studies in diabetic dogs," Diabetes — American Diabetes Association 68' Scientific Sessions: Abstract 420-P, pp. A125-A126, United States (Jun. 2008). Accessed at http://diabetes.diabetesjournals.org.
Matschinsky, M.F., "Banting Lecture 1995. A lesson in metabolic regulation inspired by the glucokinase glucose sensor paradigm," Diabetes 45(2):223-241, American Diabetes Association, Inc., United States (1996).
O'Brien, T., "Gene Therapy for Type 1 Diabetes Moves a Step Closer to Reality," Diabetes 62(5):1396-1397, American Diabetes Association, United States (2013).
Oh, T.K., et al., "Gene therapy for diabetes mellitus in rats by intramuscular injection of lentivirus containing insulin gene," Diabetes Research and Clinical Practice 71(3):233- 240, Elsevier Ireland Ltd., Ireland (2006).
Otaegui, P., et al., "Expression of Glucokinase in Skeletal Muscle: a New Approach to Counteract Diabetic Hyperglycemia," Human Gene Therapy 11(11):1543-1552, Mary Ann Liebert, Inc., United States (2000).
Printz, R.L., et al., "Mammalian glucokinase," Annu Rev Nutr 13:463-496, Annual Reviews Inc., United States (1993).
Sharp, P.M., and Li, W-H., "The codon adaptation index - a measure of directional synonymous codon usage bias, and its potential applications," Nucleic Acids Res. 15(3):1281-1295, Oxford University Press, United Kingdom (1987).
Zarrin, A.A., et al., "Comparison of CMV, RSV, SV40 viral and Vlambda1 cellular promoters in B and T lymphoid and non-lymphoid cell lines," *Biochim Biophys Acta* 1446(1-2):135-139, Elsevier, Netherlands (1999).
Anguela, X.M. et al., "Nonviral-Mediated Hepatic Expression of IGF-I Increases Treg Levels and Suppresses Autoimmune Diabetes in Mice," Diabetes, 62(2): 551-560, The American Diabetes Association, United States (2013).
Ayuso, E., and Bosch, F., "Highlights On AAV Mediated Gene Transfer: Introduction," in *The Clinibook: Clinical Gene Transfer State Of The Art*, Cohen-Haguenauer, O., ed., pp. 31-34, Éditions EDK, Paris (2012).
Ayuso, E., et al., "AAV Gene Therapy For Diabetes Mellitus," in *The Clinibook: Clinical Gene Transfer State of the Art*, Cohen-Haguenauer, O., ed., pp. 62-70, Éditions EDK, Paris (2012).
Ayuso, E., et al., "Reference Materials for the Characterization of Adeno-Associated Viral Vectors," in *The Clinibook: Clinical Gene Transfer State of the Art*, Cohen-Haguenauer, O., ed., pp. 83-90, Éditions EDK, Paris (2012).
Ayuso, E., et al., "High AAV vector purity results in serotype- and tissue- independent enhancement of transduction effiiency," *Gene Therapy*, 17(4):503-10, Macmillan Publishers Limited, United States (2010).
Ayuso, E., et al., "Production, Purification and Characterization of Adeno-Associated Vectors," *Current Gene Therapy*, 10(6): 423-426, Bentham Science Publishers Ltd., Netherlands (2010).
Fagoe, ND., "A compact dual promoter adeno-associated viral vector for effiient delivery of two genes to dorsal root ganglion neurons," *Gene Therapy*, 21: 242-252, Macmillan Publishers Limited, United States (2014).
Garcia, M., et al., "Phosphofructo-1-Kinase Deficiency Leads To A Severe Cardiac And Hematological Disorder In Addition To Skeletal Muscle Glycogenosis," *PLoS Genetics*, 5(8): e1000615, pp. 1-12, Public Library of Science, United States (2009).
Gros, L., et al., "Insulin Production By Engineered Muscle Cells," *Human Gene Therapy*. 10:1207-1217, Mary Ann Liebert, Inc., United States (1999).
Haurigot, V., et al., "Future Directions: Gene Therapy For Diabetes," Part 13, Ch. 70, in Textbook of *Diabetes*, 5th Edition, Holt, R., et al., edds., pp. 1029-1037, Wiley-Blackwell, United States (2017).
Mann, C.J., et al., "Molecular Signature Of The Immune And Tissue Response To Non-Coding Plasmid DNA In Skeletal Muscle After Electrotransfer," *Gene Therapy* 19(12):1177-1186, Macmillan Publishers Limited, United States (2012).

(56) References Cited

OTHER PUBLICATIONS

Otaegui, P., et al., "Expression Of Glucokinase In Skeletal Muscle: A New Approach To Counteract Diabetic Hyperglycemia," *Human Gene Therapy*, 11: 1543-1552, Mary Ann Liebert, Inc., United States (2000).

Riu, E., et al., "Counteraction Of Type 1 Diabetic Alterations By Engineering Skeletal Muscle to Produce Insulin, Insights From Transgenic Mice," *Diabetes*, 51:704-711, American Diabetes Association (2002).

Vilà, L. et al., Aav-mediated Sirt1 Overexpression In Skeletal Muscle Activates Oxidative Capacity But Does Not Prevent Insulin Resistance. Molecular Therapy-*Methods & Clinical Development*, 5:16072, eCollection (Nov. 2016).

\* cited by examiner

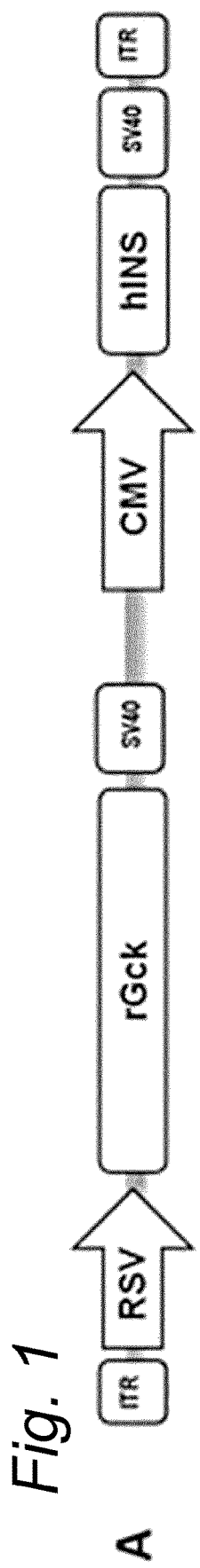
Fig. 1
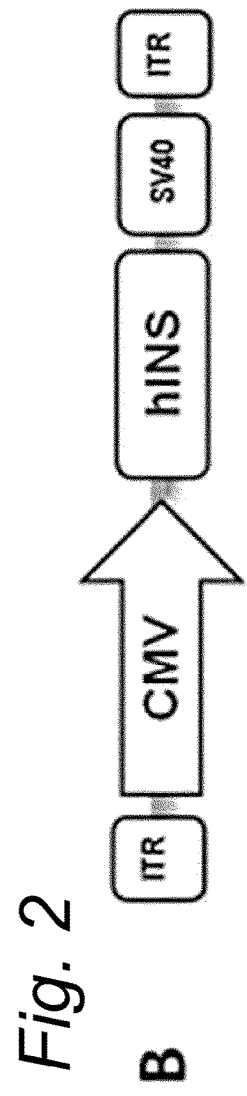
Fig. 2
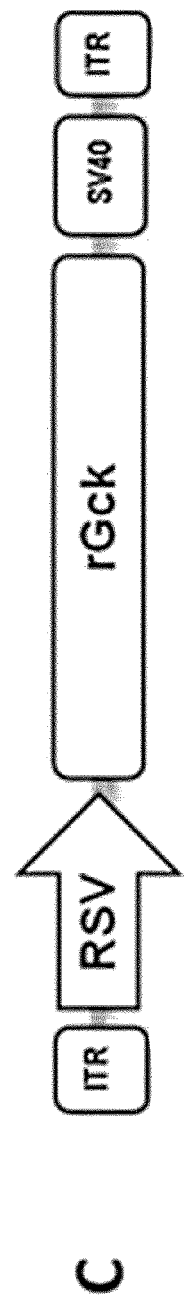
Fig. 3
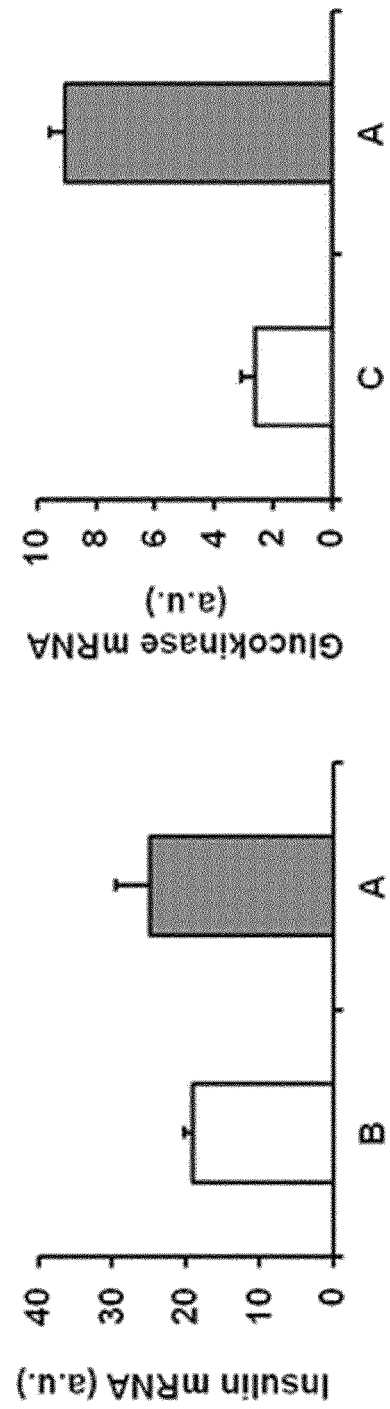

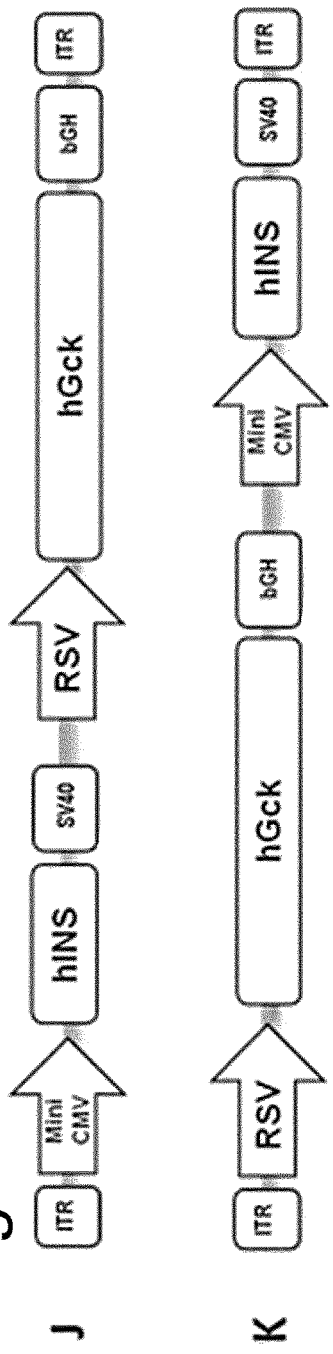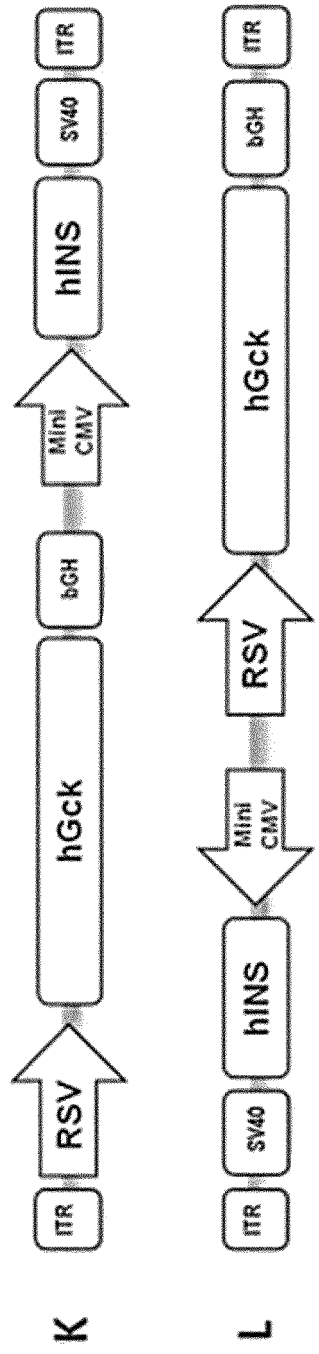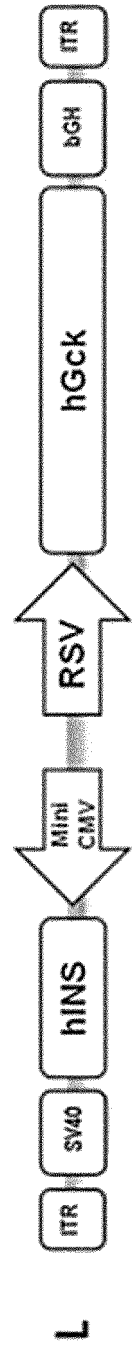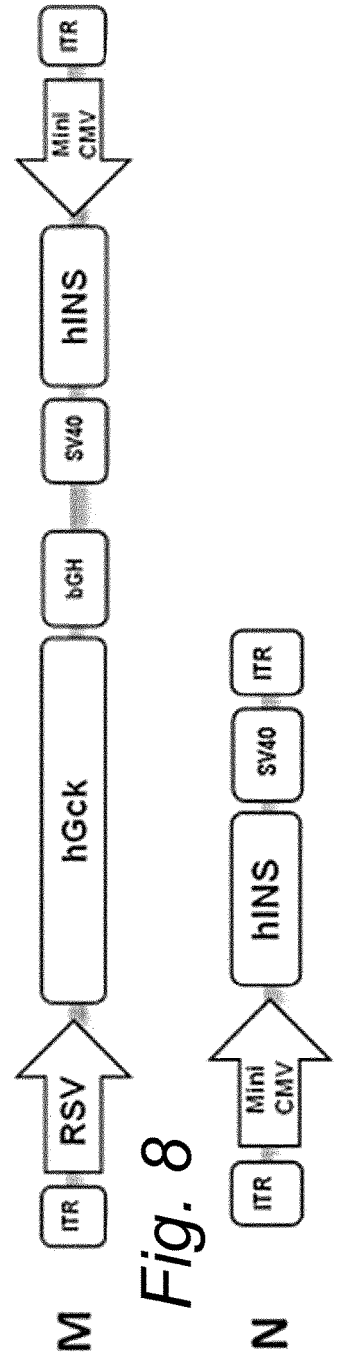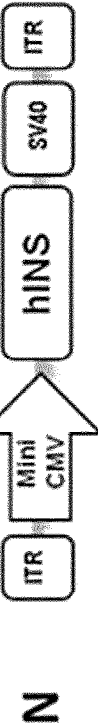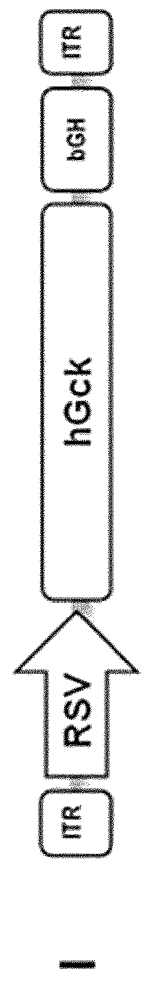
Fig. 7
Fig. 8

SEQUENCE LISTING

<160> NUMBER OF SEQ ID NOS: 33

<210> SEQ ID NO 1
<211> LENGTH: 349
<212> TYPE: DNA
<213> ORGANISM: Homo sapiens
<220> FEATURE:
<221> NAME/KEY: Human Insulin(A718) Cdna
<222> LOCATION: (1)..(349)

<400> SEQUENCE: 1

```
cttctgccat ggccctgtgg atgcgcctcc tgcccctgct ggcgctgctg gccctctggg      60
gacctgaccc agccgcagcc tttgtgaacc aacacctgtg cggctcagat ctggtggaag     120
ctctctacct agtgtgcggg gaacgaggct tcttctacac acccaggacc aagcgggagg     180
cagaggacct gcaggtgggg caggtggagc tgggcggggg ccctggtgca ggcagcctgc     240
agcccttggc cctggagggg tcgcgacaga agcgtggcat tgtggaacaa tgctgtacca     300
gcatctgctc cctctaccag ctggagaact actgcaacta gacgcagcc                 349
```

<210> SEQ ID NO 2
<211> LENGTH: 1409
<212> TYPE: DNA
<213> ORGANISM: Homo sapiens
<220> FEATURE:
<221> NAME/KEY: cDNA human glucokinase
<222> LOCATION: (1)..(1409)

<400> SEQUENCE: 2

```
tcgagaccat ggcgatggat gtcacaagga gccaggccca gacagccttg actctggtag      60
agcagatcct ggcagagttc cagctgcagg aggaggacct gaagaaggtg atgagacgga    120
tgcagaagga gatggaccgc ggcctgaggc tggagaccca tgaagaggcc agtgtgaaga    180
tgctgcccac ctacgtgcgc tccacccag aaggctcaga agtcgggac ttcctctccc      240 tggacctggg tggcactaac ttcagggtga tgctggtgaa ggtgggagaa ggtgaggagg    300
ggcagtggag cgtgaagacc aaacaccaga tgtactccat ccccgaggac gccatgaccg    360
gcactgctga gatgctcttc gactacatct ctgagtgcat ctccgacttc ctggacaagc    420
atcagatgaa acacaagaag ctgccccctgg gcttcaccctt ctcctttcct gtgaggcacg    480
aagacatcga taagggcatc cttctcaact ggaccaaggg cttcaaggcc tcaggagcag    540
aagggaacaa tgtcgtgggg cttctgcgag acgctatcaa acggagggg gactttgaaa    600 tggatgtggt ggcaatggtg aatgacacgg tggccacgat gatctcctgc tactacgaag    660
accatcagtg cgaggtcggc atgatcgtgg gcacgggctg caatgcctgc tacatggagg    720
agatgcagaa tgtggagctg gtggagggg acagggccg catgtgcgtc aataccgagt    780
ggggcgcctt cggggactcc ggcgagctgg acgagttcct gctggagtat gaccgcctgg    840
tggacgagag ctctgcaaac cccggtcagc agctgtatga aagctcata ggtggcaagt    900 acatgggcga gctggtgcgg cttgtgctgc tcaggctcgt ggacgaaaac ctgctcttcc    960
acggggaggc ctccgagcag ctgcgcacac gcggagcctt cgagacgcgc ttcgtgtcgc   1020
```

```
aggtggagag cgacacgggc gaccgcaagc agatctacaa catcctgagc acgctggggc   1080
tgcgaccctc gaccaccgac tgcgacatcg tgcgccgcgc ctgcgagagc gtgtctacgc   1140
gcgctgcgca catgtgctcg gcggggctgg cgggcgtcat caaccgcatg cgcgagagcc   1200
gcagcgagga cgtaatgcgc atcactgtgg gcgtggatgg ctccgtgtac aagctgcacc   1260
ccagcttcaa ggagcggttc catgccagcg tgcgcaggct gacgcccagc tgcgagatca   1320
ccttcatcga gtcggaggag ggcagtggcc ggggcgcggc cctggtctcg gcggtggcct   1380
gtaagaaggc ctgtatgctg ggccagtga                                    1409

<210> SEQ ID NO 3
<211> LENGTH: 797
<212> TYPE: DNA
<213> ORGANISM: Artificial
<220> FEATURE:
<223> OTHER INFORMATION: CMV promoter

<400> SEQUENCE: 3
tgtagttaat gattaacccg ccatgctact tatctacaga tctcaatatt ggccattagc    60
catattattc attggttata tagcataaat caatattggc tattggccat tgcatacgtt   120
gtatctatat cataatatgt acatttatat ggctcatgt ccaatatgac cgccatgttg    180
gcattgatta ttgactagtt attaatagta tcaattacg gggtcattag ttcatagccc    240
atatatggag ttccgcgtta cataacttac ggtaaatggc ccgcctggct gaccgcccaa    300 cgaccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagtc cgccccctat tgacgtcaat gacggtaaat ggcccgcctg    480
gcattatgcc cagtacatga ccttacggga ctttcctact tggcagtaca tctacgtatt    540
agtcatcgct attaccatgg tgatgcggtt ttggcagtac accaatgggc gtggatagcg    600
gtttgactca cggggatttc caagtctcca ccccattgac gtcaatggga gtttgttttg    660
gcaccaaaat caacgggact ttccaaaatg tcgtaacaac tgcgatcgcc cgccccgttg    720
acgcaaatgg gcggtaggcg tgtacggtgg gaggtctata taagcagagc tcgtttagtg    780
aaccgtcaga tcactag                                                  797

<210> SEQ ID NO 4
<211> LENGTH: 346
<212> TYPE: DNA
<213> ORGANISM: Artificial
<220> FEATURE:
<223> OTHER INFORMATION: intronic sequence associated with CMV promoter
<220> FEATURE:
<221> NAME/KEY: Intronic sequence associated with CMV promoter
<222> LOCATION: (1)..(346)

<400> SEQUENCE: 4
tattgcggta gtttatcaca gttaaattgc taacgcagtc agtgcttctg acacaacagt    60
ctcgaactta agctgcagtg actctcttaa ggtagccttg cagaagttgg tcgtgaggca   120
ctgggcaggt aagtatcaag gttacaagac aggtttaagg agaccaatag aaactgggct   180
tgtcgagaca gagaagactc ttgcgtttct gataggcacc tattggtctt actgacatcc   240
actttgcctt tctctccaca ggtgtccact cccagttcaa ttacagctct taaggctaga   300
gtacttaata cgactcacta tagaatacga ctcactatag ggagac                  346

<210> SEQ ID NO 5
```

```
<211> LENGTH: 411
<212> TYPE: DNA
<213> ORGANISM: Artificial
<220> FEATURE:
<223> OTHER INFORMATION: Mini CMV promoter
<220> FEATURE:
<221> NAME/KEY: Mini CMV promoter
<222> LOCATION: (1)..(411)

<400> SEQUENCE: 5
tatgccaagt acgcccccta ttgacgtcaa tgacggtaaa tggcccgcct ggcattatgc        60
ccagtacatg acctTatggg actttcctac ttggcagtac atctacgtat tagtcatcgc       120
tattaccatg gtgatgcggt tttggcagta catcaatggg cgtggatagc ggtttgactc       180
acggggattt ccaagtctcc accccattga cgtcaatggg agtttgtttt ggcaccaaaa       240
tcaacgggac tttccaaaat gtcgtaacaa ctccgcccca ttgacgcaaa tgggcggtag       300
gcgtgtacgg tgggaggtct atataagcag agctctctgg ctaactagag aacccactgc       360
ttaactggct tatcgaaatt aatacgactc actataggga gacccaagct t                411

<210> SEQ ID NO 6
<211> LENGTH: 623
<212> TYPE: DNA
<213> ORGANISM: Artificial
<220> FEATURE:
<223> OTHER INFORMATION: RSV promoter
<220> FEATURE:
<221> NAME/KEY: RSV promoter
<222> LOCATION: (1)..(623)

<400> SEQUENCE: 6
catgtttgac agcttatcat cgcagatccg tatggtgcac tctcagtaca atctgctctg        60
atgccgcata gttaagccag tatctgctcc ctgcttgtgt gttggaggtc gctgagtagt       120
gcgcgagcaa aatttaagct acaacaaggc aaggcttgac cgacaattgc atgaagaatc       180
tgcttagggt taggcgtttt gcgctgcttc gcgatgtacg ggccagatat tcgcgtatct       240
gaggggacta gggtgtgttt aggcgaaaag cggggcttcg gttgtacgcg gttaggagtc       300
ccctcaggat atagtagttt cgcttttgca tagggagggg gaaatgtagt cttatgcaat       360
actcttgtag tcttgcaaca tggtaacgat gagttagcaa catgccttac aaggagagaa       420
aaagcaccgt gcatgccgat tggtggaagt aaggtggtac gatcgtgcct tattaggaag       480
gcaacagacg ggtctgacat ggattggacg aaccactaaa ttccgcattg cagagatatt       540
gtatttaagt gcctagctcg atacaataaa cgccatttga ccattcacca cattggtgtg       600
cacctccaag ctgggtacca gct                                                623

<210> SEQ ID NO 7
<211> LENGTH: 259
<212> TYPE: DNA
<213> ORGANISM: Artificial
<220> FEATURE:
<223> OTHER INFORMATION: bGH polyadenylation signal

<400> SEQUENCE: 7
cacgtggagc tcgctgatca gcctcgactg tgccttctag ttgccagcca tctgttgttt        60
gcccctcccc cgtgccttcc ttgaccctgg aaggtgccac tcccactgtc ctttcctaat       120
aaaatgagga aattgcatcg cattgtctga gtaggtgtca ttctattctg ggggtgggg       180 tggggcagga cagcaagggg gaggattggg aagacaatag caggcatgct ggggatgcgg       240
tgggctctat ggccacgtg                                                     259
```

<210> SEQ ID NO 8
<211> LENGTH: 8520
<212> TYPE: DNA
<213> ORGANISM: Artificial
<220> FEATURE:
<223> OTHER INFORMATION: Construct A
<220> FEATURE:
<221> NAME/KEY: Construct A
<222> LOCATION: (1)..(8520)

<400> SEQUENCE: 8

```
ctagacatgg ctcgacagat ctcaatattg gccattagcc atattattca ttggttatat      60
agcataaatc aatattggct attggccatt gcatacgttg tatctatatc ataatatgta     120
catttatatt ggctcatgtc caatatgacc gccatgttgg cattgattat tgactagtta     180
ttaatagtaa tcaattacgg ggtcattagt tcatagccca tatatggagt tccgcgttac     240
ataacttacg gtaaatggcc cgcctggctg accgcccaac gacccccgcc cattgacgtc     300
aataatgacg tatgttccca tagtaacgcc aatagggact ttccattgac gtcaatgggt     360
ggagtattta cggtaaactg cccacttggc agtacatcaa gtgtatcata tgccaagtcc     420 gcccctatt gacgtcaatg acggtaaatg gcccgcctgg cattatgccc agtacatgac     480
cttacgggac tttcctactt ggcagtacat ctacgtatta gtcatcgcta ttaccatggt     540
gatgcggttt tggcagtaca ccaatgggcg tggatagcgg tttgactcac ggggatttcc     600
aagtctccac cccattgacg tcaatgggag tttgttttgg caccaaaatc aacgggactt     660
tccaaaatgt cgtaacaact gcgatcgccc gccccgttga gcaaatggg cggtaggcgt     720 gtacggtggg aggtctatat aagcagagct cgtttagtga accgtcagat cactagaagc     780
tttattgcgg tagtttatca cagttaaatt gctaacgcag tcagtgcttc tgacacaaca     840
gtctcgaact taagctgcag tgactctctt aaggtagcct gcagaagtt ggtcgtgagg     900 cactgggcag gtaagtatca aggttacaag acaggtttaa ggagaccaat agaaactggg     960
cttgtcgaga cagagaagac tcttgcgttt ctgataggca cctattggtc ttactgacat    1020
ccactttgcc tttctctcca caggtgtcca ctcccagttc aattacagct cttaaggcta    1080
gagtacttaa tacgactcac tataggctag cctcgagaat tctgccatgg ccctgtggat    1140
gcgcctcctg cccctgctgg cgctgctggc cctctgggga cctgacccag ccgcagcctt    1200
tgtgaaccaa cacctgtgcg gctcagatct ggtggaagct ctctacctag tgtgcgggga    1260
acgaggcttc ttctacacac ccaggaccaa gcgggaggca gaggacctgc aggtggggca    1320
ggtggagctg ggcgggggcc ctggtgcagg cagcctgcag cccttggccc tggaggggtc    1380
gcgacagaag cgtggcattg tggaacaatg ctgtaccagc atctgctccc tctaccagct    1440
ggagaactac tgcaactaga cgcagctgca agcttatcga taccgtcgac ccgggcggcc    1500
gcttcccttt agtgagggtt aatgcttcga gcagacatga taagatacat tgatgagttt    1560
ggacaaacca caactagaat gcagtgaaaa aaatgcttta tttgtgaaat ttgtgatgct    1620
attgctttat ttgtaaccat tataagctgc aataaacaag ttaacaacaa caattgcatt    1680
cattttatgt ttcaggttca ggggagatg tgggaggttt tttaaagcaa gtaaaacctc    1740
tacaaatgtg gtaaaatccg ataagggact agagcatggc tacgtagata agtagcatgg    1800
cgggttaatc attaactaca aggaaccct agtgatggag ttggccactc cctctctgcg    1860
cgctcgctcg ctcactgagg ccgggcgacc aaaggtcgcc cgacgcccgg ctttgcccg    1920 ggcggcctca gtgagcgagc gagcgcgcca gctggcgtaa tagcgaagag gcccgcaccg    1980
```

```
atcgcccttc caacagttg cgcagcctga atggcgaatg gaattccaga cgattgagcg    2040
tcaaaatgta ggtatttcca tgagcgtttt tccgttgcaa tggctggcgg taatattgtt    2100
ctggatatta ccagcaaggc cgatagtttg agttcttcta ctcaggcaag tgatgttatt    2160
actaatcaaa gaagtattgc gacaacggtt aatttgcgtg atggacagac tcttttactc    2220
ggtggcctca ctgattataa aaacacttct caggattctg gcgtaccgtt cctgtctaaa    2280
atcccttta tcggcctcct gtttagctcc cgctctgatt ctaacgagga aagcacgtta    2340
tacgtgctcg tcaaagcaac catagtacgc gccctgtagc ggcgcattaa gcgcggcggg    2400
tgtggtggtt acgcgcagcg tgaccgctac acttgccagc gccctagcgc ccgctccttt    2460
cgctttcttc ccttcctttc tcgccacgtt cgccggcttt ccccgtcaag ctctaaatcg    2520
ggggctccct ttagggttcc gatttagtgc tttacggcac ctcgacccca aaaaacttga    2580
ttagggtgat ggttcacgta gtgggccatc gccctgatag acggtttttc gccctttgac    2640
gttggagtcc acgttcttta atagtggact cttgttccaa actggaacaa cactcaaccc    2700
tatctcggtc tattctttg atttataagg gattttgccg atttcggcct attggttaaa    2760
aaatgagctg atttaacaaa aatttaacgc gaattttaac aaaatattaa cgtctacaat    2820
ttaaatattt gcttatacaa tcttcctgtt tttggggctt ttctgattat caaccggggt    2880
acatatgatt gacatgctag ttttacgatt accgttcatc gattctcttg tttgctccag    2940
actctcaggc aatgacctga tagcctttgt agagacctct caaaaatagc taccctctcc    3000
ggcatgaatt tatcagctag aacggttgaa tatcatattg atggtgattt gactgtctcc    3060
ggcctttctc acccgtttga atctttacct acacattact caggcattgc atttaaaata    3120
tatgagggtt ctaaaaattt ttatccttgc gttgaaataa aggcttctcc cgcaaaagta    3180
ttacagggtc ataatgtttt tggtacaacc gatttagctt tatgctctga ggctttattg    3240
cttaattttg ctaattcttt gccttgcctg tatgatttat tggatgttgg aatcgcctga    3300
tgcggtattt tctccttacg catctgtgcg gtatttcaca ccgcatatgg tgcactctca    3360
gtacaatctg ctctgatgcc gcatagttaa gccagccccg acaccgcca acaccgctg     3420
acgcgccctg acgggcttgt ctgctcccgg catccgctta cagacaagct gtgaccgtct    3480
ccggagctg catgtgtcag aggttttcac cgtcatcacc gaaacgcgcg agacgaaagg     3540
gcctcgtgat acgcctattt ttataggtta atgtcatgat aataatggtt tcttagacgt    3600
caggtggcac ttttcgggga atgtgcgcg gaacccctat ttgtttattt ttctaaatac    3660
attcaaatat gtatccgctc atgagacaat aaccctgata aatgcttcaa taatattgaa    3720
aaaggaagag tatgagtatt caacatttcc gtgtcgccct tattcccttt tttgcggcat    3780
tttgccttcc tgttttgct cacccagaaa cgctggtgaa agtaaaagat gctgaagatc    3840
agttgggtgc acgagtgggt tacatcgaac tggatctcaa cagcggtaag atccttgaga    3900
gttttcgccc cgaagaacgt tttccaatga tgagcacttt taaagttctg ctatgtggcg    3960
cggtattatc ccgtattgac gccgggcaag agcaactcgg tcgccgcata cactattctc    4020
agaatgactt ggttgagtac tcaccagtca cagaaaagca tcttacggat ggcatgacag    4080
taagagaatt atgcagtgct gccataacca tgagtgataa cactgcggcc aacttacttc    4140
tgacaacgat cggaggaccg aaggagctaa ccgcttttt gcacaacatg gggatcatg     4200
taactcgcct tgatcgttgg gaaccggagc tgaatgaagc cataccaaac gacgagcgtg    4260
acaccacgat gcctgtagca atggcaacaa cgttgcgcaa actattaact ggcgaactac    4320
```

```
ttactctagc ttcccggcaa caattaatag actggatgga ggcggataaa gttgcaggac    4380
cacttctgcg ctcggccctt ccggctggct ggtttattgc tgataaatct ggagccggtg    4440
agcgtgggtc tcgcggtatc attgcagcac tggggccaga tggtaagccc tcccgtatcg    4500
tagttatcta cacgacgggg agtcaggcaa ctatggatga acgaaataga cagatcgctg    4560
agataggtgc ctcactgatt aagcattggt aactgtcaga ccaagtttac tcatatatac    4620
tttagattga tttaaaactt catttttaat ttaaaaggat ctaggtgaag atccttttg     4680
ataatctcat gaccaaaatc ccttaacgtg agttttcgtt ccactgagcg tcagaccccg    4740
tagaaaagat caaaggatct tcttgagatc cttttttcct gcgcgtaatc tgctgcttgc    4800
aaacaaaaaa accaccgcta ccagcggtgg tttgtttgcc ggatcaagag ctaccaactc    4860
tttttccgaa ggtaactggc ttcagcagag cgcagatacc aaatactgtc cttctagtgt    4920
agccgtagtt aggccaccac ttcaagaact ctgtagcacc gcctacatac ctcgctctgc    4980
taatcctgtt accagtggct gctgccagtg gcgataagtc gtgtcttacc gggttggact    5040
caagacgata gttaccggat aaggcgcagc ggtcgggctg aacggggggt tcgtgcacac    5100
agcccagctt ggagcgaacg acctacaccg aactgagata cctacagcgt gagctatgag    5160
aaagcgccac gcttcccgaa gggagaaagg cggacaggta tccggtaagc ggcagggtcg    5220
gaacaggaga gcgcacgagg gagcttccag ggggaaacgc ctggtatctt tatagtcctg    5280
tcgggtttcg ccacctctga cttgagcgtc gatttttgtg atgctcgtca ggggggcgga    5340
gcctatggaa aaacgccagc aacgcggcct ttttacggtt cctggccttt tgctggcctt    5400
ttgctcacat gttctttcct gcgttatccc ctgattctgt ggataaccgt attaccgcct    5460
ttgagtgagc tgataccgct cgccgcagcc gaacgaccga gcgcagcgag tcagtgagcg    5520
aggaagcgga agagcgccca atacgcaaac cgcctctccc cgcgcgttgg ccgattcatt    5580
aatgcagcag ctgcgcgctc gctcgctcac tgaggccgcc cgggcaaagc ccgggcgtcg    5640
ggcgaccttt ggtcgcccgg cctcagtgag cgagcgagcg cgcagagagg gagtggccaa    5700
ctccatcact aggggttcct tgtagttaat gattaacccg ccatgctact tatctacgta    5760
gccatgctct aggtagccat gctctggaag atccgacgc gtcatgtttg acagcttatc     5820
atcgcagatc cgtatggtgc actctcagta caatctgctc tgatgccgca tagttaagcc    5880
agtatctgct ccctgcttgt gtgttggagg tcgctgagta gtgcgcgagc aaaatttaag    5940
ctacaacaag gcaaggcttg accgacaatt gcatgaagaa tctgcttagg gttaggcgtt    6000
ttgcgctgct tcgcgatgta cgggccagat attcgcgtat ctgaggggac tagggtgtgt    6060
ttaggcgaaa agcggggctt cggttgtacg cggttaggag tcccctcagg atatagtagt    6120
ttcgcttttg catagggagg gggaaatgta gtcttatgca atactcttgt agtcttgcaa    6180
catggtaacg atgagttagc aacatgcctt acaaggagag aaaaagcacc gtgcatgccg    6240
attggtggaa gtaaggtggt acgatcgtgc cttattagga aggcaacaga cgggtctgac    6300
atggattgga cgaaccacta aattccgcat tgcagagata ttgtatttaa gtgcctagct    6360
cgatacaata aacgccattt gaccattcac cacattggtg tgcacctcca agctgggtac    6420
cagctgctag caagcttgag atctgcttca gctggaggca ctgggcaggt aagtatcaag    6480
gttacaagac aggtttaagg agaccaatag aaactgggct tgtcgagaca gagaagactc    6540
ttgcgtttct gataggcacc tattggtctt actgacatcc actttgcctt tctctccaca    6600
ggtgcagctg ctgcagcggg aattcaacag gtggcctcag gagtcaggaa catctctact    6660
tccccaacga cccctgggtt gtcctctcag agatggctat ggatactaca aggtgtggag    6720
```

```
cccagttgtt gactctggtc gagcagatcc tggcagagtt ccagctgcag gaggaagacc    6780
tgaagaaggt gatgagccgg atgcagaagg agatggaccg tggcctgagg ctggagaccc    6840
acgaggaggc cagtgtaaag atgttaccca cctacgtgcg ttccacccca gaaggctcag    6900
aagtcggaga ctttctctcc ttagacctgg gaggaaccaa cttcagagtg atgctggtca    6960
aagtgggaga gggggaggca gggcagtgga gcgtgaagac aaaacaccag atgtactcca    7020
tccccgagga cgccatgacg ggcactgccg agatgctctt tgactacatc tctgaatgca    7080
tctctgactt ccttgacaag catcagatga agcacaagaa actgcccctg ggcttcacct    7140
tctccttccc tgtgaggcac gaagacctag acaagggcat cctcctcaat tggaccaagg    7200
gcttcaaggc ctctggagca gaagggaaca acatcgtagg acttctccga gatgctatca    7260
agaggagagg ggactttgag atggatgtgg tggcaatggt gaacgacaca gtggccacaa    7320
tgatctcctg ctactatgaa gaccgccaat gtgaggtcgg catgattgtg ggcactggct    7380
gcaatgcctg ctacatggag gaaatgcaga atgtggagct ggtggaaggg gatgagggac    7440
gcatgtgcgt caacacggag tggggcgcct tcggggactc gggcgagctg gatgagttcc    7500
tactggagta tgaccggatg gtggatgaaa gctcagcgaa ccccggtcag cagctgtacg    7560
agaagatcat cggtgggaag tatatgggcg agctggtacg acttgtgctg cttaagctgg    7620
tggacgagaa ccttctgttc cacggagagg cctcggagca gctgcgcacg cgtggtgctt    7680
ttgagacccg tttcgtgtca caagtggaga gcgactccgg ggaccgaaag cagatccaca    7740
acatcctaag cactctgggg cttcgaccct ctgtcaccga ctgcgacatt gtgcgccgtg    7800
cctgtgaaag cgtgtccact cgcgccgccc atatgtgctc cgcaggacta gctggggtca    7860
taaatcgcat gcgcgaaagc cgcagtgagg acgtgatgcg catcactgtg ggcgtggatg    7920
gctccgtgta caagctgcac ccgagcttca aggagcggtt tcacgccagt gtgcgcaggc    7980
tgacacccaa ctgcgaaatc accttcatcg aatcagagga gggcagcggc agggagccg    8040
cactggtctc tgcggtggcc tgcaagaagg cttgcatgct ggcccagtga atccaggtc    8100
atatggaccg ggacctgggt tccacgggga ctccacacac cacaaatgct cccagcccac    8160
cggggcagga gacctattct gctgctaccc ctggaaaatg gggagaggcc cctgcaagcc    8220
gagtcggcca gtgggacagc cctaggctgg atcggccgct tcgagcagac atgataagat    8280
acattgatga gtttggacaa accacaacta gaatgcagtg aaaaaaatgc tttatttgtg    8340
aaatttgtga tgctattgct ttatttgtaa ccattataag ctgcaataaa caagttaaca    8400
acaacaattg cattcatttt atgtttcagg ttcaggggga gatgtgggag gttttttaaa    8460
gcaagtaaaa cctctacaaa tgtggtaaaa tcgattagga tcttcctaga gcatggctac    8520
```

<210> SEQ ID NO 9
<211> LENGTH: 7260
<212> TYPE: DNA
<213> ORGANISM: Artificial
<220> FEATURE:
<223> OTHER INFORMATION: Construct D
<220> FEATURE:
<221> NAME/KEY: Construct D
<222> LOCATION: (1)..(7260)

<400> SEQUENCE: 9

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgcg atatctgtag ttaatgatta accgccatg     180
```

```
ctacttatct acagatctca atattggcca ttagccatat tattcattgg ttatatagca    240
taaatcaata ttggctattg gccattgcat acgttgtatc tatatcataa tatgtacatt    300
tatattggct catgtccaat atgaccgcca tgttggcatt gattattgac tagttattaa    360
tagtaatcaa ttacggggtc attagttcat agcccatata tggagttccg cgttacataa    420
cttacggtaa atggcccgcc tggctgaccg cccaacgacc cccgcccatt gacgtcaata    480
atgacgtatg ttcccatagt aacgccaata gggactttcc attgacgtca atgggtggag    540
tatttacggt aaactgccca cttggcagta catcaagtgt atcatatgcc aagtccgccc    600
cctattgacg tcaatgacgg taaatggccc gcctggcatt atgcccagta catgacctta    660
cgggactttc ctacttggca gtacatctac gtattagtca tcgctattac catggtgatg    720
cggttttggc agtacaccaa tgggcgtgga tagcggtttg actcacgggg atttccaagt    780
ctccacccca ttgacgtcaa tgggagtttg ttttggcacc aaaatcaacg ggactttcca    840
aaatgtcgta acaactgcga tcgcccgccc cgttgacgca aatgggcggt aggcgtgtac    900
ggtgggaggt ctatataagc agagctcgtt tagtgaaccg tcagatcact aggctagcta    960
ttgcggtagt ttatcacagt taaattgcta acgcagtcag tgcttctgac acaacagtct   1020
cgaacttaag ctgcagtgac tctcttaagg tagccttgca gaagttggtc gtgaggcact   1080
gggcaggtaa gtatcaaggt tacaagacag gtttaaggag accaatagaa actgggcttg   1140
tcgagacaga gaagactctt gcgtttctga taggcaccta ttggtcttac tgacatccac   1200
tttgcctttc tctccacagg tgtccactcc cagttcaatt acagctctta aggctagagt   1260
acttaatacg actcactata gaatacgact cactataggg agacgctagc gtcgaccttc   1320
tgccatggcc ctgtggatgc gcctcctgcc cctgctggcg ctgctggccc tctggggacc   1380
tgacccagcc gcagcctttg tgaaccaaca cctgtgcggc tcagatctgg tggaagctct   1440
ctacctagtg tgcggggaac gaggcttctt ctacacaccc aggaccaagc gggaggcaga   1500
ggacctgcag gtggggcagg tggagctggg cggggggcct ggtgcaggca gcctgcagcc   1560
cttggccctg gaggggtcgc gacagaagcg tggcattgtg gaacaatgct gtaccagcat   1620
ctgctccctc taccagctgg agaactactg caactagacg cagccgtcga cggtaccagc   1680
gctgtcgagg ccgcttcgag cagacatgat aagatacatt gatgagtttg gacaaaccac   1740
aactagaatg cagtgaaaaa aatgctttat ttgtgaaatt tgtgatgcta ttgctttatt   1800
tgtaaccatt ataagctgca ataaacaagt taacaacaac aattgcattc attttatgtt   1860
tcaggttcag ggggagatgt gggaggtttt ttaaagcaag taaaacctct acaaatgtgg   1920
taaaatcgat taggatcttc ctagagcatg gctacctaga catggctcga cagatcagcg   1980
ctcatgctct ggaagatctc gatttatcca tgtttgacag cttatcatcg cagatccgta   2040
tggtgcactc tcagtacaat ctgctctgat gccgcatagt taagccagta tctgctccct   2100
gcttgtgtgt tggaggtcgc tgagtagtgc gcgagcaaaa tttaagctac aacaaggcaa   2160
ggcttgaccg acaattgcat gaagaatctg cttagggtta ggcgttttgc gctgcttcgc   2220
gatgtacggg ccagatattc gcgtatctga ggggactagg gtgtgtttag gcgaaaagcg   2280
gggcttcggt tgtacgcggt taggagtccc ctcaggatat agtagtttcg cttttgcata   2340
gggaggggga aatgtagtct tatgcaatac tcttgtagtc ttgcaacatg gtaacgatga   2400
gttagcaaca tgccttacaa ggagagaaaa agcaccgtgc atgccgattg gtggaagtaa   2460
ggtggtacga tcgtgcctta ttaggaaggc aacagacggg tctgacatgg attggacgaa   2520
```

```
ccactaaatt ccgcattgca gagatattgt atttaagtgc ctagctcgat acaataaacg    2580
ccatttgacc attcaccaca ttggtgtgca cctccaagct gggtaccagc ttctagagag    2640
atctgcttca gctggaggca ctgggcaggt aagtatcaag gttacaagac aggtttaagg    2700
agaccaatag aaactgggct tgtcgagaca gagaagactc ttgcgtttct gataggcacc    2760
tattggtctt actgacatcc actttgcctt tctctccaca ggtgcagctg ctgcagcggt    2820
ctagaactcg agtcgagacc atggcgatgg atgtcacaag gagccaggcc cagacagcct    2880
tgactctggt agagcagatc ctggcagagt tccagctgca ggaggaggac ctgaagaagg    2940
tgatgagacg gatgcagaag gagatggacc gcggcctgag gctggagacc catgaagagg    3000
ccagtgtgaa gatgctgccc acctacgtgc gctccacccc agaaggctca gaagtcgggg    3060
acttcctctc cctggacctg ggtggcacta acttcagggt gatgctggtg aaggtgggag    3120
aaggtgagga ggggcagtgg agcgtgaaga ccaaacacca gatgtactcc atccccgagg    3180
acgccatgac cggcactgct gagatgctct tcgactacat ctctgagtgc atctccgact    3240
tcctggacaa gcatcagatg aaacacaaga agctgcccct gggcttcacc ttctcctttc    3300
ctgtgaggca cgaagacatc gataagggca tccttctcaa ctggaccaag ggcttcaagg    3360
cctcaggagc agaagggaac aatgtcgtgg ggcttctgcg agacgctatc aaacggagag    3420
gggactttga aatggatgtg gtggcaatgg tgaatgacac ggtggccacg atgatctcct    3480
gctactacga agaccatcag tgcgaggtcg gcatgatcgt gggcacgggc tgcaatgcct    3540
gctacatgga ggagatgcag aatgtggagc tggtggaggg ggacgagggc cgcatgtgcg    3600
tcaataccga gtggggcgcc ttcggggact ccggcgagct ggacgagttc ctgctggagt    3660
atgaccgcct ggtggacgag agctctgcaa accccggtca gcagctgtat gagaagctca    3720
taggtggcaa gtacatgggc gagctggtgc ggcttgtgct gctcaggctc gtggacgaaa    3780
acctgctctt ccacggggag gcctccgagc agctgcgcac acgcggagcc ttcgagacgc    3840
gcttcgtgtc gcaggtggag agcgacacgg gcgaccgcaa gcagatctac aacatcctga    3900
gcacgctggg gctgcgaccc tcgaccaccg actgcgacat cgtgcgccgc cctgcgaga    3960 gcgtgtctac gcgcgctgcg cacatgtgct cggcggggct ggcgggcgtc atcaaccgca    4020
tgcgcgagag ccgcagcgag gacgtaatgc gcatcactgt gggcgtggat ggctccgtgt    4080
acaagctgca ccccagcttc aaggagcggt tccatgccag cgtgcgcagg ctgacgccca    4140
gctgcgagat caccttcatc gagtcggagg agggcagtgg ccggggcgcg ccctggtct    4200 cggcggtggc ctgtaagaag gcctgtatgc tgggccagtg actcgagcac gtggagctcg    4260
ctgatcagcc tcgactgtgc cttctagttg ccagccatct gttgtttgcc cctcccccgt    4320
gccttccttg accctggaag gtgccactcc cactgtcctt tcctaataaa atgaggaaat    4380
tgcatcgcat tgtctgagta ggtgtcattc tattctgggg gtgggtgg ggcaggacag    4440 caagggggag gattggaag acaatagcag catgctggg gatgcggtgg gctctatggc    4500
cacgtgattt aaatgcggcc gcaggaaccc ctagtgatgg agttggccac tccctctctg    4560
cgcgctcgct cgctcactga ggccgggcga ccaaaggtcg cccgacgccc gggctttgcc    4620
cgggcggcct cagtgagcga gcgagcgcgc agctgcctgc aggggcgcct gatgcggtat    4680
tttctcctta cgcatctgtg cggtatttca caccgcatac gtcaaagcaa ccatagtacg    4740
cgccctgtag cggcgcatta agcgcggcgg gtgtggtggt tacgcgcagc gtgaccgcta    4800
cacttgccag cgccctagcg cccgctcctt tcgctttctt cccttccttt ctcgccacgt    4860
tcgccggctt tccccgtcaa gctctaaatc ggggggctccc tttagggttc cgatttagtg    4920
```

```
ctttacggca cctcgacccc aaaaaacttg atttgggtga tggttcacgt agtgggccat    4980
cgccctgata gacggttttt cgcccttga cgttggagtc cacgttcttt aatagtggac    5040
tcttgttcca aactggaaca acactcaacc ctatctcggg ctattctttt gatttataag    5100
ggattttgcc gatttcggcc tattggttaa aaaatgagct gatttaacaa aaatttaacg    5160
cgaattttaa caaaatatta acgtttacaa ttttatggtg cactctcagt acaatctgct    5220
ctgatgccgc atagttaagc cagccccgac acccgccaac acccgctgac gcgccctgac    5280
gggcttgtct gctcccggca tccgcttaca gacaagctgt gaccgtctcc gggagctgca    5340
tgtgtcagag gttttcaccg tcatcaccga acgcgcgag acgaaagggc ctcgtgatac    5400
gcctattttt ataggttaat gtcatgataa taatggtttc ttagacgtca ggtggcactt    5460
ttcggggaaa tgtgcgcgga acccctattt gtttattttt ctaaatacat tcaaatatgt    5520
atccgctcat gagacaataa ccctgataaa tgcttcaata atattgaaaa aggaagagta    5580
tgagtattca acatttccgt gtcgccctta ttccctttt tgcggcattt tgccttcctg    5640 ttttgctca cccagaaacg ctggtgaaag taaaagatgc tgaagatcag ttgggtgcac    5700
gagtgggtta catcgaactg gatctcaaca gcggtaagat ccttgagagt tttcgccccg    5760
aagaacgttt tccaatgatg agcactttta aagttctgct atgtggcgcg gtattatccc    5820
gtattgacgc cgggcaagag caactcggtc gccgcataca ctattctcag aatgacttgg    5880
ttgagtactc accagtcaca gaaaagcatc ttacggatgg catgacagta agagaattat    5940
gcagtgctgc cataaccatg agtgataaca ctgcggccaa cttacttctg acaacgatcg    6000
gaggaccgaa ggagctaacc gcttttttgc acaacatggg ggatcatgta actcgccttg    6060
atcgttggga accggagctg aatgaagcca taccaaacga cgagcgtgac accacgatgc    6120
ctgtagcaat ggcaacaacg ttgcgcaaac tattaactgg cgaactactt actctagctt    6180
cccggcaaca attaatagac tggatggagg cggataaagt tgcaggacca cttctgcgct    6240
cggcccttcc ggctggctgg tttattgctg ataaatctgg agccggtgag cgtgggtctc    6300
gcggtatcat tgcagcactg gggccagatg gtaagccctc ccgtatcgta gttatctaca    6360
cgacggggag tcaggcaact atggatgaac gaaatagaca gatcgctgag ataggtgcct    6420
cactgattaa gcattggtaa ctgtcagacc aagtttactc atatatactt tagattgatt    6480
taaaacttca ttttaattt aaaaggatct aggtgaagat cctttttgat aatctcatga    6540
ccaaaatccc ttaacgtgag ttttcgttcc actgagcgtc agaccccgta gaaaagatca    6600
aaggatcttc ttgagatcct ttttttctgc gcgtaatctg ctgcttgcaa acaaaaaaac    6660
caccgctacc agcggtggtt tgtttgccgg atcaagagct accaactctt tttccgaagg    6720
taactggctt cagcagagcg cagataccaa atactgtcct tctagtgtag ccgtagttag    6780
gccaccactt caagaactct gtagcaccgc ctacatacct cgctctgcta atcctgttac    6840
cagtggctgc tgccagtggc gataagtcgt gtcttaccgg gttggactca agacgatagt    6900
taccggataa ggcgcagcgg tcgggctgaa cggggggttc gtgcacacag cccagcttgg    6960
agcgaacgac ctacaccgaa ctgagatacc tacagcgtga gctatgagaa agcgccacgc    7020
ttcccgaagg gagaaaggcg gacaggtatc cggtaagcgg cagggtcgga acaggagagc    7080
gcacgaggga gcttccaggg ggaaacgcct ggtatcttta gtcctgtc gggtttcgcc    7140 acctctgact tgagcgtcga tttttgtgat gctcgtcagg gggcggagc ctatggaaaa    7200 acgccagcaa cgcggccttt ttacggttcc tggccttttg ctggccttt gctcacatgt    7260
```

<210> SEQ ID NO 10
<211> LENGTH: 7260
<212> TYPE: DNA
<213> ORGANISM: Artificial
<220> FEATURE:
<223> OTHER INFORMATION: Construct E
<220> FEATURE:
<221> NAME/KEY: Construct E
<222> LOCATION: (1)..(7260)

<400> SEQUENCE: 10

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | taggggttcc | tgcggccgcg | atatccatgt | ttgacagctt | atcatcgcag | 180 |
| atccgtatgg | tgcactctca | gtacaatctg | ctctgatgcc | gcatagttaa | gccagtatct | 240 |
| gctccctgct | tgtgtgttgg | aggtcgctga | gtagtgcgcg | agcaaaattt | aagctacaac | 300 |
| aaggcaaggc | ttgaccgaca | attgcatgaa | gaatctgctt | agggttaggc | gttttgcgct | 360 |
| gcttcgcgat | gtacgggcca | gatattcgcg | tatctgaggg | gactagggtg | tgtttaggcg | 420 |
| aaaagcgggg | cttcggttgt | acgcggttag | gagtcccctc | aggatatagt | agtttcgctt | 480 |
| ttgcataggg | aggggggaaat | gtagtcttat | gcaatactct | tgtagtcttg | caacatggta | 540 |
| acgatgagtt | agcaacatgc | cttacaagga | gagaaaaagc | accgtgcatg | ccgattggtg | 600 |
| gaagtaaggt | ggtacgatcg | tgccttatta | ggaaggcaac | agacgggtct | gacatggatt | 660 |
| ggacgaacca | ctaaattccg | cattgcagag | atattgtatt | taagtgccta | gctcgataca | 720 |
| ataaacgcca | tttgaccatt | caccacattg | gtgtgcacct | ccaagctggg | taccagcttc | 780 |
| tagagagatc | tgcttcagct | ggaggcactg | ggcaggtaag | tatcaaggtt | acaagacagg | 840 |
| tttaaggaga | ccaatagaaa | ctgggcttgt | cgagacagag | aagactcttg | cgtttctgat | 900 |
| aggcacctat | tggtcttact | gacatccact | ttgcctttct | ctccacaggt | gcagctgctg | 960 |
| cagcggtcta | gaactcgagt | cgagaccatg | gcgatggatg | tcacaaggag | ccaggcccag | 1020 |
| acagccttga | ctctggtaga | gcagatcctg | gcagagttcc | agctgcagga | ggaggacctg | 1080 |
| aagaaggtga | tgagacggat | gcagaaggag | atggaccgcg | gcctgaggct | ggagacccat | 1140 |
| gaagaggcca | gtgtgaagat | gctgcccacc | tacgtgcgct | ccacccccaga | aggctcagaa | 1200 |
| gtcgggggact | tcctctccct | ggacctgggt | ggcactaact | tcagggtgat | gctggtgaag | 1260 |
| gtgggagaag | gtgaggaggg | gcagtggagc | gtgaagacca | aacaccagat | gtactccatc | 1320 |
| cccgaggacg | ccatgaccgg | cactgctgag | atgctcttcg | actacatctc | tgagtgcatc | 1380 |
| tccgacttcc | tggacaagca | tcagatgaaa | cacaagaagc | tgccccctggg | cttcaccttc | 1440 |
| tcctttcctg | tgaggcacga | agacatcgat | aagggcatcc | ttctcaactg | gaccaagggc | 1500 |
| ttcaaggcct | caggagcaga | agggaacaat | gtcgtggggc | ttctgcgaga | cgctatcaaa | 1560 |
| cggagagggg | actttgaaat | ggatgtggtg | gcaatggtga | atgacacggt | ggccacgatg | 1620 |
| atctcctgct | actacgaaga | ccatcagtgc | gaggtcggca | tgatcgtggg | cacgggctgc | 1680 |
| aatgcctgct | acatggagga | gatgcagaat | gtggagctgg | tggagggggga | cgagggccgc | 1740 |
| atgtgcgtca | ataccgagtg | gggcgccttc | ggggactccg | gcgagctgga | cgagttcctg | 1800 |
| ctggagtatg | accgcctggt | ggacgagagc | tctgcaaacc | ccggtcagca | gctgtatgag | 1860 |
| aagctcatag | gtggcaagta | catgggcgag | ctggtgcggc | ttgtgctgct | caggctcgtg | 1920 |
| gacgaaaacc | tgctcttcca | cggggaggcc | tccgagcagc | tgcgcacacg | cggagccttc | 1980 |

```
gagacgcgct tcgtgtcgca ggtggagagc gacacgggcg accgcaagca gatctacaac    2040
atcctgagca cgctggggct gcgaccctcg accaccgact gcgacatcgt gcgccgcgcc    2100
tgcgagagcg tgtctacgcg cgctgcgcac atgtgctcgg cggggctggc gggcgtcatc    2160
aaccgcatgc gcgagagccg cagcgaggac gtaatgcgca tcactgtggg cgtggatggc    2220
tccgtgtaca agctgcaccc cagcttcaag gagcggttcc atgccagcgt gcgcaggctg    2280
acgcccagct gcgagatcac cttcatcgag tcggaggagg gcagtggccg gggcgcggcc    2340
ctggtctcgg cggtggcctg taagaaggcc tgtatgctgg gccagtgact cgagcacgtg    2400
gagctcgctg atcagcctcg actgtgcctt ctagttgcca gccatctgtt gtttgcccct    2460
cccccgtgcc ttccttgacc ctggaaggtg ccactcccac tgtcctttcc taataaaatg    2520
aggaaattgc atcgcattgt ctgagtaggt gtcattctat tctgggggt ggggtggggc    2580 aggacagcaa gggggaggat tgggaagaca atagcaggca tgctggggat gcggtgggct    2640
ctatggccac gtgatttatc tgtagttaat gattaacccg ccatgctact tatctacaga    2700
tctcaatatt ggccattagc catattattc attggttata tagcataaat caatattggc    2760
tattggccat tgcatacgtt gtatctatat cataatatgt acatttatat tggctcatgt    2820
ccaatatgac cgccatgttg gcattgatta ttgactagtt attaatagta atcaattacg    2880
gggtcattag ttcatagccc atatatggag ttccgcgtta cataacttac ggtaaatggc    2940
ccgcctggct gaccgcccaa cgaccccgc ccattgacgt caataatgac gtatgttccc    3000
atagtaacgc caatagggac tttccattga cgtcaatggg tggagtattt acggtaaact    3060
gcccacttgg cagtacatca agtgtatcat atgccaagtc cgccccctat tgacgtcaat    3120
gacggtaaat ggcccgcctg gcattatgcc cagtacatga ccttacggga ctttcctact    3180
tggcagtaca tctacgtatt agtcatcgct attaccatgg tgatgcggtt ttggcagtac    3240
accaatgggc gtggatagcg gtttgactca cggggatttc caagtctcca ccccattgac    3300
gtcaatggga gtttgttttg gcaccaaaat caacgggact ttccaaaatg tcgtaacaac    3360
tgcgatcgcc cgccccgttg acgcaaatgg gcggtaggcg tgtacggtgg gaggtctata    3420
taagcagagc tcgtttagtg aaccgtcaga tcactaggct agctattgcg gtagtttatc    3480
acagttaaat tgctaacgca gtcagtgctt ctgacacaac agtctcgaac ttaagctgca    3540
gtgactctct taaggtagcc ttgcagaagt tggtcgtgag gcactgggca ggtaagtatc    3600
aaggttacaa gacaggttta aggagaccaa tagaaactgg gcttgtcgag acagagaaga    3660
ctcttgcgtt tctgataggc acctattggt cttactgaca tccactttgc ctttctctcc    3720
acaggtgtcc actcccagtt caattacagc tcttaaggct agagtactta atacgactca    3780
ctatagaata cgactcacta tagggagacg ctagcgtcga ccttctgcca tggccctgtg    3840
gatgcgcctc ctgcccctgc tggcgctgct ggccctctgg ggacctgacc cagccgcagc    3900
ctttgtgaac caacctgt gcggctcaga tctggtggaa gctctctacc tagtgtgcgg    3960
ggaacgaggc ttcttctaca cacccaggac caagcgggag gcagaggacc tgcaggtggg    4020
gcaggtggag ctgggcgggg gccctggtgc aggcagcctg cagcccttgg ccctggaggg    4080 gtcgcgcacag aagcgtggca ttgtggaaca atgctgtacc agcatctgct ccctctacca    4140
gctggagaac tactgcaact agacgcagcc gtcgacggta ccagcgctgt cgaggccgct    4200
tcgagcagac atgataagat acattgatga gtttggacaa accacaacta gaatgcagtg    4260
aaaaaaatgc tttatttgtg aaatttgtga tgctattgct ttatttgtaa ccattataag    4320
ctgcaataaa caagttaaca acaacaattg cattcatttt atgtttcagg ttcaggggga    4380
```

```
gatgtgggag gttttttaaa gcaagtaaaa cctctacaaa tgtggtaaaa tcgattagga    4440
tcttcctaga gcatggctac ctagacatgg ctcgacagat cagcgctcat gctctgaag    4500 atctcgattt aaatgcggcc gcaggaaccc ctagtgatgg agttggccac tccctctctg    4560
cgcgctcgct cgctcactga ggccgggcga ccaaaggtcg cccgacgccc gggctttgcc    4620
cgggcggcct cagtgagcga gcgagcgcgc agctgcctgc aggggcgcct gatgcggtat    4680
tttctcctta cgcatctgtg cggtatttca caccgcatac gtcaaagcaa ccatagtacg    4740
cgccctgtag cggcgcatta agcgcggcgg gtgtggtggt tacgcgcagc gtgaccgcta    4800
cacttgccag cgccctagcg cccgctcctt tcgctttctt ccttcctttt ctcgccacgt    4860
tcgccggctt tccccgtcaa gctctaaatc ggggctccc tttagggttc cgatttagtg    4920
ctttacggca cctcgacccc aaaaaacttg atttgggtga tggttcacgt agtgggccat    4980
cgccctgata gacggttttt cgccctttga cgttggagtc cacgttcttt aatagtggac    5040
tcttgttcca aactgaaaca acactcaacc ctatctcggg ctattctttt gatttataag    5100
ggattttgcc gatttcggcc tattggttaa aaaatgagct gatttaacaa aaatttaacg    5160
cgaattttaa caaaatatta acgtttacaa ttttatggtg cactctcagt acaatctgct    5220
ctgatgccgc atagttaagc cagccccgac acccgccaac acccgctgac gcgccctgac    5280
gggcttgtct gctcccggca tccgcttaca gacaagctgt gaccgtctcc gggagctgca    5340
tgtgtcagag gttttcaccg tcatcaccga aacgcgcgag acgaaagggc ctcgtgatac    5400
gcctattttt ataggttaat gtcatgataa taatggtttc ttagacgtca ggtggcactt    5460
ttcggggaaa tgtgcgcgga acccctattt gtttattttt ctaaatacat tcaaatatgt    5520
atccgctcat gagacaataa ccctgataaa tgcttcaata atattgaaaa aggaagagta    5580
tgagtattca acatttccgt gtcgccctta ttcccttttt tgcggcattt tgccttcctg    5640
tttttgctca cccagaaacg ctggtgaaag taaaagatgc tgaagatcag ttgggtgcac    5700
gagtgggtta catcgaactg gatctcaaca gcggtaagat ccttgagagt tttcgccccg    5760
aagaacgttt tccaatgatg agcactttta aagttctgct atgtggcgcg gtattatccc    5820
gtattgacgc cgggcaagag caactcggtc gccgcataca ctattctcag aatgacttgg    5880
ttgagtactc accagtcaca gaaaagcatc ttacggatgg catgacagta agagaattat    5940
gcagtgctgc cataaccatg agtgataaca ctgcggccaa cttacttctg acaacgatcg    6000
gaggaccgaa ggagctaacc gcttttttgc acaacatggg ggatcatgta actcgccttg    6060
atcgttggga accggagctg aatgaagcca taccaaacga cgagcgtgac accacgatgc    6120
ctgtagcaat ggcaacaacg ttgcgcaaac tattaactgg cgaactactt actctagctt    6180
cccggcaaca attaatagac tggatggagg cggataaagt tgcaggacca cttctgcgct    6240
cggcccttcc ggctggctgg tttattgctg ataaatctgg agccggtgag cgtgggtctc    6300
gcggtatcat tgcagcactg gggccagatg gtaagccctc ccgtatcgta gttatctaca    6360
cgacggggag tcaggcaact atggatgaac gaaatagaca gatcgctgag ataggtgcct    6420
cactgattaa gcattggtaa ctgtcagacc aagtttactc atatatactt tagattgatt    6480
taaaacttca tttttaattt aaaaggatct aggtgaagat cctttttgat aatctcatga    6540
ccaaaatccc ttaacgtgag ttttcgttcc actgagcgtc agaccccgta gaaaagatca    6600
aaggatcttc ttgagatcct ttttttctgc gcgtaatctg ctgcttgcaa acaaaaaaac    6660
caccgctacc agcggtggtt tgtttgccgg atcaagagct accaactctt tttccgaagg    6720
```

| | | |
|---|---|---|
| taactggctt cagcagagcg cagataccaa atactgtcct tctagtgtag ccgtagttag | 6780 |
| gccaccactt caagaactct gtagcaccgc ctacatacct cgctctgcta atcctgttac | 6840 |
| cagtggctgc tgccagtggc gataagtcgt gtcttaccgg gttggactca agacgatagt | 6900 |
| taccggataa ggcgcagcgg tcgggctgaa cggggggttc gtgcacacag cccagcttgg | 6960 |
| agcgaacgac ctacaccgaa ctgagatacc tacagcgtga gctatgagaa agcgccacgc | 7020 |
| ttcccgaagg gagaaaggcg gacaggtatc cggtaagcgg cagggtcgga acaggagagc | 7080 |
| gcacgaggga gcttccaggg ggaaacgcct ggtatcttta tagtcctgtc gggtttcgcc | 7140 |
| acctctgact tgagcgtcga ttttgtgat gctcgtcagg ggggcggagc ctatggaaaa | 7200 |
| acgccagcaa cgcggccttt ttacggttcc tggccttttg ctggcctttt gctcacatgt | 7260 |

<210> SEQ ID NO 11
<211> LENGTH: 7260
<212> TYPE: DNA
<213> ORGANISM: Artificial
<220> FEATURE:
<223> OTHER INFORMATION: Construct F
<220> FEATURE:
<221> NAME/KEY: Construct F
<222> LOCATION: (1)..(7260)

<400> SEQUENCE: 11

| | | |
|---|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgcg ataaatcgag atcttccaga gcatgagcgc | 180 |
| tgatctgtcg agccatgtct aggtagccat gctctaggaa gatcctaatc gattttacca | 240 |
| catttgtaga ggttttactt gctttaaaaa acctcccaca tctcccccctg aacctgaaac | 300 |
| ataaaatgaa tgcaattgtt gttgttaact tgtttattgc agcttataat ggttacaaat | 360 |
| aaagcaatag catcacaaat ttcacaaata aagcattttt ttcactgcat tctagttgtg | 420 |
| gtttgtccaa actcatcaat gtatcttatc atgtctgctc gaagcggcct cgacagcgct | 480 |
| ggtaccgtcg acggctgcgt ctagttgcag tagttctcca gctggtagag ggagcagatg | 540 |
| ctggtacagc attgttccac aatgccacgc ttctgtcgcg acccctccag ggccaagggc | 600 |
| tgcaggctgc ctgcaccagg gccccgccc agctccacct gccccacctg caggtcctct | 660 |
| gcctcccgct tggtcctggg tgtgtagaag aagcctcgtt ccccgcacac taggtagaga | 720 |
| gcttccacca gatctgagcc gcacaggtgt tggttcacaa aggctgcggc tgggtcaggt | 780 |
| ccccagaggg ccagcagcgc cagcaggggc aggaggcgca tccacagggc catggcagaa | 840 |
| ggtcgacgct agcgtctccc tatagtgagt cgtattctat agtgagtcgt attaagtact | 900 |
| ctagccttaa gagctgtaat tgaactggga gtggacacct gtggagagaa aggcaaagtg | 960 |
| gatgtcagta agaccaatag gtgcctatca gaaacgcaag agtcttctct gtctcgacaa | 1020 |
| gcccagtttc tattggtctc cttaaacctg tcttgtaacc ttgatactta cctgcccagt | 1080 |
| gcctcacgac caacttctgc aaggctacct taagagagtc actgcagctt aagttcgaga | 1140 |
| ctgttgtgtc agaagcactg actgcgttag caatttaact gtgataaact accgcaatag | 1200 |
| ctagcctagt gatctgacgg ttcactaaac gagctctgct tatatagacc tcccaccgta | 1260 |
| cacgcctacc gcccatttgc gtcaacgggg cgggcgatcg cagttgttac gacattttgg | 1320 |
| aaagtcccgt tgattttggt gccaaaacaa actcccattg acgtcaatgg ggtggagact | 1380 |
| tggaaatccc cgtgagtcaa accgctatcc acgcccattg gtgtactgcc aaaaccgcat | 1440 |

```
caccatggta atagcgatga ctaatacgta gatgtactgc caagtaggaa agtcccgtaa    1500
ggtcatgtac tgggcataat gccaggcggg ccatttaccg tcattgacgt caatagggggg   1560 cggacttggc atatgataca cttgatgtac tgccaagtgg gcagtttacc gtaaatactc    1620
cacccattga cgtcaatgga aagtccctat tggcgttact atgggaacat acgtcattat    1680
tgacgtcaat gggcggggggt cgttgggcgg tcagccaggc gggccattta ccgtaagtta    1740
tgtaacgcgg aactccatat atgggctatg aactaatgac cccgtaattg attactatta    1800
ataactagtc aataatcaat gccaacatgg cggtcatatt ggacatgagc caatataaat    1860
gtacatatta tgatatagat acaacgtatg caatggccaa tagccaatat tgatttatgc    1920
tatataacca atgaataata tggctaatgg ccaatattga gatctgtaga taagtagcat    1980
ggcgggttaa tcattaacta cagatatcca tgtttgacag cttatcatcg cagatccgta    2040
tggtgcactc tcagtacaat ctgctctgat gccgcatagt taagccagta tctgctccct    2100
gcttgtgtgt tggaggtcgc tgagtagtgc gcgagcaaaa tttaagctac aacaaggcaa    2160
ggcttgaccg acaattgcat gaagaatctg cttagggtta ggcgttttgc gctgcttcgc    2220
gatgtacggg ccagatattc gcgtatctga ggggactagg gtgtgtttag gcgaaaagcg    2280
gggcttcggt tgtacgcggt taggagtccc ctcaggatat agtagtttcg cttttgcata    2340 gggagggggga aatgtagtct tatgcaatac tcttgtagtc ttgcaacatg gtaacgatga    2400
gttagcaaca tgccttacaa ggagagaaaa agcaccgtgc atgccgattg gtggaagtaa    2460
ggtggtacga tcgtgcctta ttaggaaggc aacagacggg tctgacatgg attggacgaa    2520
ccactaaatt ccgcattgca gagatattgt atttaagtgc ctagctcgat acaataaacg    2580
ccatttgacc attcaccaca ttggtgtgca cctccaagct gggtaccagc ttctagagag    2640
atctgcttca gctggaggca ctgggcaggt aagtatcaag gttacaagac aggtttaagg    2700
agaccaatag aaactgggct tgtcgagaca gagaagactc ttgcgtttct gataggcacc    2760
tattggtctt actgacatcc actttgcctt tctctccaca ggtgcagctg ctgcagcggt    2820
ctagaactcg agtcgagacc atggcgatgg atgtcacaag gagccaggcc cagacagcct    2880
tgactctggt agagcagatc ctggcagagt tccagctgca ggaggaggac ctgaagaagg    2940
tgatgagacg gatgcagaag gagatggacc gcggcctgag gctggagacc catgaagagg    3000
ccagtgtgaa gatgctgccc acctacgtgc gctccacccc agaaggctca gaagtcgggg    3060
acttcctctc cctggacctg ggtggcacta acttcagggt gatgctggtg aaggtgggag    3120
aaggtgagga ggggcagtgg agcgtgaaga ccaaacacca gatgtactcc atccccgagg    3180
acgccatgac cggcactgct gagatgctct tcgactacat ctctgagtgc atctccgact    3240
tcctggacaa gcatcagatg aaacacaaga agctgccct gggcttcacc ttctccttc    3300 ctgtgaggca cgaagacatc gataagggca tccttctcaa ctggaccaag ggcttcaagg    3360
cctcaggagc agaagggaac aatgtcgtgg gcttctgcg agacgctatc aaacggagag    3420
gggactttga aatggatgtg gtggcaatgg tgaatgacac ggtggccacg atgatctcct    3480
gctactacga agaccatcag tgcgaggtcg gcatgatcgt gggcacgggc tgcaatgcct    3540
gctacatgga ggagatgcag aatgtggagc tggtggaggg gacgagggc cgcatgtgcg    3600 tcaataccga gtggggcgcc ttcggggact ccggcgagct ggacgagttc ctgctggagt    3660
atgaccgcct ggtggacgag agctctgcaa accccggtca gcagctgtat gagaagctca    3720
taggtggcaa gtacatgggc gagctggtgc ggcttgtgct gctcaggctc gtggacgaaa    3780
acctgctctt ccacggggag gcctccgagc agctgcgcac acgcggagcc ttcgagacgc    3840
```

```
gcttcgtgtc gcaggtggag agcgacacgg gcgaccgcaa gcagatctac aacatcctga    3900
gcacgctggg gctgcgaccc tcgaccaccg actgcgacat cgtgcgccgc gcctgcgaga    3960
gcgtgtctac gcgcgctgcg cacatgtgct cggcggggct ggcgggcgtc atcaaccgca    4020
tgcgcgagag ccgcagcgag gacgtaatgc gcatcactgt gggcgtggat ggctccgtgt    4080
acaagctgca ccccagcttc aaggagcggt tccatgccag cgtgcgcagg ctgacgccca    4140
gctgcgagat caccttcatc gagtcggagg agggcagtgg ccggggcgcg ccctggtct    4200 cggcggtggc ctgtaagaag gcctgtatgc tgggccagtg actcgagcac gtggagctcg    4260
ctgatcagcc tcgactgtgc cttctagttg ccagccatct gttgtttgcc cctcccccgt    4320
gccttccttg accctggaag gtgccactcc cactgtcctt tcctaataaa atgaggaaat    4380
tgcatcgcat tgtctgagta ggtgtcattc tattctgggg ggtggggtgg ggcaggacag    4440 caaggggag gattgggaag acaatagcag gcatgctggg gatgcggtgg gctctatggc    4500
cacgtgattt aaatgcggcc gcaggaaccc ctagtgatgg agttggccac tccctctctg    4560
cgcgctcgct cgctcactga ggccgggcga ccaaggtcg cccgacgccc gggctttgcc    4620
cgggcggcct cagtgagcga gcgagcgcgc agctgcctgc aggggcgcct gatgcggtat    4680
tttctcctta cgcatctgtg cggtatttca caccgcatac gtcaaagcaa ccatagtacg    4740
cgccctgtag cggcgcatta gcgcggcgg gtgtggtggt tacgcgcagc gtgaccgcta    4800
cacttgccag cgccctagcg cccgctcctt tcgctttctt cccttccttt ctcgccacgt    4860
tcgccggctt tccccgtcaa gctctaaatc ggggctccc tttagggttc cgatttagtg    4920
ctttacggca cctcgacccc aaaaaacttg atttgggtga tggttcacgt agtgggccat    4980
cgccctgata cacggttttt cgccctttga cgttggagtc cacgttcttt aatagtggac    5040
tcttgttcca aactggaaca cactcaacc ctatctcggg ctattctttt gatttataag    5100 ggatttgcc gatttcggcc tattggttaa aaaatgagct gatttaacaa aaatttaacg    5160
cgaattttaa caaaatatta cgtttacaa ttttatggtg cactctcagt acaatctgct    5220
ctgatgccgc atagttaagc cagccccgac acccgccaac accgctgac gcgccctgac    5280 gggcttgtct gctcccggca tccgcttaca gacaagctgt gaccgtctcc gggagctgca    5340
tgtgtcagag gttttcaccg tcatcaccga aacgcgcgag acgaaagggc ctcgtgatac    5400
gcctattttt ataggttaat gtcatgataa taatggtttc ttagacgtca ggtggcactt    5460
ttcggggaaa tgtgcgcgga acccctattt gtttattttt ctaaatacat tcaaatatgt    5520
atccgctcat gagacaataa ccctgataaa tgcttcaata atattgaaaa aggaagagta    5580
tgagtattca acatttccgt gtcgccctta ttcccttttt tgcggcattt gccttcctg    5640 tttttgctca cccagaaacg ctggtgaaag taaaagatgc tgaagatcag ttgggtgcac    5700
gagtgggtta catcgaactg gatctcaaca gcggtaagat ccttgagagt tttcgccccg    5760
aagaacgttt tccaatgatg agcactttta aagttctgct atgtggcgcg gtattatccc    5820
gtattgacgc cgggcaagag caactcggtc gccgcataca ctattctcag aatgacttgg    5880
ttgagtactc accagtcaca gaaaagcatc ttacggatgg catgacagta agagaattat    5940
gcagtgctgc cataaccatg agtgataaca ctgcggccaa cttacttctg acaacgatcg    6000
gaggaccgaa ggagctaacc gcttttttgc acaacatggg ggatcatgta actcgccttg    6060
atcgttggga accggagctg aatgaagcca taccaaacga cgagcgtgac accacgatgc    6120
ctgtagcaat ggcaacaacg ttgcgcaaac tattaactgg cgaactactt actctagctt    6180
```

```
cccggcaaca attaatagac tggatggagg cggataaagt tgcaggacca cttctgcgct      6240
cggcccttcc ggctggctgg tttattgctg ataaatctgg agccggtgag cgtgggtctc      6300
gcggtatcat tgcagcactg gggccagatg gtaagccctc ccgtatcgta gttatctaca      6360
cgacggggag tcaggcaact atggatgaac gaaatagaca gatcgctgag ataggtgcct      6420
cactgattaa gcattggtaa ctgtcagacc aagtttactc atatatactt tagattgatt      6480
taaaacttca ttttaatttt aaaaggatct aggtgaagat cctttttgat aatctcatga      6540
ccaaaatccc ttaacgtgag ttttcgttcc actgagcgtc agaccccgta gaaaagatca      6600
aaggatcttc ttgagatcct ttttttctgc gcgtaatctg ctgcttgcaa acaaaaaaac      6660
caccgctacc agcggtggtt tgtttgccgg atcaagagct accaactctt tttccgaagg      6720
taactggctt cagcagagcg cagataccaa atactgtcct tctagtgtag ccgtagttag      6780
gccaccactt caagaactct gtagcaccgc ctacatacct cgctctgcta atcctgttac      6840
cagtggctgc tgccagtggc gataagtcgt gtcttaccgg gttggactca agacgatagt      6900
taccggataa ggcgcagcgg tcgggctgaa cggggggttc gtgcacacag cccagcttgg      6960
agcgaacgac ctacaccgaa ctgagatacc tacagcgtga gctatgagaa agcgccacgc      7020
ttcccgaagg gagaaaggcg gacaggtatc cggtaagcgg cagggtcgga acaggagagc      7080
gcacgaggga gcttccaggg ggaaacgcct ggtatcttta tagtcctgtc gggtttcgcc      7140
acctctgact tgagcgtcga ttttgtgat gctcgtcagg gggcggagc ctatggaaaa      7200 acgccagcaa cgcggccttt ttacggttcc tggccttttg ctggccttt gctcacatgt      7260
```

<210> SEQ ID NO 12
<211> LENGTH: 7260
<212> TYPE: DNA
<213> ORGANISM: Artificial
<220> FEATURE:
<223> OTHER INFORMATION: Construct G
<220> FEATURE:
<221> NAME/KEY: Construct G
<222> LOCATION: (1)..(7260)

<400> SEQUENCE: 12

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgcg atatccatgt ttgacagctt atcatcgcag       180
atccgtatgg tgcactctca gtacaatctg ctctgatgcc gcatagttaa gccagtatct       240
gctccctgct tgtgtgttgg aggtcgctga gtagtgcgcg agcaaaattt aagctacaac       300
aaggcaaggc ttgaccgaca attgcatgaa gaatctgctt agggttaggc gttttgcgct       360
gcttcgcgat gtacgggcca gatattgcg tatctgaggg gactagggtg tgtttaggcg       420
aaaagcgggg cttcggttgt acgcggttag gagtcccctc aggatatagt agtttcgctt       480
ttgcataggg agggggaaat gtagtcttat gcaatactct tgtagtcttg caacatggta       540
acgatgagtt agcaacatgc cttacaagga gagaaaaagc accgtgcatg ccgattggtg       600
gaagtaaggt ggtacgatcg tgccttatta ggaaggcaac agacgggtct gacatggatt       660
ggacgaacca ctaaattccg cattgcagag atattgtatt taagtgccta gctcgataca       720
ataaacgcca tttgaccatt caccacattg gtgtgcacct ccaagctggg taccagcttc       780
tagagagatc tgcttcagct ggaggcactg gcaggtaag tatcaaggtt acaagacagg       840
tttaaggaga ccaatagaaa ctgggcttgt cgagacagag aagactcttg cgtttctgat       900
```

```
aggcacctat tggtcttact gacatccact ttgcctttct ctccacaggt gcagctgctg     960
cagcggtcta gaactcgagt cgagaccatg gcgatggatg tcacaaggag ccaggcccag    1020
acagccttga ctctggtaga gcagatcctg gcagagttcc agctgcagga ggaggacctg    1080
aagaaggtga tgagacggat gcagaaggag atggaccgcg gcctgaggct ggagacccat    1140
gaagaggcca gtgtgaagat gctgcccacc tacgtgcgct ccaccccaga aggctcagaa    1200
gtcggggact cctctccct ggacctgggt ggcactaact tcaggtgat gctggtgaag    1260
gtgggagaag gtgaggaggg gcagtggagc gtgaagacca acaccagat gtactccatc    1320
cccgaggacg ccatgaccgg cactgctgag atgctcttcg actacatctc tgagtgcatc    1380
tccgacttcc tggacaagca tcagatgaaa cacaagaagc tgcccctggg cttcaccttc    1440
tcctttcctg tgaggcacga agacatcgat aagggcatcc ttctcaactg gaccaagggc    1500
ttcaaggcct caggagcaga agggaacaat gtcgtggggc ttctgcgaga cgctatcaaa    1560
cggagagggg actttgaaat ggatgtggtg gcaatggtga atgacacggt ggccacgatg    1620
atctcctgct actacgaaga ccatcagtgc gaggtcggca tgatcgtggg cacgggctgc    1680
aatgcctgct acatggagga gatgcagaat gtggagctgg tggaggggga cgagggccgc    1740
atgtgcgtca ataccgagtg gggcgccttc ggggactccg gcgagctgga cgagttcctg    1800
ctggagtatg accgcctggt ggacgagagc tctgcaaacc ccggtcagca gctgtatgag    1860
aagctcatag gtggcaagta catgggcgag ctggtgcggc ttgtgctgct caggctcgtg    1920
gacgaaaacc tgctcttcca cggggaggcc tccgagcagc tgcgcacacg cggagccttc    1980
gagacgcgct tcgtgtcgca ggtggagagc gacacgggcg accgcaagca gatctacaac    2040
atcctgagca cgctggggct gcgaccctcg accaccgact gcgacatcgt gcgccgcgcc    2100
tgcgagagcg tgtctacgcg cgctgcgcac atgtgctcgg cggggctggc gggcgtcatc    2160
aaccgcatgc gcgagagccg cagcgaggac gtaatgcgca tcactgtggg cgtggatggc    2220
tccgtgtaca agctgcaccc cagcttcaag gagcggttcc atgccagcgt gcgcaggctg    2280
acgcccagct gcgagatcac cttcatcgag tcggaggagg gcagtggccg gggcgcggcc    2340
ctggtctcgg cggtggcctg taagaaggcc tgtatgctgg gccagtgact cgagcacgtg    2400
gagctcgctg atcagcctcg actgtgcctt ctagttgcca gccatctgtt gtttgcccct    2460
cccccgtgcc ttccttgacc ctggaaggtg ccactcccac tgtcctttcc taataaaatg    2520
aggaaattgc atcgcattgt ctgagtaggt gtcattctat tctgggggt ggggtggggc    2580
aggacagcaa gggggaggat tgggaagaca atagcaggca tgctggggat gcggtgggct    2640
ctatggccac gtgatttaaa tcgagatctt ccagagcatg agcgctgatc tgtcgagcca    2700
tgtctaggta gccatgctct aggaagatcc taatcgattt taccacattt gtagaggttt    2760
tacttgcttt aaaaaacctc ccacatctcc ccctgaacct gaaacataaa atgaatgcaa    2820
ttgttgttgt taacttgttt attgcagctt ataatggtta caaataaagc aatagcatca    2880
caaatttcac aaataaagca tttttttcac tgcattctag ttgtggtttg tccaaactca    2940
tcaatgtatc ttatcatgtc tgctcgaagc ggcctcgaca gcgctggtac cgtcgacggc    3000
tgcgtctagt tgcagtagtt ctccagctgg tagagggagc agatgctggt acagcattgt    3060
tccacaatgc cacgcttctg tcgcgacccc tccagggcca agggctgcag gctgcctgca    3120
ccagggcccc cgcccagctc cacctgcccc acctgcaggt cctctgcctc ccgcttggtc    3180
ctgggtgtgt agaagaagcc tcgttccccg cacactagga agagagcttc caccagatct    3240
gagccgcaca ggtgttggtt cacaaaggct gcggctgggt caggtcccca gagggccagc    3300
```

```
agcgccagca ggggcaggag gcgcatccac agggccatgg cagaaggtcg acgctagcgt    3360
ctccctatag tgagtcgtat tctatagtga gtcgtattaa gtactctagc cttaagagct    3420
gtaattgaac tgggagtgga cacctgtgga gagaaaggca aagtggatgt cagtaagacc    3480
aataggtgcc tatcagaaac gcaagagtct tctctgtctc gacaagccca gtttctattg    3540
gtctccttaa acctgtcttg taaccttgat acttacctgc ccagtgcctc acgaccaact    3600
tctgcaaggc taccttaaga gagtcactgc agcttaagtt cgagactgtt gtgtcagaag    3660
cactgactgc gttagcaatt taactgtgat aaactaccgc aatagctagc ctagtgatct    3720
gacggttcac taaacgagct ctgcttatat agacctccca ccgtacacgc ctaccgccca    3780
tttgcgtcaa cggggcgggc gatcgcagtt gttacgacat tttggaaagt cccgttgatt    3840
ttggtgccaa aacaaactcc cattgacgtc aatggggtgg agacttggaa atccccgtga    3900
gtcaaaccgc tatccacgcc cattggtgta ctgccaaaac cgcatcacca tggtaatagc    3960
gatgactaat acgtagatgt actgccaagt aggaaagtcc cgtaaggtca tgtactgggc    4020
ataatgccag gcgggccatt taccgtcatt gacgtcaata ggggcggac ttggcatatg    4080 atacacttga tgtactgcca agtgggcagt ttaccgtaaa tactccaccc attgacgtca    4140
atggaaagtc cctattggcg ttactatggg aacatacgtc attattgacg tcaatgggcg    4200
ggggtcgttg ggcggtcagc caggcgggcc atttaccgta agttatgtaa cgcggaactc    4260
catatatggg ctatgaacta atgaccccgt aattgattac tattaataac tagtcaataa    4320
tcaatgccaa catggcggtc atattggaca tgagccaata taaatgtaca tattatgata    4380
tagatacaac gtatgcaatg ccaatagcc aatattgatt tatgctatat aaccaatgaa    4440
taatatggct aatggccaat attgagatct gtagataagt agcatggcgg gttaatcatt    4500
aactacagat aaatgcggcc gcaggaaccc ctagtgatgg agttggccac tccctctctg    4560
cgcgctcgct cgctcactga ggccgggcga ccaaaggtcg cccgacgccc gggctttgcc    4620
cgggcggcct cagtgagcga gcgagcgcgc agctgcctgc aggggcgcct gatgcggtat    4680
tttctcctta cgcatctgtg cggtatttca caccgcatac gtcaaagcaa ccatagtacg    4740
cgccctgtag cggcgcatta agcgcggcgg gtgtggtggt tacgcgcagc gtgaccgcta    4800
cacttgccag cgccctagcg cccgctcctt tcgctttctt cccttccttt ctcgccacgt    4860
tcgccggctt tccccgtcaa gctctaaatc gggggctccc tttagggttc cgatttagtg    4920
ctttacggca cctcgacccc aaaaaacttg atttgggtga tggttcacgt agtgggccat    4980
cgccctgata gacggttttt cgccctttga cgttggagtc acgttctttt aatagtggac    5040
tcttgttcca aactggaaca acactcaacc ctatctcggg ctattctttt gatttataag    5100
ggattttgcc gatttcggcc tattggttaa aaatgagct gatttaacaa aatttaacg    5160 cgaattttaa caaaatatta acgtttacaa ttttatggtg cactctcagt acaatctgct    5220
ctgatgccgc atagttaagc cagccccgac acccgccaac acccgctgac gcgccctgac    5280
gggcttgtct gctcccggca tccgcttaca dacaagctgt gaccgtctcc gggagctgca    5340
tgtgtcagag gttttcaccg tcatcaccga aacgcgcgag acgaaagggc ctcgtgatac    5400
gcctattttt ataggttaat gtcatgataa taatggtttc ttagacgtca ggtggcactt    5460
ttcggggaaa tgtgcgcgga accctatttg tttatttttt ctaaatacat tcaaatatgt    5520
atccgctcat gagacaataa ccctgataaa tgcttcaata atattgaaaa aggaagagta    5580
tgagtattca acatttccgt gtcgccctta ttcccttttt tgcggcattt tgccttcctg    5640
```

| ttttttgctca cccagaaacg ctggtgaaag taaaagatgc tgaagatcag ttgggtgcac | 5700 |
| gagtgggtta catcgaactg gatctcaaca gcggtaagat ccttgagagt tttcgccccg | 5760 |
| aagaacgttt tccaatgatg agcactttta aagttctgct atgtggcgcg gtattatccc | 5820 |
| gtattgacgc cgggcaagag caactcggtc gccgcataca ctattctcag aatgacttgg | 5880 |
| ttgagtactc accagtcaca gaaaagcatc ttacggatgg catgacagta agagaattat | 5940 |
| gcagtgctgc cataaccatg agtgataaca ctgcggccaa cttacttctg acaacgatcg | 6000 |
| gaggaccgaa ggagctaacc gcttttttgc acaacatggg ggatcatgta actcgccttg | 6060 |
| atcgttggga accggagctg aatgaagcca taccaaacga cgagcgtgac accacgatgc | 6120 |
| ctgtagcaat ggcaacaacg ttgcgcaaac tattaactgg cgaactactt actctagctt | 6180 |
| cccggcaaca attaatagac tggatggagg cggataaagt tgcaggacca cttctgcgct | 6240 |
| cggcccttcc ggctggctgg tttattgctg ataaatctgg agccggtgag cgtgggtctc | 6300 |
| gcggtatcat tgcagcactg gggccagatg gtaagccctc ccgtatcgta gttatctaca | 6360 |
| cgacggggag tcaggcaact atggatgaac gaaatagaca gatcgctgag ataggtgcct | 6420 |
| cactgattaa gcattggtaa ctgtcagacc aagtttactc atatatactt tagattgatt | 6480 |
| taaaacttca tttttaattt aaaaggatct aggtgaagat cctttttgat aatctcatga | 6540 |
| ccaaaatccc ttaacgtgag ttttcgttcc actgagcgtc agaccccgta gaaaagatca | 6600 |
| aaggatcttc ttgagatcct ttttttctgc gcgtaatctg ctgcttgcaa acaaaaaaac | 6660 |
| caccgctacc agcggtggtt tgtttgccgg atcaagagct accaactctt tttccgaagg | 6720 |
| taactggctt cagcagagcg cagataccaa atactgtcct tctagtgtag ccgtagttag | 6780 |
| gccaccactt caagaactct gtagcaccgc ctacatacct cgctctgcta atcctgttac | 6840 |
| cagtggctgc tgccagtggc gataagtcgt gtcttaccgg gttggactca agacgatagt | 6900 |
| taccggataa ggcgcagcgg tcgggctgaa cggggggttc gtgcacacag cccagcttgg | 6960 |
| agcgaacgac ctacaccgaa ctgagatacc tacagcgtga gctatgagaa agcgccacgc | 7020 |
| ttcccgaagg gagaaaggcg gacaggtatc cggtaagcgg cagggtcgga acaggagagc | 7080 |
| gcacgaggga gcttccaggg ggaaacgcct ggtatcttta tagtcctgtc gggtttcgcc | 7140 |
| acctctgact tgagcgtcga ttttttgtgat gctcgtcagg gggcggagc ctatggaaaa | 7200 |
| acgccagcaa cgcggccttt ttacggttcc tggccttttg ctggcctttt gctcacatgt | 7260 |

<210> SEQ ID NO 13
<211> LENGTH: 6522
<212> TYPE: DNA
<213> ORGANISM: Artificial
<220> FEATURE:
<223> OTHER INFORMATION: Construct J
<220> FEATURE:
<221> NAME/KEY: Construct J
<222> LOCATION: (1)..(6522)

<400> SEQUENCE: 13

| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgcg atatctatgc caagtacgcc ccctattgac | 180 |
| gtcaatgacg gtaaatggcc cgcctggcat tatgcccagt acatgacctt atgggacttt | 240 |
| cctacttggc agtacatcta cgtattagtc atcgctatta ccatggtgat gcggttttgg | 300 |
| cagtacatca atgggcgtgg atagcggttt gactcacggg gatttccaag tctccacccc | 360 |

-continued

```
attgacgtca atgggagttt gttttggcac caaaatcaac gggactttcc aaaatgtcgt    420
aacaactccg ccccattgac gcaaatgggc ggtaggcgtg tacggtggga ggtctatata    480
agcagagctc tctggctaac tagagaaccc actgcttaac tggcttatcg aaattaatac    540
gactcactat agggagaccc aagcttgcta gcgtcgacct tctgccatgg ccctgtggat    600
gcgcctcctg cccctgctgg cgctgctggc cctctgggga cctgacccag ccgcagcctt    660
tgtgaaccaa cacctgtgcg gctcagatct ggtggaagct ctctacctag tgtgcgggga    720
acgaggcttc ttctacacac ccaggaccaa gcgggaggca gaggacctgc aggtggggca    780
ggtggagctg gcgggggcc ctggtgcagg cagcctgcag cccttggccc tggagggggtc    840 gcgacagaag cgtggcattg tggaacaatg ctgtaccagc atctgctccc tctaccagct    900
ggagaactac tgcaactaga cgcagccgtc gacggtacca gcgctgtcga ggccgcttcg    960
agcagacatg ataagataca ttgatgagtt tggacaaacc acaactagaa tgcagtgaaa    1020
aaaatgcttt atttgtgaaa tttgtgatgc tattgctta tttgtaacca ttataagctg    1080
caataaacaa gttaacaaca acaattgcat tcattttatg tttcaggttc aggggggagat    1140 gtgggaggtt ttttaaagca agtaaaacct ctacaaatgt ggtaaaatcg attaggatct    1200
tcctagagca tggctaccta gacatggctc gacagatcag cgctcatgct ctggaagatc    1260
tcgatttatc catgtttgac agcttatcat cgcagatccg tatggtgcac tctcagtaca    1320
atctgctctg atgccgcata gttaagccag tatctgctcc ctgcttgtgt gttggaggtc    1380
gctgagtagt gcgcgagcaa aatttaagct acaacaaggc aaggcttgac cgacaattgc    1440
atgaagaatc tgcttagggt taggcgtttt gcgctgcttc gcgatgtacg ggccagatat    1500
tcgcgtatct gaggggacta gggtgtgttt aggcgaaaag cggggcttcg gttgtacgcg    1560
gttaggagtc ccctcaggat atagtagttt cgcttttgca tagggagggg gaaatgtagt    1620
cttatgcaat actcttgtag tcttgcaaca tggtaacgat gagttagcaa catgccttac    1680
aaggagagaa aaagcaccgt gcatgccgat tggtggaagt aaggtggtac gatcgtgcct    1740
tattaggaag gcaacagacg ggtctgacat ggattggacg aaccactaaa ttccgcattg    1800
cagagatatt gtatttaagt gcctagctcg atacaataaa cgccatttga ccattcacca    1860
cattggtgtg cacctccaag ctgggtacca gcttctagag agatctgctt cagctggagg    1920
cactgggcag gtaagtatca aggttacaag acaggtttaa ggagaccaat agaaactggg    1980
cttgtcgaga cagagaagac tcttgcgttt ctgataggca cctattggtc ttactgacat    2040
ccactttgcc tttctctcca caggtgcagc tgctgcagcg gtctagaact cgagtcgaga    2100
ccatggcgat ggatgtcaca aggagccagg cccagacagc cttgactctg gtagagcaga    2160
tcctggcaga gttccagctg caggaggagg acctgaagaa ggtgatgaga cggatgcaga    2220
aggagatgga ccgcggcctg aggctggaga ccatgaaga ggccagtgtg aagatgctgc    2280
ccacctacgt gcgctccacc ccagaaggct cagaagtcgg ggacttcctc tccctggacc    2340
tgggtggcac taacttcagg gtgatgctgg tgaaggtggg agaaggtgag gaggggcagt    2400
ggagcgtgaa gaccaaacac cagatgtact ccatccccga ggacgccatg accggcactg    2460
ctgagatgct cttcgactac atctctgagt gcatctccga cttcctggac aagcatcaga    2520
tgaaacacaa gaagctgccc ctgggcttca ccttctcctt tcctgtgagg cacgaagaca    2580
tcgataaggg catccttctc aactggacca agggcttcaa ggcctcagga gcagaaggga    2640
acaatgtcgt ggggcttctg cgagacgcta tcaaacggag aggggacttt gaaatggatg    2700
tggtggcaat ggtgaatgac acggtggcca cgatgatctc ctgctactac gaagaccatc    2760
```

-continued

```
agtgcgaggt cggcatgatc gtgggcacgg gctgcaatgc ctgctacatg gaggagatgc    2820
agaatgtgga gctggtggag ggggacgagg gccgcatgtg cgtcaatacc gagtggggcg    2880
ccttcgggga ctccggcgag ctggacgagt tcctgctgga gtatgaccgc ctggtggacg    2940
agagctctgc aaaccccggt cagcagctgt atgagaagct cataggtggc aagtacatgg    3000
gcgagctggt gcggcttgtg ctgctcaggc tcgtggacga aaacctgctc ttccacgggg    3060
aggcctccga gcagctgcgc acacgcggag ccttcgagac gcgcttcgtg tcgcaggtgg    3120
agagcgacac gggcgaccgc aagcagatct acaacatcct gagcacgctg gggctgcgac    3180
cctcgaccac cgactgcgac atcgtgcgcc gcgcctgcga gagcgtgtct acgcgcgctg    3240
cgcacatgtg ctcggcgggg ctggcgggcg tcatcaaccg catgcgcgag agccgcagcg    3300
aggacgtaat gcgcatcact gtgggcgtgg atggctccgt gtacaagctg caccccagct    3360
tcaaggagcg gttccatgcc agcgtgcgca ggctgacgcc cagctgcgag atcaccttca    3420
tcgagtcgga ggagggcagt ggccggggcg cggccctggt ctcggcggtg gcctgtaaga    3480
aggcctgtat gctgggccag tgactcgagc acgtggagct cgctgatcag cctcgactgt    3540
gccttctagt tgccagccat ctgttgtttg cccctcccc gtgccttcct tgaccctgga    3600
aggtgccact cccactgtcc tttcctaata aaatgaggaa attgcatcgc attgtctgag    3660
taggtgtcat tctattctgg ggggtgggt ggggcaggac agcaagggg aggattggga    3720 agacaatagc aggcatgctg gggatgcggt gggctctatg gccacgtgat ttaaatgcgg    3780
ccgcaggaac ccctagtgat ggagttggcc actccctctc tgcgcgctcg ctcgctcact    3840
gaggccgggc gaccaaaggt cgcccgacgc ccgggctttg cccgggcggc ctcagtgagc    3900
gagcgagcgc gcagctgcct gcaggggcgc ctgatgcggt attttctcct tacgcatctg    3960
tgcggtattt cacaccgcat acgtcaaagc aaccatagta cgcgccctgt agcggcgcat    4020
taagcgcggc gggtgtggtg gttacgcgca gcgtgaccgc tacacttgcc agcgccctag    4080
cgcccgctcc tttcgctttc ttcccttcct ttctcgccac gttcgccggc tttccccgtc    4140
aagctctaaa tcggggctc cctttagggt tccgatttag tgctttacgg cacctcgacc    4200
ccaaaaaact tgatttgggt gatggttcac gtagtgggcc atcgccctga tagacggttt    4260
ttcgcccttt gacgttggag tccacgttct ttaatagtgg actcttgttc caaactggaa    4320
caacactcaa ccctatctcg gctattctt ttgatttata agggattttg ccgatttcgg    4380
cctattggtt aaaaatgag ctgatttaac aaaaatttaa cgcgaatttt aacaaaatat    4440
taacgtttac aattttatgg tgcactctca gtacaatctg ctctgatgcc gcatagttaa    4500
gccagccccg acacccgcca acacccgctg acgcgccctg acgggcttgt ctgctcccgg    4560
catccgctta cagacaagct gtgaccgtct ccggagctg catgtgtcag aggttttcac    4620
cgtcatcacc gaaacgcgcg agacgaaagg gcctcgtgat acgcctattt ttataggtta    4680
atgtcatgat aataatggtt tcttagacgt caggtggcac ttttcgggga aatgtgcgcg    4740
gaacccctat ttgtttattt ttctaaatac attcaaatat gtatccgctc atgagacaat    4800
aaccctgata aatgcttcaa taatattgaa aaaggaagag tatgagtatt caacatttcc    4860
gtgtcgccct tattccctt tttgcggcat tttgccttcc tgtttttgct cacccagaaa    4920
cgctggtgaa agtaaaagat gctgaagatc agttgggtgc acgagtgggt tacatcgaac    4980
tggatctcaa cagcggtaag atccttgaga gttttcgccc cgaagaacgt tttccaatga    5040
tgagcacttt taaagttctg ctatgtggcg cggtattatc ccgtattgac gccgggcaag    5100
```

| | |
|---|---|
| agcaactcgg tcgccgcata cactattctc agaatgactt ggttgagtac tcaccagtca | 5160 |
| cagaaaagca tcttacggat ggcatgacag taagagaatt atgcagtgct gccataacca | 5220 |
| tgagtgataa cactgcggcc aacttacttc tgacaacgat cggaggaccg aaggagctaa | 5280 |
| ccgcttttttt gcacaacatg ggggatcatg taactcgcct tgatcgttgg gaaccggagc | 5340 |
| tgaatgaagc cataccaaac gacgagcgtg acaccacgat gcctgtagca atggcaacaa | 5400 |
| cgttgcgcaa actattaact ggcgaactac ttactctagc ttcccggcaa caattaatag | 5460 |
| actggatgga ggcggataaa gttgcaggac cacttctgcg ctcggccctt ccggctggct | 5520 |
| ggtttattgc tgataaatct ggagccgtg agcgtgggtc tcgcggtatc attgcagcac | 5580 |
| tggggccaga tggtaagccc tcccgtatcg tagttatcta cacgacgggg agtcaggcaa | 5640 |
| ctatggatga acgaaataga cagatcgctg atagggtgc ctcactgatt aagcattggt | 5700 |
| aactgtcaga ccaagtttac tcatatatac tttagattga tttaaaactt cattttttaat | 5760 |
| ttaaaaggat ctaggtgaag atcctttttg ataatctcat gaccaaaatc ccttaacgtg | 5820 |
| agtttcgtt ccactgagcg tcagaccccg tagaaaagat caaaggatct tcttgagatc | 5880 |
| ctttttttct gcgcgtaatc tgctgcttgc aaacaaaaaa accaccgcta ccagcggtgg | 5940 |
| tttgtttgcc ggatcaagag ctaccaactc ttttccgaa ggtaactggc ttcagcagag | 6000 |
| cgcagatacc aaatactgtc cttctagtgt agccgtagtt aggccaccac ttcaagaact | 6060 |
| ctgtagcacc gcctacatac ctcgctctgc taatcctgtt accagtggct gctgccagtg | 6120 |
| gcgataagtc gtgtcttacc gggttggact caagacgata gttaccggat aaggcgcagc | 6180 |
| ggtcgggctg aacggggggt tcgtgcacac agcccagctt ggagcgaacg acctacaccg | 6240 |
| aactgagata cctacagcgt gagctatgag aaagcgccac gcttcccgaa gggagaaagg | 6300 |
| cggacaggta tccggtaagc ggcagggtcg aacaggaga gcgcacgagg gagcttccag | 6360 |
| ggggaaacgc ctggtatctt tatagtcctg tcgggtttcg ccacctctga cttgagcgtc | 6420 |
| gattttgtg atgctcgtca ggggggcgga gcctatggaa aaacgccagc aacgcggcct | 6480 |
| ttttacggtt cctggccttt tgctggcctt ttgctcacat gt | 6522 |

<210> SEQ ID NO 14
<211> LENGTH: 6522
<212> TYPE: DNA
<213> ORGANISM: Artificial
<220> FEATURE:
<223> OTHER INFORMATION: Construct K
<220> FEATURE:
<221> NAME/KEY: Construct L
<222> LOCATION: (1)..(6522)
<220> FEATURE:
<221> NAME/KEY: Construct K
<222> LOCATION: (1)..(6522)

<400> SEQUENCE: 14

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgcg atatccatgt ttgacagctt atcatcgcag | 180 |
| atccgtatgg tgcactctca gtacaatctg ctctgatgcc gcatagttaa gccagtatct | 240 |
| gctccctgct tgtgtgttgg aggtcgctga gtagtgcgcg agcaaaattt aagctacaac | 300 |
| aaggcaaggc ttgaccgaca attgcatgaa gaatctgctt agggttaggc gttttgcgct | 360 |
| gcttcgcgat gtacgggcca gatattgcgc tatctgaggg gactagggtg tgtttaggcg | 420 |
| aaaagcgggg cttcggttgt acgcggttag gagtcccctc aggatatagt agtttcgctt | 480 |

```
ttgcataggg aggggggaaat gtagtcttat gcaatactct tgtagtcttg caacatggta    540
acgatgagtt agcaacatgc cttacaagga gagaaaaagc accgtgcatg ccgattggtg    600
gaagtaaggt ggtacgatcg tgccttatta ggaaggcaac agacgggtct gacatggatt    660
ggacgaacca ctaaattccg cattgcagag atattgtatt taagtgccta gctcgataca    720
ataaacgcca tttgaccatt caccacattg gtgtgcacct ccaagctggg taccagcttc    780
tagagagatc tgcttcagct ggaggcactg ggcaggtaag tatcaaggtt acaagacagg    840
tttaaggaga ccaatagaaa ctgggcttgt cgagacagag aagactcttg cgtttctgat    900
aggcacctat tggtcttact gacatccact ttgcctttct ctccacaggt gcagctgctg    960
cagcggtcta gaactcgagt cgagaccatg gcgatggatg tcacaaggag ccaggcccag   1020
acagccttga ctctggtaga gcagatcctg gcagagttcc agctgcagga ggaggacctg   1080
aagaaggtga tgagacggat gcagaaggag atggaccgcg gcctgaggct ggagacccat   1140
gaagaggcca gtgtgaagat gctgcccacc tacgtgcgct ccaccccaga aggctcagaa   1200
gtcggggact tcctctccct ggacctgggt ggcactaact tcagggtgat gctggtgaag   1260
gtgggagaag gtgaggaggg gcagtggagc gtgaagacca acaccagat gtactccatc    1320 cccgaggacg ccatgaccgg cactgctgag atgctcttcg actacatctc tgagtgcatc   1380
tccgacttcc tggacaagca tcagatgaaa cacaagaagc tgcccctggg cttcaccttc   1440
tcctttcctg tgaggcacga agacatcgat aagggcatcc ttctcaactg gaccaagggc   1500
ttcaaggcct caggagcaga agggaacaat gtcgtgggc ttctgcgaga cgctatcaaa    1560
cggagagggg actttgaaat ggatgtggtg gcaatggtga atgacacggt ggccacgatg   1620
atctcctgct actacgaaga ccatcagtgc gaggtcggca tgatcgtggg cacgggctgc   1680
aatgcctgct acatggagga gatgcagaat gtggagctgg tgaggggga cgagggccgc   1740 atgtgcgtca ataccgagtg gggcgccttc ggggactccg cgagctgga cgagttcctg    1800 ctggagtatg accgcctggt ggacgagagc tctgcaaacc ccggtcagca gctgtatgag   1860
aagctcatag gtggcaagta catgggcgag ctggtgcggc ttgtgctgct caggctcgtg   1920
gacgaaaacc tgctcttcca cggggaggcc tccgagcagc tgcgcacacg cggagccttc   1980
gagacgcgct tcgtgtcgca ggtggagagc gacacgggcg accgcaagca gatctacaac   2040
atcctgagca cgctggggct gcgacccctcg accaccgact gcgacatcgt gcgccgcgcc   2100
tgcgagagcg tgtctacgcg cgctgcgcac atgtgctcgg cggggctggc gggcgtcatc   2160
aaccgcatgc gcgagagccg cagcgaggac gtaatgcgca tcactgtggg cgtggatggc   2220
tccgtgtaca agctgcaccc cagcttcaag gagcggttcc atgccagcgt gcgcaggctg   2280
acgcccagct gcgagatcac cttcatcgag tcggaggagg cgtggccgg gggcgcggcc   2340 ctggtctcgg cggtggcctg taagaaggcc tgtatgctgg gccagtgact cgagcacgtg   2400
gagctcgctg atcagcctcg actgtgcctt ctagttgcca gccatctgtt gtttgccct    2460 cccccgtgcc ttccttgacc ctggaaggtg ccactcccac tgtcctttcc taataaaatg   2520
aggaaattgc atcgcattgt ctgagtaggt gtcattctat tctgggggt ggggtgggc    2580 aggacagcaa gggggaggat tgggaagaca atagcaggca tgctgggat gcggtgggct    2640 ctatggccac gtgatttatc tatgccaagt acgcccccta ttgacgtcaa tgacggtaaa   2700
tggcccgcct ggcattatgc ccagtacatg accttatggg actttcctac ttggcagtac   2760
atctacgtat tagtcatcgc tattaccatg gtgatgcggt tttggcagta catcaatggg   2820
```

```
cgtggatagc ggtttgactc acggggattt ccaagtctcc accccattga cgtcaatggg    2880
agtttgtttt ggcaccaaaa tcaacgggac tttccaaaat gtcgtaacaa ctccgcccca    2940
ttgacgcaaa tgggcggtag gcgtgtacgg tgggaggtct atataagcag agctctctgg    3000
ctaactagag aacccactgc ttaactggct tatcgaaatt aatacgactc actataggga    3060
gacccaagct tgctagcgtc gaccttctgc catggccctg tggatgcgcc tcctgccct     3120 gctggcgctg ctggccctct ggggacctga cccagccgca gcctttgtga accaacacct    3180
gtgcggctca gatctggtgg aagctctcta cctagtgtgc ggggaacgag gcttcttcta    3240
cacacccagg accaagcggg aggcagagga cctgcaggtg gggcaggtgg agctgggcgg    3300
gggccctggt gcaggcagcc tgcagccctt ggccctggag gggtcgcgac agaagcgtgg    3360
cattgtggaa caatgctgta ccagcatctg ctccctctac cagctggaga actactgcaa    3420
ctagacgcag ccgtcgacgg taccagcgct gtcgaggccg cttcgagcag acatgataag    3480
atacattgat gagtttggac aaaccacaac tagaatgcag tgaaaaaaat gctttatttg    3540
tgaaatttgt gatgctattg ctttatttgt aaccattata agctgcaata aacaagttaa    3600
caacaacaat tgcattcatt ttatgtttca ggttcagggg gagatgtggg aggtttttta    3660
aagcaagtaa aacctctaca aatgtggtaa atcgattag gatcttccta gagcatggct    3720
acctagacat ggctcgacag atcagcgctc atgctctgga agatctcgat ttaaatgcgg    3780
ccgcaggaac ccctagtgat ggagttggcc actccctctc tgcgcgctcg ctcgctcact    3840
gaggccgggc gaccaaaggt cgcccgacgc ccgggctttg cccgggcggc ctcagtgagc    3900
gagcgagcgc gcagctgcct gcaggggcgc ctgatgcggt attttctcct tacgcatctg    3960
tgcggtattt cacaccgcat acgtcaaagc aaccatagta cgcgccctgt agcggcgcat    4020
taagcgcggc gggtgtggtg gttacgcgca gcgtgaccgc tacacttgcc agcgccctag    4080
cgcccgctcc tttcgctttc ttcccttcct ttctcgccac gttcgccggc tttccccgtc    4140
aagctctaaa tcgggggctc cctttagggt tccgatttag tgctttacgg cacctcgacc    4200
ccaaaaaact tgatttgggt gatggttcac gtagtgggcc atcgccctga tagacggttt    4260
ttcgcccttt gacgttggag tccacgttct ttaatagtgg actcttgttc caaactggaa    4320
caacactcaa ccctatctcg ggctattctt ttgatttata agggattttg ccgatttcgg    4380
cctattggtt aaaaaatgag ctgatttaac aaaaatttaa cgcgaatttt aacaaaatat    4440
taacgtttac aattttatgg tgcactctca gtacaatctg ctctgatgcc gcatagttaa    4500
gccagccccg acaccgcca acaccgctg acgcgcctg acgggctgt ctgctcccgg       4560 catccgctta cagacaagct gtgaccgtct ccgggagctg catgtgtcag aggttttcac    4620
cgtcatcacc gaaacgcgcg agacgaaagg gcctcgtgat acgcctattt ttataggtta    4680
atgtcatgat aataatggtt tcttagacgt caggtggcac ttttcgggga aatgtgcgcg    4740
gaacccctat ttgtttattt ttctaaatac attcaaatat gtatccgctc atgagacaat    4800
aaccctgata aatgcttcaa taatattgaa aaaggaagag tatgagtatt caacatttcc    4860
gtgtcgccct tattcccttt tttgcggcat tttgccttcc tgtttttgct cacccagaaa    4920
cgctggtgaa agtaaaagat gctgaagatc agttgggtgc acgagtgggt tacatcgaac    4980
tggatctcaa cagcggtaag atccttgaga gttttcgccc cgaagaacgt tttccaatga    5040
tgagcacttt taaagttctg ctatgtggcg cggtattatc ccgtattgac gccgggcaag    5100
agcaactcgg tcgccgcata cactattctc agaatgactt ggttgagtac tcaccagtca    5160
cagaaaagca tcttacggat ggcatgacag taagagaatt atgcagtgct gccataacca    5220
```

| | |
|---|---|
| tgagtgataa cactgcggcc aacttacttc tgacaacgat cggaggaccg aaggagctaa | 5280 |
| ccgcttttt gcacaacatg ggggatcatg taactcgcct tgatcgttgg gaaccggagc | 5340 |
| tgaatgaagc cataccaaac gacgagcgtg acaccacgat gcctgtagca atggcaacaa | 5400 |
| cgttgcgcaa actattaact ggcgaactac ttactctagc ttcccggcaa caattaatag | 5460 |
| actggatgga ggcggataaa gttgcaggac cacttctgcg ctcggccctt ccggctggct | 5520 |
| ggtttattgc tgataaatct ggagccggtg agcgtgggtc tcgcggtatc attgcagcac | 5580 |
| tggggccaga tggtaagccc tcccgtatcg tagttatcta cacgacgggg agtcaggcaa | 5640 |
| ctatggatga acgaaataga cagatcgctg agataggtgc ctcactgatt aagcattggt | 5700 |
| aactgtcaga ccaagtttac tcatatatac tttagattga tttaaaactt cattttaat | 5760 |
| ttaaaaggat ctaggtgaag atcctttttg ataatctcat gaccaaaatc ccttaacgtg | 5820 |
| agttttcgtt ccactgagcg tcagaccccg tagaaaagat caaaggatct tcttgagatc | 5880 |
| ctttttttct gcgcgtaatc tgctgcttgc aaacaaaaaa accaccgcta ccagcggtgg | 5940 |
| tttgtttgcc ggatcaagag ctaccaactc tttttccgaa ggtaactggc ttcagcagag | 6000 |
| cgcagatacc aaatactgtc cttctagtgt agccgtagtt aggccaccac ttcaagaact | 6060 |
| ctgtagcacc gcctacatac ctcgctctgc taatcctgtt accagtggct gctgccagtg | 6120 |
| gcgataagtc gtgtcttacc gggttggact caagacgata gttaccggat aaggcgcagc | 6180 |
| ggtcgggctg aacggggggt tcgtgcacac agcccagctt ggagcgaacg acctacaccg | 6240 |
| aactgagata cctacagcgt gagctatgag aaagcgccac gcttcccgaa gggagaaagg | 6300 |
| cggacaggta tccggtaagc ggcagggtcg aacaggaga gcgcacgagg gagcttccag | 6360 |
| ggggaaacgc ctggtatctt tatagtcctg tcgggtttcg ccacctctga cttgagcgtc | 6420 |
| gatttttgtg atgctcgtca ggggggcgga gcctatggaa aaacgccagc aacgcggcct | 6480 |
| ttttacggtt cctggccttt tgctggcctt ttgctcacat gt | 6522 |

<210> SEQ ID NO 15
<211> LENGTH: 6522
<212> TYPE: DNA
<213> ORGANISM: Artificial
<220> FEATURE:
<223> OTHER INFORMATION: Construct L
<220> FEATURE:
<221> NAME/KEY: Construct L
<222> LOCATION: (1)..(6522)

<400> SEQUENCE: 15

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgcg ataaatcgag atcttccaga gcatgagcgc | 180 |
| tgatctgtcg agccatgtct aggtagccat gctctaggaa gatcctaatc gattttacca | 240 |
| catttgtaga ggttttactt gctttaaaaa acctcccaca tctcccctg aacctgaaac | 300 |
| ataaaatgaa tgcaattgtt gttgttaact tgtttattgc agcttataat ggttacaaat | 360 |
| aaagcaatag catcacaaat ttcacaaata aagcattttt ttcactgcat tctagttgtg | 420 |
| gtttgtccaa actcatcaat gtatcttatc atgtctgctc gaagcggcct cgacagcgct | 480 |
| ggtaccgtcg acggctgcgt ctagttgcag tagttctcca gctggtagag ggagcagatg | 540 |
| ctggtacagc attgttccac aatgccacgc ttctgtcgcg accctccag ggccaagggc | 600 |
| tgcaggctgc ctgcaccagg gcccccgccc agctccacct gccccacctg caggtcctct | 660 |

```
gcctcccgct tggtcctggg tgtgtagaag aagcctcgtt ccccgcacac taggtagaga    720
gcttccacca gatctgagcc gcacaggtgt tggttcacaa aggctgcggc tgggtcaggt    780
ccccagaggg ccagcagcgc cagcaggggc aggaggcgca tccacagggc catggcagaa    840
ggtcgacgct agcaagcttg gtctcccta tagtgagtcg tattaatttc gataagccag     900
ttaagcagtg ggttctctag ttagccagag agctctgctt atatagacct cccaccgtac    960
acgcctaccg cccatttgcg tcaatggggc ggagttgtta cgacattttg gaaagtcccg   1020
ttgattttgg tgccaaaaca aactcccatt gacgtcaatg gggtggagac ttggaaatcc   1080
ccgtgagtca aaccgctatc cacgcccatt gatgtactgc caaaaccgca tcaccatggt   1140
aatagcgatg actaatacgt agatgtactg ccaagtagga aagtcccata aggtcatgta   1200
ctgggcataa tgccaggcgg gccatttacc gtcattgacg tcaataggg gcgtacttgg    1260 catagatatc catgtttgac agcttatcat cgcagatccg tatggtgcac tctcagtaca   1320
atctgctctg atgccgcata gttaagccag tatctgctcc ctgcttgtgt gttggaggtc   1380
gctgagtagt gcgcgagcaa aatttaagct acaacaaggc aaggcttgac cgacaattgc   1440
atgaagaatc tgcttagggt taggcgtttt gcgctgcttc gcgatgtacg ggccagatat   1500
tcgcgtatct gaggggacta gggtgtgttt aggcgaaaag cggggcttcg gttgtacgcg   1560
gttaggagtc ccctcaggat atagtagttt cgcttttgca tagggagggg gaaatgtagt   1620
cttatgcaat actcttgtag tcttgcaaca tggtaacgat gagttagcaa catgccttac   1680
aaggagagaa aaagcaccgt gcatgccgat tggtggaagt aaggtggtac gatcgtgcct   1740
tattaggaag gcaacagacg ggtctgacat ggattggacg aaccactaaa ttccgcattg   1800
cagagatatt gtatttaagt gcctagctcg atacaataaa cgccatttga ccattcacca   1860
cattggtgtg cacctccaag ctgggtacca gcttctagag agatctgctt cagctggagg   1920
cactgggcag gtaagtatca aggttacaag acaggtttaa ggagaccaat agaaactggg   1980
cttgtcgaga cagagaagac tcttgcgttt ctgataggca cctattggtc ttactgacat   2040
ccactttgcc tttctctcca caggtgcagc tgctgcagcg gtctagaact cgagtcgaga   2100
ccatggcgat ggatgtcaca aggagccagg cccagacagc cttgactctg gtagagcaga   2160
tcctggcaga gttccagctg caggaggagg acctgaagaa ggtgatgaga cggatgcaga   2220
aggagatgga ccgcggcctg aggctggaga cccatgaaga ggccagtgtg aagatgctgc   2280
ccacctacgt gcgctccacc ccagaaggct cagaagtcgg ggacttcctc tccctggacc   2340
tgggtggcac taacttcagg gtgatgctgg tgaaggtggg agaaggtgag gaggggcagt   2400
ggagcgtgaa gaccaaacac cagatgtact ccatccccga ggacgccatg accggcactg   2460
ctgagatgct cttcgactac atctctgagt gcatctccga cttcctggac aagcatcaga   2520
tgaaacacaa gaagctgccc ctgggcttca ccttctcctt tcctgtgagg cacgaagaca   2580
tcgataaggg catccttctc aactggacca agggcttcaa ggcctcagga gcagaaggga   2640
acaatgtcgt ggggcttctg cgagacgcta tcaaacggag aggggacttt gaaatggatg   2700
tggtggcaat ggtgaatgac acggtggcca cgatgatctc ctgctactac gaagaccatc   2760
agtgcgaggt cggcatgatc gtgggcacgg gctgcaatgc ctgctacatg gaggagatgc   2820
agaatgtgga gctggtggag ggggacgagg gccgcatgtg cgtcaatacc gagtggggcg   2880 ccttcggga ctccggcgag ctggacgagt cctgctgga gtatgaccgc ctggtggacg    2940
agagctctgc aaaccccggt cagcagctgt atgagaagct cataggtggc aagtacatgg   3000
```

```
gcgagctggt gcggcttgtg ctgctcaggc tcgtggacga aaacctgctc ttccacgggg    3060
aggcctccga gcagctgcgc acacgcggag ccttcgagac gcgcttcgtg tcgcaggtgg    3120
agagcgacac gggcgaccgc aagcagatct acaacatcct gagcacgctg gggctgcgac    3180
cctcgaccac cgactgcgac atcgtgcgcc gcgcctgcga gagcgtgtct acgcgcgctg    3240
cgcacatgtg ctcggcgggg ctggcgggcg tcatcaaccg catgcgcgag agccgcagcg    3300
aggacgtaat gcgcatcact gtgggcgtgg atggctccgt gtacaagctg caccccagct    3360
tcaaggagcg gttccatgcc agcgtgcgca ggctgacgcc cagctgcgag atcaccttca    3420
tcgagtcgga ggagggcagt ggccggggcg cggccctggt ctcggcggtg gcctgtaaga    3480
aggcctgtat gctgggccag tgactcgagc acgtggagct cgctgatcag cctcgactgt    3540
gccttctagt tgccagccat ctgttgtttg ccctccccc gtgccttcct tgaccctgga    3600
aggtgccact cccactgtcc tttcctaata aaatgaggaa attgcatcgc attgtctgag    3660
taggtgtcat tctattctgg ggggtggggt ggggcaggac agcaagggggg aggattggga    3720
agacaatagc aggcatgctg gggatgcggt gggctctatg ccacgtgat ttaaatgcgg    3780
ccgcaggaac ccctagtgat ggagttggcc actccctctc tgcgcgctcg ctcgctcact    3840
gaggccgggc gaccaaaggt cgcccgacgc ccgggctttg cccgggcggc ctcagtgagc    3900
gagcgagcgc gcagctgcct gcaggggcgc ctgatgcggt attttctcct tacgcatctg    3960
tgcggtattt cacaccgcat acgtcaaagc aaccatagta cgcgccctgt agcggcgcat    4020
taagcgcggc gggtgtggtg gttacgcgca gcgtgaccgc tacacttgcc agcgccctag    4080
cgcccgctcc tttcgctttc ttcccttcct ttctcgccac gttcgccggc tttccccgtc    4140
aagctctaaa tcggggggctc cctttagggt tccgatttag tgctttacgg cacctcgacc    4200
ccaaaaaact tgatttgggt gatggttcac gtagtgggcc atcgccctga tagacggttt    4260
ttcgcccttt gacgttggag tccacgttct ttaatagtgg actcttgttc caaactggaa    4320
caacactcaa ccctatctcg gctattcttt tgatttata agggattttg ccgatttcgg    4380
cctattggtt aaaaaatgag ctgatttaac aaaaatttaa cgcgaatttt aacaaaatat    4440
taacgtttac aattttatgg tgcactctca gtacaatctg ctctgatgcc gcatagttaa    4500
gccagccccg acacccgcca cacccgctg acgcgccctg acgggcttgt ctgctcccgg    4560
catccgctta cagacaagct gtgaccgtct ccgggagctg catgtgtcag aggttttcac    4620
cgtcatcacc gaaacgcgcg agacgaaagg gcctcgtgat acgcctattt ttataggtta    4680
atgtcatgat aataatggtt tcttagacgt caggtggcac ttttcgggga aatgtgcgcg    4740
gaacccctat ttgtttattt ttctaaatac attcaaatat gtatccgctc atgagacaat    4800
aaccctgata aatgcttcaa taatattgaa aaaggaagag tatgagtatt caacatttcc    4860
gtgtcgccct tattcccttt tttgcggcat tttgccttcc tgtttttgct cacccagaaa    4920
cgctggtgaa agtaaaagat gctgaagatc agttgggtgc acgagtgggt tacatcgaac    4980
tggatctcaa cagcggtaag atccttgaga gttttcgccc cgaagaacgt tttccaatga    5040
tgagcacttt taaagttctg ctatgtggcg cggtattatc ccgtattgac gccgggcaag    5100
agcaactcgg tcgccgcata cactattctc agaatgactt ggttgagtac tcaccagtca    5160
cagaaaagca tcttacggat ggcatgacag taagagaatt atgcagtgct gccataacca    5220
tgagtgataa cactgcggcc aacttacttc tgacaacgat cggaggaccg aaggagctaa    5280
ccgcttttt gcacaacatg ggggatcatg taactcgcct tgatcgttgg gaaccggagc    5340
tgaatgaagc cataccaaac gacgagcgtg acaccacgat gcctgtagca atggcaacaa    5400
```

```
cgttgcgcaa actattaact ggcgaactac ttactctagc ttcccggcaa caattaatag    5460
actggatgga ggcggataaa gttgcaggac cacttctgcg ctcggccctt ccggctggct    5520
ggtttattgc tgataaatct ggagccggtg agcgtgggtc tcgcggtatc attgcagcac    5580
tggggccaga tggtaagccc tcccgtatcg tagttatcta cacgacgggg agtcaggcaa    5640
ctatggatga acgaaataga cagatcgctg agataggtgc ctcactgatt aagcattggt    5700
aactgtcaga ccaagtttac tcatatatac tttagattga tttaaaactt catttttaat    5760
ttaaaaggat ctaggtgaag atcctttttg ataatctcat gaccaaaatc ccttaacgtg    5820
agttttcgtt ccactgagcg tcagaccccg tagaaaagat caaaggatct tcttgagatc    5880
ctttttttct gcgcgtaatc tgctgcttgc aaacaaaaaa accaccgcta ccagcggtgg    5940
tttgtttgcc ggatcaagag ctaccaactc tttttccgaa ggtaactggc ttcagcagag    6000
cgcagatacc aaatactgtc cttctagtgt agccgtagtt aggccaccac ttcaagaact    6060
ctgtagcacc gcctacatac ctcgctctgc taatcctgtt accagtggct gctgccagtg    6120
gcgataagtc gtgtcttacc gggttggact caagacgata gttaccggat aaggcgcagc    6180
ggtcgggctg aacggggggt tcgtgcacac agcccagctt ggagcgaacg acctacaccg    6240
aactgagata cctacagcgt gagctatgag aaagcgccac gcttcccgaa gggagaaagg    6300
cggacaggta tccggtaagc ggcagggtcg gaacaggaga gcgcacgagg gagcttccag    6360
ggggaaacgc ctggtatctt tatagtcctg tcgggtttcg ccacctctga cttgagcgtc    6420
gatttttgtg atgctcgtca ggggggcgga gcctatggaa aaacgccagc aacgcggcct    6480
ttttacggtt cctggccttt tgctggcctt ttgctcacat gt                      6522

<210> SEQ ID NO 16
<211> LENGTH: 6522
<212> TYPE: DNA
<213> ORGANISM: Artificial
<220> FEATURE:
<223> OTHER INFORMATION: Construct M
<220> FEATURE:
<221> NAME/KEY: Construct M
<222> LOCATION: (1)..(6522)

<400> SEQUENCE: 16
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tcggccgcg atatccatgt ttgacagctt atcatcgcag     180
atccgtatgg tgcactctca gtacaatctg ctctgatgcc gcatagttaa gccagtatct     240
gctccctgct tgtgtgttgg aggtcgctga gtagtgcgcg agcaaaattt aagctacaac     300
aaggcaaggc ttgaccgaca attgcatgaa gaatctgctt agggttaggc gttttgcgct     360
gcttcgcgat gtacgggcca gatattgcgc tatctgaggg gactagggtg tgtttaggcg     420
aaaagcgggg cttcggttgt acgcggttag gagtcccctc aggatatagt agtttcgctt     480
ttgcataggg aggggggaaat gtagtcttat gcaatactct tgtagtcttg caacatggta     540
acgatgagtt agcaacatgc cttacaagga gagaaaagc accgtgcatg ccgattggtg     600
gaagtaaggt ggtacgatcg tgccttatta ggaaggcaac agacgggtct gacatggatt     660
ggacgaacca ctaaattccg cattgcagag atattgtatt taagtgccta gctcgataca     720
ataaacgcca tttgaccatt caccacattg gtgtgcacct ccaagctggg taccagcttc     780
tagagagatc tgcttcagct ggaggcactg gcaggtaag tatcaaggtt acaagacagg     840
```

-continued

```
tttaaggaga ccaatagaaa ctgggcttgt cgagacagag aagactcttg cgtttctgat      900
aggcacctat tggtcttact gacatccact ttgcctttct ctccacaggt gcagctgctg      960
cagcggtcta gaactcgagt cgagaccatg gcgatggatg tcacaaggag ccaggcccag     1020
acagccttga ctctggtaga gcagatcctg cagagttcc agctgcagga ggaggacctg     1080
aagaaggtga tgagacggat gcagaaggag atggaccgcg gcctgaggct ggagacccat     1140
gaagaggcca gtgtgaagat gctgcccacc tacgtgcgct ccaccccaga aggctcagaa     1200 gtcgggact tcctctccct ggacctgggt ggcactaact tcagggtgat gctggtgaag     1260
gtgggagaag gtgaggaggg gcagtggagc gtgaagacca acaccagat gtactccatc     1320 cccgaggacg ccatgaccgg cactgctgag atgctcttcg actacatctc tgagtgcatc     1380
tccgacttcc tggacaagca tcagatgaaa cacaagaagc tgcccctggg cttcaccttc     1440
tcctttcctg tgaggcacga agacatcgat aagggcatcc ttctcaactg gaccaagggc     1500
ttcaaggcct caggagcaga agggaacaat gtcgtgggc ttctgcgaga cgctatcaaa     1560
cggagagggg actttgaaat ggatgtggtg gcaatggtga atgacacggt ggccacgatg     1620
atctcctgct actacgaaga ccatcagtgc gaggtcggca tgatcgtggg cacgggctgc     1680
aatgcctgct acatggagga gatgcagaat gtggagctgg tggaggggga cgagggccgc     1740
atgtgcgtca ataccgagtg gggcgccttc ggggactccg cgagctgga cgagttcctg     1800 ctggagtatg accgcctggt ggacgagagc tctgcaaacc ccggtcagca gctgtatgag     1860
aagctcatag gtggcaagta catgggcgag ctggtgcggc ttgtgctgct caggctcgtg     1920
gacgaaaacc tgctcttcca cggggaggcc tccgagcagc tgcgcacacg cggagccttc     1980
gagacgcgct tcgtgtcgca ggtggagagc gacacgggcg accgcaagca gatctacaac     2040
atcctgagca cgctggggct gcgaccctcg accaccgact gcgacatcgt gcgccgcgcc     2100
tgcgagagcg tgtctacgcg cgctgcgcac atgtgctcgg cggggctggc gggcgtcatc     2160
aaccgcatgc gcgagagccg cagcgaggac gtaatgcgca tcactgtggg cgtggatggc     2220
tccgtgtaca agctgcaccc cagcttcaag gagcggttcc atgccagcgt gcgcaggctg     2280
acgcccagct gcgagatcac cttcatcgag tcggaggagg gcagtggccg gggcgcggcc     2340
ctggtctcgg cggtggcctg taagaaggcc tgtatgctgg gccagtgact cgagcacgtg     2400
gagctcgctg atcagcctcg actgtgcctt ctagttgcca gccatctgtt gtttgccccct     2460 cccccgtgcc ttccttgacc ctggaaggtg ccactcccac tgtcctttcc taataaaatg     2520
aggaaattgc atcgcattgt ctgagtaggt gtcattctat tctgggggt ggggtggggc     2580 aggacagcaa gggggaggat tgggaagaca atagcaggca tgctggggat gcggtgggct     2640
ctatggccac gtgattttaaa tcgagatctt ccagagcatg agcgctgatc tgtcgagcca     2700
tgtctaggta gccatgctct aggaagatcc taatcgattt taccacattt gtagaggttt     2760
tacttgcttt aaaaaacctc ccacatctcc ccctgaacct gaaacataaa atgaatgcaa     2820 tgttgttgt taacttgttt attgcagctt ataatggtta caaataaagc aatagcatca     2880
caaatttcac aaataaagca ttttttcac tgcattctag ttgtggtttg tccaaactca     2940
tcaatgtatc ttatcatgtc tgctcgaagc ggcctcgaca cgcgctggtac cgtcgacggc     3000 tgcgtctagt tgcagtagtt ctccagctgg tagagggagc agatgctggt acagcattgt     3060
tccacaatgc cacgcttctg tcgcgacccc tccaggccaa agggctgcag gctgcctgca     3120
ccagggcccc cgcccagctc cacctgcccc acctgcaggt cctctgcctc ccgcttggtc     3180
```

```
ctgggtgtgt agaagaagcc tcgttccccg cacactaggt agagagcttc caccagatct    3240
gagccgcaca ggtgttggtt cacaaaggct gcggctgggt caggtcccca gagggccagc    3300
agcgccagca ggggcaggag gcgcatccac agggccatgg cagaaggtcg acgctagcaa    3360
gcttgggtct ccctatagtg agtcgtatta atttcgataa gccagttaag cagtgggttc    3420
tctagttagc cagagagctc tgcttatata gacctcccac cgtacacgcc taccgcccat    3480
ttgcgtcaat ggggcggagt tgttacgaca ttttggaaag tcccgttgat tttggtgcca    3540
aaacaaactc ccattgacgt caatggggtg gagacttgga aatccccgtg agtcaaaccg    3600
ctatccacgc ccattgatgt actgccaaaa ccgcatcacc atggtaatag cgatgactaa    3660
tacgtagatg tactgccaag taggaaagtc ccataaggtc atgtactggg cataatgcca    3720
ggcgggccat ttaccgtcat tgacgtcaat aggggcgta cttggcatag ataaatgcgg    3780
ccgcaggaac ccctagtgat ggagttggcc actccctctc tgcgcgctcg ctcgctcact    3840
gaggccgggc gaccaaaggt cgcccgacgc ccgggctttg cccgggcggc ctcagtgagc    3900
gagcgagcgc gcagctgcct gcaggggcgc ctgatgcggt attttctcct tacgcatctg    3960
tgcggtattt cacaccgcat acgtcaaagc aaccatagta cgcgccctgt agcggcgcat    4020
taagcgcggc gggtgtggtg gttacgcgca gcgtgaccgc tacacttgcc agcgccctag    4080
cgcccgctcc tttcgctttc ttcccttcct ttctcgccac gttcgccggc tttccccgtc    4140
aagctctaaa tcggggctc cctttagggt tccgatttag tgctttacgg cacctcgacc    4200
ccaaaaaact tgatttgggt gatggttcac gtagtgggcc atcgccctga tagacggttt    4260
ttcgcccttt gacgttggag tccacgttct ttaatagtgg actcttgttc caaactggaa    4320
caacactcaa ccctatctcg gctattcttt tgatttata agggattttg ccgatttcgg    4380
cctattggtt aaaaaatgag ctgatttaac aaaaatttaa cgcgaatttt aacaaaatat    4440
taacgtttac aattttatgg tgcactctca gtacaatctg ctctgatgcc gcatagttaa    4500
gccagccccg acacccgcca cacccgctg acgcgccctg acgggcttgt ctgctcccgg    4560
catccgctta cagacaagct gtgaccgtct ccgggagctg catgtgtcag aggttttcac    4620
cgtcatcacc gaaacgcgcg agacgaaagg gcctcgtgat acgcctattt ttataggtta    4680
atgtcatgat aataatggtt tcttagacgt caggtggcac ttttcgggga aatgtgcgcg    4740
gaacccctat ttgtttattt ttctaaatac attcaaatat gtatccgctc atgagacaat    4800
aaccctgata aatgcttcaa taatattgaa aaaggaagag tatgagtatt caacatttcc    4860
gtgtcgccct tattccctt tttgcggcat tttgccttcc tgttttgct cacccagaaa    4920 cgctggtgaa agtaaaagat gctgaagatc agttgggtgc acgagtgggt tacatcgaac    4980
tggatctcaa cagcggtaag atccttgaga gttttcgccc cgaagaacgt tttccaatga    5040
tgagcacttt taaagttctg ctatgtggcg cggtattatc ccgtattgac gccgggcaag    5100
agcaactcgg tcgccgcata cactattctc agaatgactt ggttgagtac tcaccagtca    5160
cagaaaagca tcttacggat ggcatgacag taagagaatt atgcagtgct gccataacca    5220
tgagtgataa cactgcggcc aacttacttc tgacaacgat cggaggaccg aaggagctaa    5280 ccgcttttt gcacaacatg ggggatcatg taactcgcct tgatcgttgg aaccggagc    5340 tgaatgaagc cataccaaac gacgagcgtg acaccacgat gcctgtagca atggcaacaa    5400
cgttgcgcaa actattaact ggcgaactac ttactctagc ttcccggcaa caattaatag    5460
actggatgga ggcggataaa gttgcaggac cacttctgcg ctcggccctt ccggctggct    5520
ggtttattgc tgataaatct ggagccggtg agcgtgggtc tcgcggtatc attgcagcac    5580
```

```
tggggccaga tggtaagccc tcccgtatcg tagttatcta cacgacgggg agtcaggcaa    5640
ctatggatga acgaaataga cagatcgctg agataggtgc ctcactgatt aagcattggt    5700
aactgtcaga ccaagtttac tcatatatac tttagattga tttaaaactt catttttaat    5760 ttaaaggat ctaggtgaag atccttttg ataatctcat gaccaaaatc ccttaacgtg     5820
agttttcgtt ccactgagcg tcagaccccg tagaaaagat caaaggatct tcttgagatc    5880 cttttttct gcgcgtaatc tgctgcttgc aaacaaaaaa accaccgcta ccagcggtgg    5940
tttgtttgcc ggatcaagag ctaccaactc tttttccgaa ggtaactggc ttcagcagag    6000
cgcagatacc aaatactgtc cttctagtgt agccgtagtt aggccaccac ttcaagaact    6060
ctgtagcacc gcctacatac ctcgctctgc taatcctgtt accagtggct gctgccagtg    6120
gcgataagtc gtgtcttacc gggttggact caagacgata gttaccggat aaggcgcagc    6180
ggtcgggctg aacggggggt tcgtgcacac agcccagctt ggagcgaacg acctacaccg    6240
aactgagata cctacagcgt gagctatgag aaagcgccac gcttcccgaa gggagaaagg    6300
cggacaggta tccggtaagc ggcagggtcg aacaggaga gcgcacgagg gagcttccag    6360
ggggaaacgc ctggtatctt tatagtcctg tcgggtttcg ccacctctga cttgagcgtc    6420
gatttttgtg atgctcgtca ggggggcgga gcctatggaa aaacgccagc aacgcggcct    6480
ttttacggtt cctggccttt tgctggcctt tgctcacat gt                       6522
```

<210> SEQ ID NO 17
<211> LENGTH: 5804
<212> TYPE: DNA
<213> ORGANISM: Artificial
<220> FEATURE:
<223> OTHER INFORMATION: Construct B
<220> FEATURE:
<221> NAME/KEY: Construct B
<222> LOCATION: (1)..(5804)

<400> SEQUENCE: 17

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca    180
tgctctagac atggctcgac agatctcaat attggccatt agccatatta ttcattggtt    240
atatagcata aatcaatatt ggctattggc cattgcatac gttgtatcta tatcataata    300
tgtacattta tattggctca tgtccaatat gaccgccatg ttggcattga ttattgacta    360
gttattaata gtaatcaatt acgggtcat tagttcatag cccatatatg gagttccgcg     420
ttacataact tacggtaaat ggcccgcctg gctgaccgcc caacgacccc cgcccattga    480
cgtcaataat gacgtatgtt cccatagtaa cgccaatagg gactttccat tgacgtcaat    540
gggtggagta tttacggtaa actgcccact tggcagtaca tcaagtgtat catatgccaa    600 gtccgcccc tattgacgtc aatgacggta aatggcccgc ctggcattat gcccagtaca     660
tgaccttacg ggactttcct acttggcagt acatctacgt attagtcatc gctattacca    720
tggtgatgcg gttttggcag tacaccaatg ggcgtggata gcggtttgac tcacggggat    780
ttccaagtct ccaccccatt gacgtcaatg ggagtttgtt ttggcaccaa aatcaacggg    840
actttccaaa atgtcgtaac aactgcgatc gcccgcccg ttgacgcaaa tgggcggtag    900
gcgtgtacgg tgggaggtct atataagcag agctcgttta gtgaaccgtc agatcactag    960
aagctttatt gcggtagttt atcacagtta aattgctaac gcagtcagtg cttctgacac   1020
```

```
aacagtctcg aacttaagct gcagtgactc tcttaaggta gccttgcaga agttggtcgt    1080
gaggcactgg gcaggtaagt atcaaggtta caagacaggt ttaaggagac caatagaaac    1140
tgggcttgtc gagacagaga agactcttgc gtttctgata ggcacctatt ggtcttactg    1200
acatccactt tgcctttctc tccacaggtg tccactccca gttcaattac agctcttaag    1260
gctagagtac ttaatacgac tcactatagg ctagcctcga gaattctgcc atggccctgt    1320
ggatgcgcct cctgcccctg ctggcgctgc tggccctctg ggacctgac ccagccgcag     1380 cctttgtgaa ccaacacctg tgcggctcag atctggtgga agctctctac ctagtgtgcg    1440
gggaacgagg cttcttctac acacccagga ccaagcggga ggcagaggac ctgcaggtgg    1500
ggcaggtgga gctgggcggg ggccctggtg caggcagcct gcagcccttg gccctggagg    1560
ggtcgcgaca aagcgtggc attgtggaac aatgctgtac cagcatctgc tccctctacc      1620
agctggagaa ctactgcaac tagacgcagc tgcaagctta tcgataccgt cgacctcgag     1680
gaattcacgc gtggtacctc tagagtcgac ccgggcggcc gcttcccttt agtgagggtt     1740
aatgcttcga gcagacatga taagatacat tgatgagttt ggacaaacca caactagaat    1800
gcagtgaaaa aaatgcttta tttgtgaaat ttgtgatgct attgctttat ttgtaaccat     1860
tataagctgc aataaacaag ttaacaacaa caattgcatt cattttatgt ttcaggttca     1920 ggggagatg tgggaggttt tttaaagcaa gtaaacctc tacaaatgtg gtaaaatccg       1980
ataagggact agagcatggc tacgtagata agtagcatgg cgggttaatc attaactaca    2040
aggaacccct agtgatggag ttggccactc cctctctgcg cgctcgctcg ctcactgagg    2100
ccgggcgacc aaaggtcgcc cgacgcccgg gctttgcccg ggcggcctca gtgagcgagc    2160
gagcgcgcca gctggcgtaa tagcgaagag gcccgcaccg atcgcccttc ccaacagttg    2220
cgcagcctga atggcgaatg gaattccaga cgattgagcg tcaaaatgta ggtatttcca    2280
tgagcgtttt tccgttgcaa tggctggcgg taatattgtt ctggatatta ccagcaaggc    2340
cgatagtttg agttcttcta ctcaggcaag tgatgttatt actaatcaaa gaagtattgc    2400
gacaacggtt aatttgcgtg atggacagac tcttttactc ggtggcctca ctgattataa    2460
aaacacttct caggattctg gcgtaccgtt cctgtctaaa atccctttaa tcggcctcct    2520
gtttagctcc cgctctgatt ctaacgagga agcacgtta tacgtgctcg tcaaagcaac    2580
catagtacgc gccctgtagc ggcgcattaa gcgcggcggg tgtggtggtt acgcgcagcg    2640
tgaccgctac acttgccagc gccctagcgc ccgctccttt cgctttcttc ccttcctttc    2700
tcgccacgtt cgccggcttt ccccgtcaag ctctaaatcg gggctccct ttagggttcc     2760 gatttagtgc tttacggcac ctcgacccca aaaaacttga ttagggtgat ggttcacgta    2820
gtgggccatc gccctgatag acggttttc gccctttgac gttggagtcc acgttcttta     2880
atagtggact cttgttccaa actggaacaa cactcaaccc tatctcggtc tattcttttg    2940
atttataagg gattttgccg atttcggcct attggttaaa aaatgagctg atttaacaaa    3000
aatttaacgc gaattttaac aaaatattaa cgtctacaat ttaaatattt gcttatacaa    3060
tcttcctgtt tttggggctt ttctgattat caaccggggt acatatgatt gacatgctag    3120
ttttacgatt accgttcatc gattctcttg tttgctccag actctcaggc aatgacctga    3180
tagcctttgt agagacctct caaaaatagc taccctctcc ggcatgaatt tatcagctag    3240
aacggttgaa tatcatattg atggtgattt gactgtctcc ggcctttctc acccgtttga    3300
atctttacct acacattact caggcattgc atttaaaata tatgagggtt ctaaaaattt    3360
```

```
ttatccttgc gttgaaataa aggcttctcc cgcaaaagta ttacagggtc ataatgtttt    3420
tggtacaacc gatttagctt tatgctctga ggctttattg cttaattttg ctaattcttt    3480
gccttgcctg tatgatttat tggatgttgg aatcgcctga tgcggtattt tctccttacg    3540
catctgtgcg gtatttcaca ccgcatatgg tgcactctca gtacaatctg ctctgatgcc    3600
gcatagttaa gccagccccg acacccgcca acacccgctg acgcgccctg acgggcttgt    3660
ctgctcccgg catccgctta cagacaagct gtgaccgtct ccgggagctg catgtgtcag    3720
aggttttcac cgtcatcacc gaaacgcgcg agacgaaagg cctcgtgat acgcctattt     3780 ttataggtta atgtcatgat aataatggtt tcttagacgt caggtggcac ttttcgggga    3840
aatgtgcgcg gaacccctat ttgtttattt ttctaaatac attcaaatat gtatccgctc    3900
atgagacaat aaccctgata aatgcttcaa taatattgaa aaaggaagag tatgagtatt    3960
caacatttcc gtgtcgccct tattcccttt tttgcggcat tttgccttcc tgttttgct     4020 cacccagaaa cgctggtgaa agtaaaagat gctgaagatc agttgggtgc acgagtgggt    4080
tacatcgaac tggatctcaa cagcggtaag atccttgaga gttttcgccc cgaagaacgt    4140
tttccaatga tgagcacttt taaagttctg ctatgtggcg cggtattatc ccgtattgac    4200
gccgggcaag agcaactcgg tcgccgcata cactattctc agaatgactt ggttgagtac    4260
tcaccagtca cagaaaagca tcttacggat ggcatgacag taagagaatt atgcagtgct    4320
gccataacca tgagtgataa cactgcggcc aacttacttc tgacaacgat cggaggaccg    4380
aaggagctaa ccgcttttt gcacaacatg ggggatcatg taactcgcct tgatcgttgg     4440
gaaccggagc tgaatgaagc cataccaaac gacgagcgtg acaccacgat gcctgtagca    4500
atggcaacaa cgttgcgcaa actattaact ggcgaactac ttactctagc ttcccggcaa    4560
caattaatag actggatgga ggcggataaa gttgcaggac cacttctgcg ctcggccctt    4620
ccggctggct ggtttattgc tgataaatct ggagccggtg agcgtgggtc tcgcggtatc    4680
attgcagcac tggggccaga tggtaagccc tcccgtatcg tagttatcta cacgacgggg    4740
agtcaggcaa ctatggatga acgaaataga cagatcgctg agataggtgc ctcactgatt    4800
aagcattggt aactgtcaga ccaagtttac tcatatatac tttagattga tttaaaactt    4860
catttttaat ttaaaaggat ctaggtgaag atcctttttg ataatctcat gaccaaaatc    4920
ccttaacgtg agttttcgtt ccactgagcg tcagaccccg tagaaaagat caaaggatct    4980
tcttgagatc ctttttttct gcgcgtaatc tgctgcttgc aaacaaaaaa accaccgcta    5040
ccagcggtgg tttgtttgcc ggatcaagag ctaccaactc tttttccgaa ggtaactggc    5100
ttcagcagag cgcagatacc aaatactgtc cttctagtgt agccgtagtt aggccaccac    5160
ttcaagaact ctgtagcacc gcctacatac ctcgctctgc taatcctgtt accagtggct    5220
gctgccagtg gcgataagtc gtgtcttacc gggttggact caagacgata gttaccggat    5280
aaggcgcagc ggtcgggctg aacggggggt tcgtgcacac agcccagctt ggagcgaacg    5340
acctacaccg aactgagata cctacagcgt gagctatgag aaagcgccac gcttcccgaa    5400
gggagaaagg cggacaggta tccggtaagc ggcagggtcg aacaggaga gcgcacgagg     5460 gagcttccag ggggaaacgc ctggtatctt tatagtcctg tcgggtttcg ccacctctga    5520
cttgagcgtc gatttttgtg atgctcgtca gggggcgga gccatggaa aaacgccagc      5580 aacgcggcct ttttacggtt cctggccttt tgctggcctt tgctcacat gttctttcct     5640 gcgttatccc ctgattctgt ggataaccgt attaccgcct tgagtgagc tgataccgct     5700 cgccgcagcc gaacgaccga gcgcagcgag tcagtgagcg aggaagcgga agagcgccca    5760
```

<210> SEQ ID NO 18
<211> LENGTH: 6722
<212> TYPE: DNA
<213> ORGANISM: Artificial
<220> FEATURE:
<223> OTHER INFORMATION: Construct C
<220> FEATURE:
<221> NAME/KEY: Construct C
<222> LOCATION: (1)..(6722)

<400> SEQUENCE: 18

```
                                                                      atacgcaaac cgcctctccc cgcgcgttgg ccgattcatt aatg          5804 gtagataagt agcatggcgg gttaatcatt aactacaagg aacccctagt gatggagttg      60
gccactccct ctctgcgcgc tcgctcgctc actgaggccg ggcgaccaaa ggtcgcccga     120
cgcccgggct ttgcccgggc ggcctcagtg agcgagcgag cgcgccagct ggcgtaatag     180
cgaagaggcc cgcaccgatc gcccttccca cagttgcgc agcctgaatg gcgaatggaa      240
ttccagacga ttgagcgtca aaatgtaggt atttccatga gcgttttcc gttgcaatgg      300
ctggcggtaa tattgttctg gatattacca gcaaggccga tagtttgagt tcttctactc     360
aggcaagtga tgttattact aatcaaagaa gtattgcgca acggttaat ttgcgtgatg      420
gacagactct tttactcggt ggcctcactg attataaaaa cacttctcag gattctggcg     480
taccgttcct gtctaaaatc cctttaatcg gcctcctgtt tagctcccgc tctgattcta     540
acgaggaaag cacgttatac gtgctcgtca agcaaccat agtacgcgcc ctgtagcggc      600
gcattaagcg cggcgggtgt ggtggttacg cgcagcgtga ccgctacact tgccagcgcc     660
ctagcgcccg ctcctttcgc tttcttccct tcctttctcg ccacgttcgc cggctttccc     720
cgtcaagctc taaatcgggg gctcccttta gggttccgat ttagtgcttt acggcacctc     780
gaccccaaaa aacttgatta gggtgatggt tcacgtagtg ggccatcgcc ctgatagacg     840
gttttttcgcc ctttgacgtt ggagtccacg ttctttaata gtggactctt gttccaaact    900
ggaacaacac tcaaccctat ctcggtctat tcttttgatt tataagggat tttgccgatt     960
tcggcctatt ggttaaaaaa tgagctgatt taacaaaaat ttaacgcgaa ttttaacaaa    1020
atattaacgt ctacaatttta aatatttgct tatacaatct tcctgttttt ggggcttttc    1080
tgattatcaa ccggggtaca tatgattgac atgctagttt tacgattacc gttcatcgat    1140
tctcttgttt gctccagact ctcaggcaat gacctgatag cctttgtaga gacctctcaa    1200
aaatagctac cctctccggc atgaatttat cagctagaac ggttgaatat catattgatg    1260
gtgatttgac tgtctccggc ctttctcacc cgtttgaatc tttacctaca cattactcag    1320
gcattgcatt taaaatatat gagggttcta aaaattttta tccttgcgtt gaataaaagg    1380
cttctcccgc aaaagtatta cagggtcata atgtttttgg tacaaccgat ttagctttat    1440
gctctgaggc tttattgctt aattttgcta attctttgcc ttgcctgtat gatttattgg    1500
atgttggaat cgcctgatgc ggtatttttct ccttacgcat ctgtgcggta tttcacaccg    1560
catatggtgc actctcagta caatctgctc tgatgccgca tagttaagcc agccccgaca    1620
cccgccaaca cccgctgacg cgccctgacg ggcttgtctg ctcccggcat ccgcttacag    1680
acaagctgtg accgtctccg ggagctgcat gtgtcagagg ttttcaccgt catcaccgaa    1740
acgcgcgaga cgaaagggcc tcgtgatacg cctatttta taggttaatg tcatgataat    1800
aatggtttct tagacgtcag gtggcacttt tcggggaaat gtgcgcggaa ccccatttg     1860
tttattttc taaatacatt caaatatgta tccgctcatg agacaataac cctgataaat    1920
```

```
gcttcaataa tattgaaaaa ggaagagtat gagtattcaa catttccgtg tcgcccttat    1980
tccctttttt gcggcatttt gccttcctgt ttttgctcac ccagaaacgc tggtgaaagt    2040
aaaagatgct gaagatcagt tgggtgcacg agtgggttac atcgaactgg atctcaacag    2100
cggtaagatc cttgagagtt ttcgccccga gaacgttttt ccaatgatga gcacttttaa    2160
agttctgcta tgtggcgcgg tattatcccg tattgacgcc gggcaagagc aactcggtcg    2220
ccgcatacac tattctcaga atgacttggt tgagtactca ccagtcacag aaagcatct    2280 tacggatggc atgacagtaa gagaattatg cagtgctgcc ataaccatga gtgataacac    2340
tgcggccaac ttacttctga caacgatcgg aggaccgaag gagctaaccg cttttttgca    2400
caacatgggg gatcatgtaa ctcgccttga tcgttgggaa ccggagctga atgaagccat    2460
accaaacgac gagcgtgaca ccacgatgcc tgtagcaatg gcaacaacgt tgcgcaaact    2520
attaactggc gaactactta ctctagcttc ccggcaacaa ttaatagact ggatggaggc    2580
ggataaagtt gcaggaccac ttctgcgctc ggcccttccg gctggctggt ttattgctga    2640
taaatctgga gccggtgagc gtgggtctcg cggtatcatt gcagcactgg ggccagatgg    2700
taagccctcc cgtatcgtag ttatctacac gacggggagt caggcaacta tggatgaacg    2760
aaatagacag atcgctgaga taggtgcctc actgattaag cattggtaac tgtcagacca    2820
agtttactca tatatacttt agattgattt aaaacttcat ttttaattta aaaggatcta    2880
ggtgaagatc cttttgata atctcatgac caaaatccct taacgtgagt tttcgttcca    2940
ctgagcgtca gacccgtag aaaagatcaa aggatcttct tgagatcctt ttttctgcg    3000 cgtaatctgc tgcttgcaaa caaaaaaacc accgctacca gcggtggttt gtttgccgga    3060
tcaagagcta ccaactcttt ttccgaaggt aactggcttc agcagagcgc agataccaaa    3120
tactgtcctt ctagtgtagc cgtagttagg ccaccacttc aagaactctg tagcaccgcc    3180
tacatacctc gctctgctaa tcctgttacc agtggctgct gccagtggcg ataagtcgtg    3240
tcttaccggg ttggactcaa gacgatagtt accggataag gcgcagcggt cgggctgaac    3300
ggggggttcg tgcacacagc ccagcttgga gcgaacgacc tacaccgaac tgagatacct    3360
acagcgtgag ctatgagaaa gcgccacgct tcccgaaggg agaaaggcgg acaggtatcc    3420
ggtaagcggc agggtcggaa caggagagcg cacgagggag cttccagggg gaaacgcctg    3480
gtatctttat agtcctgtcg ggtttcgcca cctctgactt gagcgtcgat ttttgtgatg    3540
ctcgtcaggg gggcggagcc tatggaaaaa cgccagcaac gcggcctttt tacggttcct    3600
ggccttttgc tggccttttg ctcacatgtt ctttcctgcg ttatcccctg attctgtgga    3660
taaccgtatt accgcctttg agtgagctga taccgctcgc cgcagccgaa cgaccgagcg    3720
cagcgagtca gtgagcgagg aagcggaaga gcgcccaata cgcaaaccgc ctctccccgc    3780
gcgttggccg attcattaat gcagcagctg gcgctcgct cgctcactga ggccgcccgg    3840
gcaaagcccg ggcgtcgggc gacctttggt cgcccggcct cagtgagcga gcgagcgcgc    3900
agagagggag tggccaactc catcactagg ggttccttgt agttaatgat taacccgcca    3960
tgctacttat ctacgtagcc atgctctgga agatctcgac gcgtcatgtt tgacagctta    4020
tcatcgcaga tccgtatggt gcactctcag tacaatctgc tctgatgccg catagttaag    4080
ccagtatctg ctccctgctt gtgtgttgga ggtcgctgag tagtgcgcga gcaaaattta    4140
agctacaaca aggcaaggct tgaccgacaa ttgcatgaag aatctgctta gggttaggcg    4200
ttttgcgctg cttcgcgatg tacgggccag atattcgcgt atctgagggg actagggtgt    4260
```

```
gtttaggcga aaagcggggc ttcggttgta cgcggttagg agtcccctca ggatatagta   4320
gtttcgcttt tgcataggga gggggaaatg tagtcttatg caatactctt gtagtcttgc   4380
aacatggtaa cgatgagtta gcaacatgcc ttacaaggag agaaaaagca ccgtgcatgc   4440
cgattggtgg aagtaaggtg gtacgatcgt gccttattag gaaggcaaca gacgggtctg   4500
acatggattg gacgaaccac taaattccgc attgcagaga tattgtattt aagtgcctag   4560
ctcgatacaa taaacgccat ttgaccattc accacattgg tgtgcacctc caagctgggt   4620
accagctgct agcaagcttg agatctgctt cagctggagg cactgggcag gtaagtatca   4680
aggttacaag acaggtttaa ggagaccaat agaaactggg cttgtcgaga cagagaagac   4740
tcttgcgttt ctgataggca cctattggtc ttactgacat ccactttgcc tttctctcca   4800
caggtgcagc tgctgcagcg ggaattcaac aggtggcctc aggagtcagg aacatctcta   4860
cttccccaac gacccctggg ttgtcctctc agagatggct atggatacta caaggtgtgg   4920
agcccagttg ttgactctgg tcgagcagat cctggcagag ttccagctgc aggaggaaga   4980
cctgaagaag gtgatgagcc ggatgcagaa ggagatggac cgtggcctga gctgggagac   5040
ccacgaggag gccagtgtaa agatgttacc cacctacgtg cgttccaccc cagaaggctc   5100
agaagtcgga gactttctct ccttagacct gggaggaacc aacttcagag tgatgctggt   5160
caaagtggga gaggggagg cagggcagtg gagcgtgaag acaaaacacc agatgtactc   5220
catccccgag gacgccatga cgggcactgc cgagatgctc tttgactaca tctctgaatg   5280
catctctgac ttccttgaca agcatcagat gaagcacaag aaactgcccc tgggcttcac   5340
cttctccttc cctgtgaggc acgaagacct agacaagggc atcctcctca attggaccaa   5400
gggcttcaag gcctctggag cagaagggaa caacatcgta ggacttctcc gagatgctat   5460
caagaggaga gggacttttg agatggatgt ggtggcaatg gtgaacgaca cagtggccac   5520
aatgatctcc tgctactatg aagaccgcca atgtgaggtc ggcatgattg tgggcactgg   5580
ctgcaatgcc tgctacatgg aggaaatgca gaatgtggag ctggtggaag gggatgaggg   5640
acgcatgtgc gtcaacacgg agtggggcgc cttcgggac tcgggcgagc tggatgagtt   5700
cctactggag tatgaccgga tggtggatga aagctcagcg aaccccggtc agcagctgta   5760
cgagaagatc atcggtggga agtatatggg cgagctggta cgacttgtgc tgcttaagct   5820
ggtggacgag aaccttctgt tccacggaga ggcctcggag cagctgcgca cgcgtggtgc   5880
ttttgagacc cgtttcgtgt cacaagtgga gagcgactcc ggggaccgaa agcagatcca   5940
caacatccta agcactctgg ggcttcgacc ctctgtcacc gactgcgaca ttgtgcgccg   6000
tgcctgtgaa agcgtgtcca ctcgcgccgc ccatatgtgc tccgcaggac tagctggggt   6060
cataaatcgc atgcgcgaaa gccgcagtga ggacgtgatg cgcatcactg tgggcgtgga   6120
tggctccgtg tacaagctgc acccgagctt caaggagcgg tttcacgcca gtgtgcgcag   6180
gctgacaccc aactgcgaaa tcaccttcat cgaatcagag gagggcagcg caggggagc   6240
cgcactggtc tctgcggtgg cctgcaagaa ggcttgcatg ctggcccagt gaaatccagg   6300
tcatatggac cgggacctgg gttccacggg gactccacac accacaaatg ctcccagccc   6360
accggggcag gagacctatt ctgctgctac ccctggaaaa tggggagagg ccctgcaag   6420
ccgagtcggc cagtgggaca gccctaggct ggatcggccg cttcgagcag acatgataag   6480
atacattgat gagtttggac aaaccacaac tagaatgcag tgaaaaaaat gctttatttg   6540
tgaaatttgt gatgctattg ctttatttgt aaccattata agctgcaata aacaagttaa   6600
caacaacaat tgcattcatt ttatgtttca ggttcagggg gagatgtggg aggttttta   6660
```

-continued

```
aagcaagtaa aacctctaca aatgtggtaa aatcgattag gatcttccta gagcatggct    6720
ac                                                                   6722
```

<210> SEQ ID NO 19
<211> LENGTH: 4755
<212> TYPE: DNA
<213> ORGANISM: Artificial
<220> FEATURE:
<223> OTHER INFORMATION: Construct H
<220> FEATURE:
<221> NAME/KEY: Construct H
<222> LOCATION: (1)..(4755)

<400> SEQUENCE: 19

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgcg atatctgtag ttaatgatta acccgccatg     180
ctacttatct acagatctca atattggcca ttagccatat tattcattgg ttatatagca     240
taaatcaata ttggctattg gccattgcat acgttgtatc tatatcataa tatgtacatt     300
tatattggct catgtccaat atgaccgcca tgttggcatt gattattgac tagttattaa     360
tagtaatcaa ttacggggtc attagttcat agcccatata tggagttccg cgttacataa     420
cttacggtaa atggcccgcc tggctgaccg cccaacgacc cccgcccatt gacgtcaata     480
atgacgtatg ttcccatagt aacgccaata gggactttcc attgacgtca atgggtggag     540
tatttacggt aaactgccca cttggcagta catcaagtgt atcatatgcc aagtccgccc     600
cctattgacg tcaatgacgg taaatggccc gcctggcatt atgcccagta catgacctta     660
cgggactttc ctacttggca gtacatctac gtattagtca tcgctattac catggtgatg     720
cggttttggc agtacaccaa tgggcgtgga tagcggtttg actcacgggg atttccaagt     780 ctccaccccca ttgacgtcaa tgggagtttg ttttggcacc aaaatcaacg ggactttcca     840
aaatgtcgta acaactgcga tcgccgccc cgttgacgca aatgggcggt aggcgtgtac     900
ggtgggaggt ctatataagc agagctcgtt tagtgaaccg tcagatcact aggctagcta     960
ttgcggtagt ttatcacagt taaattgcta acgcagtcag tgcttctgac acaacagtct    1020
cgaacttaag ctgcagtgac tctcttaagg tagccttgca gaagttggtc gtgaggcact    1080
gggcaggtaa gtatcaaggt tacaagacag gtttaaggag accaatagaa actgggcttg    1140
tcgagacaga gaagactctt gcgtttctga taggcaccta ttggtcttac tgacatccac    1200
tttgcctttc tctccacagg tgtccactcc cagttcaatt acagctctta aggctagagt    1260
acttaatacg actcactata gaatacgact cactataggg agacgctagc gtcgaccttc    1320
tgccatggcc ctgtggatgc gcctcctgcc cctgctggcg ctgctggccc tctggggacc    1380
tgacccagcc gcagcctttg tgaaccaaca cctgtgcggc tcagatctgg tggaagctct    1440
ctacctagtg tgcggggaac gaggcttctt ctacacaccc aggaccaagc gggaggcaga    1500
ggacctgcag gtggggcagg tggagctggg cggggccct ggtgcaggca gcctgcagcc    1560
cttggccctg gagggtcgc gacagaagcg tggcattgtg gaacaatgct gtaccagcat    1620
ctgctccctc taccagctgg agaactactg caactagacg cagccgtcga cggtaccagc    1680
gctgtcgagg ccgcttcgag cagacatgat aagatacatt gatgagtttg gacaaaccac    1740
aactagaatg cagtgaaaaa aatgctttat ttgtgaaatt tgtgatgcta ttgctttatt    1800
tgtaaccatt ataagctgca ataaacaagt taacaacaac aattgcattc attttatgtt    1860
```

-continued

```
tcaggttcag ggggagatgt gggaggtttt ttaaagcaag taaaacctct acaaatgtgg   1920
taaaatcgat taggatcttc ctagagcatg gctacctaga catggctcga cagatcagcg   1980
ctcatgctct ggaagatctc gatttaaatg cggccgcagg aacccctagt gatggagttg   2040
gccactccct ctctgcgcgc tcgctcgctc actgaggccg ggcgaccaaa ggtcgcccga   2100
cgcccgggct tgcccgggc ggcctcagtg agcgagcgag cgcgcagctg cctgcagggg   2160
cgcctgatgc ggtattttct ccttacgcat ctgtgcggta tttcacaccg catacgtcaa   2220
agcaaccata gtacgcgccc tgtagcggcg cattaagcgc ggcgggtgtg gtggttacgc   2280
gcagcgtgac cgctacactt gccagcgccc tagcgcccgc tcctttcgct ttcttccctt   2340
cctttctcgc cacgttcgcc ggctttcccc gtcaagctct aaatcggggg ctccctttag   2400
ggttccgatt tagtgcttta cggcacctcg accccaaaaa acttgatttg ggtgatggtt   2460
cacgtagtgg gccatcgccc tgatagacgg ttttttcgcc tttgacgttg gagtccacgt   2520
tctttaatag tggactcttg ttccaaactg gaacaacact caaccctatc tcgggctatt   2580
cttttgattt ataagggatt ttgccgattt cggcctattg gttaaaaaat gagctgattt   2640
aacaaaaatt taacgcgaat tttaacaaaa tattaacgtt tacaattttta tggtgcactc   2700 tcagtacaat ctgctctgat gccgcatagt taagccagcc ccgacacccg ccaacacccg   2760
ctgacgcgcc ctgacgggct tgtctgctcc cggcatccgc ttacagacaa gctgtgaccg   2820
tctccgggag ctgcatgtgt cagaggtttt caccgtcatc accgaaacgc gcgagacgaa   2880
agggcctcgt gatacgccta ttttttatagg ttaatgtcat gataataatg gtttcttaga   2940
cgtcaggtgg cacttttcgg ggaaatgtgc gcggaacccc tatttgtttta ttttttctaaa   3000 tacattcaaa tatgtatccg ctcatgagac aataaccctg ataaatgctt caataatatt   3060
gaaaaaggaa gagtatgagt attcaacatt tccgtgtcgc ccttattccc ttttttgcgg   3120
cattttgcct tcctgttttt gctcacccag aaacgctggt gaaagtaaaa gatgctgaag   3180
atcagttggg tgcacgagtg ggttacatcg aactggatct caacagcggt aagatccttg   3240
agagttttcg ccccgaagaa cgttttccaa tgatgagcac ttttaaagtt ctgctatgtg   3300
gcgcggtatt atcccgtatt gacgccgggc aagagcaact cggtcgccgc atacactatt   3360
ctcagaatga cttggttgag tactcaccag tcacagaaaa gcatcttacg gatggcatga   3420
cagtaagaga attatgcagt gctgccataa ccatgagtga taacactgcg gccaacttac   3480
ttctgacaac gatcggagga ccgaaggagc taaccgcttt tttgcacaac atgggggatc   3540
atgtaactcg ccttgatcgt tgggaaccgg agctgaatga agccatacca aacgacgagc   3600
gtgacaccac gatgcctgta gcaatggcaa caacgttgcg caaactatta actggcgaac   3660
tacttactct agcttcccgg caacaattaa tagactggat ggaggcggat aaagttgcag   3720
gaccacttct gcgctcggcc cttccggctg gctggtttat tgctgataaa tctggagccg   3780
gtgagcgtgg gtctcgcggt atcattgcag cactggggcc agatggtaag ccctcccgta   3840
tcgtagttat ctacacgacg gggagtcagg caactatgga tgaacgaaat agacagatcg   3900
ctgagatagg tgcctcactg attaagcatt ggtaactgtc agaccaagtt tactcatata   3960
tactttagat tgatttaaaa cttcattttt aatttaaaag gatctaggtg aagatccttt   4020
ttgataatct catgaccaaa atcccttaac gtgagttttc gttccactga gcgtcagacc   4080
ccgtagaaaa gatcaaagga tcttcttgag atcctttttt tctgcgcgta atctgctgct   4140
tgcaaacaaa aaaaccaccg ctaccagcgg tggtttgttt gccggatcaa gagctaccaa   4200
```

| | |
|---|---|
| ctcttttcc gaaggtaact ggcttcagca gagcgcagat accaaatact gtccttctag | 4260 |
| tgtagccgta gttaggccac cacttcaaga actctgtagc accgcctaca tacctcgctc | 4320 |
| tgctaatcct gttaccagtg gctgctgcca gtggcgataa gtcgtgtctt accgggttgg | 4380 |
| actcaagacg atagttaccg gataaggcgc agcggtcggg ctgaacgggg ggttcgtgca | 4440 |
| cacagcccag cttggagcga acgacctaca ccgaactgag atacctacag cgtgagctat | 4500 |
| gagaaagcgc cacgcttccc gaagggagaa aggcggacag gtatccggta agcggcaggg | 4560 |
| tcggaacagg agagcgcacg agggagcttc caggggggaaa cgcctggtat ctttatagtc | 4620 |
| ctgtcgggtt tcgccacctc tgacttgagc gtcgattttt gtgatgctcg tcagggggggc | 4680 |
| ggagcctatg gaaaaacgcc agcaacgcgg cctttttacg gttcctggcc ttttgctggc | 4740 |
| cttttgctca catgt | 4755 |

<210> SEQ ID NO 20
<211> LENGTH: 5417
<212> TYPE: DNA
<213> ORGANISM: Artificial
<220> FEATURE:
<223> OTHER INFORMATION: Construct I
<220> FEATURE:
<221> NAME/KEY: Construct I
<222> LOCATION: (1)..(5407)

<400> SEQUENCE: 20

| | |
|---|---|
| artcaartca cctgcaggca gctgcgcgct cgctcgctca ctgaggccgc ccgggcaaag | 60 |
| cccgggcgtc gggcgacctt tggtcgcccg gcctcagtga gcgagcgagc gcgcagagag | 120 |
| ggagtggcca actccatcac tagggggttcc tgcggccgcg atatccatgt ttgacagctt | 180 |
| atcatcgcag atccgtatgg tgcactctca gtacaatctg ctctgatgcc gcatagttaa | 240 |
| gccagtatct gctccctgct tgtgtgttgg aggtcgctga gtagtgcgcg agcaaaattt | 300 |
| aagctacaac aaggcaaggc ttgaccgaca attgcatgaa gaatctgctt agggttaggc | 360 |
| gttttgcgct gcttcgcgat gtacgggcca gatattcgcg tatctgaggg gactagggtg | 420 |
| tgtttaggcg aaaagcgggg cttcggttgt acgcggttag gagtcccctc aggatatagt | 480 |
| agtttcgctt ttgcataggg aggggggaaat gtagtcttat gcaatactct tgtagtcttg | 540 |
| caacatggta acgatgagtt agcaacatgc cttacaagga gagaaaaagc accgtgcatg | 600 |
| ccgattggtg gaagtaaggt ggtacgatcg tgccttatta ggaaggcaac agacgggtct | 660 |
| gacatggatt ggacgaacca ctaaattccg cattgcagag atattgtatt taagtgccta | 720 |
| gctcgataca ataaacgcca tttgaccatt caccacattg gtgtgcacct ccaagctggg | 780 |
| taccagcttc tagagagatc tgcttcagct ggaggcactg ggcaggtaag tatcaaggtt | 840 |
| acaagacagg tttaaggaga ccaatagaaa ctgggcttgt cgagacagag aagactcttg | 900 |
| cgtttctgat aggcacctat tggtcttact gacatccact ttgccttttct ctccacaggt | 960 |
| gcagctgctg cagcggtcta gaactcgagt cgagaccatg gcgatggatg tcacaaggag | 1020 |
| ccaggcccag acagccttga ctctggtaga gcagatcctg gcagagttcc agctgcagga | 1080 |
| ggaggacctg aagaaggtga tgagacggat gcagaaggag atggaccgcg gcctgaggct | 1140 |
| ggagacccat gaagaggcca gtgtgaagat gctgcccacc tacgtgcgct ccaccccaga | 1200 |
| aggctcagaa gtcggggact tcctctccct ggacctgggt ggcactaact tcagggtgat | 1260 |
| gctggtgaag gtgggagaag gtgaggaggg gcagtggagc gtgaagacca aacaccagat | 1320 |
| gtactccatc cccgaggacg ccatgaccgg cactgctgag atgctcttcg actacatctc | 1380 |

```
tgagtgcatc tccgacttcc tggacaagca tcagatgaaa cacaagaagc tgcccctggg    1440
cttcaccttc tcctttcctg tgaggcacga agacatcgat aagggcatcc ttctcaactg    1500
gaccaagggc ttcaaggcct caggagcaga agggaacaat gtcgtggggc ttctgcgaga    1560
cgctatcaaa cggagagggg actttgaaat ggatgtggtg caatggtgga atgacacggt    1620
ggccacgatg atctcctgct actacgaaga ccatcagtgc gaggtcggca tgatcgtggg    1680
cacgggctgc aatgcctgct acatggagga gatgcagaat gtggagctgg tggaggggga    1740
cgagggccgc atgtgcgtca ataccgagtg gggcgccttc ggggactccg gcgagctgga    1800
cgagttcctg ctggagtatg accgcctggt ggacgagagc tctgcaaacc ccggtcagca    1860
gctgtatgag aagctcatag gtggcaagta catgggcgag ctggtgcggc ttgtgctgct    1920
caggctcgtg gacgaaaacc tgctcttcca cggggaggcc tccgagcagc tgcgcacacg    1980
cggagccttc gagacgcgct tcgtgtcgca ggtggagagc gacacgggcg accgcaagca    2040
gatctacaac atcctgagca cgctggggct gcgacccgtcg accaccgact gcgacatcgt    2100
gcgccgcgcc tgcgagagcg tgtctacgcg cgctgcgcac atgtgctcgg cggggctggc    2160
gggcgtcatc aaccgcatgc gcgagagccg cagcgaggac gtaatgcgca tcactgtggg    2220
cgtggatggc tccgtgtaca agctgcaccc cagcttcaag gagcggttcc atgccagcgt    2280
gcgcaggctg acgcccagct gcgagatcac cttcatcgag tcggaggagg gcagtggccg    2340
gggcgcggcc ctggtctcgg cggtggcctg taagaaggcc tgtatgctgg gccagtgact    2400
cgagcacgtg gagctcgctg atcagcctcg actgtgcctt ctagttgcca gccatctgtt    2460
gtttgcccct ccccgtgcc ttccttgacc ctggaaggtg ccactcccac tgtcctttcc    2520
taataaaatg aggaaattgc atcgcattgt ctgagtaggt gtcattctat tctgggggt    2580 ggggtggggc aggacagcaa gggggaggat tgggaagaca atagcaggca tgctggggat    2640
gcggtgggct ctatggccac gtgatttaaa tgcggccgca ggaacccta gtgatggagt    2700 tggccactcc ctctctgcgc gctcgctcgc tcactgaggc cgggcgacca aaggtcgccc    2760
gacgcccggg cttttgcccgg gcggcctcag tgagcgagcg agcgcgcagc tgcctgcagg    2820
ggcgcctgat gcggtatttt ctccttacgc atctgtgcgg tatttcacac cgcatacgtc    2880
aaagcaacca tagtacgcgc cctgtagcgg cgcattaagc gcggcgggtg tggtggttac    2940
gcgcagcgtg accgctacac ttgccagcgc cctagcgccc gctcctttcg ctttcttccc    3000
ttcctttctc gccacgttcg ccggctttcc ccgtcaagct ctaaatcggg ggctcccttt    3060
agggttccga tttagtgctt tacggcacct cgaccccaaa aaacttgatt tgggtgatgg    3120
ttcacgtagt gggccatcgc cctgatagac ggtttttcgc cctttgacgt tggagtccac    3180
gttctttaat agtggactct tgttccaaac tggaacaaca ctcaaccta tctcgggcta    3240 ttcttttgat ttataaggga ttttgccgat ttcggcctat tggttaaaaa atgagctgat    3300
ttaacaaaaa tttaacgcga attttaacaa aatattaacg tttacaattt tatggtgcac    3360
tctcagtaca atctgctctg atgccgcata gttaagccag ccccgacacc cgccaacacc    3420
cgctgacgcg ccctgacggg cttgtctgct cccggcatcc gcttacagac aagctgtgac    3480
cgtctccggg agctgcatgt gtcagaggtt ttcaccgtca tcaccgaaac gcgcgagacg    3540
aaagggcctc gtgatacgcc tatttttata ggttaatgtc atgataataa tggtttctta    3600
gacgtcaggt ggcacttttc ggggaaatgt gcgcggaacc cctatttgtt tatttttcta    3660
aatacattca aatatgtatc cgctcatgag acaataaccc tgataaatgc ttcaataata    3720
ttgaaaaagg aagagtatga gtattcaaca tttccgtgtc gcccttattc cctttttgc     3780
```

-continued

| | |
|---|---|
| ggcattttgc cttcctgttt ttgctcaccc agaaacgctg gtgaaagtaa aagatgctga | 3840 |
| agatcagttg ggtgcacgag tgggttacat cgaactggat ctcaacagcg gtaagatcct | 3900 |
| tgagagtttt cgccccgaag aacgttttcc aatgatgagc acttttaaag ttctgctatg | 3960 |
| tggcgcggta ttatcccgta ttgacgccgg gcaagagcaa ctcggtcgcc gcatacacta | 4020 |
| ttctcagaat gacttggttg agtactcacc agtcacagaa aagcatctta cggatggcat | 4080 |
| gacagtaaga gaattatgca gtgctgccat aaccatgagt gataacactg cggccaactt | 4140 |
| acttctgaca acgatcggag gaccgaagga gctaaccgct tttttgcaca acatggggga | 4200 |
| tcatgtaact cgccttgatc gttgggaacc ggagctgaat gaagccatac caaacgacga | 4260 |
| gcgtgacacc acgatgcctg tagcaatggc aacaacgttg cgcaaactat taactggcga | 4320 |
| actacttact ctagcttccc ggcaacaatt aatagactgg atggaggcgg ataaagttgc | 4380 |
| aggaccactt ctgcgctcgg cccttccggc tggctggttt attgctgata aatctggagc | 4440 |
| cggtgagcgt gggtctcgcg gtatcattgc agcactgggg ccagatggta agccctcccg | 4500 |
| tatcgtagtt atctacacga cggggagtca ggcaactatg gatgaacgaa atagacagat | 4560 |
| cgctgagata ggtgcctcac tgattaagca ttggtaactg tcagaccaag tttactcata | 4620 |
| tatactttag attgatttaa aacttcattt ttaatttaaa aggatctagg tgaagatcct | 4680 |
| ttttgataat ctcatgacca aaatccctta acgtgagttt cgttccact gagcgtcaga | 4740 |
| ccccgtagaa aagatcaaag gatcttcttg agatcctttt tttctgcgcg taatctgctg | 4800 |
| cttgcaaaca aaaaaaccac cgctaccagc ggtggtttgt ttgccggatc aagagctacc | 4860 |
| aactcttttt ccgaaggtaa ctggcttcag cagagcgcag ataccaaata ctgtccttct | 4920 |
| agtgtagccg tagttaggcc accacttcaa gaactctgta gcaccgccta catacctcgc | 4980 |
| tctgctaatc ctgttaccag tggctgctgc cagtggcgat aagtcgtgtc ttaccgggtt | 5040 |
| ggactcaaga cgatagttac cggataaggc gcagcggtcg ggctgaacgg ggggttcgtg | 5100 |
| cacacagccc agcttggagc gaacgaccta caccgaactg agatacctac agcgtgagct | 5160 |
| atgagaaagc gccacgcttc ccgaagggag aaaggcggac aggtatccgg taagcggcag | 5220 |
| ggtcggaaca ggagagcgca cgagggagct tccaggggga aacgcctggt atctttatag | 5280 |
| tcctgtcggg tttcgccacc tctgacttga gcgtcgattt ttgtgatgct cgtcaggggg | 5340 |
| gcggagccta tggaaaaacg ccagcaacgc ggcctttta cggttcctgg ccttttgctg | 5400 |
| gccttttgct cacatgt | 5417 |

<210> SEQ ID NO 21
<211> LENGTH: 4017
<212> TYPE: DNA
<213> ORGANISM: Artificial
<220> FEATURE:
<223> OTHER INFORMATION: Construct N
<220> FEATURE:
<221> NAME/KEY: Construct N
<222> LOCATION: (1)..(4017)

<400> SEQUENCE: 21

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgcg atatctatgc caagtacgcc ccctattgac | 180 |
| gtcaatgacg gtaaatggcc cgcctggcat tatgcccagt acatgacctt atgggacttt | 240 |
| cctacttggc agtacatcta cgtattagtc atcgctatta ccatggtgat gcggttttgg | 300 |

-continued

```
cagtacatca atgggcgtgg atagcggttt gactcacggg gatttccaag tctccacccc      360
attgacgtca atgggagttt gttttggcac caaaatcaac gggactttcc aaaatgtcgt      420
aacaactccg ccccattgac gcaaatgggc ggtaggcgtg tacggtggga ggtctatata      480
agcagagctc tctggctaac tagagaaccc actgcttaac tggcttatcg aaattaatac      540
gactcactat agggagaccc aagcttgcta gcgtcgacct tctgccatgg ccctgtggat      600
gcgcctcctg cccctgctgg cgctgctggc cctctgggga cctgacccag ccgcagcctt      660
tgtgaaccaa cacctgtgcg gctcagatct ggtggaagct ctctacctag tgtgcgggga      720
acgaggcttc ttctacacac ccaggaccaa gcgggaggca gaggacctgc aggtggggca      780
ggtggagctg ggcgggggcc ctggtgcagg cagcctgcag cccttggccc tggaggggtc      840
gcgacagaag cgtggcattg tggaacaatg ctgtaccagc atctgctccc tctaccagct      900
ggagaactac tgcaactaga cgcagccgtc gacggtacca gcgctgtcga ggccgcttcg      960
agcagacatg ataagataca ttgatgagtt tggacaaacc acaactagaa tgcagtgaaa     1020
aaaatgcttt atttgtgaaa tttgtgatgc tattgcttta tttgtaacca ttataagctg     1080
caataaacaa gttaacaaca acaattgcat tcattttatg tttcaggttc agggggagat     1140
gtgggaggtt ttttaaagca agtaaaacct ctacaaatgt ggtaaaatcg attaggatct     1200
tcctagagca tggctaccta gacatggctc gacagatcag cgctcatgct ctggaagatc     1260
tcgatttaaa tgcggccgca ggaacccta gtgatggagt tggccactcc ctctctgcgc     1320
gctcgctcgc tcactgaggc cgggcgacca aggtcgccc gacgcccggg ctttgccegg     1380
gcggcctcag tgagcgagcg agcgcgcagc tgcctgcagg ggcgcctgat gcggtatttt     1440
ctccttacgc atctgtgcgg tatttcacac cgcatacgtc aaagcaacca tagtacgcgc     1500
cctgtagcgg cgcattaagc gcggcgggtg tggtggttac gcgcagcgtg accgctacac     1560
ttgccagcgc cctagcgccc gctcctttcg ctttcttccc ttcctttctc gccacgttcg     1620
ccggctttcc ccgtcaagct ctaaatcggg ggctcccttt agggttccga tttagtgctt     1680
tacggcacct cgaccccaaa aaacttgatt tgggtgatgg ttcacgtagt gggccatcgc     1740
cctgatagac ggtttttcgc cctttgacgt tggagtccac gttctttaat agtggactct     1800
tgttccaaac tggaacaaca ctcaacccta tctcgggcta ttcttttgat ttataaggga     1860
ttttgccgat ttcggcctat tggttaaaaa atgagctgat ttaacaaaaa tttaacgcga     1920
attttaacaa aatattaacg tttacaattt tatggtgcac tctcagtaca atctgctctg     1980
atgccgcata gttaagccag ccccgacacc cgccaacacc cgctgacgcg ccctgacggg     2040
cttgtctgct cccggcatcc gcttacagac aagctgtgac cgtctccggg agctgcatgt     2100
gtcagaggtt ttcaccgtca tcaccgaaac gcgcgagacg aaagggcctc gtgatacgcc     2160
tatttttata ggttaatgtc atgataataa tggtttctta gacgtcaggt ggcacttttc     2220
ggggaaatgt gcgcggaacc cctatttgtt tatttttcta aatacattca aatatgtatc     2280
cgctcatgag acaataaccc tgataaatgc ttcaataata ttgaaaaagg aagagtatga     2340
gtattcaaca tttccgtgtc gcccttattc ccttttttgc ggcattttgc cttcctgttt     2400
ttgctcaccc agaaacgctg gtgaaagtaa aagatgctga agatcagttg ggtgcacgag     2460
tgggttacat cgaactggat ctcaacagcg gtaagatcct tgagagtttt cgccccgaag     2520
aacgttttcc aatgatgagc acttttaaag ttctgctatg tggcgcggta ttatcccgta     2580
ttgacgccgg gcaagagcaa ctcggtcgcc gcatacacta ttctcagaat gacttggttg     2640
```

```
agtactcacc agtcacagaa aagcatctta cggatggcat gacagtaaga gaattatgca    2700
gtgctgccat aaccatgagt gataacactg cggccaactt acttctgaca acgatcggag    2760
gaccgaagga gctaaccgct tttttgcaca acatggggga tcatgtaact cgccttgatc    2820
gttgggaacc ggagctgaat gaagccatac caaacgacga gcgtgacacc acgatgcctg    2880
tagcaatggc aacaacgttg cgcaaactat taactggcga actacttact ctagcttccc    2940
ggcaacaatt aatagactgg atggaggcgg ataaagttgc aggaccactt ctgcgctcgg    3000
cccttccggc tggctggttt attgctgata atctggagcc cggtgagcgt gggtctcgcg    3060
gtatcattgc agcactgggg ccagatggta agccctcccg tatcgtagtt atctacacga    3120
cggggagtca ggcaactatg gatgaacgaa atagacagat cgctgagata ggtgcctcac    3180
tgattaagca ttggtaactg tcagaccaag tttactcata tatactttag attgatttaa    3240
aacttcattt ttaatttaaa aggatctagg tgaagatcct ttttgataat ctcatgacca    3300
aaatccctta acgtgagttt tcgttccact gagcgtcaga ccccgtagaa aagatcaaag    3360
gatcttcttg agatcctttt tttctgcgcg taatctgctg cttgcaaaca aaaaaaccac    3420
cgctaccagc ggtggtttgt ttgccggatc aagagctacc aactcttttt ccgaaggtaa    3480
ctggcttcag cagagcgcag ataccaaata ctgtccttct agtgtagccg tagttaggcc    3540
accacttcaa gaactctgta gcaccgccta catacctcgc tctgctaatc ctgttaccag    3600
tggctgctgc cagtggcgat aagtcgtgtc ttaccgggtt ggactcaaga cgatagttac    3660
cggataaggc gcagcggtcg ggctgaacgg ggggttcgtg cacacagccc agcttggagc    3720
gaacgaccta caccgaactg agatacctac agcgtgagct atgagaaagc gccacgcttc    3780
ccgaagggag aaaggcggac aggtatccgg taagcggcag ggtcggaaca ggagagcgca    3840
cgagggagct tccaggggga aacgcctggt atctttatag tcctgtcggg tttcgccacc    3900
tctgacttga gcgtcgattt tgtgatgct cgtcaggggg cggagccta tggaaaaacg    3960 ccagcaacgc ggccttttta cggttcctgg ccttttgctg ccttttgct cacatgt     4017
```

<210> SEQ ID NO 22
<211> LENGTH: 330
<212> TYPE: DNA
<213> ORGANISM: Artificial
<220> FEATURE:
<223> OTHER INFORMATION: SV40 polyadenylation signal
<220> FEATURE:
<221> NAME/KEY: SV40
<222> LOCATION: (1)..(330)

<400> SEQUENCE: 22

```
ggtaccagcg ctgtcgaggc cgcttcgagc agacatgata agatacattg atgagtttgg     60
acaaaccaca actagaatgc agtgaaaaaa atgctttatt tgtgaaattt gtgatgctat    120
tgctttattt gtaaccatta taagctgcaa taaacaagtt aacaacaaca attgcattca    180
ttttatgttt caggttcagg gggagatgtg gggaggtttt taaagcaagt aaaacctcta    240
caaatgtggt aaaatcgatt aggatcttcc tagagcatgg ctacctagac atggctcgac    300
agatcagcgc tcatgctctg gaagatctcg                                    330
```

<210> SEQ ID NO 23
<211> LENGTH: 182
<212> TYPE: DNA
<213> ORGANISM: Artificial
<220> FEATURE:
<223> OTHER INFORMATION: Intronic sequence associated with RSV promoter
<220> FEATURE:

```
<221> NAME/KEY: Intronic sequence associated with RSV promoter
<222> LOCATION: (1)..(182)

<400> SEQUENCE: 23
gagatctgct tcagctggag gcactgggca ggtaagtatc aaggttacaa gacaggttta    60
aggagaccaa tagaaactgg gcttgtcgag acagagaaga ctcttgcgtt tctgataggc   120
acctattggt cttactgaca tccactttgc ctttctctcc acaggtgcag ctgctgcagc   180
gg                                                                 182

<210> SEQ ID NO 24
<211> LENGTH: 94
<212> TYPE: DNA
<213> ORGANISM: Artificial
<220> FEATURE:
<223> OTHER INFORMATION: Equivalent mini CMV promoter
<220> FEATURE:
<221> NAME/KEY: Equivalent mini CMV promoter
<222> LOCATION: (1)..(94)

<400> SEQUENCE: 24
taggcgtgta cggtgggagg tctatataag cagagctctc tggctaacta gagaacccac    60
tgcttaactg gcttatcgaa attaatacga ctca                                94

<210> SEQ ID NO 25
<211> LENGTH: 3971
<212> TYPE: DNA
<213> ORGANISM: Artificial
<220> FEATURE:
<223> OTHER INFORMATION: Construct O

<400> SEQUENCE: 25
gctcatgctc tggaagatct cgatttaaat gcggccgcag gaacccctag tgatggagtt    60
ggccactccc tctctgcgcg ctcgctcgct cactgaggcc gggcgaccaa aggtcgcccg   120
acgcccgggc tttgcccggg cggcctcagt gagcgagcga gcgcgcagct gcctgcaggg   180
gcgcctgatg cggtattttc tccttacgca tctgtgcggt atttcacacc gcatacgtca   240
aagcaaccat agtacgcgcc ctgtagcggc gcattaagcg cggcgggtgt ggtggttacg   300
cgcagcgtga ccgctacact tgccagcgcc ctagcgcccg ctcctttcgc tttcttccct   360
tcctttctcg ccacgttcgc cggctttccc cgtcaagctc taaatcgggg gctcccttta   420
gggttccgat ttagtgcttt acggcacctc gaccccaaaa aacttgattt gggtgatggt   480
tcacgtagtg ggccatcgcc ctgatagacg gtttttcgcc ctttgacgtt ggagtccacg   540
ttctttaata gtggactctt gttccaaact ggaacaacac tcaaccctat ctcgggctat   600
tcttttgatt tataagggat tttgccgatt tcggcctatt ggttaaaaaa tgagctgatt   660
taacaaaaat ttaacgcgaa ttttaacaaa atattaacgt ttacaatttt atggtgcact   720
ctcagtacaa tctgctctga tgccgcatag ttaagccagc cccgacaccc gccaacaccc   780
gctgacgcgc cctgacgggc ttgtctgctc ccggcatccg cttacagaca agctgtgacc   840
gtctccggga gctgcatgtg tcagaggttt tcaccgtcat caccgaaacg cgcgagacga   900
aagggcctcg tgatacgcct atttttatag gttaatgtca tgataataat ggtttcttag   960
acgtcaggtg gcacttttcg gggaaatgtg cgcggaaccc ctatttgttt attttttctaa  1020 atacattcaa atatgtatcc gctcatgaga caataaccct gataaatgct tcaataatat  1080
tgaaaaagga agagtatgag tattcaacat ttccgtgtcg cccttattcc cttttttgcg  1140
gcattttgcc ttcctgtttt tgctcaccca gaaacgctgg tgaaagtaaa agatgctgaa  1200
```

```
gatcagttgg gtgcacgagt gggttacatc gaactggatc tcaacagcgg taagatcctt    1260
gagagttttc gccccgaaga acgttttcca atgatgagca cttttaaagt tctgctatgt    1320
ggcgcggtat tatcccgtat tgacgccggg caagagcaac tcggtcgccg catacactat    1380
tctcagaatg acttggttga gtactcacca gtcacagaaa agcatcttac ggatggcatg    1440
acagtaagag aattatgcag tgctgccata accatgagtg ataacactgc ggccaactta    1500
cttctgacaa cgatcggagg accgaaggag ctaaccgctt ttttgcacaa catgggggat    1560
catgtaactc gccttgatcg ttgggaaccg gagctgaatg aagccatacc aaacgacgag    1620
cgtgacacca cgatgcctgt agcaatggca acaacgttgc gcaaactatt aactggcgaa    1680
ctacttactc tagcttcccg gcaacaatta atagactgga tggaggcgga taaagttgca    1740
ggaccacttc tgcgctcggc ccttccggct ggctggttta ttgctgataa atctggagcc    1800
ggtgagcgtg ggtctcgcgg tatcattgca gcactggggc cagatggtaa gccctcccgt    1860
atcgtagtta tctacacgac ggggagtcag gcaactatgg atgaacgaaa tagacagatc    1920
gctgagatag gtgcctcact gattaagcat tggtaactgt cagaccaagt ttactcatat    1980
atactttaga ttgatttaaa acttcatttt taatttaaaa ggatctaggt gaagatcctt    2040
tttgataatc tcatgaccaa aatcccttaa cgtgagtttt cgttccactg agcgtcagac    2100
cccgtagaaa agatcaaagg atcttcttga gatcctttt ttctgcgcgt aatctgctgc    2160
ttgcaaacaa aaaaccacc gctaccagcg gtggtttgtt tgccggatca agagctacca    2220
actctttttc cgaaggtaac tggcttcagc agagcgcaga taccaaatac tgtccttcta    2280
gtgtagccgt agttaggcca ccacttcaag aactctgtag caccgcctac atacctcgct    2340
ctgctaatcc tgttaccagt ggctgctgcc agtggcgata gtcgtgtct taccgggttg    2400 gactcaagac gatagttacc ggataaggcg cagcggtcgg gctgaacggg gggttcgtgc    2460
acacagccca gcttggagcg aacgacctac accgaactga gatacctaca gcgtgagcta    2520
tgagaaagcg ccacgcttcc cgaagggaga aaggcggaca ggtatccggt aagcggcagg    2580
gtcggaacag gagagcgcac gagggagctt ccagggggaa acgcctggta tctttatagt    2640
cctgtcgggt ttcgccacct ctgacttgag cgtcgatttt tgtgatgctc gtcagggggg    2700
cggagcctat ggaaaaacgc cagcaacgcg gccttttac ggttcctggc cttttgctgg    2760
ccttttgctc acatgtcctg caggcagctg cgcgctcgct cgctcactga ggccgcccgg    2820
gcaaagcccg ggcgtcgggc gacctttggt cgcccggcct cagtgagcga gcgagcgcgc    2880
agagagggag tggccaactc catcactagg ggttcctgcg gccgcgatat ctatgccaag    2940 tacgcccct attgacgtca atgacggtaa atggcccgcc tggcattatg cccagtacat    3000
gaccttatgg gactttccta cttggcagta catctacgta ttagtcatcg ctattaccat    3060
ggtgatgcgg ttttggcagt acatcaatgg gcgtggatag cggtttgact cacggggatt    3120
tccaagtctc cacccattg acgtcaatgg gagtttgttt tggcaccaaa atcaacggga    3180
ctttccaaaa tgtcgtaaca actccgcccc attgacgcaa atgggcggta ggcgtgtacg    3240
gtgggaggtc tatataagca gagctctctg gctaactaga gaacccactg cttaactggc    3300
ttatcgaaat taatacgact cactataggg agacccaagc ttgctagcgt cgaccttctg    3360
ccatggccct gtggatgcgc ctcctgcccc tgctggcgct gctggccctc tggggacctg    3420
acccagccgc agcctttgtg aaccaacacc tgtgcggctc agatctggtg aagctctct    3480 acctagtgtg cggggaacga ggcttcttct acacacccag gaccaagcgg gaggcagagg    3540
```

| | | | | |
|---|---|---|---|---|
| acctgcaggt | ggggcaggtg | gagctgggcg | ggggccctgg | tgcaggcagc | ctgcagccct | 3600 |
| tggccctgga | ggggtcgcga | cagaagcgtg | gcattgtgga | acaatgctgt | accagcatct | 3660 |
| gctccctcta | ccagctggag | aactactgca | actagacgca | gccgtcgacg | gtaccagcgt | 3720 |
| ggagctcgct | gatcagcctc | gactgtgcct | tctagttgcc | agccatctgt | tgtttgcccc | 3780 |
| tccccgtgc | cttccttgac | cctggaaggt | gccactccca | ctgtcctttc | ctaataaaat | 3840 |
| gaggaaattg | catcgcattg | tctgagtagg | tgtcattcta | ttctgggggg | tggggtgggg | 3900 |
| caggacagca | agggggagga | ttgggaagac | aatagcaggc | atgctgggga | tgcggtgggc | 3960 |
| tctatggcca | c | | | | | 3971 |

<210> SEQ ID NO 26
<211> LENGTH: 5453
<212> TYPE: DNA
<213> ORGANISM: Artificial
<220> FEATURE:
<223> OTHER INFORMATION: Construct P

<400> SEQUENCE: 26

| | | | | | | |
|---|---|---|---|---|---|---|
| gtgatttaaa | tgcggccgca | ggaacccta | gtgatggagt | tggccactcc | ctctctgcgc | 60 |
| gctcgctcgc | tcactgaggc | cgggcgacca | aaggtcgccc | gacgcccggg | ctttgcccgg | 120 |
| gcggcctcag | tgagcgagcg | agcgcgcagc | tgcctgcagg | ggcgcctgat | gcggtatttt | 180 |
| ctccttacgc | atctgtgcgg | tatttcacac | cgcatacgtc | aaagcaacca | tagtacgcgc | 240 |
| cctgtagcgg | cgcattaagc | gcggcgggtg | tggtggttac | gcgcagcgtg | accgctacac | 300 |
| ttgccagcgc | cctagcgccc | gctcctttcg | ctttcttccc | ttcctttctc | gccacgttcg | 360 |
| ccggctttcc | ccgtcaagct | ctaaatcggg | ggctcccttt | agggttccga | tttagtgctt | 420 |
| tacggcacct | cgaccccaaa | aaacttgatt | tgggtgatgg | ttcacgtagt | gggccatcgc | 480 |
| cctgatagac | ggttttcgc | cctttgacgt | tggagtccac | gttctttaat | agtggactct | 540 |
| tgttccaaac | tggaacaaca | ctcaacccta | tctcggcta | ttcttttgat | ttataaggga | 600 |
| ttttgccgat | ttcggcctat | tggttaaaaa | atgagctgat | ttaacaaaaa | tttaacgcga | 660 |
| attttaacaa | aatattaacg | tttacaattt | tatggtgcac | tctcagtaca | atctgctctg | 720 |
| atgccgcata | gttaagccag | ccccgacacc | cgccaacacc | cgctgacgcg | ccctgacggg | 780 |
| cttgtctgct | cccggcatcc | gcttacagac | aagctgtgac | cgtctccggg | agctgcatgt | 840 |
| gtcagaggtt | ttcaccgtca | tcaccgaaac | gcgcgagacg | aaagggcctc | gtgatacgcc | 900 |
| tatttttata | ggttaatgtc | atgataataa | tggtttctta | gacgtcaggt | ggcacttttc | 960 |
| ggggaaatgt | gcgcggaacc | cctatttgtt | tattttcta | aatacattca | aatatgtatc | 1020 |
| cgctcatgag | acaataaccc | tgataaatgc | ttcaataata | ttgaaaaagg | aagagtatga | 1080 |
| gtattcaaca | tttccgtgtc | gcccttattc | ccttttttgc | ggcattttgc | cttcctgttt | 1140 |
| ttgctcaccc | agaaacgctg | gtgaaagtaa | aagatgctga | agatcagttg | ggtgcacgag | 1200 |
| tgggttacat | cgaactggat | ctcaacagcg | gtaagatcct | tgagagtttt | cgccccgaag | 1260 |
| aacgttttcc | aatgatgagc | acttttaaag | ttctgctatg | tggcgcggta | ttatcccgta | 1320 |
| ttgacgccgg | gcaagagcaa | ctcggtcgcc | gcatacacta | ttctcagaat | gacttggttg | 1380 |
| agtactcacc | agtcacagaa | aagcatctta | cggatggcat | gacagtaaga | gaattatgca | 1440 |
| gtgctgccat | aaccatgagt | gataacactg | cggccaactt | acttctgaca | acgatcggag | 1500 |
| gaccgaagga | gctaaccgct | tttttgcaca | acatggggga | tcatgtaact | cgccttgatc | 1560 |
| gttgggaacc | ggagctgaat | gaagccatac | caaacgacga | gcgtgacacc | acgatgcctg | 1620 |

```
tagcaatggc aacaacgttg cgcaaactat taactggcga actacttact ctagcttccc    1680
ggcaacaatt aatagactgg atggaggcgg ataaagttgc aggaccactt ctgcgctcgg    1740
cccttccggc tggctggttt attgctgata atctggagc cggtgagcgt gggtctcgcg     1800
gtatcattgc agcactgggg ccagatggta agccctcccg tatcgtagtt atctacacga    1860
cggggagtca ggcaactatg gatgaacgaa atagacagat cgctgagata ggtgcctcac    1920
tgattaagca ttggtaactg tcagaccaag tttactcata tactttag attgatttaa      1980 aacttcattt ttaatttaaa aggatctagg tgaagatcct ttttgataat ctcatgacca    2040 aaatcccta acgtgagttt tcgttccact gagcgtcaga ccccgtagaa aagatcaaag     2100
gatcttcttg agatcctttt tttctgcgcg taatctgctg cttgcaaaca aaaaaaccac    2160
cgctaccagc ggtggtttgt tgccggatc aagagctacc aactcttttt ccgaaggtaa     2220
ctggcttcag cagagcgcag ataccaaata ctgtccttct agtgtagccg tagttaggcc    2280
accacttcaa gaactctgta gcaccgccta catacctcgc tctgctaatc ctgttaccag    2340
tggctgctgc cagtggcgat aagtcgtgtc ttaccgggtt ggactcaaga cgatagttac    2400
cggataaggc gcagcggtcg ggctgaacgg ggggttcgtg cacacagccc agcttggagc    2460
gaacgaccta caccgaactg agatacctac agcgtgagct atgagaaagc gccacgcttc    2520
ccgaagggag aaaggcggac aggtatccgg taagcggcag ggtcggaaca ggagagcgca    2580
cgagggagct ccaggggga aacgcctggt atctttatag tcctgtcggg tttcgccacc     2640
tctgacttga gcgtcgattt tgtgatgct cgtcaggggg gcggagccta tggaaaaacg     2700
ccagcaacgc ggcctttta cggttcctgg ccttttgctg gccttttgct cacatgtcct     2760
gcaggcagct gcgcgctcgc tcgctcactg aggccgcccg gcaaagccc gggcgtcggg     2820 cgacctttgg tcgcccggcc tcagtgagcg agcgagcgcg cagagaggga gtggccaact    2880
ccatcactag gggttcctgc ggccgcgata tccatgtttg acagcttatc atcgcagatc    2940
cgtatggtgc actctcagta caatctgctc tgatgccgca tagttaagcc agtatctgct    3000
ccctgcttgt gtgttggagg tcgctgagta gtgcgcgagc aaaatttaag ctacaacaag    3060
gcaaggcttg accgacaatt gcatgaagaa tctgcttagg gttaggcgtt ttgcgctgct    3120
tcgcgatgta cgggccagat attgcgtat ctgagggac tagggtgtgt ttaggcgaaa      3180
agcgggcgtt cggttgtacg cggttaggag tcccctcagg atatagtagt ttcgcttttg    3240
catagggagg gggaaatgta gtcttatgca atactcttgt agtcttgcaa catggtaacg    3300
atgagttagc aacatgcctt acaaggagag aaaagcacc gtgcatgccg attggtggaa     3360
gtaaggtggt acgatcgtgc cttattagga aggcaacaga cgggtctgac atggattgga    3420
cgaaccacta aattccgcat tgcagagata ttgtatttaa gtgcctagct cgatacaata    3480
aacgccattt gaccattcac cacattggtg tgcacctcca agctgggtac cagcttctag    3540
agagatctgc ttcagctgga ggcactgggc aggtaagtat caaggttaca agacaggttt    3600
aaggagacca atagaaactg ggcttgtcga gacagagaag actcttgcgt ttctgatagg    3660
cacctattgg tcttactgac atccactttg cctttctctc cacaggtgca gctgctgcag    3720
cggtctagaa ctcgagtcga gaccatgcg atggatgtca caaggagcca ggcccagaca    3780
gccttgactc tggtagagca gatcctggca gagttccagc tgcaggagga ggacctgaag    3840
aaggtgatga acggatgca gaaggagatg gaccgcggcc tgaggctgga gacccatgaa    3900
gaggccagtg tgaagatgct gccccaccta cgtgcgctcca ccccagaagg ctcagaagtc    3960
```

```
gggggacttcc tctccctgga cctgggtggc actaacttca gggtgatgct ggtgaaggtg    4020
ggagaaggtg aggaggggca gtggagcgtg aagaccaaac accagatgta ctccatcccc    4080
gaggacgcca tgaccggcac tgctgagatg ctcttcgact acatctctga gtgcatctcc    4140
gacttcctgg acaagcatca gatgaaacac aagaagctgc ccctgggctt caccttctcc    4200
tttcctgtga ggcacgaaga catcgataag gcatccttc tcaactggac caagggcttc     4260
aaggcctcag gagcagaagg gaacaatgtc gtgggcttc tgcgagacgc tatcaaacgg      4320 agagggact ttgaaatgga tgtggtggca atggtgaatg acacggtggc cacgatgatc      4380
tcctgctact acgaagacca tcagtgcgag gtcggcatga tcgtgggcac gggctgcaat    4440
gcctgctaca tggaggagat gcagaatgtg gagctggtgg aggggacga gggccgcatg     4500 tgcgtcaata ccgagtgggg cgccttcggg gactccggcg agctggacga gttcctgctg    4560
gagtatgacc gcctggtgga cgagagctct gcaaaccccg gtcagcagct gtatgagaag   4620
ctcataggtg gcaagtacat gggcgagctg gtgcggcttg tgctgctcag gctcgtggac    4680
gaaaacctgc tcttccacgg ggaggcctcc gagcagctgc gcacacgcgg agccttcgag   4740
acgcgcttcg tgtcgcaggt ggagagcgac acgggcgacc gcaagcagat ctacaacatc   4800
ctgagcacgc tggggctgcg accctcgacc accgactgcg acatcgtgcg ccgcgcctgc   4860
gagagcgtgt ctacgcgcgc tgcgcacatg tgctcggcgg ggctggcggg cgtcatcaac    4920
cgcatgcgcg agagccgcag cgaggacgta atgcgcatca ctgtgggcgt ggatggctcc    4980
gtgtacaagc tgcaccccag cttcaaggag cggttccatg ccagcgtgcg caggctgacg    5040
cccagctgcg agatcacctt catcgagtcg gaggagggca gtggccgggg gcgggccctg   5100
gtctcggcgg tggcctgtaa gaaggcctgt atgctgggcc agtgactcga gcacgctgtc   5160
gaggccgctt cgagcagaca tgataagata cattgatgag tttggacaaa ccacaactag   5220
aatgcagtga aaaaatgct ttatttgtga aatttgtgat gctattgctt tatttgtaac    5280
cattataagc tgcaataaac aagttaacaa caacaattgc attcatttta tgtttcaggt    5340
tcagggggag atgtgggagg tttttttaaag caagtaaaac ctctacaaat gtggtaaaat   5400
cgattaggat cttcctagag catggctacc tagacatggc tcgacagatc agc            5453

<210> SEQ ID NO 27
<211> LENGTH: 6522
<212> TYPE: DNA
<213> ORGANISM: Artificial
<220> FEATURE:
<223> OTHER INFORMATION: Construct Q

<400> SEQUENCE: 27
atccatgttt gacagcttat catcgcagat ccgtatggtg cactctcagt acaatctgct      60
ctgatgccgc atagttaagc cagtatctgc tccctgcttg tgtgttggag gtcgctgagt     120
agtgcgcgag caaatttaa gctacaacaa ggcaaggctt gaccgacaat tgcatgaaga     180
atctgcttag ggttaggcgt tttgcgctgc ttcgcgatgt acgggccaga tattcgcgta    240
tctgagggga ctagggtgtg tttaggcgaa aagcggggct tcggttgtac gcggttagga     300
gtcccctcag gatatagtag tttcgctttt gcatagggag ggggaaatgt agtcttatgc    360
aatactcttg tagtcttgca acatggtaac gatgagttag caacatgcct tacaaggaga    420
gaaaaagcac cgtgcatgcc gattggtgga agtaaggtgg tacgatcgtg ccttattagg    480
aaggcaacag acgggtctga catggattgg acgaaccact aaattccgca ttgcagagat    540
attgtattta agtgcctagc tcgatacaat aaacgccatt tgaccattca ccacattggt    600
```

-continued

```
gtgcacctcc aagctgggta ccagcttcta gagagatctg cttcagctgg aggcactggg    660
caggtaagta tcaaggttac aagacaggtt taaggagacc aatagaaact gggcttgtcg    720
agacagagaa gactcttgcg tttctgatag gcacctattg gtcttactga catccacttt    780
gcctttctct ccacaggtgc agctgctgca gcggtctaga actcgagtcg agaccatggc    840
gatggatgtc acaaggagcc aggcccagac agccttgact ctggtagagc agatcctggc    900
agagttccag ctgcaggagg aggacctgaa gaaggtgatg agacggatgc agaaggagat    960
ggaccgcggc ctgaggctgg agacccatga agaggccagt gtgaagatgc tgcccaccta   1020
cgtgcgctcc accccagaag gctcagaagt cggggacttc ctctccctgg acctgggtgg   1080
cactaacttc agggtgatgc tggtgaaggt gggagaaggt gaggaggggc agtggagcgt   1140
gaagaccaaa caccagatgt actccatccc cgaggacgcc atgaccggca ctgctgagat   1200
gctcttcgac tacatctctg agtgcatctc cgacttcctg acaagcatc agatgaaaca    1260
caagaagctg cccctgggct tcaccttctc ctttcctgtg aggcacgaag acatcgataa   1320
gggcatcctt ctcaactgga ccaagggctt caaggcctca ggagcagaag gaacaatgt    1380
cgtgggcctt ctgcgagacg ctatcaaacg gagaggggac tttgaaatgg atgtggtggc   1440
aatggtgaat gacacggtgg ccacgatgat ctcctgctac tacgaagacc atcagtgcga   1500
ggtcggcatg atcgtgggca cgggctgcaa tgcctgctac atggaggaga tgcagaatgt   1560
ggagctggtg gaggggacg agggccgcat gtgcgtcaat accgagtggg gcgccttcgg   1620
ggactccggc gagctggacg agttcctgct ggagtatgac cgcctggtgg acgagagctc   1680
tgcaaacccc ggtcagcagc tgtatgagaa gctcataggt ggcaagtaca tgggcgagct   1740
ggtgcggctt gtgctgctca ggctcgtgga cgaaaacctg ctcttccacg ggaggcctc    1800
cgagcagctg cgcacacgcg gagccttcga gacgcgcttc gtgtcgcagg tggagagcga   1860
cacgggcgac cgcaagcaga tctacaacat cctgagcacg ctgggctgc gaccctcgac    1920
caccgactgc gacatcgtgc gccgcgcctg cgagagcgtg tctacgcgcg ctgcgcacat   1980
gtgctcggcg ggctggcgg gcgtcatcaa ccgcatgcgc gagagccgca gcaggacgt    2040
aatgcgcatc actgtgggcg tggatggctc cgtgtacaag ctgcaccca gcttcaagga    2100
gcggttccat gccagcgtgc gcaggctgac gcccagctgc gagatcacct tcatcgagtc   2160
ggaggagggc agtggccggg gcgcggccct ggtctcggcg gtggcctgta gaaggcctg    2220
tatgctgggc cagtgactcg agcacgctgt cgaggccgct tcgagcagac atgataagat   2280
acattgatga gtttggacaa accacaacta gaatgcagta aaaaaatgc tttatttgtg    2340
aaatttgtga tgctattgct ttatttgtaa ccattataag ctgcaataaa caagttaaca   2400
acaacaattg cattcatttt atgtttcagg ttcaggggga gatgtgggag gtttttaaa    2460
gcaagtaaaa cctctacaaa tgtggtaaaa tcgattagga tcttcctaga gcatggctac   2520
ctagacatgg ctcgacagat cagcgtgatt taaatgcggc gcaggaacc cctagtgatg    2580
gagttggcca ctccctctct gcgcgctcgc tcgctcactg aggccgggcg accaaaggtc   2640
gcccgacgcc cgggctttgc ccgggcggcc tcagtgagcg agcgagcgcg cagctgcctg   2700
cagggcgcc tgatgcggta tttctccctt acgcatctgt gcggtatttc acaccgcata    2760
cgtcaaagca accatagtac gcgccctgta gcggcgcatt aagcgcggcg ggtgtggtgg   2820
ttacgcgcag cgtgaccgct acacttgcca gcgccctagc gcccgctcct ttcgctttct   2880
tcccttcctt tctcgccacg ttcgccggct ttccccgtca gctctaaat cggggggctcc    2940
```

```
ctttagggtt ccgatttagt gctttacggc acctcgaccc caaaaaactt gatttgggtg   3000
atggttcacg tagtgggcca tcgccctgat agacggtttt tcgcccttg acgttggagt   3060
ccacgttctt taatagtgga ctcttgttcc aaactggaac aacactcaac cctatctcgg   3120
gctattcttt tgatttataa gggattttgc cgatttcggc ctattggtta aaaaatgagc   3180
tgatttaaca aaaatttaac gcgaatttta acaaaatatt aacgtttaca attttatggt   3240
gcactctcag tacaatctgc tctgatgccg catagttaag ccagcccga cacccgccaa   3300
cacccgctga cgcgccctga cgggcttgtc tgctcccggc atccgcttac agacaagctg   3360
tgaccgtctc cggagctgc atgtgtcaga ggttttcacc gtcatcaccg aaacgcgcga   3420
gacgaaaggg cctcgtgata cgcctatttt tataggttaa tgtcatgata ataatggttt   3480
cttagacgtc aggtggcact tttcggggaa atgtgcgcgg aacccctatt tgtttattt   3540
tctaaataca ttcaaatatg tatccgctca tgagacaata accctgataa atgcttcaat   3600
aatattgaaa aaggaagagt atgagtattc aacatttccg tgtcgccctt attccctttt   3660
ttgcggcatt ttgccttcct gttttgctc acccagaaac gctggtgaaa gtaaaagatg   3720
ctgaagatca gttgggtgca cgagtgggtt acatcgaact ggatctcaac agcggtaaga   3780
tccttgagag ttttcgcccc gaagaacgtt ttccaatgat gagcactttt aaagttctgc   3840
tatgtggcgc ggtattatcc cgtattgacg ccgggcaaga gcaactcggt cgccgcatac   3900
actattctca gaatgacttg gttgagtact caccagtcac agaaaagcat cttacggatg   3960
gcatgacagt aagagaatta tgcagtgctg ccataaccat gagtgataac actgcggcca   4020
acttacttct gacaacgatc ggaggaccga aggagctaac cgcttttttg cacaacatgg   4080
gggatcatgt aactcgcctt gatcgttggg aaccggagct gaatgaagcc ataccaaacg   4140
acgagcgtga ccaccgatg cctgtagcaa tggcaacaac gttgcgcaaa ctattaactg   4200
gcgaactact tactctagct tcccggcaac aattaataga ctggatggag gcggataaag   4260
ttgcaggacc acttctgcgc tcggcccttc cggctggctg gtttattgct gataaatctg   4320
gagccggtga gcgtgggtct cgcggtatca ttgcagcact ggggccagat ggtaagccct   4380
cccgtatcgt agttatctac acgacgggga gtcaggcaac tatggatgaa cgaaatagac   4440
agatcgctga gataggtgcc tcactgatta agcattggta actgtcagac caagtttact   4500
catatatact ttagattgat ttaaaacttc attttaatt taaaggatc taggtgaaga   4560
tccttttga taatctcatg accaaaatcc cttaacgtga gttttcgttc cactgagcgt   4620
cagacccg agaaaagatc aaaggatctt cttgagatcc ttttttttctg cgcgtaatct   4680
gctgcttgca acaaaaaaa ccaccgctac cagcggtggt ttgtttgccg gatcaagagc   4740
taccaactct ttttccgaag gtaactggct tcagcagagc gcagatacca atactgtcc   4800
ttctagtgta gccgtagtta ggccaccact tcaagaactc tgtagcaccg cctacatacc   4860
tcgctctgct aatcctgtta ccagtggctg ctgccagtgg cgataagtcg tgtcttaccg   4920
ggttggactc aagacgatag ttaccggata aggcgcagcg tcgggctga cgggggggtt   4980
cgtgcacaca gcccagcttg gagcgaacga cctacaccga actgagatac ctacagcgtg   5040
agctatgaga aagcgccacg cttcccgaag ggagaaaggc ggacaggtat ccggtaagcg   5100
gcagggtcgg aacaggagag cgcacgaggg agcttccagg gggaaacgcc tggtatcttt   5160
atagtcctgt cgggtttcgc cacctctgac ttgagcgtcg attttgtga tgctcgtcag   5220
gggggcggag cctatggaaa aacgccagca acgcggcctt tttacggttc ctggccttt   5280
gctggccttt tgctcacatg ttcctgcaggc agctgcgcgc tcgctcgctc actgaggccg   5340
```

-continued

```
cccgggcaaa gcccgggcgt cgggcgacct ttggtcgccc ggcctcagtg agcgagcgag    5400
cgcgcagaga gggagtggcc aactccatca ctaggggttc ctgcggccgc gataaatcga    5460
gatcttccag agcatgagcg tggccataga gcccaccgca tccccagcat gcctgctatt    5520
gtcttcccaa tcctccccct tgctgtcctg ccccaccccc cccccagaa tagaatgaca     5580 cctactcaga caatgcgatg caatttcctc attttattag gaaaggacag tgggagtggc    5640
accttccagg gtcaaggaag gcacggggga ggggcaaaca acagatggct ggcaactaga    5700
aggcacagtc gaggctgatc agcgagctcc acgctggtac cgtcgacggc tgcgtctagt    5760
tgcagtagtt ctccagctgg tagagggagc agatgctggt acagcattgt tccacaatgc    5820
cacgcttctg tcgcgacccc tccagggcca agggctgcag gctgcctgca ccagggcccc    5880
cgcccagctc cacctgcccc acctgcaggt cctctgcctc ccgcttggtc ctgggtgtgt    5940
agaagaagcc tcgttccccg cacactaggt agagagcttc caccagatct gagccgcaca    6000
ggtgttggtt cacaaaggct gcggctgggt caggtcccca gagggccagc agcgccagca    6060
ggggcaggag gcgcatccac agggccatgg cagaaggtcg acgctagcaa gcttgggtct    6120
ccctatagtg agtcgtatta atttcgataa gccagttaag cagtgggttc tctagttagc    6180
cagagagctc tgcttatata gacctcccac cgtacacgcc taccgcccat ttgcgtcaat    6240
ggggcggagt tgttacgaca ttttggaaag tcccgttgat tttggtgcca aaacaaactc    6300
ccattgacgt caatggggtg gagacttgga atccccgtg agtcaaaccg ctatccacgc     6360
ccattgatgt actgccaaaa ccgcatcacc atggtaatag cgatgactaa tacgtagatg    6420
tactgccaag taggaaagtc ccataaggtc atgtactggg cataatgcca ggcgggccat    6480
ttaccgtcat tgacgtcaat aggggggcgta cttggcatag at                      6522
```

<210> SEQ ID NO 28
<211> LENGTH: 4238
<212> TYPE: DNA
<213> ORGANISM: Artificial
<220> FEATURE:
<223> OTHER INFORMATION: Construct R

<400> SEQUENCE: 28

```
gctcatgctc tggaagatct cgatttaaat gcggccgcag gaacccctag tgatggagtt     60
ggccactccc tctctgcgcg ctcgctcgct cactgaggcc gggcgaccaa aggtcgcccg    120
acgcccgggc tttgcccggg cggcctcagt gagcgagcga gcgcgcagct gcctgcaggg    180
gcgcctgatg cggtattttc tccttacgca tctgtgcggt atttcacacc gcatacgtca    240
aagcaaccat agtacgcgcc ctgtagcggc gcattaagcg cggcgggtgt ggtggttacg    300
cgcagcgtga ccgctacact tgccagcgcc ctagcgcccg ctcctttcgc tttcttccct    360
tcctttctcg ccacgttcgc cggctttccc cgtcaagctc taaatcgggg gctcccttta    420
gggttccgat ttagtgcttt acggcacctc gaccccaaaa aacttgattt gggtgatggt    480
tcacgtagtg ggccatcgcc ctgatagacg gttttttcgcc ctttgacgtt ggagtccacg    540
ttctttaata gtggactctt gttccaaact ggaacaacac tcaaccctat ctcgggctat    600
tcttttgatt tataagggat tttgccgatt tcggcctatt ggttaaaaaa tgagctgatt    660
taacaaaaat ttaacgcgaa ttttaacaaa atattaacgt ttacaatttt atggtgcact    720
ctcagtacaa tctgctctga tgccgcatag ttaagccagc cccgacaccc gccaacaccc    780
gctgacgcgc cctgacgggc ttgtctgctc ccggcatccg cttacagaca agctgtgacc    840
```

```
gtctccggga gctgcatgtg tcagaggttt tcaccgtcat caccgaaacg cgcgagacga    900
aagggcctcg tgatacgcct attttatag gttaatgtca tgataataat ggtttcttag    960
acgtcaggtg gcacttttcg gggaaatgtg cgcggaaccc ctatttgttt attttctaa   1020
atacattcaa atatgtatcc gctcatgaga caataaccct gataaatgct tcaataatat   1080
tgaaaaagga gagtatgag tattcaacat ttccgtgtcg cccttattcc cttttttgcg   1140
gcattttgcc ttcctgtttt tgctcaccca gaaacgctgg tgaaagtaaa agatgctgaa   1200
gatcagttgg gtgcacgagt gggttacatc gaactggatc tcaacagcgg taagatcctt   1260
gagagttttc gccccgaaga acgttttcca atgatgagca cttttaaagt tctgctatgt   1320
ggcgcggtat tatcccgtat tgacgccggg caagagcaac tcggtcgccg catacactat   1380
tctcagaatg acttggttga gtactcacca gtcacagaaa agcatcttac ggatggcatg   1440
acagtaagag aattatgcag tgctgccata accatgagtg ataacactgc ggccaactta   1500
cttctgacaa cgatcggagg accgaaggag ctaaccgctt ttttgcacaa catgggggat   1560
catgtaactc gccttgatcg ttgggaaccg gagctgaatg aagccatacc aaacgacgag   1620
cgtgacacca cgatgcctgt agcaatggca acaacgttgc gcaaactatt aactggcgaa   1680
ctacttactc tagcttcccg gcaacaatta atagactgga tggaggcgga taaagttgca   1740
ggaccacttc tgcgctcggc ccttccggct ggctggttta ttgctgataa atctggagcc   1800
ggtgagcgtg ggtctcgcgg tatcattgca gcactggggc cagatggtaa gccctcccgt   1860
atcgtagtta tctacacgac ggggagtcag gcaactatgg atgaacgaaa tagacagatc   1920
gctgagatag gtgcctcact gattaagcat tggtaactgt cagaccaagt ttactcatat   1980
atactttaga ttgatttaaa acttcatttt taatttaaaa ggatctaggt gaagatcctt   2040
tttgataatc tcatgaccaa aatcccttaa cgtgagtttt cgttccactg agcgtcagac   2100
cccgtagaaa agatcaaagg atcttcttga gatcctttt ttctgcgcgt aatctgctgc   2160
ttgcaaacaa aaaaaccacc gctaccagcg gtggtttgtt tgccggatca agagctacca   2220
actcttttc cgaaggtaac tggcttcagc agagcgcaga taccaaatac tgtccttcta   2280
gtgtagccgt agttaggcca ccacttcaag aactctgtag caccgcctac atacctcgct   2340
ctgctaatcc tgttaccagt ggctgctgcc agtggcgata agtcgtgtct taccgggttg   2400
gactcaagac gatagttacc ggataaggcg cagcggtcgg gctgaacggg gggttcgtgc   2460
acacagccca gcttggagcg aacgacctac accgaactga gatacctaca gcgtgagcta   2520
tgagaaagcg ccacgcttcc cgaagggaga aaggcggaca ggtatccggt aagcggcagg   2580
gtcggaacag gagagcgcac gagggagctt ccagggggaa acgcctggta tctttatagt   2640
cctgtcgggt ttcgccacct ctgacttgag cgtcgatttt tgtgatgctc gtcaggggg    2700
cggagcctat ggaaaaacgc cagcaacgcg gcctttttac ggttcctggc cttttgctgg   2760
ccttttgctc acatgtcctg caggcagctg gcgctcgct cgctcactga ggccgcccgg   2820
gcaaagcccg ggcgtcgggc gacctttggt cgcccggcct cagtgagcga gcgagcgcgc   2880
agagagggag tggccaactc catcactagg ggttcctgcg gccgcgatat ctatgccaag   2940
tacgccccct attgacgtca atgacggtaa atggcccgcc tggcattatg cccagtacat   3000
gaccttatgg gactttccta cttggcagta catctacgta ttagtcatcg ctattaccat   3060
ggtgatgcgg ttttggcagt acatcaatgg gcgtggatag cggtttgact cacggggatt   3120
tccaagtctc cacccattg acgtcaatgg gagtttgttt tggcaccaaa atcaacggga   3180
cttttccaaaa tgtcgtaaca actccgcccc attgacgcaa atgggcggta ggcgtgtacg   3240
```

-continued

| | |
|---|---|
| gtgggaggtc tatataagca gagctctctg gctaactaga gaacccactg cttaactggc | 3300 |
| ttatcgaaat taatacgact cactataggg agacccaagc ttgctagcgt cgaccttctg | 3360 |
| ccatggccct gtggatgcgc ctcctgcccc tgctggcgct gctggccctc tggggacctg | 3420 |
| acccagccgc agcctttgtg aaccaacacc tgtgcggctc agatctggtg gaagctctct | 3480 |
| acctagtgtg cggggaacga ggcttcttct acacacccag gaccaagcgg gaggcagagg | 3540 |
| acctgcaggt ggggcaggtg gagctgggcg ggggccctgg tgcaggcagc ctgcagccct | 3600 |
| tggccctgga ggggtcgcga cagaagcgtg gcattgtgga acaatgctgt accagcatct | 3660 |
| gctccctcta ccagctggag aactactgca actagacgca gccgtcgacg gtaccagcgc | 3720 |
| tgagtcgggg cggccggccg cttcgagcag acatgataag atacattgat gagtttggac | 3780 |
| aaaccacaac tagaatgcag tgaaaaaaat gctttatttg tgaaatttgt gatgctattg | 3840 |
| ctttatttgt aaccattata agctgcaata acaagttaa caacaacaat tgcattcatt | 3900 |
| ttatgtttca ggttcagggg gaggtgtggg aggtttttta aagcaagtaa aacctctaca | 3960 |
| aatttggtaa aatcgataag gatctgaacg atggagcgga gaatgggcgg aactgggcgg | 4020 |
| agttaggggc gggatgggcg gagttagggg cgggactatg gttgctgact aattgagatg | 4080 |
| catgctttgc atacttctgc ctgctgggga gcctgggac tttccacacc tggttgctga | 4140 |
| ctaattgaga tgcatgcttt gcatacttct gcctgctggg gagcctgggg actttccaca | 4200 |
| ccctaactga cacacattcc acagcggcaa atttgagc | 4238 |

<210> SEQ ID NO 29
<211> LENGTH: 6743
<212> TYPE: DNA
<213> ORGANISM: Artificial
<220> FEATURE:
<223> OTHER INFORMATION: Construct S

<400> SEQUENCE: 29

| | |
|---|---|
| atccatgttt gacagcttat catcgcagat ccgtatggtg cactctcagt acaatctgct | 60 |
| ctgatgccgc atagttaagc cagtatctgc tccctgcttg tgtgttggag gtcgctgagt | 120 |
| agtgcgcgag caaaatttaa gctacaacaa ggcaaggctt gaccgacaat tgcatgaaga | 180 |
| atctgcttag ggttaggcgt tttgcgctgc ttcgcgatgt acgggccaga tattcgcgta | 240 |
| tctgagggga ctagggtgtg tttaggcgaa aagcgggct tcggttgtac gcggttagga | 300 |
| gtccccctcag gatatagtag tttcgctttt gcatagggag ggggaaatgt agtcttatgc | 360 |
| aatactcttg tagtcttgca acatggtaac gatgagttag caacatgcct tacaaggaga | 420 |
| gaaaaagcac cgtgcatgcc gattggtgga agtaaggtgg tacgatcgtg ccttattagg | 480 |
| aaggcaacag acgggtctga catggattgg acgaaccact aaattccgca ttgcagagat | 540 |
| attgtattta agtgcctagc tcgatacaat aaacgccatt tgaccattca ccacattggt | 600 |
| gtgcacctcc aagctgggta ccagcttcta gagagatctg cttcagctgg aggcactggg | 660 |
| caggtaagta tcaaggttac aagacaggtt taaggagacc aatagaaact gggcttgtcg | 720 |
| agacagagaa gactcttgcg tttctgatag gcacctattg gtcttactga catccacttt | 780 |
| gcctttctct ccacaggtgc agctgctgca gcggtctaga actcgagtcg agaccatggc | 840 |
| gatggatgtc acaaggagcc aggcccagac agccttgact ctggtagagc agatcctggc | 900 |
| agagttccag ctgcaggagg aggacctgaa gaaggtgatg agacgatgc agaaggagat | 960 |
| ggaccgcggc ctgaggctgg agacccatga agaggccagt gtgaagatgc tgcccaccta | 1020 |

```
cgtgcgctcc accccagaag gctcagaagt cggggacttc ctctccctgg acctgggtgg    1080
cactaacttc agggtgatgc tggtgaaggt gggagaaggt gaggaggggc agtggagcgt    1140
gaagaccaaa caccagatgt actccatccc cgaggacgcc atgaccggca ctgctgagat    1200
gctcttcgac tacatctctg agtgcatctc cgacttcctg acaagcatc agatgaaaca     1260 caagaagctg cccctgggct tcaccttctc ctttcctgtg aggcacgaag acatcgataa    1320
gggcatcctt ctcaactgga ccaagggctt caaggcctca ggagcagaag gaacaatgt     1380 cgtggggctt ctgcgagacg ctatcaaacg gagaggggac tttgaaatgg atgtggtggc    1440
aatggtgaat gacacggtgg ccacgatgat ctcctgctac tacgaagacc atcagtgcga    1500
ggtcggcatg atcgtgggca cgggctgcaa tgcctgctac atggaggaga tgcagaatgt    1560
ggagctggtg gaggggacg agggccgcat gtgcgtcaat accgagtggg gcgccttcgg     1620
ggactccggc gagctggacg agttcctgct ggagtatgac cgcctggtgg acgagagctc    1680
tgcaaacccc ggtcagcagc tgtatgagaa gctcataggt ggcaagtaca tgggcgagct    1740
ggtgcggctt gtgctgctca ggctcgtgga cgaaaacctg ctcttccacg gggaggcctc    1800
cgagcagctg cgcacacgcg gagccttcga cgcgcttc gtgtcgcagg tggagagcga     1860
cacgggcgac cgcaagcaga tctacaacat cctgagcacg ctggggctgc gaccctcgac    1920
caccgactgc gacatcgtgc gccgcgcctg cgagagcgtg tctacgcgcg ctgcgcacat    1980
gtgctcggcg gggctggcgg gcgtcatcaa ccgcatgcgc gagagccgca gcgaggacgt    2040
aatgcgcatc actgtgggcg tggatggctc cgtgtacaag ctgcaccccca gcttcaagga   2100 gcggttccat gccagcgtgc gcaggctgac gcccagctgc gagatcacct tcatcgagtc    2160
ggaggagggc agtggccggg gcgcggccct ggtctcggcg gtggcctgta agaaggcctg    2220
tatgctgggc cagtgactcg agcacgtgga gctcgctgat cagcctcgac tgtgccttct    2280
agttgccagc catctgttgt ttgcccctcc ccgtgccttt ccttgaccct ggaaggtgcc    2340
actcccactg tcctttccta ataaaatgag gaaattgcat cgcattgtct gagtaggtgt    2400
cattctattc tggggggtgg ggtggggcag gacagcaagg gggaggattg gaagacaat     2460 agcaggcatg ctgggatgc ggtgggctct atggccacgt gatttaaatg cggccgcagg     2520 aaccccctagt gatggagttg gccactccct ctctgcgcgc tcgctcgctc actgaggccg    2580
ggcgaccaaa ggtcgcccga cgcccgggct ttgcccgggc ggcctcagtg agcgagcgag    2640
cgcgcagctg cctgcagggg cgcctgatgc ggtatttct ccttacgcat ctgtgcggta     2700
tttcacaccg catacgtcaa agcaaccata gtacgcgccc tgtagcggcg cattaagcgc    2760
ggcgggtgtg gtggttacgc gcagcgtgac cgctacactt gccagcgccc tagcgcccgc    2820
tcctttcgct ttcttccctt cctttctcgc cacgttcgcc ggcttccccc gtcaagctct    2880
aaatcggggg ctcccttag ggttccgatt tagtgcttta cggcacctcg accccaaaaa     2940
acttgatttg ggtgatggtt cacgtagtgg ccatcgccc tgatagacgg ttttcgccc      3000 tttgacgttg gagtccacgt tctttaatag tggactcttg ttccaaactg gaacaacact    3060
caaccctatc tcgggctatt cttttgattt ataagggatt ttgccgattt cggcctattg    3120
gttaaaaaat gagctgattt aacaaaaatt taacgcgaat tttaacaaaa tattaacgtt    3180
tacaatttta tggtgcactc tcagtacaat ctgctctgat gccgcatagt taagccagcc    3240
ccgacacccg ccaacacccg ctgacgcgcc ctgacgggct tgtctgctcc cggcatccgc    3300
ttacagacaa gctgtgaccg tctccgggag ctgcatgtgt cagaggtttt caccgtcatc    3360
accgaaacgc gcgagacgaa agggcctcgt gatacgccta ttttataggt taatgtcat    3420
```

```
gataataatg gtttcttaga cgtcaggtgg cactttccgg ggaaatgtgc gcggaacccc    3480
tatttgttta tttttctaaa tacattcaaa tatgtatccg ctcatgagac aataaccctg    3540
ataaatgctt caataatatt gaaaaaggaa gagtatgagt attcaacatt tccgtgtcgc    3600
ccttattccc ttttttgcgg cattttgcct tcctgttttt gctcacccag aaacgctggt    3660
gaaagtaaaa gatgctgaag atcagttggg tgcacgagtg ggttacatcg aactggatct    3720
caacagcggt aagatccttg agagttttcg ccccgaagaa cgttttccaa tgatgagcac    3780
ttttaaagtt ctgctatgtg gcgcggtatt atcccgtatt gacgccgggc aagagcaact    3840
cggtcgccgc atacactatt ctcagaatga cttggttgag tactcaccag tcacagaaaa    3900
gcatcttacg gatggcatga cagtaagaga attatgcagt gctgccataa ccatgagtga    3960
taacactgcg gccaacttac ttctgacaac gatcggagga ccgaaggagc taaccgcttt    4020
tttgcacaac atgggggatc atgtaactcg ccttgatcgt tgggaaccgg agctgaatga    4080
agccatacca aacgacgagc gtgacaccac gatgcctgta gcaatggcaa caacgttgcg    4140
caaactatta actggcgaac tacttactct agcttcccgg caacaattaa tagactggat    4200
ggaggcggat aaagttgcag gaccacttct gcgctcggcc cttccggctg gctggtttat    4260
tgctgataaa tctggagccg gtgagcgtgg gtctcgcggt atcattgcag cactggggcc    4320
agatggtaag ccctcccgta tcgtagttat ctacacgacg gggagtcagg caactatgga    4380
tgaacgaaat agacagatcg ctgagatagg tgcctcactg attaagcatt ggtaactgtc    4440
agaccaagtt tactcatata tactttagat tgatttaaaa cttcattttt aatttaaaag    4500
gatctaggtg aagatccttt ttgataatct catgaccaaa atcccttaac gtgagttttc    4560
gttccactga gcgtcagacc ccgtagaaaa gatcaaagga tcttcttgag atcctttttt    4620
tctgcgcgta atctgctgct tgcaaacaaa aaaaccaccg ctaccagcgg tggtttgttt    4680
gccggatcaa gagctaccaa ctcttttttcc gaaggtaact ggcttcagca gagcgcagat    4740
accaaatact gtccttctag tgtagccgta gttaggccac cacttcaaga actctgtagc    4800
accgcctaca tacctcgctc tgctaatcct gttaccagtg gctgctgcca gtggcgataa    4860
gtcgtgtctt accgggttgg actcaagacg atagttaccg gataaggcgc agcggtcggg    4920
ctgaacgggg ggttcgtgca cacagcccag cttggagcga acgacctaca ccgaactgag    4980
atacctacag cgtgagctat gagaaagcgc cacgcttccc gaagggagaa aggcggacag    5040
gtatccggta agcggcaggg tcggaacagg agagcgcacg agggagcttc caggggggaaa    5100
cgcctggtat ctttatagtc ctgtcgggtt tcgccacctc tgacttgagc gtcgattttt    5160
gtgatgctcg tcagggggggc ggagcctatg gaaaaacgcc agcaacgcgg ccttttacg    5220
gttcctggcc ttttgctggc cttttgctca catgtcctgc aggcagctgc gcgctcgctc    5280
gctcactgag gccgcccggg caaagcccgg gcgtcgggcg acctttggtc gcccggcctc    5340
agtgagcgag cgagcgcgca gagggagt ggccaactcc atcactaggg gttcctgcgg    5400
ccgcgataaa tcgagatctt ccagagcatg agcgctcaaa tttgccgctg tggaatgtgt    5460
gtcagttagg gtgtggaaag tccccaggct ccccagcagg cagaagtatg caaagcatgc    5520
atctcaatta gtcagcaacc aggtgtggaa agtcccagg ctccccagca ggcagaagta    5580
tgcaaagcat gcatctcaat tagtcagcaa ccatagtccc gcccctaact ccgcccatcc    5640
cgcccctaac tccgcccagt tccgcccatt ctccgctcca tcgttcagat ccttatcgat    5700
tttaccaaat ttgtagaggt tttacttgct ttaaaaaacc tcccacacct ccccctgaac    5760
```

| | |
|---|---|
| ctgaaacata aaatgaatgc aattgttgtt gttaacttgt ttattgcagc ttataatggt | 5820 |
| tacaaataaa gcaatagcat cacaaatttc acaaataaag catttttttc actgcattct | 5880 |
| agttgtggtt tgtccaaact catcaatgta tcttatcatg tctgctcgaa gcggccggcc | 5940 |
| gccccgactc agcgctggta ccgtcgacgg ctgcgtctag ttgcagtagt tctccagctg | 6000 |
| gtagagggag cagatgctgg tacagcattg ttccacaatg ccacgcttct gtcgcgaccc | 6060 |
| ctccagggcc aagggctgca ggctgcctgc accagggccc cgccagct ccacctgccc | 6120 |
| cacctgcagg tcctctgcct cccgcttggt cctgggtgtg tagaagaagc ctcgttcccc | 6180 |
| gcacactagg tagagagctt ccaccagatc tgagccgcac aggtgttggt tcacaaaggc | 6240 |
| tgcggctggg tcaggtcccc agagggccag cagcgccagc aggggcagga ggcgcatcca | 6300 |
| cagggccatg gcagaaggtc gacgctagca agcttgggtc tccctatagt gagtcgtatt | 6360 |
| aatttcgata agccagttaa gcagtgggtt ctctagttag ccagagagct ctgcttatat | 6420 |
| agacctccca ccgtacacgc ctaccgccca tttgcgtcaa tggggcggag ttgttacgac | 6480 |
| attttggaaa gtcccgttga ttttggtgcc aaaacaaact cccattgacg tcaatgggt | 6540 |
| ggagacttgg aaatccccgt gagtcaaacc gctatccacg cccattgatg tactgccaaa | 6600 |
| accgcatcac catggtaata gcgatgacta atacgtagat gtactgccaa gtaggaaagt | 6660 |
| cccataaggt catgtactgg gcataatgcc aggcgggcca tttaccgtca ttgacgtcaa | 6720 |
| taggggcgt acttggcata gat | 6743 |

<210> SEQ ID NO 30
<211> LENGTH: 520
<212> TYPE: DNA
<213> ORGANISM: Artificial
<220> FEATURE:
<223> OTHER INFORMATION: SV40 polyadenylation signal and enhancer
      sequence

<400> SEQUENCE: 30

| | |
|---|---|
| gctgagtcgg ggcggccggc cgcttcgagc agacatgata agatacattg atgagtttgg | 60 |
| acaaaccaca actagaatgc agtgaaaaaa atgctttatt tgtgaaattt gtgatgctat | 120 |
| tgctttattt gtaaccatta taagctgcaa taaacaagtt aacaacaaca attgcattca | 180 |
| ttttatgttt caggttcagg gggaggtgtg ggaggttttt taaagcaagt aaaacctcta | 240 |
| caaattggt aaaatcgata aggatctgaa cgatggagcg gagaatgggc ggaactgggc | 300 |
| ggagttaggg gcgggatggg cggagttagg ggcgggacta tggttgctga ctaattgaga | 360 |
| tgcatgcttt gcatacttct gcctgctggg gagcctgggg actttccaca cctggttgct | 420 |
| gactaattga gatgcatgct ttgcatactt ctgcctgctg gggagcctgg ggactttcca | 480 |
| caccctaact gacacacatt ccacagcggc aaatttgagc | 520 |

<210> SEQ ID NO 31
<211> LENGTH: 141
<212> TYPE: DNA
<213> ORGANISM: Artificial
<220> FEATURE:
<223> OTHER INFORMATION: 5' ITR AAV2

<400> SEQUENCE: 31

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc t | 141 |

```
<210> SEQ ID NO 32
<211> LENGTH: 141
<212> TYPE: DNA
<213> ORGANISM: Artificial
<220> FEATURE:
<223> OTHER INFORMATION: 3' ITR AAV2

<400> SEQUENCE: 32
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                              141

<210> SEQ ID NO 33
<211> LENGTH: 230
<212> TYPE: DNA
<213> ORGANISM: Artificial
<220> FEATURE:
<223> OTHER INFORMATION: SV40 enhancer sequence

<400> SEQUENCE: 33
gcggagaatg ggcggaactg ggcggagtta ggggcgggat gggcggagtt aggggcggga      60
ctatggttgc tgactaattg agatgcatgc tttgcatact tctgcctgct ggggagcctg     120
gggactttcc acacctggtt gctgactaat tgagatgcat gctttgcata cttctgcctg     180
ctggggagcc tggggacttt ccacacccta actgacacac attccacagc                230
```

SINGLE-VECTOR GENE CONSTRUCT COMPRISING INSULIN AND GLUCOKINASE GENES

CROSS REFERENCE TO RELATED APPLICATIONS

The present application is the 35 U.S.C. 371 National Stage of International Application Number PCT/EP2016/050147, filed Jan. 7, 2016, which claims priority from European patent application 15150376.0, filed Jan. 7, 2015, the contents of which are incorporated herein by reference.

SEQUENCE LISTING SUBMISSION VIA EFS-WEB

A computer readable text file, entitled "031902-5028-US-Sequence-Listing.txt", created on or about Jul. 5, 2017 with a file size of about 159 KB contains the sequence listing for this application and is hereby incorporated by reference in its entirety.

FIELD OF THE INVENTION

The invention pertains to the medical field, comprising gene therapy compositions for use in the treatment of Diabetes Type 1 (T1D), Diabetes Type 2 (T2D) and/or Monogenic Diabetes, either in higher mammals, particularly pets and more particularly dogs; or in human beings.

BACKGROUND OF THE INVENTION

The two main forms of diabetes mellitus are type 1 (T1D) and type 2 (T2D) (Diabetes care, 1997, 20-1183-1197). TED is characterized by a severe lack of insulin production due to specific destruction of the pancreatic β-cells. β-cell loss in T1D is the result of an autoimmune mediated process, where a chronic inflammation called insulitis causes β-cell destruction (Eizirik D. L. et al, 2001, Diabetologia, 44:2115-2133 and Mathis D et al, 2001, Nature, 414: 792-798).

T1D is one of the most common endocrine and metabolic conditions in childhood; incidence is rapidly increasing, especially among young children. T1D is diagnosed when the autoimmune-mediated β-cell destruction is almost complete and patients need insulin-replacement therapy to survive. T1D in an adult may present itself as T2D, with a slow deterioration in metabolic control, and subsequent progression to insulin dependency. This form is called latent autoimmune diabetes mellitus in adults (LADA) (Diabetes Atlas 4th edition, 2009, International Diabetes Federation).

Lifelong insulin treatment is the therapy of choice for T1D. While lifelong treatment with exogenous insulin successfully manages diabetes, correct maintenance of a normoglycemic state can be challenging, Chronic hyperglycemia leads to severe microvascular (retinopathy and nephropathy), macrovascular (stroke, myocardial infarction), and neurological complications. These devastating complications can be prevented by normalization of blood glucose levels. Brittle diabetes is one example of a difficult-to-manage disease. Additionally, in many underdeveloped countries, especially in less privileged families, access to self-care tools and also to insulin is limited and this may lead to severe handicap and early death in diabetic children (Diabetes Atlas 4th edition, 2009, International Diabetes Federation, Beran D. et al 2006, Lancet, 368: 1689-1695, and Gale E. A., et al, 2006, Lancet, 368: 1626-1628). The most common cause of death in a child with diabetes, from a global perspective, is lack of access to insulin; thus the availability of a one-time gene therapy approach could make a difference in terms of prognosis when access to insulin is limited (Greenwood H. L. et al, 2006, PLoS Med 3. e381).

The reduction of hyperglycemia and maintenance of normoglycemia is a goal of any therapeutic approach to T1D. The current therapy for most diabetic patients is based on regular subcutaneous injections of mixtures of soluble (short-acting) insulin and lente (long-acting) insulin preparations. Other therapeutical approaches include gene therapy, which would offer the potential advantage of an administration of a viral vector, which could ideally provide the necessary insulin through the lifetime of the diabetic subject. WO 2012/007458 discloses the generation of two viral vectors, one expressing the insulin gene and one expressing the glucokinase gene as a treatment of diabetes. However, there is still a need for an improved diabetes treatment wherein a lower dose of vector could be used, wherein a concomitant expression of each gene is provided in each transfected cell, wherein an attractive yield of the virus could be obtained and/or wherein potential induced side effects due to immunological properties of the capsid are lowered.

Therefore there is still a need for designing new treatments for diabetes which do not have all the drawbacks of existing treatments.

DESCRIPTION OF THE INVENTION

The inventors designed improved gene therapy strategies based on adeno-associated viral (AAV) vector-mediated insulin/glucokinase muscle gene transfer to counteract diabetic hyperglycemia, dual-gene viral constructs encoding insulin and glucokinase were generated to ensure concomitant expression of both transgenes in transduced muscle cells.

Generation of dual-gene vectors will also allow decreasing vector dose, which in turn, should result in reduced risk of capsid-triggered immunity or other toxicities. From a regulatory point of view, the use of a dual vector will greatly facilitate the development of the treatment. Moreover, the use of a dual vector will allow for a dramatic reduction in the cost of manufacturing of AAV vectors. However, the skilled person knows that such a dual vector due to its size may not always be produced in sufficient yields to be used in a therapeutic setting and may not always be found to ensure acceptable expression levels of both transgenes. All dual vectors tested in the experimental part could be produced at acceptable titers and were found to be able to ensure acceptable expression levels of both transgenes.

Therefore the generation of such AAV dual vectors that contain both the insulin and glucokinase transgenes and potentially have improved therapeutic efficacy is not routine for a person skilled in the art, as demonstrated in the experimental part.

Viral Expression Construct

In a first aspect there is provided a viral expression construct comprising the elements a) and b):

a) a nucleotide sequence encoding an insulin operably linked to a first promoter, b) a nucleotide sequence encoding a glucokinase operably linked to a second promoter, and said viral expression construct comprises at least one of elements c), d) and e)

c) the first and the second promoters are positioned in reverse orientation within the expression construct, d) the first and the second promoters are positioned in reverse orientation within the expression construct and are located adjacent to each other and e) the first promoter is a CMV promoter, preferably a mini CMV promoter.

The definition of "viral expression construct", "promoter", "operatively linked" has been provided in the part of the description entitled "general definitions". Within the context of the invention, elements a) and b) define the expression cassette of a viral expression construct of the invention as further explained in the part of the description entitled "general definitions".

In the context of the invention, a nucleotide sequence encoding an insulin could be replaced by:
  i. a nucleotide sequence comprising a nucleotide sequence that has at least 60% sequence identity or similarity with SEQ ID NO: 1;
  ii. a nucleotide sequence the complementary strand of which hybridizes to a nucleic acid molecule of sequence of (i);
  iii. a nucleotide sequence the sequence of which differs from the sequence of a nucleic acid molecule of (i) or (ii) due to the degeneracy of the genetic code; or,
  iv. a nucleotide sequence that encodes an amino acid sequence that has at least 60% amino acid identity or similarity with an amino acid sequence encoded by a nucleotide sequence SEQ ID NO: 1.

A preferred nucleotide sequence encoding an insulin has at least 60%, 65%, 70%, 75%, 80%, 85%, 90%, 95%, 99%, 100% identity with SEQ ID NO:1. Identity may be assessed over the whole SEQ ID NO or over part thereof as explained in the part of the description entitled "general definitions". SEQ ID NO:1 is a nucleotide sequence encoding human insulin. The nucleotide sequence encoding an insulin may be derived from any insulin gene, preferably from dog, human or rat; or a mutated insulin gene, or a codon optimized insulin gene, preferably from human, dog or rat as for example disclosed in WO 2012/007458 which is incorporated by reference in its entirety.

An insulin as used herein exerts at least a detectable level of an activity of an insulin as known to the skilled person. An activity of an insulin is the regulation of hyperglycemia. This could be assessed using any technique known to the skilled person or as was done in the experimental part.

In the context of the invention, a nucleotide sequence encoding a glucokinase could be replaced by:
  i. a nucleotide sequence comprising a nucleotide sequence that has at least 60% sequence identity or similarity with SEQ ID NO: 2;
  ii. a nucleotide sequences the complementary strand of which hybridizes to a nucleic acid molecule of sequence of (i);
  iii. a nucleotide sequence the sequence of which differs from the sequence of a nucleic acid molecule of (i) or (ii) due to the degeneracy of the genetic code; or,
  iv. a nucleotide sequence that encodes an amino acid sequence that has at least 60% amino acid identity or similarity with an amino acid sequence encoded by a nucleotide sequence SEQ ID NO: 2.

A preferred nucleotide sequence encoding an insulin has at least 60%, 65%, 70%, 75%, 80%, 85%, 90%, 95%, 99%, 100% identity with SEQ ID NO:2. Identity may be assessed over the whole SEQ ID NO or over part thereof as explained in the part of the description entitled "general definitions". SEQ ID NO:2 is a nucleotide sequence encoding human glucokinase. The nucleotide sequence encoding a glucokinase may be derived from any glucokinase gene, preferably from human or rat; or a mutated glucokinase gene, or a codon optimized glucokinase gene, preferably from human or rat as for example disclosed in WO 2012/007458 which is incorporated by reference in its entirety.

A glucokinase as used herein exerts at least a detectable level of an activity of a glucokinase as known to the skilled person. An activity of a glucokinase is to phosphorylate glucose. This activity could be assessed using assays known to the skilled person.

In the context of the invention, a first promoter is a promoter which is operatively linked to the insulin nucleotide sequence defined above and a second promoter is a promoter which is operatively linked to the glucokinase nucleotide sequence defined above.

In one embodiment, the first and second promoters are different. It is therefore not excluded that the first and second promoters are identical. In one embodiment, both promoters are cell-specific and/or tissue-specific, preferably both promoters are specific for skeletal muscle.

A preferred first promoter is a CMV promoter (element e).

In the context of the invention, a nucleotide sequence of a CMV promoter could be replaced by a nucleotide sequence comprising a nucleotide sequence that has at least 60% sequence identity or similarity with SEQ ID NO: 3. A preferred nucleotide sequence has at least 60%, 65%, 70%, 75%, 80%, 85%, 90%, 95%, 99%, 100% identity with SEQ ID NO:3. Identity may be assessed over the whole SEQ ID NO or over part thereof as explained in the part of the description entitled "general definitions".

A first promoter as used herein (especially when his sequence is defined has having a minimal identity percentage with a given SEQ ID NO) should exert at least an activity of a promoter as known to the skilled person. Please be referred to the part of the description entitled "general definitions" for a definition of such activity. Preferably a first promoter defined has having a minimal identity percentage with a given SEQ ID NO should control transcription of the nucleotide sequence it is operably linked thereto (i.e. a nucleotide sequence encoding an insulin for the first promoter) as assessed in an assay known to the skilled person. The same holds for a second promoter with a nucleotide sequence encoding a glucokinase).

Preferably said CMV promoter is used together with an intronic sequence. In this context an intronic sequence may be replaced by a nucleotide sequence comprising a nucleotide sequence that has at least 60% sequence identity or similarity with SEQ ID NO: 4. A preferred nucleotide sequence has at least 60%, 65%, 70%, 75%, 80%, 85%, 90%, 95%, 99%, 100% identity with SEQ ID NO:4. Identity may be assessed over the whole SEQ ID NO or over part thereof as explained in the part of the description entitled "general definitions".

In a more preferred embodiment, a CMV promoter is a mini CMV promoter. In the context of the invention, a nucleotide sequence of a mini CMV promoter could be replaced by a nucleotide sequence comprising a nucleotide sequence that has at least 60% sequence identity or similarity with SEQ ID NO: 5. A preferred nucleotide sequence has at least 60%, 65%, 70%, 75%, 80%, 85%, 90%, 95%, 99%, 100% identity with SEQ ID NO:5. Identity may be assessed over the whole SEQ ID NO or over part thereof as explained in the part of the description entitled "general definitions".

In an even more preferred embodiment, a nucleotide sequence of a mini CMV promoter comprising a nucleotide sequence that has at least 60% sequence identity or similarity with SEQ ID NO: 24. A preferred nucleotide sequence has at least 60%, 65%, 70%, 75%, 80%, 85%, 90%, 95%, 99%, 100% identity with SEQ ID NO:24. Even more preferably, a nucleotide sequence a mini CMV promoter has at least 60% sequence identity or similarity with SEQ ID NO: 24 or at least 60%, 65%, 70%, 75%, 80%, 85%, 90%, 95%, 99%, 100% identity with SEQ ID NO:24 and has a length of 93, 94, 95, 96, 97, 98, 99, 100, 101, 102, 103, 104, 105, 106, 107, 109, 110 nucleotides.

Identity may be assessed over the whole SEQ ID NO or over part thereof as explained in the part of the description entitled "general definitions".

In an embodiment, said mini CMV promoter may be used together with the intronic sequence defined above.

A preferred second promoter is a RSV promoter.

In the context of the invention, a nucleotide sequence of a RSV promoter could be replaced by a nucleotide sequence comprising a nucleotide sequence that has at least 60% sequence identity or similarity with SEQ ID NO: 6. A preferred nucleotide sequence has at least 60%, 65%, 70%, 75%, 80%, 85%, 90%, 95%, 99%, 100% identity with SEQ ID NO:6. Identity may be assessed over the whole SEQ ID NO or over part thereof as explained in the part of the description entitled "general definitions".

Preferably said RSV promoter is used together with an intronic sequence. In this context an intronic sequence may be replaced by a nucleotide sequence comprising a nucleotide sequence that has at least 60% sequence identity or similarity with SEQ ID NO: 23. A preferred nucleotide sequence has at least 60%, 65%, 70%, 75%, 80%, 85%, 90%, 95%, 99%, 100% identity with SEQ ID NO:23. Identity may be assessed over the whole SEQ ID NO or over part thereof as explained in the part of the description entitled "general definitions".

In a preferred embodiment, the first and the second promoters are positioned in reverse orientation within the viral expression construct (element c). In this embodiment, it implies that the insulin and the glucokinase nucleotide sequences are read in opposite directions. More preferably, in this configuration, the first and the second promoters are adjacent to each other (element d). In this context, "adjacent" means that 0, 2, 5, 10, 20, 30, 50, 100, 200, 300, 400, 500, 600, 700 bases are present between the first and the second promoters.

Several viral expression constructs are therefore encompassed by the present invention:
A viral expression construct comprising elements a), b) and c),
A viral expression construct comprising elements a), b) and d),
A viral expression construct comprising elements a), b) and e),
A viral expression construct comprising elements a), b) and e), wherein the CMV promoter is a mini CMV promoter,
A viral expression construct comprising elements a), b), d) and e),
A viral expression construct comprising elements a), b), d) and e), wherein the CMV promoter is a mini CMV promoter.

For each of these preferred viral expression constructs defined above, the second promoter is preferably a RSV promoter as defined herein.

In an embodiment, a viral expression construct is encompassed comprising elements a) and b) and at least one of elements c), d) and e), wherein the first promoter is a CMV promoter, preferably a mini CMV promoter and/or wherein the second promoter is a RSV promoter.

Additional sequences may be present in the viral expression construct of the invention as explained in detail in the part of the description entitled "general definitions". Preferred additional sequences include ITRs, SV40 (i.e. which means SV40 polyadenylation signal) (SEQ ID NO: 22), bGH (i.e. which means bGH polyadenylation signal) (SEQ ID NO:7), SV40 polyadenylation signal and enhancer sequence (SEQ ID NO:30), SV40 enhancer sequence (SEQ ID NO: 33). Within the context of the invention, "ITRs" is intended to encompass one 5'ITR and one 3'ITR, each being derived from the genome of a AAV. Preferred ITRs are from AAV2 and are represented by SEQ ID NO: 31 (5' ITR) and SEQ ID NO: 32 (3' ITR). Within the context of the invention, it is encompassed to use the SV40 enhancer sequence either included in the SV40 polyadenylation signal (as SEQ ID NO:30) or as a separate sequence (as SEQ ID NO:33). It is also encompassed to use the SV40 polyadenylation signal and the SV40 enhancer sequence as two separate sequences (SEQ ID NO:22 and SEQ ID NO: 33) or as a single sequence (SEQ ID NO:30).

Each of these additional sequences may be present in the viral expression construct of the invention (see for example as depicted in FIGS. 1, 2, 4, 7, 13, 16).

In an embodiment, the viral expression construct comprising elements a) and b), and at least one of elements c), d) and e) as earlier defined and further comprises:
ITRs that flank the expression cassette of said construct,
SV40 or bGH polyadenylation signals that are located at the 3' of the nucleotide sequence encoding the glucokinase or insulin and/or
SV40 polyadenylation signals and enhancer sequence that is located at the 3' of the nucleotide sequence encoding the glucokinase or insulin and/or
SV40 enhancer sequence that is located at the 5' of the nucleotide sequence encoding the glucokinase or insulin.

In a preferred embodiment, the viral expression construct comprising elements a) and b), and at least one of elements c), d) and e) as earlier defined and further comprises ITRs that flank the expression cassette of said construct and optionally
SV40 or bGH polyadenylation signals that are located at the 3' of the nucleotide sequence encoding the glucokinase or insulin and/or
SV40 polyadenylation signals and enhancer sequence that is located at the 3' of the nucleotide sequence encoding the glucokinase or insulin and/or
SV40 enhancer sequence that is located at the 5' of the nucleotide sequence encoding the glucokinase or insulin.

If the SV40 enhancer sequence is not included in the SV40 polyadenylation signal, the SV40 enhancer sequence is preferably located 5' of the nucleotide sequence encoding the glucokinase or insulin.

These sequences were used in the experimental part in some of the constructs identified herein.

Therefore in one embodiment, for each of these preferred viral expression constructs defined above an additional sequence may be present selected from the group consisting of: ITRs, SV40 polyadenylation signal, bGH polyadenylation signal, SV40 polyadenylation signal and enhancer sequence, SV40 enhancer sequence.

In a preferred embodiment, a viral expression construct is encompassed comprising elements a) and b) and at least one of elements c), d) and e),
wherein the first promoter is a CMV promoter, preferably a mini CMV promoter and/or wherein the second promoter is a RSV promoter and/or
wherein an additional sequence is present which is selected from the group consisting of: ITRs, SV40 polyadenylation signal, bGH polyadenylation signal, SV40 polyadenylation signal and enhancer sequence, SV40 enhancer sequence.

Preferred ITRs are those of AAV2 which are represented by SEQ ID NO: 31 (5' ITR) and SEQ ID NO: 32 (3' ITR).

Preferred viral expression constructs comprise elements a) and b) and at least one of elements c), d) and e) and are such that the expression cassette as defined by elements a), b) and at least one of elements c), d), e) is flanked by a 5'ITR and a 3'ITR.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 polyadenylation signals are present.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 and bGH polyadenylation signals are present.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 enhancer sequence is present.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 enhancer sequence and SV40 polyadenylation signals are present as two separate sequences.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 enhancer sequence and SV40 polyadenylation signals are present as two separate sequences. In this embodiment, bGH polyadenylation signals are also present.

Other preferred viral expression constructs comprise elements a) and b) and at least one of elements c), d) and e) and are such that the expression cassette as defined by elements a), b) and at least one of c), d), e) is flanked by a 5'ITR and a 3'ITR. In addition, SV40 polyadenylation signals and enhancer sequence are present together with bGH polyadenylation signals are present.

Most preferred designed viral expression constructs include:
Construct A (represented by a nucleotide sequence comprising SEQ ID NO: 8),
Construct D (represented by a nucleotide sequence comprising SEQ ID NO: 9),
Construct E (represented by a nucleotide sequence comprising SEQ ID NO: 10),
Construct F (represented by a nucleotide sequence comprising SEQ ID NO: 11),
Construct G (represented by a nucleotide sequence comprising SEQ ID NO: 12),
Construct J (represented by a nucleotide sequence comprising SEQ ID NO: 13),
Construct K (represented by a nucleotide sequence comprising SEQ ID NO: 14),
Construct L (represented by a nucleotide sequence comprising SEQ ID NO: 15),
Construct M (represented by a nucleotide sequence comprising SEQ ID NO: 16).
Construct Q (represented by a nucleotide sequence comprising SEQ ID NO: 27).
Construct S (represented by a nucleotide sequence comprising SEQ ID NO: 29).

As the skilled person will understand, each of these viral expression constructs already comprise two ITRs from AAV2 (i.e. SEQ ID NO: 31 (5' ITR) and SEQ ID NO: 32 (3' ITR)).

Best results were obtained with constructs F (SEQ ID NO: 11), construct J (SEQ ID NO: 13), construct K (SEQ ID NO: 14), construct L (SEQ ID NO: 15), construct M (SEQ ID NO: 16), construct Q (SEQ ID NO: 27) and construct S (SEQ ID NO: 29).

Figure 13:
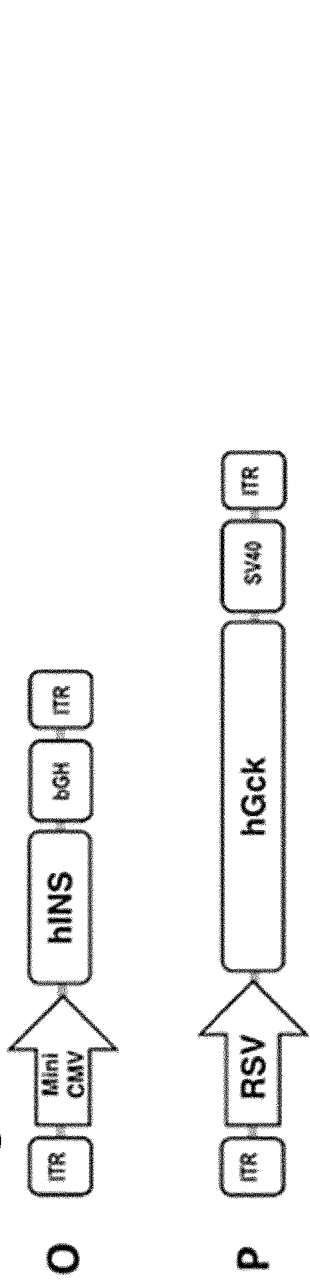

Constructs L and Q comprise both bGH polyadenylation signal and SV40 polyadenylation signal sequences, the order of each of these 3'untranslated sequences being interchanged (see FIGS. 7 and 13).

Figure 16:
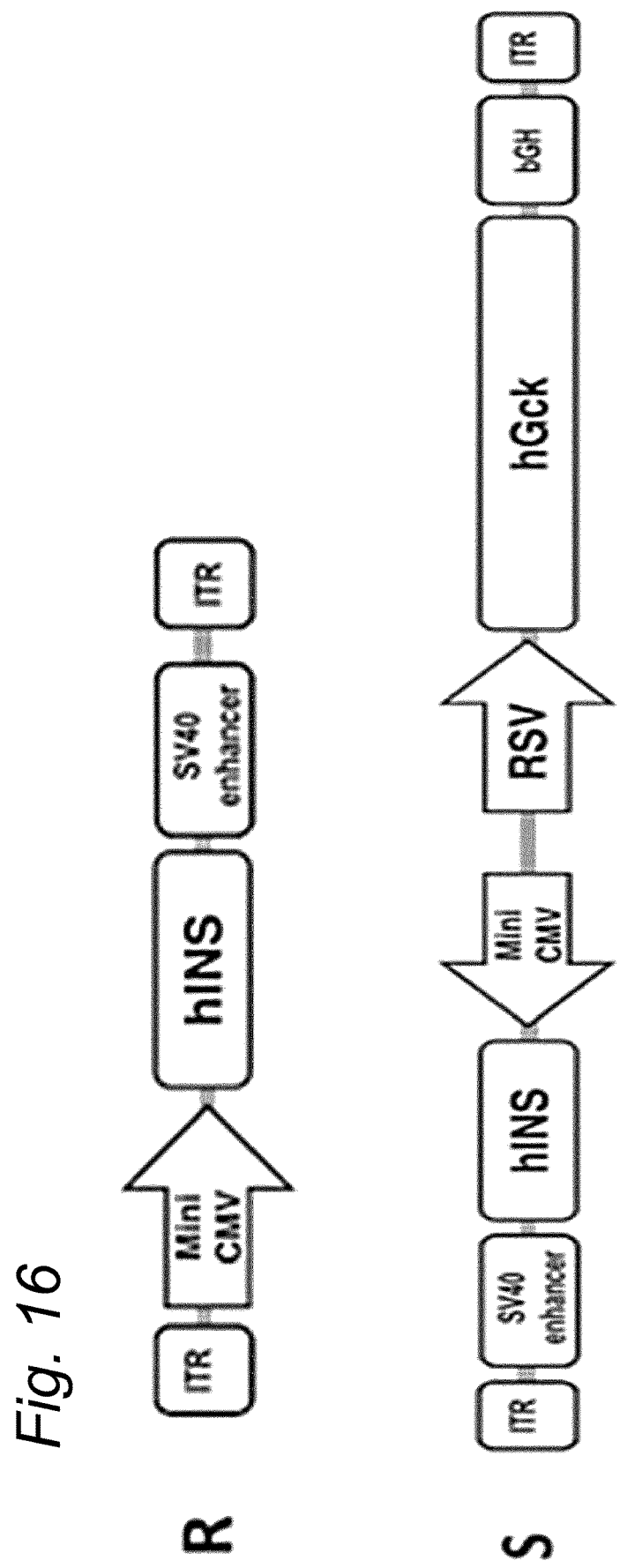

Construct S comprises both bGH polyadenylation signal and SV40 polyadenylation signal and enhancer sequences (see FIG. 16).

As explained in the general part entitled "general definitions", throughout this application, each time one refers to a specific nucleotide sequence SEQ ID NO (take SEQ ID NO: 8, 9, 10, 11, 12, 13, 14, 15, 16, 27, 29) representing the preferred constructs designed herein, one may replace it by:
  i. a nucleotide sequence comprising a nucleotide sequence that has at least 60% sequence identity or similarity with SEQ ID NO: 8, 9, 10, 11, 12, 13, 14, 15, 16, 27 or 29;
  ii. a nucleotide sequences the complementary strand of which hybridizes to a nucleic acid molecule of sequence of (i);
  iii. a nucleotide sequence the sequence of which differs from the sequence of a nucleic acid molecule of (i) or (ii) due to the degeneracy of the genetic code.

Each nucleotide sequence described herein by virtue of its identity percentage (at least 60%) with a given nucleotide sequence respectively has in a further preferred embodiment an identity of at least 65%, 70%, 75%, 80%, 85%, 90%, 95%, 97%, 98%, 99% or more identity with the given nucleotide respectively. In a preferred embodiment, sequence identity is determined by comparing the whole length of the sequences as identified herein. Unless otherwise indicated herein, identity with a given SEQ ID NO means identity or similarity based on the full length of said sequence (i.e. over its whole length or as a whole).

A construct defined by its minimum identity (i.e. at least 60%) to a given SEQ ID NO as identified above is encompassed within the scope of the invention when this construct or a viral expression construct or a viral vector comprising this construct or a composition comprising this construct or vector is able to induce the expression of insulin and glucokinase in a cell, preferably in a muscle cell. The expression of both genes could be assessed using techniques known to the skilled person. In a preferred embodiment, said expression is assessed as carried out in the experimental part.

In a preferred embodiment, a viral expression construct is such that the construct is represented by a nucleotide sequence comprising SEQ ID NO: 8, 9, 10, 11, 12, 13, 14, 15, 16, 27 or 29 or a sequence having at least 60% identity with SEQ ID NO: 8, 9, 10, 11, 12, 13, 14, 15, 16, 27 or 29.

Viral Vector

In a further aspect, there is provided a viral vector. A viral vector comprises a viral expression construct as defined above. A viral vector is further defined in the part of the description entitled "general definitions". Preferably a viral vector is a retrovirus vector, an adenovirus vector, an adeno-associated virus vector, a herpesvirus vector, a polyoma virus vector or a vaccinia virus vector. More detail is also provided in the part of the description entitled "general definitions".

In an embodiment, an adeno-associated viral vector is used comprising each of the elements defined earlier herein and a rAAV based genome comprising inverted terminal repeats (ITR) or a part thereof. Preferred ITRs are those of AAV2 which are represented by SEQ ID NO: 31 (5' ITR) and SEQ ID NO: 32 (3' ITR).

Preferably, said adeno-associated viral vector is an adeno-associated virus vector, more preferably an AAV1 vector.

A viral expression construct and a viral vector of the invention are preferably for use as a medicament. The medicament is preferably for preventing, delaying, curing, reverting and/or treating a diabetes. Diabetes may be Diabetes Type 1, Diabetes Type 2 or Monogenic Diabetes. The subject treated may be a higher mammal, e.g. cats, rodent, (preferably mice, rats, gerbils and guinea pigs, and more preferably mice and rats), or dogs, or in human beings.

Composition

In a further aspect there is provided a composition comprising a viral expression construct or a viral vector as defined earlier herein. This composition is preferably called a gene therapy composition. Preferably, the composition is a pharmaceutical composition said pharmaceutical composition comprising a pharmaceutically acceptable carrier, adjuvant, diluents, solubilizer, filler, preservative and/or excipient.

Such pharmaceutically acceptable carrier, filler, preservative, solubilizer, diluent and/or excipient may for instance be found in Remington: The Science and Practice of Pharmacy, 20th Edition. Baltimore, Md.: Lippincott Williams & Wilkins, 2000.

In a preferred embodiment, said composition is for use as a medicament, preferably for preventing, delaying, curing, reverting and/or treating a diabetes. Diabetes may be Diabetes Type 1, Diabetes Type 2 or Monogenic Diabetes. The subject treated may be a higher mammal, e.g. cats, rodent, (preferably mice, rats, gerbils and guinea pigs, and more preferably mice and rats), or dogs, or in human beings.

Said viral expression construct, viral vector and/or composition are preferably said to be able to be used for preventing, delaying, reverting, curing and/or treating a diabetes, when said viral expression construct, viral vector and/or composition are able to exhibit an anti-diabetes effect. An anti-diabetes effect may be reached when glucose disposal in blood is increased and/or when glucose tolerance is improved. This could be assessed using techniques known to the skilled person or as done in the experimental part. In this context, "increase" (respectively "improvement") means at least a detectable increase (respectively a detectable improvement) using an assay known to the skilled person or using assays as carried out in the experimental part.

An anti-diabetes effect may also be observed when the progression of a typical symptom (i.e. insulitis, beta cell loss, . . . ) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of diabetes, including clinical examination and routine laboratory tests. Such methods include both macroscopic and microscopic methods, as well as molecular methods, X-rays, biochemical, immunohistochemical and others.

A medicament as defined herein (viral expression construct, viral vector, composition) is preferably able to alleviate one symptom or one characteristic of a patient or of a cell, tissue or organ of said patient if after at least one week, one month, six month, one year or more of treatment using a viral expression vector or a composition of the invention, said symptom or characteristic is no longer detectable.

A viral expression construct or a viral vector or a composition as defined herein for use according to the invention may be suitable for administration to a cell, tissue and/or an organ in vivo of individuals affected by or at risk of developing a diabetes, and may be administered in vivo, ex vivo or in vitro. Said combination and/or composition may be directly or indirectly administrated to a cell, tissue and/or an organ in vivo of an individual affected by or at risk of developing a diabetes, and may be administered directly or indirectly in vivo, ex vivo or in vitro. A preferred administration mode is intramuscular.

A viral expression construct or a viral vector or a composition of the invention may be directly or indirectly administered using suitable means known in the art. Improvements in means for providing an individual or a cell, tissue, organ of said individual with a viral expression construct or a viral vector or a composition of the invention are anticipated, considering the progress that has already thus far been achieved. Such future improvements may of course be incorporated to achieve the mentioned effect of the invention. A viral expression construct or a viral vector or a composition can be delivered as is to an individual, a cell, tissue or organ of said individual. Depending on the disease or condition, a cell, tissue or organ of said individual may be as earlier defined herein. When administering a viral expression construct or a viral vector or a composition of the invention, it is preferred that such viral expression construct or vector or composition is dissolved in a solution that is compatible with the delivery method. For intravenous, subcutaneous, intramuscular, intrathecal, intraarticular and/or intraventricular administration it is preferred that the solution is a physiological salt solution. Intramuscular administration is a preferred administration mode. More preferably intramuscular administration is carried out using a multi-needle. As encompassed herein, a therapeutically effective dose of a viral expression construct, vector or composition as mentioned above is preferably administered in a single and unique dose hence avoiding repeated periodical administration. More preferably, the single dose is administered to muscle tissue, and even more preferably by means of a unique multi-needle injection.

A further compound may be present in a composition of the invention. Said compound may help in delivery of the composition. Below is provided a list of suitable compounds: compounds capable of forming complexes, nanoparticles, micelles and/or liposomes that deliver each constituent as defined herein, complexed or trapped in a vesicle or liposome through a cell membrane. Many of these compounds are known in the art. Suitable compounds comprise polyethylenimine (PEI), or similar cationic polymers, including polypropyleneimine or polyethylenimine copolymers (PECs) and derivatives, synthetic amphiphiles (SAINT-18), Lipofectin™, DOTAP.

Depending on their identity, the skilled person will know which type of formulation is the most appropriate for the composition, as defined herein.

In this context a further compound may be insulin that could be regularly injected.

Method/Use

In a further aspect there is provided a method for preventing, delaying, reverting, curing and/or treating a diabetes wherein a viral expression construct or viral vector or composition as defined herein as defined herein is being used.

Such a method is preferably for alleviating one or more symptom(s) of diabetes in an individual, in a cell, tissue or organ of said individual or alleviate one or more characteristic(s) or symptom(s) of a cell, tissue or organ of said individual, the method comprising administering to said individual a viral expression construct or viral vector or a composition as defined herein.

In a further aspect there is provided a use of a viral expression construct or viral vector or a composition as defined herein for the manufacture of a medicament for preventing, delaying, reverting, curing and/or treating a diabetes.

Diabetes and the type of subject treated have been earlier defined herein.

In one embodiment said method or use is performed in vitro, for instance using a cell culture. Preferably, said method or use is in vivo. Each feature of these methods/uses has already been defined herein. In a method of the invention, a viral expression construct or vector and/or a composition may be combined with an additional compound known to be used for treating diabetes in an individual.

In a preferred embodiment, a treatment in a use or in a method according to the invention does not have to be repeated. Alternatively in a use or a method according to the invention said administration of the viral expression construct or of said composition may be repeated each year or each 2, 3, 4, 5, 6 years.

GENERAL DEFINITIONS

Identity/Similarity

In the context of the invention, a protein or a protein fragment as insulin or glucokinase is represented by an amino acid sequence.

In the context of the invention, a nucleic acid molecule as a nucleic acid molecule encoding an insulin or a nucleic acid molecule encoding a glucokinase is represented by a nucleic acid or nucleotide sequence which encodes a protein or a polypeptide or a protein fragment or a peptide or a derived peptide. A nucleic acid molecule may comprise a regulatory region.

It is to be understood that each nucleic acid molecule or protein or protein fragment or peptide or derived peptide or polypeptide or construct as identified herein by a given Sequence Identity Number (SEQ ID NO) is not limited to this specific sequence as disclosed. Each gene sequence or nucleotide sequence or nucleic acid sequence as identified herein encoding a given protein or polypeptide or construct or protein fragment or peptide or derived peptide or is itself a protein or a protein fragment or polypeptide or construct or peptide or derived peptide. Throughout this application, each time one refers to a specific nucleotide sequence SEQ ID NO (take SEQ ID NO: X as example) encoding a given polypeptide, one may replace it by:

i. a nucleotide sequence comprising a nucleotide sequence that has at least 60% sequence identity or similarity with SEQ ID NO: X;
ii. a nucleotide sequences the complementary strand of which hybridizes to a nucleic acid molecule of sequence of (i);
iii. a nucleotide sequence the sequence of which differs from the sequence of a nucleic acid molecule of (i) or (ii) due to the degeneracy of the genetic code; or,
iv. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

Each non-coding nucleotide sequence (i.e. of a promoter or of another regulatory region) could be replaced by a nucleotide sequence comprising a nucleotide sequence that has at least 60% sequence identity or similarity with SEQ ID NO: A. A preferred nucleotide sequence has at least 60%, 65%, 70%, 75%, 80%, 85%, 90%, 95%, 99%, 100% identity with SEQ ID NO:A. Identity may be assessed over the whole SEQ ID NO or over part thereof as explained herein. In a preferred embodiment, such non-coding nucleotide sequence such as a promoter exhibits or exerts at least an activity of such a non-coding nucleotide sequence such as an activity of a promoter as known to the skilled person.

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10%, 20%, 30%, 40%, 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Gene or Coding Sequence

"Gene" or "coding sequence" or "nucleic acid" or "nucleic" refers to a DNA or RNA region (the transcribed region) which "encodes" a particular protein such as an insulin or a glucokinase. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3'nontranslated sequence, comprising a polyadenylation site or a signal sequence. A chimeric or recombinant gene (such as a chimeric insulin gene or a chimeric glucokinase gene) is a gene not normally found in nature, such as a gene in which for example the promoter is not associated in nature with part or all of the transcribed DNA region. "Expression of a gene" refers to the process wherein a gene is transcribed into an RNA and/or translated into an active protein.

Promoter

As used herein, the term "promoter" refers to a nucleic acid fragment that functions to control the transcription of one or more genes (or coding sequence), located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is preferentially active in specific types of differentiated cells/tissues, such as preferably a muscle cell or tissue derived therefrom.

Operably Linked

"Operably linked" is defined herein as a configuration in which a control sequence such as a promoter sequence or regulating sequence is appropriately placed at a position relative to the nucleotide sequence of interest, preferably coding for an insulin or a glucokinase such that the promoter or control or regulating sequence directs or affects the transcription and/or production or expression of the nucleotide sequence of interest, preferably encoding an insulin or a glucokinase in a cell and/or in a subject. For instance, a promoter is operably linked to a coding sequence if the promoter is able to initiate or regulate the transcription or expression of a coding sequence, in which case the coding sequence should be understood as being "under the control of" the promoter. When one or more nucleotide sequences and/or elements comprised within a construct are defined herein to be "configured to be operably linked to an optional nucleotide sequence of interest", said nucleotide sequences and/or elements are understood to be configured within said construct in such a way that these nucleotide sequences and/or elements are all operably linked to said nucleotide sequence of interest once said nucleotide sequence of interest is present in said construct.

Viral Expression Construct

An expression construct carries a genome that is able to stabilize and remain episomal in a cell. Within the context of the invention, a cell may mean to encompass a cell used to make the construct or a cell wherein the construct will be administered. Alternatively a construct is capable of integrating into a cell's genome, e.g. through homologous recombination or otherwise. A particularly preferred expression construct is one wherein a nucleotide sequence encoding an insulin and a glucokinase as defined herein, is operably linked to a first and a second promoters as defined herein wherein said promoters are capable of directing expression of said nucleotide sequences (i.e. coding sequences) in a cell. Such a preferred expression construct is said to comprise an expression cassette. An expression cassette as used herein comprises or consists of a nucleotide sequence encoding an insulin and an nucleotide sequence encoding a glucokinase, each of them being operably linked to a promoter (i.e. a first and a second promoter) wherein said promoters are capable of directing expression of said nucleotide sequences. A viral expression construct is an expression construct which is intended to be used in gene therapy. It is designed to comprise part of a viral genome as later defined herein.

Expression constructs disclosed herein could be prepared using recombinant techniques in which nucleotide sequences encoding said insulin and glucokinased are expressed in a suitable cell, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34: 315 (describing cassette mutagenesis).

Typically, a nucleic acid or nucleotide sequence encoding an insulin and a glucokinase are used in an expression construct or expression vector. The phrase "expression vector" generally refers to a nucleotide sequence that is capable of effecting expression of a gene in a host compatible with such sequences. These expression vectors typically include at least suitable promoter sequences and optionally, transcription termination signals. An additional factor necessary or helpful in effecting expression can also be used as described herein. A nucleic acid or DNA or nucleotide sequence encoding an insulin and a glucokinase is incorporated into a DNA construct capable of introduction into and expression in an in vitro cell culture. Specifically, a DNA construct is suitable for replication in a prokaryotic host, such as bacteria, e.g., *E. coli*, or can be introduced into a cultured mammalian, plant, insect, (e.g., Sf9), yeast, fungi or other eukaryotic cell lines.

A DNA construct prepared for introduction into a particular host may include a replication system recognized by the host, an intended DNA segment encoding a desired polypeptide, and transcriptional and translational initiation and termination regulatory sequences operably linked to the polypeptide-encoding segment. The term "operably linked" has already been defined herein. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression vector includes the replication system and transcriptional and translational regulatory sequences together with the insertion site for the polypeptide encoding segment can be employed. In most cases, the replication system is only functional in the cell that is used to make the vector (bacterial cell as *E. Coli*). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal.

Viral Vector

A viral vector or a gene therapy vector is a vector that comprises a viral expression construct as defined above.

A viral vector or a gene therapy vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an Adenoviral and Adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications. (Russell, 2000, J. Gen. Virol. 81: 2573-2604; Goncalves, 2005, Virol J. 2(1):43) as indicated above. AAV vectors are even more preferred since they are known to result in very stable long term expression of transgene expression (up to 9 years in dog (Niemeyer et al, Blood. 2009 Jan. 22; 113(4):797-806) and ~2 years in human (Nathwani et al, N Engl J Med. 2011 Dec. 22; 365(25): 2357-65, Simonelli et al, Mol Ther. 2010 March; 18(3):643-50. Epub 2009 Dec. 1.)). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et a, 2004, Eye 18(11):1049-55, Nathwani et al, N Engl J Med. 2011 Dec. 22; 365(25): 2357-65, Apparailly et al, Hum Gene Ther. 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and Vigna et al. (2000, J Gene Med 2000; 2: 308-16).

Other suitable gene therapy vectors include a herpes virus vector, a polyoma virus vector or a vaccinia virus vector.

A gene therapy vector comprises a nucleotide sequence encoding an insulin and a glucokinase to be expressed, whereby each of said nucleotide sequence is operably linked to the appropriate regulatory sequences. Such regulatory sequence will at least comprise a promoter sequence. Suitable promoters for expression of a nucleotide sequence encoding an insulin and a glycokinase from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Suitable promoters are described below.

Several inducible promoter systems have been described that may be induced by the administration of small organic or inorganic compounds. Such inducible promoters include those controlled by heavy metals, such as the metallothionine promoter (Brinster et al. 1982 Nature 296: 39-42; Mayo et al. 1982 Cell 29: 99-108), RU-486 (a progesterone antagonist) (Wang et al. 1994 Proc. Natl. Acad. Sci. USA 91: 8180-8184), steroids (Mader and White, 1993 Proc. Natl. Acad. Sci. USA 90: 5603-5607), tetracycline (Gossen and Bujard 1992 Proc. Natl. Acad. Sci. USA 89: 5547-5551; U.S. Pat. No. 5,464,758; Furth et al. 1994 Proc. Natl. Acad. Sci. USA 91: 9302-9306; Howe et al. 1995 J. Biol. Chem. 270: 14168-14174; Resnitzky et al. 1994 Mol. Cell. Biol. 14: 1669-1679; Shockett et al. 1995 Proc. Natl. Acad. Sci. USA 92: 6522-6526) and the tTAER system that is based on the multi-chimeric transactivator composed of a tetR polypeptide, as activation domain of VP16, and a ligand binding domain of an estrogen receptor (Yee et al., 2002, U.S. Pat. No. 6,432,705).

A gene therapy vector may optionally comprise a further nucleotide sequence coding for a further polypeptide. A further polypeptide may be a (selectable) marker polypeptide that allows for the identification, selection and/or screening for cells containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3$^{rd}$ edition), Cold Spring Harbor Laboratory, Cold Spring Harbor Laboratory Press, New York.

A gene therapy vector is preferably formulated in a pharmaceutical composition as defined herein. In this context, a pharmaceutical composition may comprise a suitable pharmaceutical carrier as earlier defined herein.

Adeno-Associated Virus Vector (AAV Vector)

A preferred viral vector or a preferred gene therapy vector is an AAV vector. An AAV vector as used herein preferably comprises a recombinant AAV vector (rAAV). A "rAAV vector" as used herein refers to a recombinant vector comprising part of an AAV genome encapsidated in a protein shell of capsid protein derived from an AAV serotype as explained herein. Part of an AAV genome may contain the inverted terminal repeats (ITR) derived from an adeno-associated virus serotype, such as AAV1, AAV2, AAV3, AAV4, AAV5 and others. Preferred ITRs are those of AAV2 which are represented by SEQ ID NO: 31 (5' ITR) and SEQ ID NO: 32 (3' ITR).

Protein shell comprised of capsid protein may be derived from an AAV serotype such as AAV1, 2, 3, 4, 5 and others. A preferred AAV capsid is a AAV1 capsid. A preferred ITR is from the AAV2. A protein shell may also be named a capsid protein shell. rAAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the rAAV vector genome ITR.

A nucleic acid molecule represented by a nucleic acid sequence of choice is preferably inserted between the rAAV genome or ITR sequences as identified above, for example an expression construct comprising an expression regulatory element operably linked to a coding sequence and a 3' termination sequence. Said nucleic acid molecule may also be called a transgene.

"AAV helper functions" generally refers to the corresponding AAV functions required for rAAV replication and packaging supplied to the rAAV vector in trans. AAV helper functions complement the AAV functions which are missing in the rAAV vector, but they lack AAV ITRs (which are provided by the rAAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct. Introduction of the helper construct into the host cell can occur e.g. by transformation, transfection, or transduction prior to or concurrently with the introduction of the rAAV genome present in the rAAV vector as identified herein. The AAV helper constructs of the invention may thus be chosen such that they produce the desired combination of serotypes for the rAAV vector's capsid protein shell on the one hand and for the rAAV genome present in said rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

A "transgene" is herein defined as a gene or a nucleic acid molecule (i.e. a molecule encoding an insulin and a molecule encoding a glucokinase) that has been newly introduced into a cell, i.e. a gene that may be present but may normally not be expressed or expressed at an insufficient level in a cell. In this context, "insufficient" means that although said insulin and glucokinase is expressed in a cell, a condition and/or disease as defined herein could still be developed. In this case, the invention allows the overexpression of an insulin and a glucokinase. The transgene may comprise sequences that are native to the cell, sequences that naturally do not occur in the cell and it may comprise combinations of both. A transgene may contain sequences coding for an insulin and a glucokinase and/or additional proteins as earlier identified herein that may be operably linked to appropriate regulatory sequences for expression of the sequences coding for an insulin and a glucokinase in the cell. Preferably, the transgene is not integrated into the host cell's genome.

"Transduction" refers to the delivery of an insulin and a glucokinase into a recipient host cell by a viral vector. For example, transduction of a target cell by a rAAV vector of the invention leads to transfer of the rAAV genome contained in that vector into the transduced cell. "Host cell" or "target cell" refers to the cell into which the DNA delivery takes place, such as the muscle cells of a subject. AAV vectors are able to transduce both dividing and non-dividing cells.

Production of an AAV Vector

The recombinant AAV vector, including all combinations of AAV serotype capsid and AAV genome ITRs, is produced using methods known in the art, as described in Pan et al. (J. of Virology 1999, Vol 73(4):3410-3417) and Clark et al. (Human Gene Therapy, 1999, 10:1031-1039), incorporated herein by reference. In short, the methods generally involve (a) the introduction of the rAAV genome into a host cell, (b) the introduction of an AAV helper construct into the host cell, wherein the helper construct comprises the viral functions missing from the rAAV genome and (c) introducing a helper virus into the host cell. All functions for rAAV vector replication and packaging need to be present, to achieve replication and packaging of the rAAV genome into rAAV vectors. The introduction into the host cell can be carried out using standard virological techniques and can be simultaneously or sequentially. Finally, the host cells are cultured to produce rAAV vectors and are purified using standard techniques such as CsCl gradients (Xiao et al. 1996, J. Virol. 70: 8098-8108). Residual helper virus activity can be inactivated using known methods, such as for example heat inactivation. The purified rAAV vector is then ready for use in the methods. High titres of more than $10^{12}$ particles per ml and high purity (free of detectable helper and wild type viruses) can be achieved (Clark et al. supra and Flotte et al. 1995, Gene Ther. 2: 29-37).

The rAAV genome present in a rAAV vector comprises at least the nucleotide sequences of the inverted terminal repeat regions (ITR) of one of the AAV serotypes (preferably the ones of serotype AAV2 as disclosed earlier herein), or nucleotide sequences substantially identical thereto or nucleotide sequences having at least 60% identity thereto, and nucleotide sequence encoding an insulin and a glucokinase (under control of a suitable regulatory element) inserted between the two ITRs. A vector genome requires the use of flanking 5' and a 3' ITR sequences to allow for efficient packaging of the vector genome into the rAAV capsid.

The complete genome of several AAV serotypes and corresponding ITR has been sequenced (Chiorini et al. 1999, J. of Virology Vol. 73, No. 2, p 1309-1319). They can be either cloned or made by chemical synthesis as known in the art, using for example an oligonucleotide synthesizer as supplied e.g. by Applied Biosystems Inc. (Fosters, Calif., USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the wild type AAV sequence between the ITRs can be replaced with the desired nucleotide sequence.

Preferably, the rAAV genome as present in a rAAV vector does not comprise any nucleotide sequences encoding viral proteins, such as the rep (replication) or cap (capsid) genes of AAV. This rAAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV genome as present in said rAAV vector further comprises a promoter sequence operably linked to the nucleotide sequence encoding an insulin and a glucokinased. Preferred promoter sequences are promoters which confer expression in muscle cells and/or muscle tissues. Examples of such promoters include a CMV and a RSV promoters as earlier defined herein.

A suitable 3' untranslated sequence may also be operably linked to the nucleotide sequence encoding an insulin and a glucokinase. Suitable 3' untranslated regions may be those naturally associated with the nucleotide sequence or may be derived from different genes, such as for example the bovine growth hormone 3' untranslated region (bGH polyadenylation signal (SEQ ID NO:7), SV40 polyadenylation signal (SEQ ID NO:22), SV40 polyadenylation signal and enhancer sequence (SEQ ID NO: 30).

Within the context of the invention, when one refers to "SV40", it means SV40 polyadenylation signal. When one refers to "SV40 enhancer sequence", it means SV40 polyadenylation signal and enhancer sequence. However, the invention also encompasses the use of SV40 polyadenylation signal (SEQ ID NO:22) and SV40 enhancer sequence (SEQ ID NO:33) as two separate sequences.

These sequences were used in the preferred constructs prepared in the experimental part. Constructs L and Q comprise both bGH polyA and SV40 polyadenylation signal sequences, the order of each of these 3'untranslated sequences being interchanged (see FIGS. 7 and 13).

Construct S comprises both bGH polyA and SV40 polyadenylation signal and enhancer sequences (see FIG. 16).

Optionally, additional nucleotide sequences may be operably linked to the nucleotide sequence(s) encoding an insulin and a glucokinase, such as nucleotide sequences encoding signal sequences, nuclear localization signals, expression enhancers, and the like.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a viral expression construct, viral vector, composition, gene therapy composition, as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. In this context WO 2012/007458 is incorporated by reference in its entirety. Each embodiment as identified herein may be combined together unless otherwise indicated.

The invention is further explained in the following examples. These examples do not limit the scope of the invention, but merely serve to clarify the invention.

FIGURE LEGENDS

FIG. 1. Schematic representation of the dual-gene RSV-rGck-CMV-hIns AAV construct described in A.2. ITR: Inverted Terminal Repeat; RSV: Rous Sarcoma Virus promoter; rGck: rat glucokinase cDNA; SV40: simian virus 40 polyadenylation signal; CMV: cytomegalovirus promoter; hINS: human insulin cDNA.

Construct A: RSV-rGck-CMV-hIns (size: 4.9 kb) (SEQ ID NO: 8) is depicted in FIG. 1.

FIG. 2. Schematic representation of the single-gene AAV constructs described in A.2. ITR: Inverted Terminal Repeat; CMV: cytomegalovirus promoter; hINS: human insulin cDNA; SV40: simian virus 40 polyadenylation signal; RSV: Rous Sarcoma Virus promoter; rGck: rat glucokinase cDNA.

Construct B is depicted in FIG. 2: CMV-hIns (SEQ ID NO: 17).

Construct C is depicted in FIG. 2: RSV-rGck (SEQ ID NO: 18).

FIG. 3. Expression of insulin and glucokinase in HEK293 cells. The left histogram represents the expression of insulin in cells transfected with CMV-hIns (B) or RSV-rGck-CMV-hIns (A) plasmids. The right histogram represents the expression of glucokinase in cells transfected with RSVrGck (C) or RSV-rGck-CMV-hIns (A).

FIG. 4. Schematic representation of the dual-gene AAV constructs described in A.3. ITR: Inverted Terminal Repeat; CMV: cytomegalovirus promoter; hINS: human insulin cDNA; SV40: simian virus 40 polyadenylation signal; RSV: Rous Sarcoma Virus promoter; hGck: human glucokinase cDNA; bGH: bovine growth hormone polyadenylation signal.

Construct D is depicted in FIG. 4: CMV-hIns-RSV-hGck (size: 4.7 kb) (SEQ ID NO:9).

Construct E is depicted in FIG. 4: RSV-hGck-CMV-hIns (size: 4.7 kb) (SEQ ID NO:10).

Construct F is depicted in FIG. 4: CMV-hIns(rev)-RSV-hGck (size: 4.7 kb) (SEQ ID NO: 11).

Construct G is depicted in FIG. 4: RSV-hGck-CMV-hIns (rev) (size: 4.7 kb) (SEQ ID NO: 12).

Figure 5:
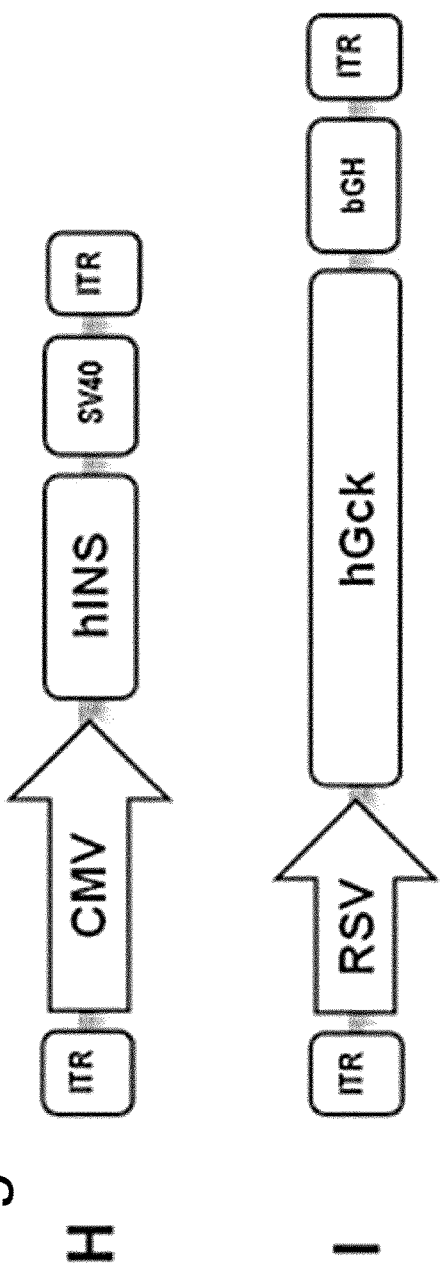

FIG. 5. Schematic representation of the single-gene AAV constructs described in A.3. ITR: Inverted Terminal Repeat; CMV: cytomegalovirus promoter; hINS: human insulin cDNA; SV40: simian virus 40 polyadenylation signal; RSV: Rous Sarcoma Virus promoter; hGck: human glucokinase cDNA; bGH: bovine growth hormone polyadenylation signal.

Construct H is depicted in FIG. 5: CMV-hIns (SEQ ID NO:19).

Construct I is depicted in FIG. 5: RSV-hGck (SEQ ID NO: 20).

Figure 6:
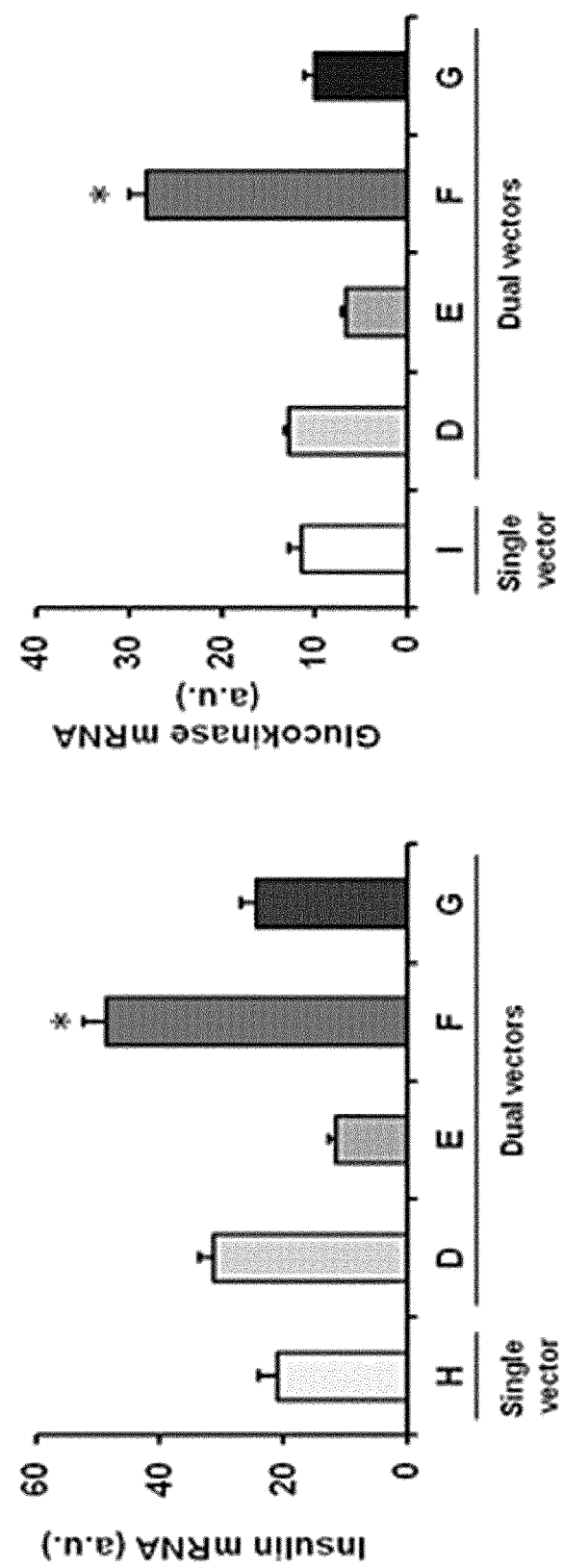

FIG. 6. Expression of insulin and glucokinase in HEK293 cells. The left histogram represents the expression of human insulin in cells transfected with CMV-hIns (construct H), CMV-hIns-RSV-hGck (construct D), RSV-hGck-CMV-hIns (construct E), CMV-hIns(rev)-RSV-hGck (construct F) or RSV-hGck-CMV-hIns(rev) (construct G) plasmids. The right histogram represents the expression of human glucokinase in cells transfected with RSV-hGck (construct I), CMV-hIns-RSV-hGck (construct D), RSV-hGck-CMV-hIns (construct E), CMV-hIns(rev)-RSV-hGck (construct F) or RSVh-Gck-CMV-hIns(rev) (construct G).

FIG. 7. Schematic representation of the dual-gene AAV constructs described in A.4. ITR: Inverted Terminal Repeat; MiniCMV: minicytomegalovirus promoter; hINS: human insulin cDNA; SV40: simian virus 40 polyadenylation signal; RSV: Rous Sarcoma Virus promoter; hGck: human glucokinase cDNA; bGH: bovine growth hormone polyadenylation signal.

Construct J is depicted in FIG. 7: miniCMV-hIns-RSV-hGck (size: 4 kb) (SEQ ID NO:13).

Construct K is depicted in FIG. 7: RSV-hGck-miniCMV-hIns (size: 4 kb) (SEQ ID NO:14).

Construct L is depicted in FIG. 7: miniCMV-hIns(rev)-RSV-hGck (size: 4 kb) (SEQ ID NO:15).

Construct M is depicted in FIG. 7: RSV-hGck-miniCMV-hIns(rev) (size: 4 kb) (SEQ ID NO:16).

FIG. 8. Schematic representation of the single-gene AAV described in A.4. ITR: Inverted Terminal Repeat; MiniCMV: minicytomegalovirus promoter; INS: human insulin cDNA; SV40: simian virus 40 polyadenylation. signal; RSV: Rous Sarcoma Virus promoter; Gck: human glucokinase cDNA; bGH: bovine growth hormone polyadenylation signal.

Construct N is depicted in FIG. 8: miniCMV-hIns (SEQ ID NO:21).

Construct I is depicted in FIG. 8: RSV-hGcK-bGH (SEQ ID NO:20).

Figure 9:
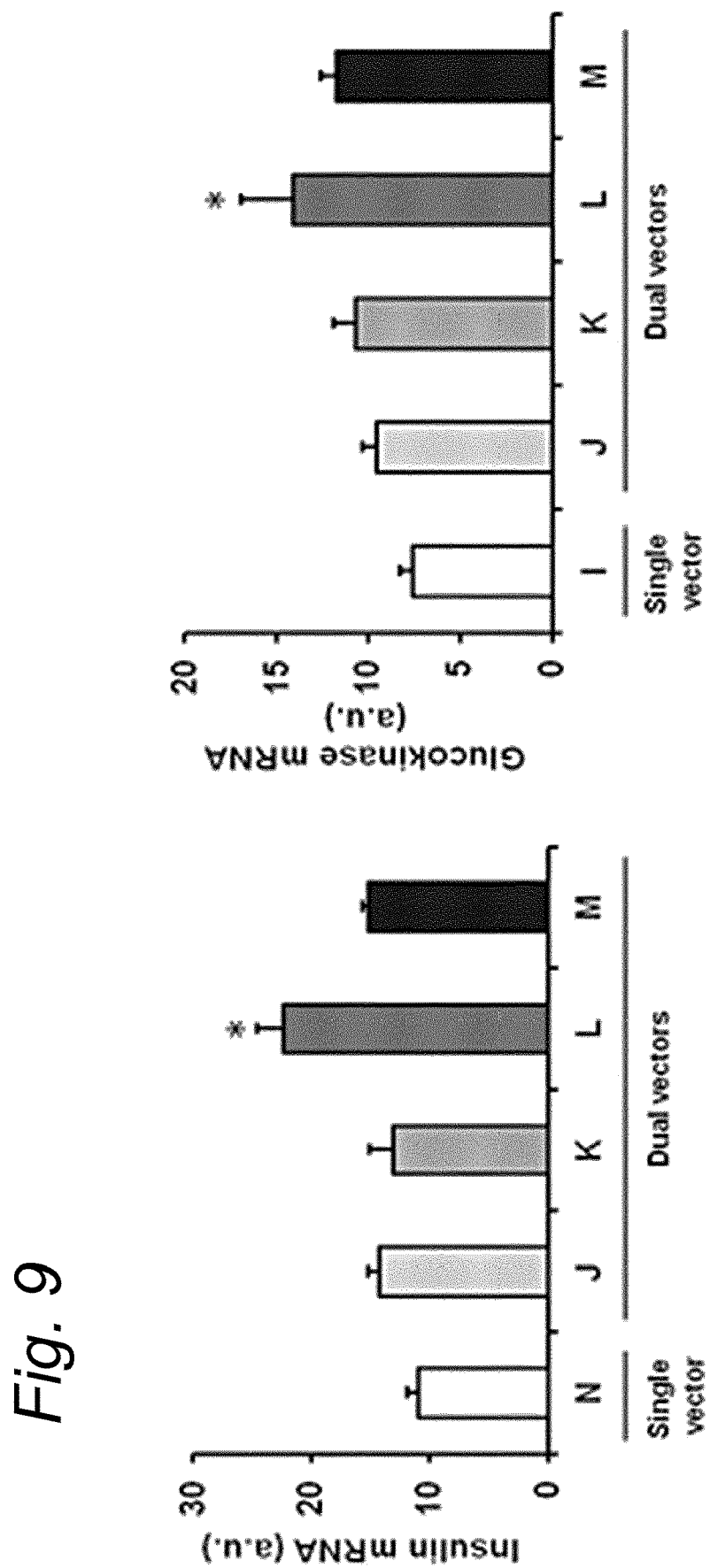

FIG. 9. Expression levels of insulin and glucokinase in HEK293 cells. The left histogram represents the expression of human insulin in cells transfected with miniCMV-Ins (construct N), miniCMV-hIns-RSV-Gck (construct J), RSV-hGck-miniCMV-hIns (construct K), miniCMV-hIns(rev)-RSV-hGck (construct L) or RSV-hGck-miniCMV-hIns(rev) (construct M) plasmids. The right histogram represents the expression of human glucokinase in cells transfected with RSV-hGck (construct I), miniCMV-hIns-RSV-hGck (construct J), RSV-hGck-miniCMV-hIns (construct K), miniCMV-hIns(rev)-RSV-hGck (construct L) or RSV-hGck-miniCMV-hIns(rev) (construct M) plasmids.

Figure 10:
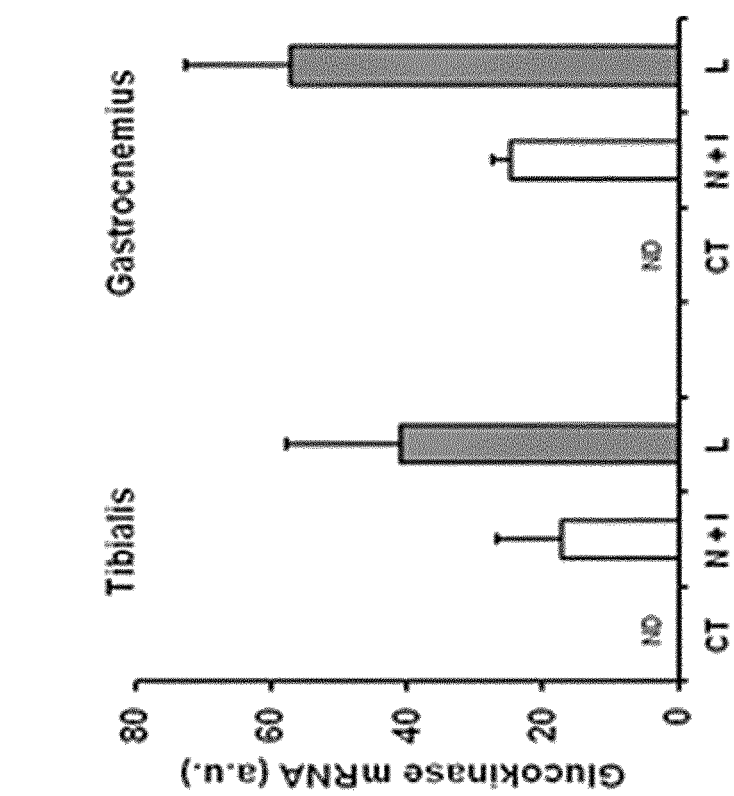
Figure 10:
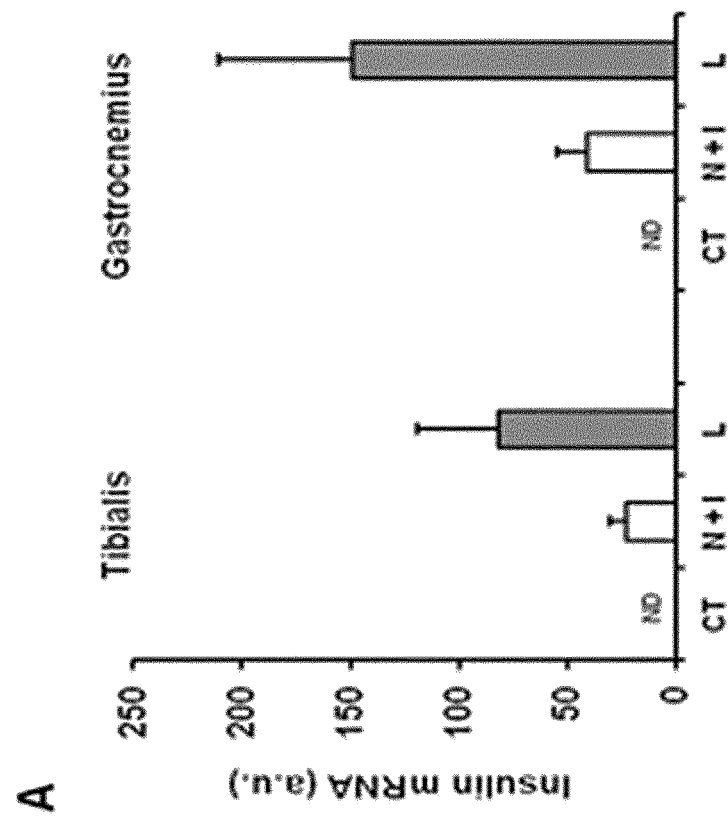

FIG. 10. AAV-mediated expression levels of insulin and glucokinase in the skeletal muscle of wild-type animals. Three weeks after vector administration, insulin (A) and glucokinase (B) expression was analysed by quantitative real time PCR in tibialis and gastrocnemius of control uninjected mice (CT), or in mice injected with the combination of the single vectors AAV1-miniCMV-hINS and AAV1-RSV-hGck (constructs N+I) or with the dual vector AAV1-miniCMV-hINS-rev-RSV-hGck (construct L). The amount of insulin and glucokinase was normalized to 36B4 expression. N.D., non detected, a.u. arbitrary units.

Figure 11:
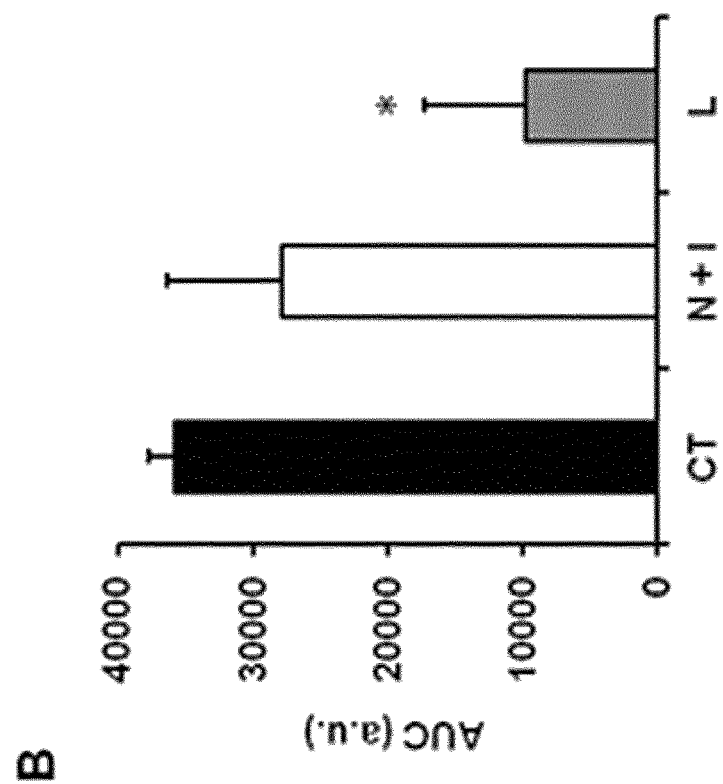
Figure 11:
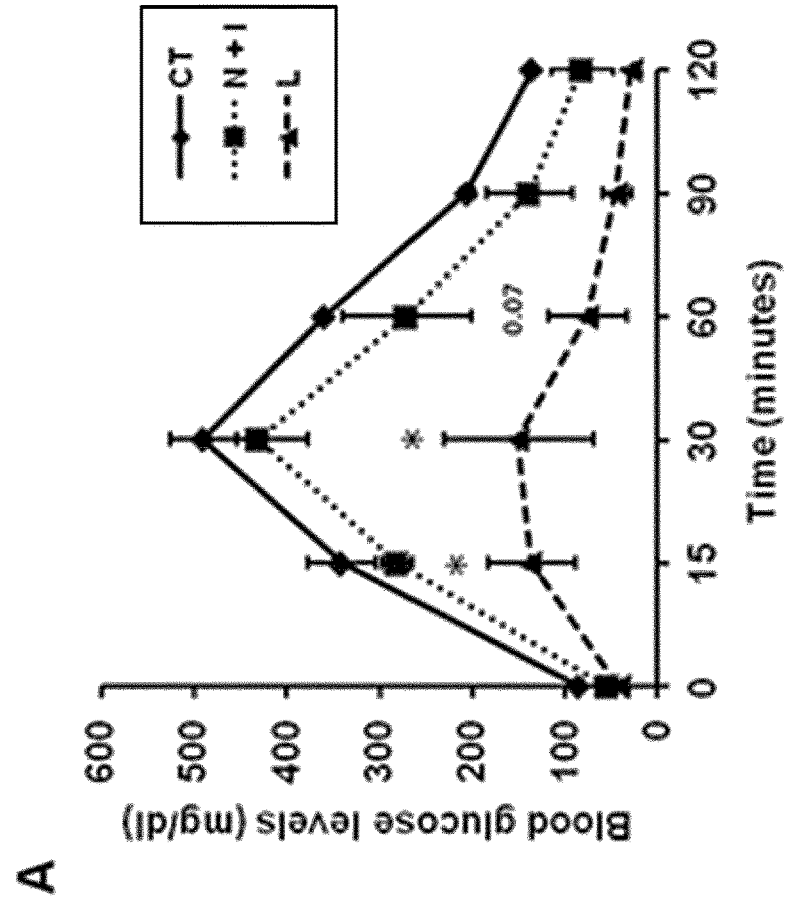

FIG. 11. Comparison of the ability to dispose of glucose after a load in animals injected with either a combination of single vectors or a dual-gene AAV vector. (A) Control mice (CT), mice injected with the combination of single vectors AAV1-miniCMV-hINS and AAV1-RSV-hGck (constructs N+I) and mice injected with the dual viral vector AAV1-miniCMV-hINS-rev-RSV-hGck (construct L) were given an intraperitoneal injection of 2 g glucose/kg body weight. Blood samples were taken from the tail of the animals at indicated time points and glucose concentration was determined. (B) The area under the curve (AUC) of the glucose tolerance test was calculated. a.u. arbitrary units. *p<0.05 vs N+I.

Figure 12:
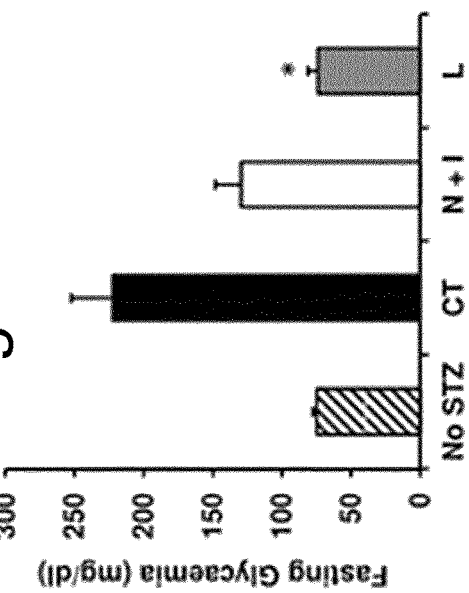
Figure 12:
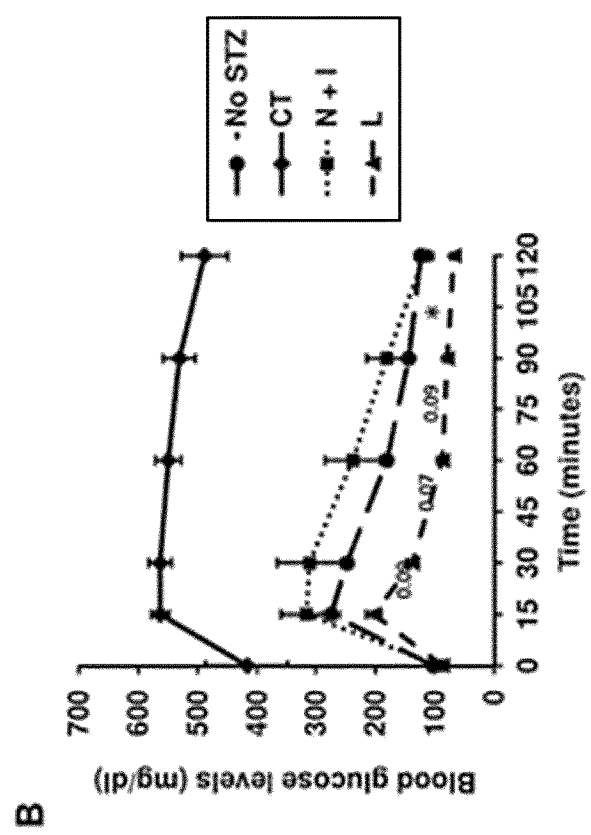
Figure 12:
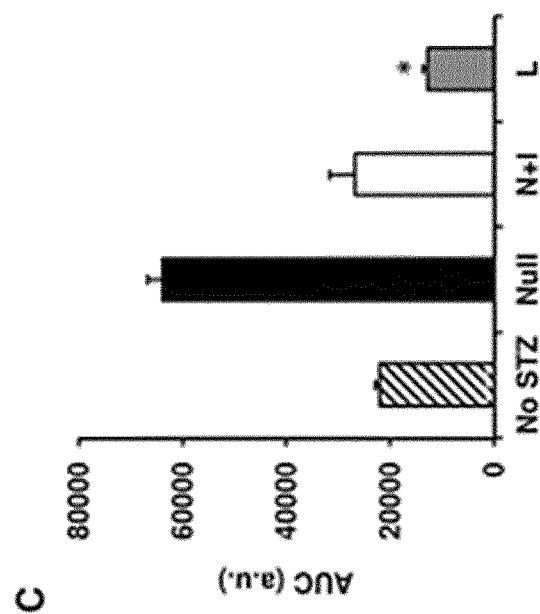

FIG. 12. Comparison of the ability to dispose of glucose after a load in diabetic animals injected with either a combination of single vectors or a dual-gene AAV vector. Healthy mice (No STZ), diabetic control mice (CT), diabetic mice injected with the combination of single vectors AAV1-miniCMV-hINS and AAV1-RSV-hGck (constructs N+I), and diabetic mice injected with the dual viral vector AAV1-miniCMV-hINS-rev-RSV-hGck (construct L) were given an intraperitoneal injection of 1 g glucose/kg body weight. (A) Fasting glucose levels. (B) Blood samples were taken from the tail of the animals at indicated time points and glucose concentration was determined. (C) The area under the curve (AUC) of the glucose tolerance test was calculated. a.u., arbitrary units. *p<0.05 vs N+I FIG. 13. Schematic representation of the dual-gene and single-gene AAV described in A.5. ITR: Inverted Terminal Repeat; MiniCMV: minicytomegalovirus promoter; INS: human insulin cDNA; SV40: simian virus 40 polyadenylation signal; RSV: Rous Sarcoma Virus promoter; Gck: human glucokinase cDNA; bGH: bovine growth hormone polyadenyilation signal.

Construct O is depicted in FIG. 13: miniCMV-hIns-bGH (size: 1.4 kb) (SEQ ID NO:25).

Construct P is depicted in FIG. 13: RSV-hGck-SV40 (size: 2.9 kb) (SEQ ID NO:26).

Construct Q is depicted in FIG. 13: miniCMV-hIns-bGH (rev)-RSV-hGck-SV40 (size: 4 kb) (SEQ ID NO:27).

Figure 14:
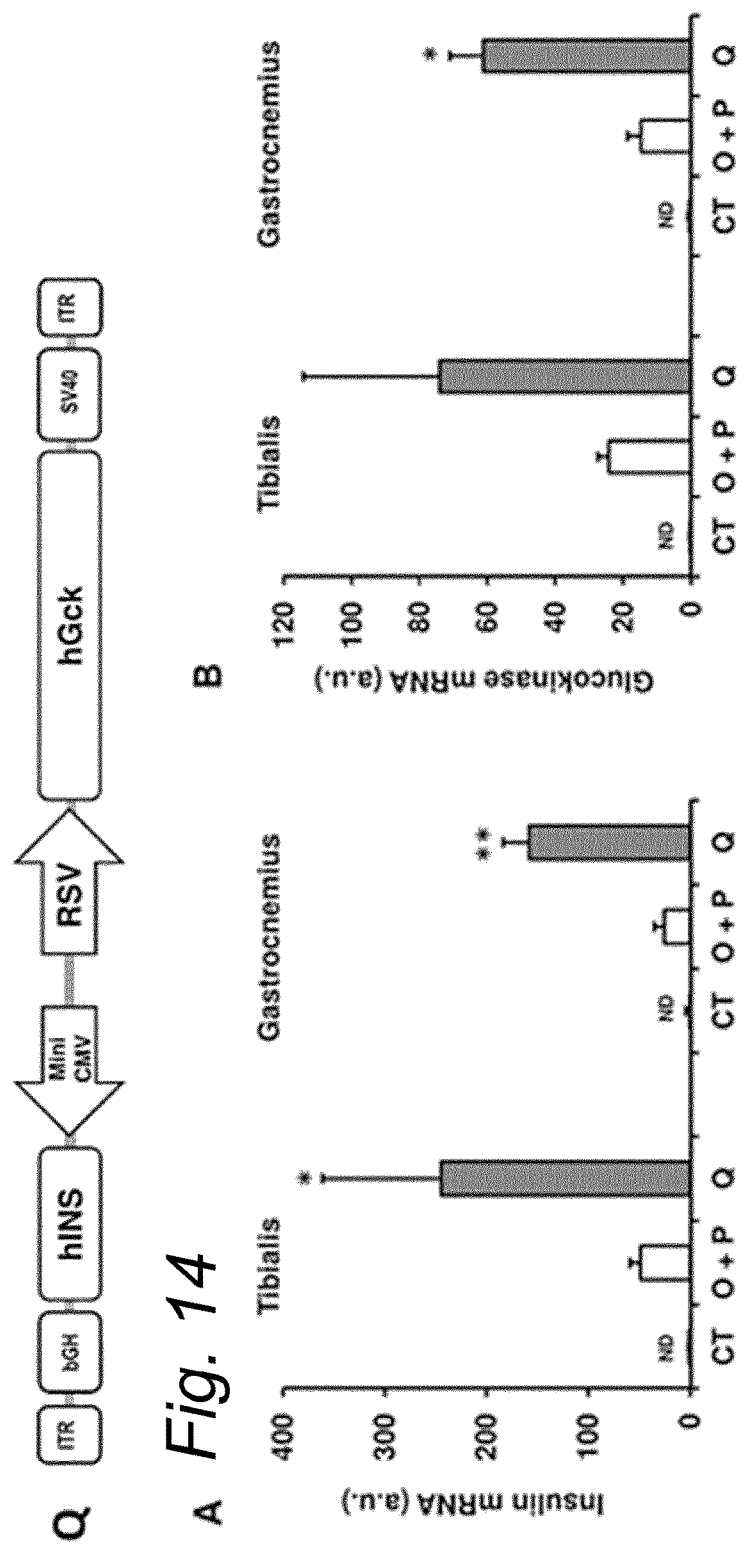

FIG. 14. AAV-mediated expression levels of insulin and glucokinase in the skeletal muscle of wild-type animals. Three weeks after vector administration, insulin (A) and glucokinase (B) expression was analysed by quantitative real time PCR in tibialis and gastrocnemius of control uninjected mice (CT), or in mice injected with the combination of the single vectors AAV1-miniCMV-hIns-bGH and AAV1-RSV-hGck-SV40 (constructs O+P) or with the dual vector AAV1-miniCMV-Insulin-bGH(rev)-RSV-Glucokinase-SV40 (construct Q). The amount of insulin and glucokinase was normalized to 36B4 expression. N.D., non detected. a.u., arbitrary units. *p<0.05 vs O+P FIG. 15. Comparison of the ability to dispose of glucose after a load in animals injected with either a combination of single vectors or a dual-gene AAV vector. (A) Control mice (CT), mice injected with the combination of single vectors AAV1-miniCMV-hIns-bGH and AAV1-RSV-hGck-SV40 (constructs O+P) and mice injected with the dual viral vector AAV1-miniCMV-Insulin-bGH(rev)-RSV-Glucokinase-SV40 (construct Q) were given an intraperitoneal injection of 2 g glucose/kg body weight. Blood samples were taken from the tail of the animals at indicated time points and glucose concentration was determined. (B) The area under the curve (AUC) of the glucose tolerance test was calculated. a.u., arbitrary units. *p<0.05 vs O+P FIG. 16. Schematic representation of the dual-gene and single-gene AAV described in A.G. ITR: Inverted Terminal Repeat; MiniCMV: minicytomegalovirus promoter; INS: human insulin cDNA; SV40 enhancer: SV40 enhancer and simian virus 40 polyadenylation signal; RSV: Rous Sarcoma Virus promoter; Gck: human glucokinase cDNA; bGH: bovine growth hormone polyadenylation signal.

Construct R is depicted in FIG. 16: miniCMV-hIns-SV40enhancer (size: 1.6 kb) (SEQ ID NO:28).

Construct S is depicted in FIG. 16: miniCMV-hIns-SV40enhancer(rev)-RSV-hGck-bGH (size: 4.2 kb) (SEQ ID NO:29).

Figure 17:
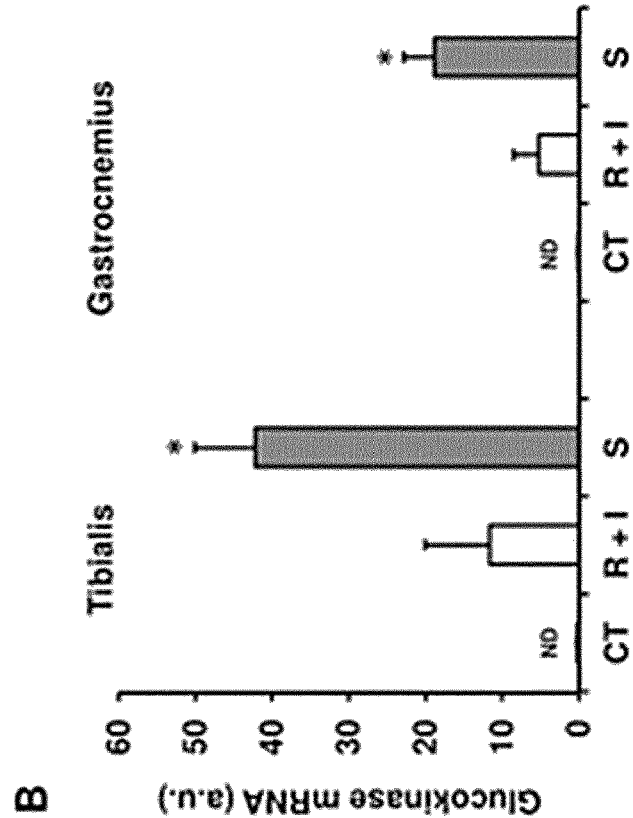
Figure 17:
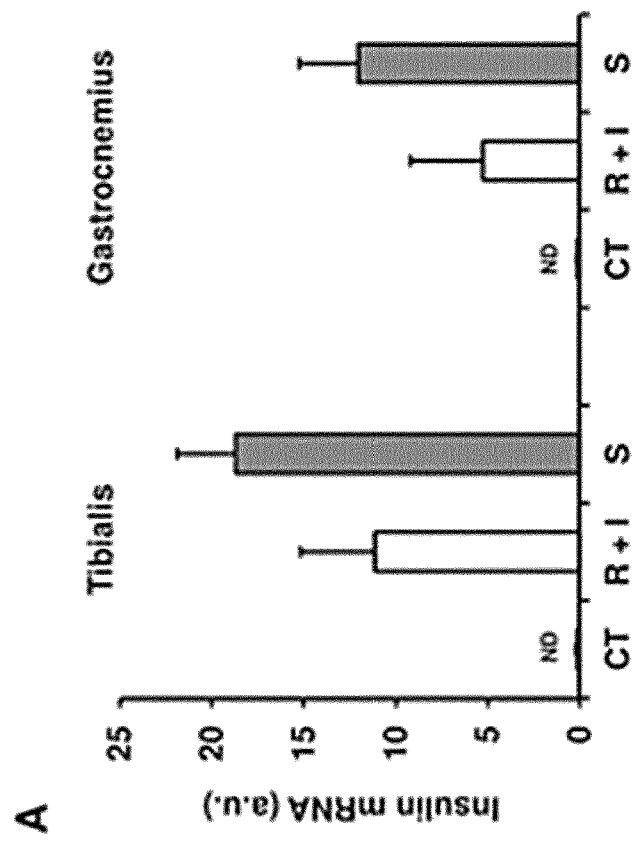

FIG. 17. AAV-mediated expression levels of insulin and glucokinase in the skeletal muscle of wild-type animals. Three weeks after vector administration, insulin (A) and glucokinase (B) expression was analysed by quantitative real time PCR in tibialis and gastrocnemius of control uninjected mice (CT), or in mice injected with the combination of the single vectors AAV1-miniCMV-hIns-SV40enhancer and AAV1-RSV-hGck (constructs R+I) or with the dual vector AAV1-miniCMV-hIns-SV40enhancer (rev)-RSV-hGck-bGH (construct S). The amount of insulin and glucokinase was normalized to 36B4 expression. N.D., non detected. a.u., arbitrary units. *p<0.05 vs R+I.

Figure 18:
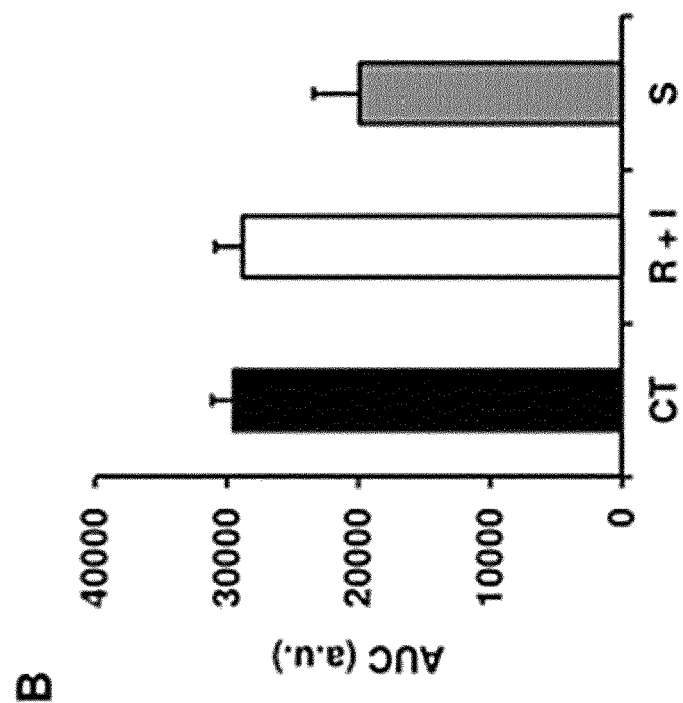
Figure 18:
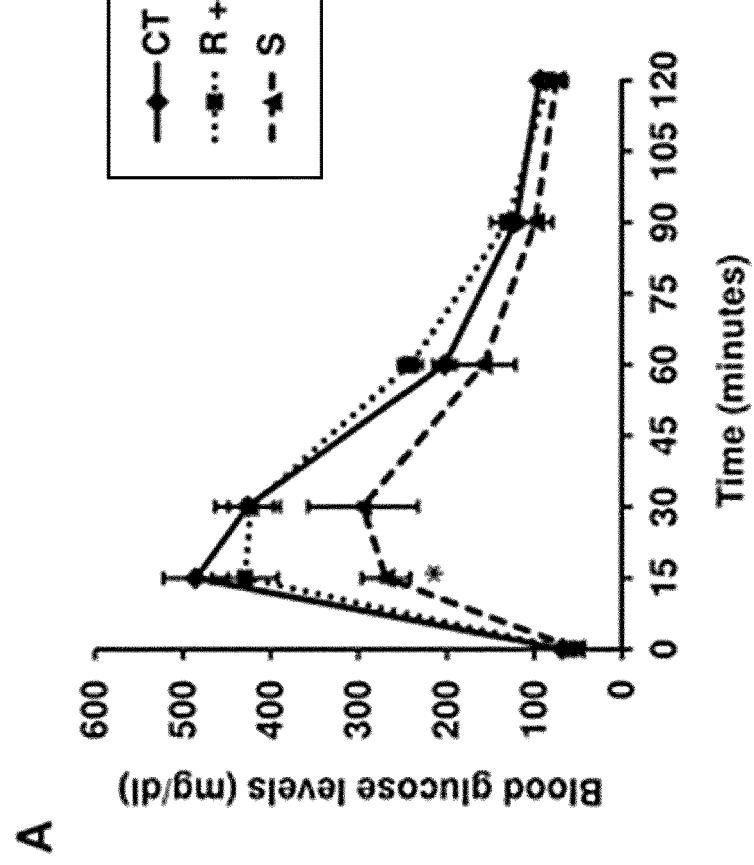

FIG. 18. Comparison of the ability to dispose of glucose after a load in animals injected with either a combination of single vectors or a dual-gene AAV vector. (A) Control mice (CT), mice injected with the combination of single vectors AAV1-miniCMV-hIns-SV40enhancer and AAV1-RSV-hGck (R+I) and mice injected with the dual viral vector AAV1-miniCMV-hIns-SV40enhancer(rev)-RSV-hGck-bGH (S) were given an intraperitoneal injection of 2 g glucose/kg body weight. Blood samples were taken from the tail of the animals at indicated time points and glucose concentration was determined. (B) The area under the curve (AUC) of the glucose tolerance test was calculated. a.u., arbitrary units. *p<0.05 vs R+I.

EXAMPLES

Throughout the application, one refers to constructs or vectors based on/comprising constructs A to S. The letter identifies the type of construct used and the same letter could be used to refer to a vector based on/derived from and/or comprising said construct. This is the reason why the ITRs are present in each of the FIG. 1, 2, 4, 5, 7, 8, 13 or 16 depicting each of the AAV viral vectors comprising said construct.

A. Generation of Dual-Gene Adeno-Associated Viral (AAV) Vector Constructs for the Concomitant Expression of Insulin and Glucokinase In order to develop more effective gene therapy strategies based on adeno-associated viral vector-mediated insulin/glucokinase muscle gene transfer to counteract diabetic hyperglycemia, dual-gene viral constructs encoding insulin and glucokinase were generated to ensure concomitant expression of both transgenes in transduced muscle cells.

Generation of dual-gene AAV1-Ins+Gck vectors will also allow decreasing vector dose, which in turn, should result in reduced risk of capsid-triggered immunity or other toxicities. From a regulatory point of view, the use of a dual vector will greatly facilitate the development of the treatment. Moreover, the use of a dual vector will allow for a dramatic reduction in the cost of manufacturing of AAV vectors.

The generation of such AAV dual vectors that contain both the insulin and glucokinase transgenes and potentially have improved therapeutic efficacy is not, however, entirely routine for a person skilled in the art, as demonstrated below.

In the experimental part, the nucleotide sequence encoding insulin was SEQ ID NO:1, the nucleotide sequence encoding glucokinase was SEQ ID NO:2. The nucleotide sequence of the CMV promoter was SEQ ID NO: 3 used with associated intronic sequence SEQ ID NO:4. The nucleotide sequence of the RSV promoter was SEQ ID NO: 6 with associated intronic sequence SEQ ID NO:23. The nucleotide sequence of the mini CMV promoter was SEQ ID NO:5. The nucleotide sequence of the bGH regulatory region was SEQ ID NO: 7. The nucleotide sequence of the SV40 was SEQ ID NO: 22.

A.1. Dual-Gene AAV-CMV-Insulin-CMV-Glucokinase Construct

In the therapeutic approach that utilized 2 different AAV1 vectors to mediate the gene transfer to the skeletal muscle of the insulin and glucokinase genes when administered to mice and dogs (Mas, A. et al., Diabetes (2006) 55:1546-1553; Callejas, D. et al. Diabetes (2013) 62:1718-1729), the expression of both transgenes was driven by the CMV promoter. Therefore, the most obvious option to be considered while generating the dual-gene AAV constructs would have been to use CMV-Insulin and CMV-Glucokinase expression cassettes within the same vector. However, this option was discarded because the presence of the same promoter in 2 regions within the same construct increases dramatically the high risk of intramolecular recombination events that are sometimes observed during AAV production due to the presence of repeated sequences.

A.2. Dual-Gene CMV-Insulin-RSV-Glucokinase AAV Constructs

Taking into account the restrictions on the use of promoters discussed above, the ubiquitous Rous Sarcoma Virus (RSV) promoter was chosen to drive expression of glucokinase in the dual-gene AAV construct. This promoter was selected because, similar to the CMV promoter, it has been reported to mediate strong transgene expression in muscle cells (Yue Y. et al, 2002, Biotechniques, 33:672, p 676 Development of Multiple Cloning Site cis-Vectors for Recombinant Adeno-Associated Virus Production). Additionally, its small size is convenient given the limited cloning capacity of AAV vectors.

A dual-gene AAV1-Ins+Gck construct bearing the human insulin coding sequence driven by the CMV promoter and the rat glucokinase coding sequence driven by the RSV promoter (FIG. 1) was generated. In this dual-gene construct the SV40 polyA sequence was cloned after the insulin and glucokinase genes:

Construct A: RSV-rGck-CMV-hIns (size: 4.9 kb) (SEQ ID NO: 8) is depicted in FIG. 1.

In addition to the previously described dual-gene AAV1-Ins+Gck construct, two additional single-gene plasmids encoding either human insulin or rat glucokinase were generated, using the same AAV backbone (FIG. 2), for comparison with the dual-gene AAV1-Ins+Gck construct:

Construct B is depicted in FIG. 2: CMV-hIns (SEQ ID NO: 17).

Construct C is depicted in FIG. 2: C: RSV-rGck (SEQ ID NO: 18).

The function of the dual-gene plasmid RSV-rGck-CMV-hIns (construct A) was assessed in vitro before AAV production and insulin and glucokinase were expressed at very high levels (FIG. 3).

Having verified the functionality of the RSV-rGck-CMV-hIns (construct A) in vitro, the plasmid was used to produce the corresponding dual-gene AAV1 vector in HEK293 cells. The yield of the vector batch was, however, low. The first production of AAV1-RSV-rGck-CMV-hIns rendered no AAV vectors and the yield of the second production run was 4E11 viral genomes (vg)/roller bottle (RB), considerably lower than our in house average yield for AAV1 production (expected yield: 2E12 vg/RB). The final size of the AAV constructs was close to the limit of encapsidation capacity of the AAV1, and the observation of low yields could be consistent with the low efficiency of encapsidation of over-sized genomes. Nevertheless, this result was not foreseeable because in some cases AAV constructs of approximately 5 kb have been successfully produced by our lab.

A.3. Optimized CMV-Insulin-RSV-Glucokinase Dual-Gene AAV Constructs

Given the relative low yield of the AAV batches produced with the previous dual-gene AAV constructs, we decided to completely remake the dual insulin and glucokinase expression cassettes. To this end, we designed a novel modular system that allowed us the test different combinations of coding sequences (optimized or not, and from different species) and cis-acting sequences (promoters, polyAs) at minimum effort and within optimal size for encapsidation. This new approached greatly simplified vector design.

First, we generated 4 additional dual-gene constructs containing the human insulin coding sequence under the control of the CMV promoter and the human glucokinase coding sequence driven by the RSV promoter. We tested the effect of positioning the insulin expression cassette upstream of the glucokinase expression cassette and viceversa, and also in reverse orientation (FIG. 4).

In addition, in this new set of constructs, the CMV-hInsulin cassette included the SV40 polyA sequence whereas the bovine growth hormone polyA sequence was cloned in the RSV-hGlucokinase cassette, as the latter is shorter and mediates higher transgene expression than the SV40 polyA (Azzoni A R, J Gene Med. 2007: The impact of polyadenylation signals on plasmid nuclease-resistance and transgene expression). The new constructs are:

Construct D is depicted in FIG. 4: CMV-hIns-RSV-hGck (size: 4.7 kb) (SEQ ID NO:9).

Construct E is depicted in FIG. 4: RSV-hGck-CMV-hIns (size: 4.7 kb) (SEQ ID NO:10).

Construct F is depicted in FIG. 4: CMV-hIns(rev)-RSV-hGck (size: 4.7 kb) (SEQ ID NO: 11).

Construct G is depicted in FIG. 4: RSV-hGck-CMV-hIns (rev) (size: 4.7 kb) (SEQ ID NO: 12).

In addition to the aforementioned 4 dual-gene AAV1-Ins+Gck constructs (constructs D, E, F and G)), two additional single-gene plasmids encoding either insulin or glucokinase were generated using the same AAV backbone (FIG. 5) for comparison with the four new dual-gene AAV1-Ins+Gck constructs:

Construct H is depicted in FIG. 5: CMV-hIns (SEQ ID NO:19).

Construct I is depicted in FIG. 5: RSV-hGck (SEQ ID NO: 20).

We assessed the function of the dual-gene constructs D, E, F and G plasmids in vitro in HEK293 cells and the F construct (CMV-hIns(rev)-RSV-rGck) mediated the highest insulin and glucokinase expression (FIG. 6). Therefore, said plasmid was used to produce the corresponding dual-gene AAV1 vector in HEK293 cells. Although the size of the CMV-hIns(rev)-RSV-rGck (construct F) genome construct was within optimal AAV encapsidation capacity, a vector batch of low yield was obtained again (5.5E11 vg/RB). Based on previous observations with other AAV constructs manufactured in our lab, we postulate that, in addition to the size of the vector genome, the conformation of the DNA may also impacts encapsidation efficiency, which could potentially explain the relative low manufacturing yield of this new dual construct.

A.4. Optimized miniCMV-Insulin-RSV-Glucokinase Dual-Gene AAV Constructs

Given that the AAV1-CMV-hIns(rev)-RSV-hGck production rendered a relative low yield, we decided to further decrease the size of the dual-gene construct replacing the CMV promoter by a short version of such promoter, named mini CMV promoter. We generated 4 new dual-gene constructs bearing the human insulin coding sequence under the control of the mini CMV promoter and the human glucokinase coding sequence driven by the RSV promoter. The SV40 and the bGH polyA were used as polyA sequences, respectively. Again, we tested the effect of positioning the insulin expression cassette upstream of the glucokinase expression cassette or viceversa, and also the effect of positioning it the glucokinase expression cassette in reverse orientation (FIG. 7). The new constructs are:

Construct J is depicted in FIG. 7: miniCMV-hIns-RSV-hGck (size: 4 kb) (SEQ ID NO:13).

Construct K is depicted in FIG. 7: RSV-hGck-miniCMV-hIns (size: 4 kb) (SEQ ID NO:14).

Construct L is depicted in FIG. 7: miniCMV-hIns(rev)-RSV-hGck (size: 4 kb) (SEQ ID NO:15).

Construct M is depicted in FIG. 7: RSV-hGck-miniCMV-hIns(rev) (size: 4 kb) (SEQ ID NO:16).

In addition to these 4 new dual-gene AAV1-Ins+Gck constructs (J, K, L and M), an additional single-gene plasmid encoding insulin was generated using the same AAV backbone for comparison with the 4 new dual-gene AAV1-Ins+Gck constructs. The single-gene plasmid encoding Gck was the previously mentioned RSV-hGCK (construct I) (FIG. 8).

Construct N is depicted in FIG. 8: miniCMV-hIns (SEQ ID NO:21).

Construct I is depicted in FIG. 8: RSV-hGCK-bGH (SEQ ID NO:20).

We assessed the function of constructs J, K, L and M dual-gene plasmids in vitro in HEK293 cells and the (L) construct, miniCMV-hIns(rev)-RSV-hGck, mediated the highest expression of insulin and glucokinase (FIG. 9).

This (L) construct (miniCMV-hIns(rev)-RSV-hGck) and the same construct (J) but in sense orientation (miniCMV-hIns-RSV-hGck dual-promoter) were used to produce the corresponding dual-gene AAV1 vectors in HEK293 cells.

In these cases, AAV production yields were within the expected value, being 2.1E12 vg/RB for AAV1-miniCMV-hIns(rev)-RSV-hGck (construct L) and 1.9E12 vg/RB for AAV1-miniCMV-hIns-RSV-hGck (construct J).

B. Increased Transgene Expression and Efficacy of Dual-Gene AAV1-miniCMV-hIns(rev)-RSV-hGck Vectors B.1. Increased Transgene Expression In Vivo To verify if the administration of the double-gene AAV1-Ins+Gck vectors was superior than the co-delivery of two single-gene AAV vectors in mediating the expression of insulin and/or glucokinase and/or in the ability to improve glucose disposal in response to a glucose overload, an in vivo experiment was performed in mice.

Two groups of wild type mice were treated with either the 2 single vectors together (constructs N+I) (AAV1-miniCMV-hINS and AAV1-RSV-hGck) or with the dual gene (construct L) (AAV1-miniCMV-hINS-rev-RSV-hGck). Vectors were administered intramuscularly into tibialis and gastrocnemius muscles of both hindlimbs at a dose of 5E10 vg/muscle of each vector (constructs N and I or L).

Three weeks after vector administration, animals were sacrificed and the expression of both transgenes (insulin and glucokinase) was analysed by real time quantitative PCR in the different experimental groups. We observed that the expression of both Insulin (FIG. 10A) and Glucokinase (FIG. 10B) was higher in the muscles obtained from the animals that received the double-gene vector (construct L), in comparison to the combination of the two single vectors (constructs N+I).

B.2. Increased Efficacy In Vivo

To demonstrate the efficacy of the newly designed dual-gene constructs, the ability of the vector to enhance glucose disposal in vivo was assessed in the previous described experimental groups. To this end, a glucose tolerance test was performed in which all groups of mice were injected intraperitoneally with 2 g glucose/kg body weight, and blood glucose levels were determined at different time points.

As observed in FIG. 11, animals injected with the L dual vector showed higher glucose tolerance than animals injected with the combination of the two single vectors.

B.3. Increased Efficacy In Vivo in Diabetic Mice

In order to assess efficacy of the dual-gene (construct L) vector (AAV1-miniCMV-hIns(rev)-RSV-hGck) in diabetic animals, a dose of 5E10 vg/muscle was administered intramuscularly into tibialis and gastrocnemius muscles of both hindlimbs of mice treated with streptozotocin (STZ) to trigger the diabetic process. As control, the 2 single vectors were administered together (construct N+I) (AAV1-miniCMV-hINS and AAV1-RSV-hGck).

Eight weeks post-AAV administration, a glucose tolerance test was performed in which all groups of mice were injected intraperitoneally with 1 g glucose/kg body weight, and blood glucose levels were determined at different time points.

As observed in FIG. 12A, diabetic animals injected with the L dual vector showed decreased levels of glycaemia in fasted conditions in comparison with animals treated with the combination of the N+I single vectors. Noticeably, glucose levels displayed by animals treated with the L dual-gene vector were similar to those of non-diabetic healthy mice (FIG. 12A). Moreover, diabetic animals injected with the L dual vector showed higher glucose tolerance than animals injected with the combination of the two single vectors (N+I) (FIG. 12B-C).

C. Increased Transgene Expression and Efficacy of Dual-Gene AAV1-miniCMV-Insulin-bGH(rev)-RSV-Glucokinase-SV40

C1. Generation of Optimized miniCMV-Insulin-bGH (rev)-RSV-Glucokinase-SV40 Dual-Gene AAV Constructs Given that polyadenylation signals have been reported to influence transgene expression (Azzoni et al., J Gene Med 2007; 9: 392-40.), we generated a new dual-gene construct bearing the human insulin coding sequence under the control of the mini CMV promoter and the bGH polyA (expression cassette in reverse orientation) and the human glucokinase coding sequence driven by the RSV promoter and SV40 polyA (construct Q; same construct as L but with polyA signals interchanged). Two additional single-gene plasmids encoding insulin and glucokinase (constructs O and P, respectively) were generated using the same AAV backbone for comparison with the new dual-gene AAV1-Ins+Gck (Q) construct (FIG. 13). The new constructs are:

Construct O is depicted in FIG. 13: miniCMV-hIns-bGH (size: 1.4 kb) (SEQ ID NO:25).

Construct P is depicted in FIG. 13: RSV-hGck-SV40 (size: 2.9 kb) (SEQ ID NO:26).

Construct Q is depicted in FIG. 13: miniCMV-hIns-bGH (rev)-RSV-hGck-SV40 (size: 4 kb) (SEQ ID NO:27).

C.2. Increased Transgene Expression In Vivo

Two groups of wild type mice were treated with either the 2 single vectors together (constructs O+P) (AAV1-miniCMV-hIns-bGH and AAV1-RSV-hGck-SV40) or with the dual gene (construct Q) (AAV1-miniCMV-Insulin-bGH (rev)-RSV-Glucokinase-SV40). Vectors were administered intramuscularly into tibialis and gastrocnemius muscles of both hindlimbs at a dose of 5E10 vg/muscle of each vector (constructs O and P or Q).

Three weeks after vector administration, animals were sacrificed and the expression of both transgenes (insulin and glucokinase) was analysed by real time quantitative PCR in the different experimental groups. We observed that the expression of both Insulin (FIG. 14A) and Glucokinase (FIG. 14B) was higher in the muscles obtained from the animals that received the double-gene vector (construct Q), in comparison to the combination of the two single vectors (constructs O+P).

C.3. Increased Efficacy In Vivo

To demonstrate the efficacy of the newly designed Q dual-gene construct (AAV1-miniCMV-Insulin-bGH(rev)-RSV-Glucokinase-SV40), the ability of the vector to enhance glucose disposal in vivo was assessed in the experimental groups previously described in section C.2. To this end, a glucose tolerance test was performed in which all groups of mice were injected intraperitoneally with 2 g glucose/kg body weight, and blood glucose levels were determined at different time points.

Figure 15:
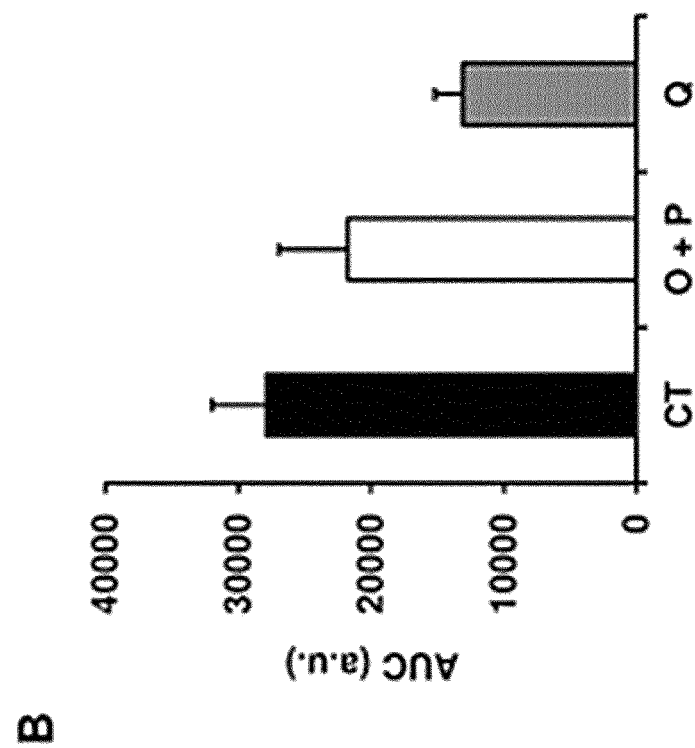
Figure 15:
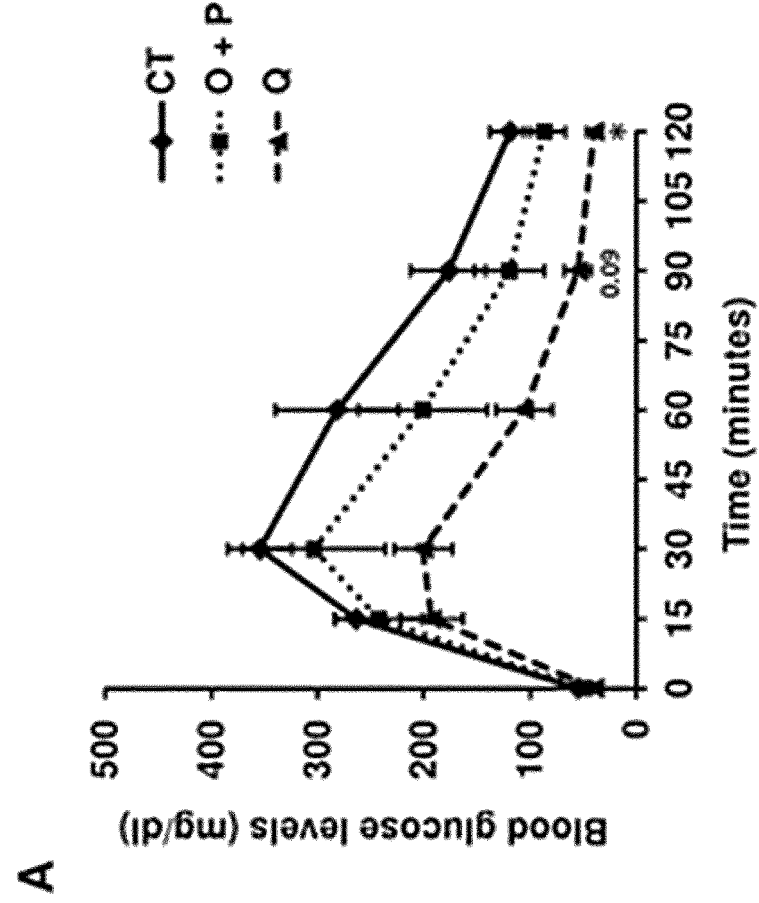

As observed in FIG. 15, animals injected with the Q dual vector showed higher glucose tolerance than animals injected with the combination of the two single vectors (O+P).

D. Increased Transgene Expression and Efficacy of Dual-Gene AAV1-miniCMV-hIns-SV40enhancer(Rev)-RSV-hGck-bGH D.1. Generation of Optimized miniCMV-Insulin-SV40enhancer-RSV-Glucokinase-bGH Dual-Gene AAV Constructs In order to increase the expression levels of insulin, the enhancer of the SV40 was incorporated at the 3' end of the polyA. A new dual-gene construct bearing the human insulin coding sequence under the control of the mini CMV promoter and the SV40 enhancer at the 3' end of the SV40 polyA (expression cassette in reverse orientation) and the human glucokinase coding sequence driven by the RSV promoter and the bGH polyA (construct S) was generated (FIG. 16). As control, a single-gene plasmid encoding insulin under the control of the mini CMV promoter and the SV40 enhancer at the 3' end of the SV40 polyA (construct R) was generated (FIG. 16). The single-gene plasmid encoding Gck was the previously mentioned RSV-hGCK (construct I) (FIG. 8). The new constructs are:

Construct R is depicted in FIG. 16: miniCMV-hIns-SV40enhancer (size: 1.6 kb) (SEQ ID NO: 28).

Construct S is depicted in FIG. 16: miniCMV-hIns-SV40enhancer(rev)-RSV-hGck-bGH (size: 4.2 kb) (SEQ ID NO: 29).

D.2. Increased Transgene Expression In Vivo

Two groups of wild type mice were treated with either the 2 single vectors together (constructs R+I) (AAV1-miniCMV-hIns-SV40enhancer and AAV1-RSV-hGck) or with the dual gene (construct S) (AAV1-miniCMV-hIns-SV40enhancer(rev)-RSV-hGck-bGH). Vectors were administered intramuscularly into tibialis and gastrocnemius muscles of both hindlimbs at a dose of 5E10 vg/muscle of each vector (constructs R and I or S).

Three weeks after vector administration, animals were sacrificed and the expression of both transgenes (insulin and glucokinase) was analysed by real time quantitative PCR in the different experimental groups. We observed that the expression of both Insulin (FIG. 17A) and Glucokinase (FIG. 17B) was higher in the muscles obtained from the animals that received the double-gene vector (construct S), in comparison to the combination of the two single vectors (construct R+I).

D.3. Increased Efficacy In Vivo

To demonstrate the efficacy of the newly designed S dual-gene construct (AAV1-miniCMV-hIns-SV40enhancer (rev)-RSV-hGck-bGH), the ability of the vector to enhance glucose disposal in vivo was assessed in the experimental groups previously described in section D.2. To this end, a glucose tolerance test was performed in which all groups of mice were injected intraperitoneally with 2 g glucose/kg body weight, and blood glucose levels were determined at different time points.

As observed in FIG. 18, animals injected with the S dual vector showed higher glucose tolerance than animals injected with the combination of the two single vectors (R+I).

In conclusion, we believe the new approach based on the use of the dual-gene AAV1-INS-Gck vector allows for more—or at least the same—expression of therapeutic transgenes at considerably lower vector doses (half the vector genomes in dual-gene-treated mice), when compared to the combination of the two single vectors.

As the actions of insulin and glucokinase are synergic to create a glucose sensor in muscle, the use of dual-gene vectors allows the delivery of adequate amounts of both transgenes to the same cell. Therefore, the new approach based on the use of the dual-gene viral vector improves glucose metabolization to a higher extent when compared to the combination of the two single vectors. Moreover, it also allows for higher levels of expression of the transgenes using half the dose of viral genomes.

Sequences

TABLE 1

| Overview of sequences | |
|---|---|
| SEQ ID NO: | Type of sequence |
| 1 | cDNA human insulin |
| 2 | cDNA human glucokinase |
| 3 | CMV promoter |
| 4 | Intronic sequence associated with CMV promoter |
| 5 | Mini CMV promoter |
| 6 | RSV promoter |
| 7 | bGH |
| 8 | Construct A |
| 9 | Construct D |
| 10 | Construct E |
| 11 | Construct F |
| 12 | Construct G |
| 13 | Construct J |
| 14 | Construct K |
| 15 | Construct L |
| 16 | Construct M |
| 17 | Construct B |
| 18 | Construct C |
| 19 | Construct H |
| 20 | Construct I |
| 21 | Construct N |
| 22 | SV40 polyadenylation signal |

TABLE 1-continued

Overview of sequences

| SEQ ID NO: | Type of sequence |
|---|---|
| 23 | Intronic sequence associated with RSV promoter |
| 24 | Equivalent mini CMV promoter |
| 25 | Construct O |
| 26 | Construct P |
| 27 | Construct Q |
| 28 | Construct R |
| 29 | Construct S |
| 30 | SV40 polyadenylation signal and enhancer sequence |
| 31 | 5'ITR |
| 32 | 3'ITR |
| 33 | SV40 enhancer sequence |

```
CMV Promoter (Full): (SEQ ID NO: 3)
Human cytomegalovirus (CMV) immediate early
enhancer and promoter
TGTAGTTAATGATTAACCCGCCATGCTACTTATCTACAGATCTCAATAT

TGGCCATTAGCCATATTATTCATTGGTTATATAGCATAAATCAATATTG

GCTATTGGCCATTGCATACGTTGTATCTATATCATAATATGTACATTTA

TATTGGCTCATGTCCAATATGACCGCCATGTTGGCATTGATTATTGACT

AGTTATTAATAGTAATCAATTACGGGGTCATTAGTTCATAGCCCATATA

TGGAGTTCCGCGTTACATAACTTACGGTAAATGGCCCGCCTGGCTGAC

CGCCCAACGACCCCCGCCCATTGACGTCAATAATGACGTATGTTCCCA

TAGTAACGCCAATAGGGACTTTCCATTGACGTCAATGGGTGGAGTATT

TACGGTAAACTGCCCACTTGGCAGTACATCAAGTGTATCATATGCCAA

GTCCGCCCCCTATTGACGTCAATGACGGTAAATGGCCCGCCTGGCATT

ATGCCCAGTACATGACCTTACGGGACTTTCCTACTTGGCAGTACATCTA

CGTATTAGTCATCGCTATTACCATGGTGATGCGGTTTTGGCAGTACACC

AATGGGCGTGGATAGCGGTTTGACTCACGGGGATTTCCAAGTCTCCAC

CCCATTGACGTCAATGGGAGTTTGTTTTGGCACCAAAATCAACGGGAC

TTTCCAAAATGTCGTAACAACTGCGATCGCCCGCCCCGTTGACGCAAA

TGGGCGGTAGGCGTGTACGGTGGGAGGTCTATATAAGCAGAGCTCGTT

TAGTGAACCGTCAGATCACTAG

Intronic sequence associated with CMV
promoter (SEQ ID NO: 4)
TATTGCGGTAGTTTATCACAGTTAAATTGCTAACGCAGTCAGTGCTTCT

GACACAACAGTCTCGAACTTAAGCTGCAGTGACTCTCTTAAGGTAGCC

TTGCAGAAGTTGGTCGTGAGGCACTGGGCAGGTAAGTATCAAGGTTAC

AAGACAGGTTTAAGGAGACCAATAGAAACTGGGCTTGTCGAGACAGAG

AAGACTCTTGCGTTTCTGATAGGCACCTATTGGTCTTACTGACATCCAC

TTTGCCTTTCTCTCCACAGGTGTCCACTCCCAGTTCAATTACAGCTCTT

AAGGCTAGAGTACTTAATACGACTCACTATAGAATACGACTCACTATAG

GGAGAC

Human Insulin(A718) Cdna (SEQ ID NO: 1)
CTTCTGCCATGGCCCTGTGGATGCGCCTCCTGCCCCTGCTGGCGCTGC

TGGCCCTCTGGGGACCTGACCCAGCCGCAGCCTTTGTGAACCAACACC

TGTGCGGCTCAGATCTGGTGGAAGCTCTCTACCTAGTGTGCGGGGAAC

GAGGCTTCTTCTACACACCCAGGACCAAGCGGGAGGCAGAGGACCTGC

AGGTGGGGCAGGTGGAGCTGGGCGGGGGCCCTGGTGCAGGCAGCCTG

CAGCCCTTGGCCCTGGAGGGGTCGCGACAGAAGCGTGGCATTGTGGA

ACAATGCTGTACCAGCATCTGCTCCCTCTACCAGCTGGAGAACTACTG

CAACTAGACGCAGCC

SV40 PolyA (SEQ ID NO: 22)
GGTACCAGCGCTGTCGAGGCCGCTTCGAGCAGACATGATAAGATACAT

TGATGAGTTTGGACAAACCACAACTAGAATGCAGTGAAAAAAATGCTT

TATTTGTGAAATTTGTGATGCTATTGCTTTATTTGTAACCATTATAAGC

TGCAATAAACAAGTTAACAACAACAATTGCATTCATTTTATGTTTCAGG

TTCAGGGGGAGATGTGGGAGGTTTTTTAAAGCAAGTAAAACCTCTACA

AATGTGGTAAAATCGATTAGGATCTTCCTAGAGCATGGCTACCTAGAC

ATGGCTCGACAGATCAGCGCTCATGTCTGGAAGATCTCG

RSV Promoter (SEQ ID NO: 6)
CATGTTTGACAGCTTATCATCGCAGATCCGTATGGTGCACTCTCAGTAC

AATCTGCTCTGATGCCGCATAGTTAAGCCAGTATCTGCTCCCTGCTTGT

GTGTTGGAGGTCGCTGAGTAGTGCGCGAGCAAAATTTAAGCTACAACA

AGGCAAGGCTTGACCGACAATTGCATGAAGAATCTGCTTAGGGTTAGG

CGTTTTGCGCTGCTTCGCGATGTACGGGCCAGATATTCGCGTATCTGA

GGGGACTAGGGTGTGTTTAGGCGAAAAGCGGGGCTTCGGTTGTACGC

GGTTAGGAGTCCCCTCAGGATATAGTAGTTTCGCTTTTGCATAGGGAG

GGGGAAATGTAGTCTTATGCAATACTCTTGTAGTCTTGCAACATGGTAA

CGATGAGTTAGCAACATGCCTTACAAGGAGAGAAAAAGCACCGTGCAT

GCCGATTGGTGGAAGTAAGGTGGTACGATCGTGCCTTATTAGGAAGGC

AACAGACGGGTCTGACATGGATTGGACGAACCACTAAATTCCGCATTG

CAGAGATATTGTATTTAAGTGCCTAGCTCGATACAATAAACGCCATTTG

ACCATTCACCACATTGGTGTGCACCTCCAAGCTGGGTACCAGCT

Intronic sequence associated with RSV
promoter (SEQ ID NO: 23)
GAGATCTGCTTCAGCTGGAGGCACTGGGCAGGTAAGTATCAAGGTTAC

AAGACAGGTTTAAGGAGACCAATAGAAACTGGGCTTGTCGAGACAGAG

AAGACTCTTGCGTTTCTGATAGGCACCTATTGGTCTTACTGACATCCAC

TTTGCCTTTCTCTCCACAGGTGCAGCTGCTGCAGCGG

Human GcK (SEQ ID NO: 2)
TCGAGACCATGGCGATGGATGTCACAAGGAGCCAGGCCCAGACAGCCT

TGACTCTGGTAGAGCAGATCCTGGCAGAGTTCCAGCTGCAGGAGGAGG

ACCTGAAGAAGGTGATGAGACGGATGCAGAAGGAGATGGACCGCGGC

CTGAGGCTGGAGACCCATGAAGAGGCCAGTGTGAAGATGCTGCCCACC

TACGTGCGCTCCACCCCAGAAGGCTCAGAAGTCGGGGACTTCCTCTCC
```

```
CTGGACCTGGGTGGCACTAACTTCAGGGTGATGCTGGTGAAGGTGGGA
GAAGGTGAGGAGGGGCAGTGGAGCGTGAAGACCAAACACCAGATGTA
CTCCATCCCCGAGGACGCCATGACCGGCACTGCTGAGATGCTCTTCGA
CTACATCTCTGAGTGCATCTCCGACTTCCTGGACAAGCATCAGATGAA
ACACAAGAAGCTGCCCCTGGGCTCACCTTCTCCTTTCCTGTGAGGCA
CGAAGACATCGATAAGGGCATCCTTCTCAACTGGACCAAGGGCTTCAA
GGCCTCAGGAGCAGAAGGGAACAATGTCGTGGGGCTTCTGCGAGACG
CTATCAAACGGAGAGGGGACTTTGAAATGGATGTGGTGGCAATGGTGA
ATGACACGGTGGCCACGATGATCTCCTGCTACTACGAAGACCATCAGT
GCGAGGTCGGCATGATCGTGGGCACGGGCTGCAATGCCTGCTACATG
GAGGAGATGCAGAATGTGGAGCTGGTGGAGGGGGACGAGGGCCGCAT
GTGCGTCAATACCGAGTGGGGCGCCTTCGGGGACTCCGGCGAGCTGG
ACGAGTTCCTGCTGGAGTATGACCGCCTGGTGGACGAGAGCTCTGCAA
ACCCCGGTCAGCAGCTGTATGAGAAGCTCATAGGTGGCAAGTACATGG
GCGAGCTGGTGCGGCTTGTGCTGCTCAGGCTCGTGGACGAAAACCTGC
TCTTCCACGGGGAGGCCTCCGAGCAGCTGCGCACACGCGGAGCCTTCG
AGACGCGCTTCGTGTCGCAGGTGGAGAGCGACACGGGCGACCGCAAG
CAGATCTACAACATCCTGAGCACGCTGGGGCTGCGACCCTCGACCACC
GACTGCGACATCGTGCGCCGCGCCTGCGAGAGCGTGTCTACGCGCGCT
GCGCACATGTGCTCGGCGGGGCTGGCGGGCGTCATCAACCGCATGCG
CGAGAGCCGCAGCGAGGACGTAATGCGCATCACTGTGGGCGTGGATG
GCTCCGTGTACAAGCTGCACCCCAGCTTCAAGGAGCGGTTCCATGCCA
GCGTGCGCAGGCTGACGCCCAGCTGCGAGATCACCTTCATCGAGTCGG
AGGAGGGCAGTGGCCGGGGCGCGGCCCTGGTCTCGGCGGTGGCCTGT
AAGAAGGCCTGTATGCTGGGCCAGTGA bGH PolyA (SEQ ID NO: 7)
CACGTGGAGCTCGCTGATCAGCCTCGACTGTGCCTTCTAGTTGCCAGC
CATCTGTTGTTTGCCCCTCCCCCGTGCCTTCCTTGACCCTGGAAGGTGC
CACTCCCACTGTCCTTTCCTAATAAAATGAGGAAATTGCATCGCATTGT
CTGAGTAGGTGTCATTCTATTCTGGGGGGTGGGGTGGGGCAGGACAG
CAAGGGGGAGGATTGGGAAGACAATAGCAGGCATGCTGGGGATGCGG
TGGGCTCTATGGCCACGTG Mini-CMV: cmv intermediate early
promoter (SEQ ID NO: 5)
TATGCCAAGTACGCCCCCTATTGACGTCAATGACGGTAAATGGCCCGC
CTGGCATTATGCCCAGTACATGACCTTATGGGACTTTCCTACTTGGCAG
TACATCTACGTATTAGTCATCGCTATTACCATGGTGATGCGGTTTTGGC
AGTACATCAATGGGCGTGGATAGCGGTTTGACTCACGGGGATTTCCAA
GTCTCCACCCCATTGACGTCAATGGGAGTTTGTTTTGGCACCAAAATCA
ACGGGACTTTCCAAAATGTCGTAACAACTCCGCCCCATTGACGCAAAT
GGGCGGTAGGCGTGTACGGTGGGAGGTCTATATAAGCAGAGCTCTCTG
GCTAACTAGAGAACCCACTGCTTAACTGGCTTATCGAAATTAATACGAC
TCACTATAGGGAGACCCAAGCTT
```

A: RSV-rGck-CMV-hIns (SEQ ID NO:8; FIG. 1)

| pGG2-RSV-rGck-CMV-hInsplasmid sequence |
|---|
| 1 CTAGACATGG CTCGACAGAT CTCAATATTG GCCATTAGCC AMATTATTCA |
| 51 TTGGTTATAT AGCAMAAATC AATATTGGCT ATTGGCCATT GCATACGTTG |
| 101 TATCTATATC ATAATATGTA CATTTATATT GGCTCATGTC AAATATGACC |
| 151 GCCATGTTGG CATTGATTAT TGACTAGTTA TTAATAGTAA TCAATTACGG |
| 201 GGTCATTAGT TCATAGCCCA TATATGGAGT TCCGCGTTAC ATAACTTACG |
| 251 GTAAATGGCC CGCCTGGCTG ACCGCCCAAC GACCCCCGCC CATTGACGTC |
| 301 AATAATGACG TATGTTCCCA TAGTAACGCC AATAGGGACT TTCCATTGAC |
| 351 GTCAATGGGT GGAGTATTTA CGGTAAACTG CCCACTTGGC AGTACATCAA |
| 401 GTGTATCATA TGCCAAGTCC GCCCCCTATT GACGTCAATG ACGGTAAATG |
| 451 GCCCGCCTGG CATTATGCCC AGTACATGAC CTTACGGGAC TTTCCTACTT |
| 501 GGCAGTACAT CTACGTATTA GTCATCGCTA TTACCATGGT GATOCGGTTT |
| 551 TGGCAGTACA CCAATGGGCG TGGATAGCGG TTTGACTCAC GGGGATTTCC |
| 601 AAGTCTCCAC CCCATTGACG TCAATGGGAG TTTGTTTTGG CACCAAAATC |
| 651 AACGGGACTT TCCAAAATGT CGTAACAACT GCGATCGCCC GCCCCGTTGA |
| 701 CGCAAATGGG CGGTAGGCGT GTACGGTGGG AGGTCTATAT AAGCAGAGCT |
| 751 CGTTTAGTGA ACCGTCAGAT CACTAGAAGC TTTATTGCGG TAGTTTATCA |
| 801 CAGTTAAATT GCTAACGCAG TCAGTGCTTC TGACACAACA GTCTCGAACT |

-continued

| pGG2-RSV-rGck-CMV-hIns plasmid sequence |
| --- |

```
 851 TAAGCTGCAG TGACTCTCTT AAGGTAGCCT TGCAGAAGTT GGTCGTGAGG
 901 CACTGGGCAG GTAAGTATCA AGGTTACAAG ACAGGTTTAA GGAGACCAAT
 951 AGAAACTGGG CTTGTCGAGA CAGAGAAGAC TCTTGCGTTT CTGATAGGCA
1001 CCTATTGGTC TTACTGACAT CCACTTTGCC TTTCTCTCCA CAGGTGTCCA
1051 CTCCCAGTTC AATTACAGCT CTTAAGGCTA GAGTACTTAA TACGACTCAC
1101 TATAGGCTAG CCTCGAGAAT TCTGCCATGG CCCTGTGGAT GCGCCTCCTG
1151 CCCCTGCTGG CGCTGCTGGC CCTCTGGGGA CCTGACCCAG CCGCAGCCTT
1201 TGTGAACCAA CACCTGTGCG GCTCAGATCT GGTGGAAGCT CTCTACCTAG
1251 TGTGCGGGGA ACGAGGCTTC TTCTACACAC CCAGGACCAA GCGGGAGGCA
1301 GAGGACCTGC AGGTGGGGCA GGTGGAGCTG GGCGGGGGCC CTGGTGCAGG
1351 CAGCCTGCAG CCCTTGGCCC TGGAGGGGTC GCGACAGAAG CGTGGCATTG
1401 TGGAACAATG CTGTACCAGC ATCTGCTCCC TCTACCAGCT GGAGAACTAC
1451 TGCAACTAGA CGCAGCTGCA AGCTTATCGA TACCGTCGAC CCGGGCGGCC
1501 GCTTCCCTTT AGTGAGGGTT AATGCTTCGA GCAGACATGA TAAGATACAT
1551 TGATGAGTTT GGACAAACCA CAACTAGAAT GCAGTGAAAA AAATGCTTTA
1601 TTTGTGAAAT TTGTGATGCT ATTGCTTTAT TTGTAACCAT TATAAGCTGC
1651 AATAAACAAG TTAACAACAA CAATTOCATT CATTTTATGT TTCAGGTTCA
1701 GGGGGAGATG TGGGAGGTTT TTTAAAGCAA GTAAAACCTC TACAAATGTG
1751 GTAAAATCCG ATAAGGGACT AGAGCATGGC TACGTAGATA AGTAGCATGG
1801 CGGGTTAATC ATTAACTACA AGGAACCCCT AGTGATGGAG TTGGCCACTC
1851 CCTCTCTGCG CGCTCGCTCG CTCACTGAGG CCGGGCGACC AAAGOTCGCC
1901 CGACGCCCGG GCTTTGCCCG GCGGCCTCA GTGAGCGAGC GAGCGCGCCA
1951 GCTGGCGTAA TAGCGAAGAG GCCCGCACCG ATCGCCCTTC CCAACAGTTG
2001 CGCAGCCTGA ATGGCGAATG GAATTCCAGA CGATTGAGCG TCAAAATGTA
2051 GGTATTTCCA TGAGCGTTTT TCCGTTGCAA TGGCTGGCGG TAATATTGTT
2101 CTGGATATTA CCAGCAAGGC CGATAGTTTG AGTTCTTCTA CTCAGGCAAG
2151 TGATGTTATT ACTAATCAAA GAAGTATTGC GACAACGGTT AATTTGCGTG
2201 ATGGACAGAC TCTTTTACTC GGTGGCCTCA CTGATTATAA AAACACTTCT
2251 CAGGATTCTG GCGTACCGTT CCTGTCTAAA ATCCCTTTAA TCGGCCTCCT
2301 GTTTAGCTCC CGCTCTGATT CTAACGAGGA AGCACGTTA TACGTGCTCG
2351 TCAAAGCAAC CATAGTACGC GCCCTGTAGC GGCGCATTAA GCGCGGCGGO
2401 TGTGGTGGTT ACGCGCAGCG TGACCGCTAC ACTTGCCAGC GCCCTAGCGC
2451 CCGCTCCTTT CGCTTTCTTC CCTTCCTTTC TCGCCACGTT CGCCGGCTTT
2501 CCCCGTCAAG CTCTAAATCG GGGGCTCCCT TTAGGGTTCC GATTTAGTGC
2551 TTTACGGCAC CTCGACCCCA AAAAACTTGA TTAGGGTGAT GGTTCACGTA
2601 GTGGGCCATC GCCCTGATAG ACGGTTTTTC GCCCTTTGAC GTTGGAGTCC
2651 ACGTTCTTTA ATAGTGGACT CTTGTTCCAA ACTGGAACAA CACTCAACCC
2701 TATCTCGGTC TATTCTTTTG ATTTATAAGG GATTTTGCCG ATTTCGGCCT
```

| pGG2-RSV-rGck-CMV-hIns plasmid sequence |
|---|
| 2751 ATTGGTTAAA AAATGAGCTG ATTTAACAAA AATTTAACGC GAATTTTAAC |
| 2801 AAAATATTAA CGTCTACAAT TTAAATATTT GCTTATACAA TCTTCCTGTT |
| 2851 TTTGGGGCTT TTCTGATTAT CAACCGGGGT ACATATGATT GACATGCTAG |
| 2901 TTTTACGATT ACCGTTCATC GATTCTCTTG TTTGCTCCAG ACTCTCAGGC |
| 2951 AATGACCTGA TAGCCTTTGT AGAGACCTCT CAAAAATAGC TACCCTCTCC |
| 3001 GGCATGAATT TATCAGCTAG AACGGTTGAA TATCATATTG ATGGTGATTT |
| 3051 GACTGTCTCC GGCCTTTCTC ACCCGTTTGA ATCTTTACCT ACACATTACT |
| 3101 CAGGCATTGC ATTTAAAATA TATGAGGGTT CTAAAAATTT TTATCCTTGC |
| 3151 GTTGAAATAA AGGCTTCTCC CGCAAAAGTA TTACAGGGTC ATAATGTTTT |
| 3201 TGGTACAACC GATTTAGCTT TATGCTCTGA GGCTTTATTG CTTAATTTTG |
| 3251 CTAATTCTTT GCCTTGCCTG TATGATTTAT GGATGTTGG AATCGCCTGA |
| 3301 TGCGGTATTT TCTCCTTACG CATCTGTGCG GTATTTCACA CCGCATATGG |
| 3351 TGCACTCTCA GTACAATCTG CTCTGATGCC CGATAGTTAA GCCAGCCCCG |
| 3401 ACACCCGCCA ACACCCGCTG ACGCGCCCTG AGGGGCTTGT CTGCTCCCGG |
| 3451 CATCCGCTTA CAGACAAGCT GTGACCGTCT CCGGGAGCTG CATGTGTCAG |
| 3501 AGGTTTTCAC CGTCATCACC GAAACGCGCG AGACGAAAGG GCCTCGTGAT |
| 3551 ACGCCTATTT TTATAGGTTA ATGTCATGAT AATAATGGTT TCTTAGACGT |
| 3601 CAGGTGGCAC TTTTCGGGGA ATGTGCGCG GAACCCCTAT TTGTTTATTT |
| 3651 TTCTAAATAC ATTCAAATAT CTATCCGCTC ATGAGACAAT AACCCTGATA |
| 3701 AATGCTTCAA TATTATTGAA AAAGGAAGAG TATGAGTATT CAACATTTCC |
| 3751 GTGTCGCCCT TATTCCCTTT TTTGCGGCAT TTTGCCTTCC TGTTTTTGCT |
| 3801 CACCCAGAAA CGCTGGTGAA AGTAAAAGAT GCTGAAGATC AGTTGGGTGC |
| 3851 ACGAGTGGGT TACATCGAAC TGGATCTCAA CAGCGGTAAG ATCCTTGAGA |
| 3901 GTTTTCGCCC CGAAGAACGT TTTCCAATGA TGAGCACTTT TAAAGTTCTG |
| 3951 CTATGTGGCG CGGTATTATC CCGTATTGAC GCCGGGCAAG AGCAACTCGG |
| 4001 TCGCCGCATA CACTATTCTC AGAATGACTT GGTTGAGTAC TCACCAGTCA |
| 4051 CAGAAAAGCA TCTTACGGAT GGCATGACAG TAAGAGAATT ATGCAGTGCT |
| 4101 GCCARAACCA TGAGTGATAA CACTFCGGCC AACTTACTTC TGACAACGAT |
| 4151 CGGAGGACCG AAGGAGCTAA CCGCTTTTTT GCACAACATG GGGGATCATG |
| 4201 TAACTCGCCT TGATCGTTGG GAACCGGAGC TGAATGAAGC CATACCAAAC |
| 4251 GACGAGCGTG ACACCACGAT GCCTGTAGCA ATGGCAACAA CGTTGCGCAA |
| 4301 ACTATTAACT GGCGAACTAC TTACTCTAGC TTCCCGGCAA CAATTAATAG |
| 4351 ACTGGATGGA GGCGGATAAA GTTGCAGGAC CACTTCTGCG CTCGGCCCTT |
| 4401 CCGGCTGGCT GGTTTATTGC TGATAAATCT GGAGCCGGTG AGCGTGGGTC |
| 4451 TCGCGGTATC ATTGCAGCAC TGGGGCCAGA TGGTAAGCCC TCCCGTATCG |
| 4501 TAGTTATCTA CACGACGGGG AGTCAGGCAA CTATGGATGA ACGAAATAGA |
| 4551 CAGATCGCTG AGATAGGTGC CTCACTGATT AAGCATTGGT AACTGTCAGA |
| 4601 CCAAGTTTAC TCATATATAC TTTAGATTGA TTTAAAACTT CATTTTTAAT |
| 4651 TTAAAAGGAT CTAGGTGAAG ATCCTTTTTG ATAATCTCAT GACCAAAATC |

| pGG2-RSV-rGck-CMV-hInsplasmid sequence |
|---|

```
4701 CCTTAACGTG AGTTTTCGTT CCACTGAGCG TCAGACCCCG TAGAAAAGAT

4751 CAAAGGATCT TCTTGAGATC CTTTTTTTCT GCGCGTAATC TGCTGCTTGC

4801 AAACAAAAAA ACCACCGCTA CCAGCGGTGG TTTGTTTGCC GGATCAAGAG

4851 CTACCAACTC TTTTTCCGAA GGTAACTGGC TTCAGCAGAG CGCAGATACC

4901 AAATACTGTC CTTCTAGTGT AGCCGTAGTT AGGCCACCAC TTCAAGAACT

4951 CTGTAGCACC GCCTACATAC CTCGCTCTGC TAATCCTGTT ACCAGTGGCT

5001 GCTGCCACTG GCGATAAGTC GTGTCTTACC GGGTTGGACT CAAGACGATA

5051 GTTACCGGAT AAGGCGCAGC GGTCGGGCTG AACGGGGGGT TCGTGCACAC

5101 AGCCCAGCTT GGAGCGAACG ACCTACACCG AACTGAGATA CCTACAGCGT

5151 GAGCTATGAG AAAGCGCCAC GCTTCCCGAA GGGAGAAAGG CGGACAGGTA

5201 TCCGGTAAGC GGCAGGGTCG GAACAGGAGA GCGCACGAGG GAGCTTCCAG

5251 GGGGAAACGC CTGGTATCTT TATAGTCCTG TCGGGTTTCG CCACCTCTGA

5301 CTTGAGCGTC GATTTTTGTG ATGCTCGTCA GGGGGGCGGA GCCTATGGAA

5351 AAACGCCAGC AACGCGGCCT TTTTACGGTT CCTGGCCTTT TGCTGGCCTT

5401 TTGCTCACAT GTTCTTTCCT GCGTTATCCC CTGATTCTGT GGATAACCGT

5451 ATTACCGCCT TTGAGTGAGC TGATACCGCT CGCCGCAGCC GAACGACCGA

5501 GCGCAGCGAG TCAGTGAGCG AGGAAGCGGA AGAGCGCCCA ATACGCAAAC

5551 CGCCTCTCCC CGCGCGTTGG CCGATTCATT AATGCAGCAG CTGCGCGCTC

5601 GCTCGCTCAC TGAGGCCGCC CGGGCAAAGC CCGGGCGTCG GGCGACCTTT

5651 GGTCGCCCGG CCTCAGTGAG CGAGCGAGCG CGCAGAGAGG GAGTGGCCAA

5701 CTCCATCACT AGGGGTTCCT TGTAGTTAAT GATTAACCCG CCATGCTACT

5751 TATCTACGTA GCCATGCTAT AGGTAGCCAT GCTCTGGAAG ATCTCGACGC

5801 GTCATGTTTG ACAGCTTATC ATCGCAGATC GCTATGGTGC ACTCTCAGTA

5851 CAATCTGCTC TGATGCCGCA TAGTTAAGCC AGTATCTGCT CCCTGCTTGT

5901 GTGTTGGAGG TCGCTGAGTA GTGCGCGAGC AAAATTTAAG CTACAACAAG

5951 GCAAGGCTTG ACCGACAATT GCATGAAGAA TCTGCTTAGG GTTAGGCGTT

6001 TTGCGCTGCT TCGCGATGTA CGGGCCAGAT ATTCGCGTAT CTGAGGGGAC

6051 TAGGGTGTGT TTAGGCGAAA AGCGGGGCTT CGGTTGTACG CGGTTAGGAG

6101 TCCCCTCAGG ATATAGTAGT TTCGCTTTTG CATAGGGAGG GGGAAATGTA

6151 GTCTTATGCA ATACTCTTGT AGTCTTGCAA CATGGTAACG ATGAGTTAGC

6201 AACATGCCTT ACAAGGAGAG AAAAAGCACC GTGCATGCCG ATTGGTGGAA

6251 GTAAGGTGGT ACGATCGTGC CTTATTAGGA AGGCAACAGA CGGGTCTGAC

6301 ATGGATTGGA CGAACCACTA AATTCCGCAT TGCAGAGATA TTGTATTTAA

6351 GTGCCTAGCT CGATACAATA AACGCCATTT GACCATTCAC CACATTGGTG

6401 TGCACCTCCA AGCTGGGTAC CAGCTGCTAG CAAGCTTGAG ATCTGCTTCA

6451 GCTGGAGGCA CTGGGCAGGT AAGTATCAAG GTTACAAGAC AGGTTTAAGG

6501 AGACCAATAG AAACTGGGCT TGTCGAGACA GAGAAGACTC TTGCGTTTCT

6551 GATAGGCACC TATTGGTCTT ACTGACATCC ACTTTGCCTT TCTCTCCACA
```

-continued pGG2-RSV-rGck-CMV-hInsplasmid sequence

6601 GGTGCAGCTG CTGCAGCGGG AATTCAACAG GTGGCCTCAG GAGTCAGGAA
6651 CATCTCTACT TCCCCAACGA CCCCTGGGTT GTCCTCTCAG AGATGGCTAT
6701 GGATACTACA AGGTGTGGAG CCCAGTTGTT GACTCTGGTC GAGCAGATCC
6751 TGGCAGAGTT CCAGCTGCAG GAGGAAGACC TGAAGAAGGT GATGAGCCGG
6801 ATGCAGAAGG AGATGGACCG TGGCCTGAGG CTGGAGACCC ACGAGGAGGC
6851 CAGTGTAAAG ATGTTACCCA CCTACGTGCG TTCCACCCCA GAAGGCTCAG
6901 AAGTCGGAGA CTTTCTCTCC TTAGACCTGG GAGGAACCAA CTTCAGAGTG
6951 ATGCTGGTCA AAGTGGGAGA GGGGGAGGCA GGGCAGTGGA GCGTGAAGAC
7001 AAAACACCAG ATGTACTCCA TCCCCGAGGA CGCCATGACG GGCACTGCCG
7051 AGATGCTCTT TGACTACATC TCTGAATGCA TCTCTGACTT CCTTGACAAG
7101 CARCAGATGA AGCACAAGAA ACTGCCCCTG GGCTTCACCT TCTCCTTCCC
7151 TGTGAGGCAC GAAGACCTAG ACAAGGGCAT CCTCCTCAAT TGGACCAAGG
7201 GCTTCAAGGC CTCTGGAGCA GAAGGGAACA ACATCGTAGG ACTTCTCCGA
7251 GATGCTATCA AGAGGAGAGG GGACTTTGAG ATGGATGTGG TGGCAATGGT
7301 GAACGACACA GTGGCCACAA TGATCTCCTG CTACTATGAA GACCGCCAAT
7351 GTGAGGTCGG CATGATTGTG GGCACTGGCT GCAATGCCTG CTACATGGAG
7401 GAAATGCAGA ATGTGGAGCT GGTGGAAGGG GATGAGGGAC GCATGTGCGT
7451 CAACACGGAG TGGGGCGCCT TCGGGGACTC GGGCGAGCTG GATGAGTTCC
7501 TACTGGAGTA TGACCGGATG GTGGATGAAA GCTCAGCGAA CCCCGGTCAG
7551 CAGCTGTACG AGAAGATCAT CGGTGGGAAG TATATGGGCG AGCTGGTACG
7601 ACTTGTGCTG CTTAAGCTGG TGGACGAGAA CCTTCTGTTC CACGGAGAGG
7651 CCTCGGAGCA GCTGCGCACG CGTGGTGCTT TTGAGACCCG TTTCGTGTCA
7701 CAAGTGGAGA GCGACTCCGG GGACCGAAAG CAGATCCACA ACATCCTAAG
7751 CACTCTGGGG CTTCGACCCT CTGTCACCGA CTGCGACATT GTGCGCCGTG
7801 CCTGTGAAAG CGTGTCCACT CGCGCCGCCC ATATGTGCTC CGCAGGACTA
7851 GCTGGGGTCA TAAATCGCAT GCGCGAAAGC CGCAGTGAGG ACGTGATGCG
7901 CATCACTGTG GGCGTGGATG GCTCCGTGTA CAAGCTGCAC CCGAGCTTCA
7951 AGGAGCGGTT TCACGCCAGT GTGCGCAGGC TGACACCCAA CTGCGAAATC
8001 ACCTTCATCG AATCAGAGGA GGGCAGCGGC AGGGGAGCCG CACTGGTCTC
8051 TGCGGTGGCC TGCAAGAAGG CTTGCATGCT GGCCCAGTGA ATCCAGGTC
8101 ATATGGACCG GGACCTGGGT TCCACGGGGA CTCCACACAC CACAAATGCT
8151 CCCAGCCCAC CGGGGCAGGA GACCTATTCT GCTGCTACCC CTHHAAAATG
8201 GGGAGAGGCC CCTGCAAGCC GAGTCGGCCA GTGGGACAGC CCTAGGCTGG
8251 ATCGGCCGCT TCGAGCAGAC ATGATAAGAT ACATTGATGA GTTTGGACAA
8301 ACCACAACTA GAATGCAGTG AAAAAAATGC TTTATTTGTG AAATTTGTGA
8351 TGCTATTGCT TTATTTGTAA CCATTATAAG CTGCAATAAA CAAGTTAACA
8401 ACAACAATTG CATTCATTTT ATGTTTCAGG TTCAGGGGGA GATGTGGGAG

-continued

| pGG2-RSV-rGck-CMV-hIns plasmid sequence |
|---|

```
8451 GTTTTTTAAA GCAAGTAAAA CCTCTACAAA TGTGGTAAAA TCGATTAGGA
8501 TCTTCCTAGA GCATGGCTAC
```

ITR 5': 5585-5720 bp
CMV promoter: 22-1043 bp
hIns: 1120-1466 bp
SV40 polyA: 1532-1754
ITR 3': 1821-1971 bp
B: CMV-hIns (SEQ ID NO:17; FIG. 2)

| pGG2-CMV-hIns plasmid seauence |
|---|

```
   1 CAGCAGCTGC GCGCTCGCTC GCTCACTGAG GCCGCCCGGG CAAAGCCCGG
  51 GCGTCGGGCG ACCTTTGGTC GCCCGGCCTC AGTGAGCGAG CGAGCGCGCA
 101 GAGAGGGAGT GGCCAACTCC ATCACTAGGG GTTCCTTGTA GTTAATGATT
 151 AACCCGCCAT GCTACTTATC TACGTAGCCA TGCTCTAGAC ATGGCTCGAC
 201 AGATCTCAAT ATTGGCCATT AGCCATATTA TTCATTGGTT ATATAGCATA
 251 AATCAATATT GGCTATTGGC CATTGCATAC GTTGTATCTA TATCATAATA
 301 TGTACATTTA TATTGGCTCA TGTCCAATAT GACCGCCATG TTGGCATTGA
 351 TTATTGACTA GTTATTAATA GTAATCAATT ACGGGGTCAT TAGTTCATAG
 401 CCCATATATG GAGTTCCGCG TTACATAACT TACGGTAAAT GGCCCGCCTG
 451 GCTGACCGCC CAACGACCCC CGCCCATTGA CGTCAATAAT GACGTATGTT
 501 CCCATAGTAA CGCCAATAGG GACTTTCCAT TGACGTCAAT GGGTGGAGTA
 551 TTTACGGTAA ACTGCCCACT TGGCAGTACA TCAAGTGTAT CATATGCCAA
 601 GTCCGCCCCC TATTGACGTC AATGACGGTA AATGGCCCGC CTGGCATTAT
 651 GCCCAGTACA TGACCTTACG GGACTTTCCT ACTTGGCAGT ACATCTACGT
 701 ATTAGTCATC GCTATTACCA TGGTGATGCG GTTTTGGCAG TACACCAATG
 751 GGCGTGGATA GCGGTTTGAC TCACGGGGAT TTCCAAGTCT CCACCCCATT
 801 GACGTCAATG GGAGTTTGTT TTGGCACCAA AATCAACGGG ACTTTCCAAA
 851 ATGTCGTAAC AACTGCGATC GCCCGCCCCG TTGACGCAAA TGGGCGGTAG
 901 GCGTGTACGG TGGGAGGTCT ATATAAGCAG AGCTCGTTTA GTGAACCGTC
 951 AGATCACTAG AAGCTTTATT GCGGTAGTTT ATCACAGTTA AATTGCTAAC
1001 GCAGTCAGTG CTTCTGACAC AACAGTCTCG AACTTAAGCT GCAGTGACTC
1051 TCTTAAGGTA GCCTTGCAGA AGTTGGTCGT GAGGCACTGG GCAGGTAAGT
1101 ATCAAGGTTA CAAGACAGGT TTAAGGAGAC CAATAGAAAC TGGGCTTGTC
1151 GAGACAGAGA AGACTCTTGC GTTTCTGATA GGCACCTATT GGTCTTACTG
1201 ACATCCACTT TGCCTTTCTC TCCACAGGTG TCCACTCCCA GTTCAATTAC
1251 AGCTCTTAAG GCTAGAGTAC TTAATACGAC TCACTATAGG CTAGCCTCGA
1301 GAATTCTGCC ATGGCCCTGT GGATGCGCCT CCTGCCCCTG CTGGCGCTGC
1351 TGGCCCTCTG GGGACCTGAC CCAGCCGCAG CCTTTGTGAA CCAACACCTG
1401 TGCGGCTCAG ATCGGTGGA AGCTCTCTAC CTAGTGTGCG GGGAACGAGG
1451 CTTCTTCTAC ACACCCAGGA CCAAGCGGGA GGCAGAGGAC CTGCAGGTGG
```

| pGG2-CMV-hIns plasmid sequence |
|---|

```
1501 GGCAGGTGGA GCTGGGCGGG GGCCCTGGTG CAGGCAGCCT GCAGCCCTTG
1551 GCCCTGGAGG GGTCGCGACA GAAGCGTGGC ATTGTGGAAC AATGCTGTAC
1601 CAGCATCTGC TCCCTCTACC AGCTGGAGAA CTACTGCAAC TAGACGCAGC
1651 TGCAAGCTTA TCGATACCGT CGACCTCGAG GAATTCACGC GTGGTACCTC
1701 TAGAGTCGAC CCGGGCGGCC GCTTCCCTTT AGTGAGGGTT AATGCTTCGA
1751 GCAGACATGA TAAGATACAT TGATGAGTTT GGACAAACCA CAACTAGAAT
1801 GCAGTGAAAA AATGCTTTA TTTGTGAAAT TTGTGATGCT ATTGCTTTAT
1851 TTGTAACCAT TATAAGCTGC AATAAACAAG TTAACAACAA CAATTGCATT
1901 CATTTTATGT TTCAGGTTCA GGGGGAGATG TGGGAGGTTT TTTAAAGCAA
1951 GTAAAACCTC TACAAATGTG GTAAAATCCG ATAAGGGACT AGAGCATGGC
2001 TACGTAGATA AGTAGCATGG CGGGTTAATC ATTAACTACA AGGAACCCCT
2051 AGTGATGGAG TTGGCCACTC CCTCTCTGCG CGCTCGCTCG CTCACTGAGG
2101 CCGGGCGACC AAAGGTCGCC CGACGCCCGG GCTTTGCCCG GCGGCCTCA
2151 GTGAGCGAGC GAGCGCGCCA GCTGGCGTAA TAGCGAAGAG GCCCGCACCG
2201 ATCGCCCTTC CCAACAGTTG CGCAGCCTGA ATGGCGAATG GAATTCCAGA
2251 CGATTGAGCG TCAAAATGTA GGTATTTCCA TGAGCGTTTT TCCGTTGCAA
2301 TGGCTGGCGG TAATATTGTT CTGGATATTA CCAGCAAGGC CGATAGTTTG
2351 AGTTCTTCTA CTCAGGCAAG TGATGTTATT ACTAATCAAA GAAGTATTGC
2401 GACAACGGTT AATTTGCGTG ATGGACAGAC TCTTTTACTC GGTGGCCTCA
2451 CTGATTATAA AAACACTTCT CAGGATTCTG GCGTACCGTT CCTGTCTAAA
2501 ATCCCTTTAA TCGGCCTCCT GTTTAGCTCC CGCTCTGATT CTAACGAGGA
2551 AAGCACGTTA TACGTGCTCG TCAAAGCAAC CATAGTACGC GCCCTGTAGC
2601 GGCGCATTAA GCGCGGCGGG TGTGGTGGTT ACGCGCAGCG TGACCGCTAC
2651 ACTTGCCAGC GCCCTAGCGC CCGCTCCTTT CGCTTTCTTC CCTTCCTTTC
2701 TCGCCACGTT CGCCGGCTTT CCCCGTCAAG CTCTAAATCG GGGGCTCCCT
2751 TTAGGGTTCC GATTTAGTGC TTTACGGCAC CTCGACCCCA AAAAACTTGA
2801 TTAGGGTGAT GGTTCACGTA GTGGGCCATC GddCTGATAG ACGGTTTTTd
2851 GCCCTTTGAC GTTGGAGTCC ACGTTCTTTA ATAGTGGACT CTTGTTCCAA
2901 ACTGGAACAA CACTCAACCC TATCTCGGTC TATTCTTTTG ATTTATAAGG
2951 GATTTTGCCG ATTTCGGCCT ATTGGTTAAA AAATGAGCTG ATTTAACAAA
3001 AATTTAACGC GAATTTTAAC AAAATATTAA CGTCTACAAT TTAAATATTT
3051 GCTTATACAA TCTTCdTGTT TTTGGGGCTT TTCTGATTAT CAACCGGGGT
3101 ACATATGATT GACATGCTAG TTTTACGATT ACCGTTCATC GATTCTCTTG
3151 TTTGCTCCAG ACTCTCAGGC AATGACCTGA TAGCCTTTGT AGAGACCTCT
3201 CAAAAATAGC TACCCTCTCC GGCATGAATT TATCAGCTAG AACGGTTGAA
3251 TATCATATTG ATGGTGATTT GACTGTCTCC GGCCTTTCTC ACCCGTTTGA
3301 ATCTTTACCT ACACATTACT CAGGCATTGC ATTTAAAAMA TATGAGGGTT
3351 CTAAAAATTT TTATCCTTGC GTTGAAATAA AGGCTTCTCC CGCAAAAGTA
```

| pGG2-CMV-hIns plasmid sequence |
|---|
| 3401 TTACAGGGTC ATAATGTTTT TGGTACAACC GATTTAGCTT TATGCTCTGA |
| 3451 GGCTTTATTG CTTAATTTTG CTAATTCTTT GCCTTGCCTG TATGATTTAT |
| 3501 TGGATGTTGG AATCGCCTGA TGCGGTATTT TCTCCTTACG CATCTGTGCG |
| 3551 GTATTTCACA CCGCATATGG TGCACTCTCA GTACAATCTG CTCTGATGCC |
| 3601 GCATAGTTAA GCCAGCCCCG ACACCCGCCA ACACCCGCTG ACGCGCCCTG |
| 3651 ACGGGCTTGT CTGCTCCCGG CATCCGCTTA CAGACAAGCT GTGACCGTCT |
| 3701 CCGGGAGCTG CATGTGTCAG AGGTTTTCAC CGTCATCACC GAAACGCGCG |
| 3751 AGACGAAAGG GCCTCGTGAT ACGCCTATTT TTATAGGTTA ATGTCATGAT |
| 3801 AATAATGGTT TCTTAGACGT CAGGTGGCAC TTTTCGGGGA AATGTGCGCG |
| 3851 GAACCCCTAT TTGTTTATTT TTCTAAATAC ATTCAAATAT GTATCCGCTC |
| 3901 ATGAGACAAT AACCCTGATA AATGCTTCAA TAATATTGAA AAAGGAAGAG |
| 3951 TATGAGTATT CAACATTTCC GTGTCGCCCT TATTCCCTTT TTTGCGGCAT |
| 4001 TTTGCCTTCC TGTTTTTGCT CACCCAGAAA CGCTGGTGAA AGTAAAAGAT |
| 4051 GCTGAAGATC AGTTGGGTGC ACGAGTGGGT TACATCGAAC TGGATCTCAA |
| 4101 CAGCGGTAAG ATCCTTGAGA GTTTTCGCCC CGAAGAACGT TTTCCAATGA |
| 4151 TGAGCACTTT TAAAGTTCTG CTATGTGGCG CGGTATTATC CCGTATTGAC |
| 4201 GCCGGGCAAG AGCAACTCGG TCGCCGCATA CACTATTCTC AGAATGACTT |
| 4251 GGTTGAGTAC TCACCAGTCA CAGAAAAGCA TCTTACGGAT GGCATGACAG |
| 4301 TAAGAGAATT ATGCAGTGCT GCCATAACCA TGAGTGATAA CACTGCGGCC |
| 4351 AACTTACTTC TGACAACGAT CGGAGGACCG AAGGAGCTAA CCGCTTTTTT |
| 4401 GCACAACATG GGGGATCATG TAACTCGCCT TGATCGTTGG GAACCGGAGC |
| 4451 TGAATGAAGC CATACCAAAC GACGAGCGTG ACACCACGAT GCCTGTAGCA |
| 4501 ATGGCAACAA CGTTGCGCAA ACTATTAACT GGCGAACTAC TTACTCTAGC |
| 4551 TTCCCGGCAA CAATTAATAG ACTGGATGGA GGCGGATAAA GTTGCAGGAC |
| 4601 CACTTCTGCG CTCGGCCCTT CCGGCTGGCT GGTTTATTGC TGATAAATCT |
| 4651 GGAGCCGGTG AGCGTGGGTC TCGCGGMATC ATTGCAGCAC TGGGGCCAGA |
| 4701 TGGTAAGCCC TCCCGTATCG TAGTTATCTA CACGACGGGG AGTCAGGCAA |
| 4751 CTATGGATGA ACGAAATAGA CAGATCGCTG AGATAGGTGC CTCACTGATT |
| 4801 AAGCATTGGT AACTGTCAGA CCAAGTTTAC TCATATATAC TTTAGATTGA |
| 4851 TTTAAAACTT CATTTTTAAT TTAAAAGGAT CTAGGTGAAG ATCCTTTTTG |
| 4901 ATAATCTCAT GACCAAAATC CCTTAACGTG AGTTTTCGTT CCACTGAGCG |
| 4951 TCAGACCCCG TAGAAAAGAT CAAAGGATCT CTTGAGATC CTTTTTTTCT |
| 5001 GCGCGTAATC TGCTGCTTGC AAACAAAAAA ACCACCGCTA CCAGCGGTGG |
| 5051 TTTGTTTGCC GGATCAAGAG CTACCAACTC TTTTTCCGAA GGTAACTGGC |
| 5101 TTCAGCAGAG CGCAGATACC AAATACTGTC CTTCTAGTGT AGCCGTAGTT |
| 5151 AGGCCACCAC TTCAAGAACT CTGTAGCACC GCCTACATAC CTCGCTCTGC |
| 5201 TAATCCTGTT ACCAGTGGCT GCTGCCAGTG GCGATAAGTC GTGTCTTACC |
| 5251 GGGTTGGACT CAAGACGATA GTTACCGGAT AAGGCGCAGC GGTCGGGCTG |
| 5301 AACGGGGGGT TCGTGCACAC AGCCCAGCTT GGAGCGAACG ACCTACACCG |

| pGG2-CMV-hIns plasmid sequence |
|---|
| 5351 AACTGAGATA CCTACAGCGT GAGCTATGAG AAAGCGCCAC GCTTCCCGAA |
| 5401 GGGAGAAAGG CGGACAGGTA TCCGGTAAGC GGCAGGGTCG GAACAGGAGA |
| 5451 GCGCACGAGG GAGCTTCCAG GGGGAAACGC CTGGTATdTT TATAGTCCTG |
| 5501 TCGGGTTTCG CCACCTCTGA CTTGAGCGTC GATTTTTGTG ATGCTCGTCA |
| 5551 GGGGGGCGGA GCCTATGGAA AAACGCCAGC AACGCGGCCT TTTTACGGTT |
| 5601 CCTGGCCTTT TGCTGGCCTT TTGCTCACAT GTTCTTTCCT GCGTTATCCC |
| 5651 CTGATTCTGT GGATAACCGT ATTACCGCCT TTGAGTGAGC TGATACCGCT |
| 5701 CGCCGCAGCC GAACGACCGA GCGCAGCGAG TCAGTGAGCG AGGAAGCGGA |
| 5751 AGAGCGCCCA ATACGCAAAC CGCCTCTCCC CGCGCGTTGG-CCGATTCATT |
| 5801 AATG |

ITR 5': 1-136 bp
CMV promoter: 206-1227 bp
hIns: 1304-1650
SV40 polyA: 1752-1974 bp
ITR 3': 2041-2191 bp
C: RSV-rGck (SEQ ID NO:18; FIG. 2)

pGG2-RSV-rGck plasmid sequence
```
   1 GTAGATAAGT AGCATGGCGG GTTAATCATT AACTACAAGG AACCCCTAGT
  51 GATGGAGTTG GCCACTCCCT CTCTGCGCGC TCGCTCGCTC ACTGAGGCCG
 101 GGCGACCAAA GGTCGCCCGA CGCCCGGGCT TTGCCCGGGC GGCCTCAGTG
 161 AGCGAGCGAG CGCGCCAGCT GGCGTAATAG CGAAGAGGCC CGCACCGATC
 201 GCCCTTCCCA ACAGTTGCGC AGCCTGAATG GCGAATGGAA TTCCAGACGA
 251 TTGAGCGTCA AAATGTAGGT ATTTCCATGA GCGTTTTTCC GTTGCAATGG
 301 CTGGCGGTAA TATTGTTCTG GATATTACCA GCAAGGCCGA TAGTTTGAGT
 351 TCTTCTACTC AGGCAAGTGA TGTTATTACT AATCAAAGAA GTATTGCGAC
 401 AACGGTTAAT TTGCGTGATG GACAGACTCT TTTACTCGGT GGCCTCACTG
 451 ATTATAAAAA CACTTCTCAG GATTCTGGCG TACCGTTCCT GTCTAAAATC
 501 CCTTTAATCG GCCTCCTGTT TAGCTCCCGC TCTGATTCTA ACGAGGAAAG
 551 CACGTTATAC GTGCTCGTCA AAGCAACCAT AGTACGCGCC CTGTAGCGGC
 601 GCATTAAGCG CGGCGGGTGT GGTGGTTACG CGCAGCGTGA CCGCTACACT
 651 TGCCAGCGCC CTAGCGCCCG CTCCTTTCGC TTTCTTCCCT TCCTTTCTCG
 701 CCACGTTCGC CGGCTTTCCC CGTCAAGCTC TAAATCGGGG GCTCCCTTTA
 751 GGGTTCCGAT TTAGTGCTTT ACGGCACCTC GACCCCAAAA AACTTGATTA
 801 GGGTGATGGT TCACGTAGTG GGCCATCGCC CTGATAGACG GTTTTTCGCC
 851 CTTTGACGTT GGAGTCCACG TTCTTTAATA GTGGACTCTT GTTCCAAACT
 901 GGAACAACAC TCAACCCTAT CTCGGTCTAT TCTTTTGATT TATAAGGGAT
 951 TTTGCCGATT TCGGCCTATT GGTTAAAAAA TGAGCTGATT TAACAAAAAT
1001 TTAACGCGAA TTTTAACAAA ATATTAACGT CTACAATTTA AATATTTGCT
1051 TATACAATCT TCCTGTTTTT GGGGCTTTTC TGATTATCAA CCGGGGTACA
```

-continued
```
1101 TATGATTGAC ATGCTAGTTT TACGATTACC GTTCATCGAT TCTCTTGTTT

1151 GCTCCAGACT CTCAGGCAAT GACCTGATAG CCTTTGTAGA GACCTCTCAA

1201 AAATAGCTAC CCTCTCCGGC ATGAATTTAT CAGCTAGAAC GGTTGAATAT

1251 CATATTGATG GTGATTTGAC TGTCTaCGGC CTTTCTCACC CGTTTGAATC

1301 TTTACCTACA CATTACTCAG GCATTGCATT TAAAATATAT GAGGGTTCTA

1351 AAAATTTTTA TCCTTGCGTT GAAATAAAGG CTTCTCCCGC AAAAGTATTA

1401 CAGGGTCATA ATGTTTTTGG TACAACCGAT TTAGCTTTAT GCTCTGAGGC

1451 TTTATTGCTT AATTTTGCTA ATTCTTTGCC TTGCCTGTAT GATTTATTGG

1501 ATGTTGGAAT CGCCTGATGC GGTATTTTCT CCTTACGCAT CTGTGCGGTA

1551 TTTCACACCG CAMATGGTGC ACTCTCAGTA CAATCTGCTC TGATGCCGCA

1601 TAGTTAAGCC AGCCCCGACA CCCGCCAACA CCCGCTGACG CGCCCTGACG

1651 GGCTTGTCTG CTCCCGGCAT CCGCTTACAG ACAAGCTGTG ACCGTCTCCG

1701 GGAGCTGCAT GTGTCAGAGG TTTTCACCGT CATCACCGAA ACGCGCGAGA

1751 CGAAAGGGCC TCGTGATACG CCTATTTTTA TAGGTTAATG TCATGATAAT

1801 AATGGTTTCT TAGACGTCAG GTGGCACTTT TCGGGGAAAT GTGCGCGGAA

1851 CCCCTATTTG TTTATTTTTC TAAATACATT CAAATATGTA TCCGCTCATG

1901 AGACAATAAC CCTGATAAAT GCTTCAATAA TATTGAAAAA GGAAGAGTAM

1951 GAGTATTCAA CATTTCCGTG TCGCCCTTAT TCCCTTTTTT GCGGCATTTT

2001 GCCTTCCTGT TTTTGCTCAC CCAGAAACGC TGGTGAAAGT AAAAGATGCT

2051 GAAGATCAGT TGGGTGCACG AGTGGGTTAC ATCGAACTGG ATCTCAACAG

2101 CGGTAAGATC CTTGAGAGTT TTCGCCCCGA AGAACGTTTT CCAATGATGA

2151 GCACTTTTAA AGTTCTGCTA TGTGGCGCGG TATTATCCCG TATTGACGCC

2201 GGGCAAGAGC AACTCGGTCG CCGCATACAC TATTCTCAGA ATGACTTGGT

2251 TGAGTACTCA CCAGTCACAG AAAAGCATCT TACGGATGGC-ATGACAGTAA

2301 GAGAATTATG CAGTGCTGCC ATAACCATGA GTGATAACAC TGCGGCCAAC

2351 TTACTTCTGA CAACGATCGG AGGACCGAAG GAGCTAACCG CTTTTTTGCA

2401 CAACATGGGG GATCATGTAA CTCGCCTTGA TCGTTGGGAA CCGGAGCTGA

2451 ATGAAGCCAT ACCAAACGAC GAGCGTGACA CCACGATGCC TGTAGCAATG

2501 GCAACAACGT TGCGCAAACT ATTAACTGGC GAACTACTTA CTCTAGCTTC

2551 CCGGCAACAA TTAATAGACT GGATGGAGGC GGATAAAGTT GCAGGACCAC

2601 TTCTGCGCTC GGCCCTTCCG GCTGGCTGGT TTATTGCTGA TAAATCTGGA

2651 GCCGGTGAGC GTGGGTCTCG CGGTATCATT GCAGCACTGG GGCCAGATGG

2701 TAAGCCCTCC CGTATCGTAG TTATCTACAC GACGGGGAGT CAGGCAACTA

2751 TGGATGAACG AAATAGACAG ATCGCTGAGA TAGGTGCCTC ACTGATTAAG

2801 CATTGGTAAC TGTCAGACCA AGTTTACTCA TATATACTTT AGATTGATTT

2851 AAAACTTCAT TTTTAATTTA AAAGGATCTA GGTGAAGATC CTTTTTGATA

2901 ATCTCATGAC CAAATCCCT TAACGTGAGT TTTCGTTCCA CTGAGCGTCA

2951 GACCCCGTAG AAAAGATCAA AGGATCTTCT TGAGATCCTT TTTTTCTGCG

3001 CGTAATCTGC TGCTTGCAAA CAAAAAAACC ACCGCTACCA GCGGTGGTTT

3051 GTTTGCCGGA TCAAGAGCTA CCAACTCTTT TTCCGAAGGT AACTGGCTTC

3101 AGCAGAGCGC AGATACCAAA TACTGTCCTT CTAGTGTAGC CGTAGTTAGG
```

-continued

```
3151 CCACCACTTC AAGAACTCTG TAGCACCGCC TACATACCTC GCTCTGCTAA

3201 TCCTGTMACC AGTGGCTGCT GCCAGTGGCG ATAAGTCGTG TCTTACCGGG

3251 TTGGACTCAA GACGATAGTT ACCGGATAAG GCGCAGCGGT CGGGCTGAAC

3301 GGGGGGTTCG TGCACACAGC CCAGCTTGGA GCGAACGACC TACACCGAAC

3351 TGAGATACCT ACAGCGTGAG CTATGAGAAA GCGCCACGCT TCCCGAAGGG

3401 AGAAAGGCGG ACAGGTATCC GGTAAGCGGC AGGGTCGGAA CAGGAGAGCG

3451 CACGAGGGAG CTTCCAGGGG GAAACGCCTG GTATCTTTAT AGTCCTGTCG

3501 GGTTTCGCCA CCTCTGACTT GAGCGTCGAT TTTTGTGATG CTCGTCAGGG

3551 GGGCGGAGCC TATGGAAAAA CGCCAGCAAC GCGGCCTTTT TACGGTTCCT

3601 GGCCTTTTGC TGGCCTTTTG CTCACATGTT CTTTCCTGCG TTATCCCCTG

3651 ATTCTGTGGA TAACCGMATT ACCGCCTTTG AGTGAGCTGA TACCGCTCGC

3701 CGCAGCCGAA CGACCGAGCG CAGCGAGTCA GTGAGCGAGG AAGCGGAAGA

3751 GCGCCCAATA CGCAAACCGC CTCTCCCCGC GCGTTGGCCG ATTCATTAAT

3801 GCAGCAGCTG CGCGCTCGCT CGCTCACTGA GGCCGCCCGG GCAAAGCCCG

3851 GGCGTCGGGC GACCTTTGGT CGCCCGGCCT CAGTGAGCGA GCGAGCGCGC

3901 AGAGAGGGAG TGGCCAACTC CATCACTAGG GGTTCCTTGT AGTTAATGAT

3951 TAACCCGCCA TGCTACTTAT CTACGTAGCC ATGCTCTGGA AGATCTCGAC

4001 GCGTCATGTT TGACAGCTTA TCATCGCAGA TCCGTATGGT GCACTCTCAG

4051 TACAATCTGC TCTGATGCCG CATAGTTAAG CCAGTATCTG CTCCCTGCTT

4101 GTGTGTTGGA GGTCGCTGAG TAGTGCGCGA GCAAAATTTA AGCTACAACA

4151 AGGCAAGGCT TGACCGACAA TTGCATGAAG AATCTGCTTA GGGTTAGGCG

4201 TTTTGCGCTG CTTCGCGATG TACGGGCCAG ATATTCGCGT ATCTGAGGGG

4251 ACTAGGGTGT GTTTAGGCGA AAAGCGGGGC TTCGGTTGTA CGCGGTTAGG

4301 AGTCCCCTCA GGATATAGTA GTTTCGCTTT TGCATAGGGA GGGGGAAATG

4351 TAGTCTTATG CAATACTCTT GTAGTCTTGC AACATGGTAA CGATGAGTTA

4401 GCAACATGCC TTACAAGGAG AGAAAAAGCA CCGTGCATGC CGATTGGTGG

4451 AAGTAAGGTG GTACGATCGT GCCTTATTAG GAAGGCAACA GACGGGTCTG

4501 ACATGGATTG GACGAACCAC TAAATTCCGC ATTGCAGAGA TATTGTATTT

4551 AAGTGCCTAG CTCGATACAA TAAACGCCAT TTGACCATTC ACCACATTGG

4601 TGTGCACCTC CAAGCTGGGT ACCAGCTGCT AGCAAGCTTG AGATCTGCTT

4651 CAGCTGGAGG CACTGGGCAG GTAAGTATCA AGGTTACAAG ACAGGTTTAA

4701 GGAGACCAAT AGAAACTGGG CTTGTCGAGA CAGAGAAGAC TCTTGCGTTT

4751 CTGATAGGCA CCTATTGGTC TTACTGACAT CCACTTTGCC TTTCTCTCCA

4801 CAGGTGCAGC TGCTGCAGCG GGAATTCAAC AGGTGGCCTC AGGAGTCAGG

4851 AACATCTCTA CTTCCCCAAC GACCCCTGGG TTGTCCTCTC AGAGATGGCT

4901 ATGGATACTA CAAGGTCTGG AGCCCAGTTG TTGACTCTGG TCGAGCAGAT

4951 CCTGGCAGAG TTCCAGCTGC AGGAGGAAGA CCTGAAGAAG GTGATGAGCC

5001 GGATGCAGAA GGAGATGGAC CGTGGCCTGA GGCTGGAGAC CCACGAGGAG

5051 GCCAGTGTAA AGATGTTACC CACCTACGTG CGTTCCACCC CAGAAGGCTC

5101 AGAAGTCGGA GACTTTCTCT CCTTAGACCT GGGAGGAACC AACTTCAGAG
```

-continued

```
5151 TGATGCTGGT CAAAGTGGGA GAGGGGGAGG CAGGGCAGTG GAGCGTGAAG

5201 ACAAAACACC AGATGTACTC CATCCCCGAG GACGCCATGA CGGGCACTGC

5251 CGAGATGCTC TTTGACTACA TCTCTGAATG CATCTCTGAC TTCCTTGACA

5301 AGCATCAGAT GAAGCACAAG AAACTGCCCC TGGGCTTCAC CTTCTCCTTC

5351 CCTGTGAGGC ACGAAGACCT AGACAAGGGC ATCCTCCTCA ATTGGACCAA

5401 GGGCTTCAAG GCCTCTGGAG CAGAAGGGAA CAACATCGTA GGACTTCTCC

5451 GAGATGCTAT CAAGAGGAGA GGGGACTTTG AGATGGATGT GGTGGCAATG

5501 GTGAACGACA CAGTGGCCAC AATGATCGCC TGCTACTATG AAGACCGCCA

5551 ATGTGAGGTC GGCATGATTG TGGGCACTGG CTGCAATGCC TGCTACATGG

5601 AGGAAATGCA GAATGTGGAG CTGGTGGAAG GGGATGAGGG ACGCATGTGC

5651 GTCAACACGG AGTGGGGCGC CTTCGGGGAC TCGGGCGAGC TGGATGAGTT

5701 CCTACTGGAG TATGACCGGA TGGTGGATGA AAGCTCAGCG AACCCCGGTC

5751 AGCAGCTGTA CGAGAAGATC ATCGGTGGGA AGTATATGGG CGAGCTGGTA

5801 CGACTTGTGC TGCTTAAGCT GGTGGACGAG AACCTTCTGT TCCACGGAGA

5851 GGCCTCGGAG CAGCTGCGCA CGCGTGGTGC TTTTGAGACC CGTTTCGTGT

5901 CACAAGTGGA GAGCGACTCC GGGGACCGAA AGCAGATCCA CAACATCCTA

5951 AGCACTCTGG GGCTTCGACC CTCTGTCACC GACTGCGACA TTGTGCGCCG

6001 TGCCTGTGAA AGCGTGTCCA CTCGCGCCGC CCATATGTGC TCCGCAGGAC

6051 TAGCTGGGGT CATAAATCGA ATGCGCGAAA GCCGCAGTGA GGACGTGATG

6101 CGCATCACTG TGGGCGTGGA TGGCTCCGTG TACAAGCTGC ACCCGAGCTT

6151 CAAGGAGCGG TTTCACGCCA GTGTGCGCAG GCTGACACCC AACTGCGAAA

6201 TCACCTTCAT CGAATCAGAG GAGGGCAGCG GCAGGGGAGC CGCACTGGTC

6251 TCTGCGGTGG CCTGCAAGAA GGCTTGCATG CTGGCCCAGT GAAATCCAGG

6301 TCATATGGAC CGGGACCTGG GTTCCACGGG GACTCCACAC ACCACAAATG

6351 CTCCCAGCCC ACCGGGGCAG GAGACCTATT CTGCTGCTAC CCCTGGAAAA

6401 TGGGGAGAGG CCCCTGCAAG CCGAGTCGGC CAGTGGGACA GCCCTAGGCT

6451 GGATCGGCCG CTTCGAGCAG ACATGATAAG ATACATTGAT GAGTTTGGAC

6501 AAACCACAAC TAGAATGCAG TGAAAAAAAT GCTTTATTTG TGAAATTTGT

6551 GATGCTATTG CTTTATTTGT AACCATTATA AGCTGCAATA AACAAGTTAA

6601 CAACAACAAT TGCATTCATT TTATGTTTCA GGTTCAGGGG GAGATGTGGG

6651 AGGTTTTTTA AAGCAAGTAA AACCTCTACA AATGTGGTAA AATCGATTAG

6701 GATCTTCCTA GAGCATGGCT AC
```

ITR 5': 3802-3937 bp
RSV promoter: 4088-4803 bp
rGck: 4915-6292 bp

SV40 polyA: 6456-6694 bp
ITR 3': 38-188 bp
D: CMV-hIns-RSV-hGck (SEQ ID NO: 9; FIG. 4)

```
pAAV-CMV-hIns-RSV-hGck plasmid sequence
  1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCGCG

151 ATATCTGTAG TTAATGATTA ACCCGCCATG CTACTTATCT ACAGATCTCA

201 ATATTGGCCA TTAGCCATAT TATTCATTGG TTATATAGCA TAAATCAATA
```

```
-continued
 251 TTGGCTATTG GCCATTGCAT ACGTTGTATC TATATCATAA TATGTACATT
 301 TATATTGGCT CATGTCCAAT ATGACCGCCA TGTTGGCATT GATTATTGAC
 351 TAGTTATTAA TAGTAATCAA TTACGGGGTC ATTAGTTCAT AGCCCATATA
 401 TGGAGTTCCG CGTTACATAA CTTACGGTAA ATGGCCCGCC TGGCTGACCG
 451 CCCAACGACC CCCGCCCATT GACGTCAATA ATGACGTATG TTCCCATAGT
 501 AACGCCAATA GGGACTTTCC ATTGACGTCA ATGGGTGGAG TATTTACGGT
 551 AAACTGCCCA CTTGGCAGTA CATCAAGTGT ATCATATGCC AAGTCCGCCC
 601 CCTATTGACG TCAATGACGG TAAATGGCCC GCCTGGCATT ATGCCCAGTA
 651 CATGACCTTA CGGGACTTTC CTACTTGGCA GTACATCTAC GTATTAGTCA
 701 TCGCTATTAC CATGGTGATG CGGTTTTGGC AGTACACCAA TGGGCGTGGA
 751 TAGCGGTTTG ACTCACGGGG ATTTCCAAGT CTCCACCCCA TTGACGTCAA
 801 TGGGAGTTTG TTTTGGCACC AAAATCAACG GGACTTTCCA AAATGTCGTA
 851 ACAACTGCGA TCGCCCGCCC CGTTGACGCA AATGGGCGGT AGGCGTGTAC
 901 GGTGGGAGGT CTATATAAGC AGAGCTCGTT TAGTGAACCG TCAGATCACT
 951 AGGCTAGCTA TTGCGGTAGT TTATCACAGT TAAATTGCTA ACGCAGTCAG
1001 TGCTTCTGAC ACAACAGTCT CGAACTTAAG CTGCAGTGAC TCTCTTAAGG
1051 TAGCCTTGCA GAAGTTGGTC GTGAGGCACT GGGCAGGTAA GTATCAAGGT
1101 TACAAGACAG GTTTAAGGAG ACCAATAGAA ACTGGGCTTG TCGAGACAGA
1151 GAAGACTCTT GCGTTTCTGA TAGGCACCTA TTGGTCTTAC TGACATCCAC
1201 TTTGCCTTTC TCTCCACAGG TGTCCACTCC CAGTTCAATT ACAGCTCTTA
1251 AGGCTAGAGT ACTTAATACG ACTCACTATA.GAATACGACT CACTATAGGG
1301 AGACGCTAGC GTCGACCTTC TGCCATGGCC CTGTGGATGC GCCTCCTGCC
1351 CCTGCTGGCG CTGCTGGCCC TCTGGGGACC TGACCCAGCC GCAGCCTTTG
1401 TGAACCAACA CCTGTGCGGC TCAGATCTGG TGGAAGCTCT CTACCTAGTG
1451 TGCGGGGAAC GAGGCTTCTT CTACACACCC AGGACCAAGC GGGAGGCAGA
1501 GGACCTGCAG GTGGGGCAGG TGGAGCTGGG CGGGGGCCCT GGTGCAGGCA
1551 GCCTGCAGCC CTTGGCCCTG GAGGGGTCGC GACAGAAGCG TGGCATTGTG
1601 GAACAATGCT GTACCAGCAT CTGCTCCCTC TACCAGCTGG AGAACTACTG
1651 CAACTAGACG CAGCCGTCGA CGGTACCAGC GCTGTCGAGG CCGCTTCGAG
1701 CAGACATGAT AAGATACATT GATGAGTTTG GACAAACCAC AACTAGAATG
1751 CAGTGAAAAA AATGCTTTAT TTGTGAAATT TGTGATGCTA TTGCTTTATT
1801 TGTAACCATT ATAAGCTGCA ATAAACAAGT TAACAACAAC AATTGCATTC
1851 ATTTMATGTT TCAGGTTCAG GGGGAGATGT GGGAGGTTTT TTAAAGCAAG
1901 TAAAACCTCT ACAAATGTGG TAAAATCGAT TAGGATCTTC CTAGAGCATG
1951 GCTACCTAGA CATGGCTCGA CAGATCAGCG CTCATGCTCT GGAAGATCTC
2001 GATTTATCCA TGTTTGACAG CTTATCATCG CAGATCCGTA TGGTGCACTC
2051 TCAGTACAAT CTGCTCTGAT GCCGCATAGT TAAGCCAGTA TCTGCTCCCT
2101 GCTTGTGTGT TGGAGGTCGC TGAGTAGTGC GCGAGCAAAA TTTAAGCTAC
2151 AACAAGGCAA GGCTTGACCG ACAATTGCAT GAAGAATCTG CTTAGGGTTA
2201 GGCGTTTTGC GCTGCTTCGC GATGTACGGG CCAGATATTC GCGTATCTGA
```

```
2251 GGGGACTAGG GTGTGTTTAG GCGAAAAGCG GGGCTTCGGT TGTACGCGGT

2301 TAGGAGTCCC CTCAGGATAT AGTAGTTTCG CTTTTGCATA GGGAGGGGGA

2351 AATGTAGTCT TATGCAATAC TCTTGTAGTC TTGCAACATG GTAACGATGA

2401 GTTAGCAACA TGCCTTACAA GGAGAGAAAA AGCACCGTGC ATGCCGATTG

2451 GTGGAAGTAA GGTGGTACGA TCGTGCCTTA TTAGGAAGGC AACAGACGGG

2501 TCTGACATGG ATTGGACGAA CCACTAAATT CCGCATTGCA GAGATATTGT

2551 ATTTAAGTGC CTAGCTCGAT ACAATAAACG CCATTTGACC ATTCACCACA

2601 TTGGTGTGCA CCTCCAAGCT GGGTACCAGC TTCTAGAGAG ATCTGCTTCA

2651 GCTGGAGGCA CTGGGCAGGT AAGTATCAAG GTTACAAGAC AGGTTTAAGG

2701 AGACCAATAG AAACTGGGCT TGTCGAGACA GAGAAGACTC TTGCGTTTCT

2751 GATAGGCACC TATTGGTCTT ACTGACATCC ACTTTGCCTT TCTCTCCACA

2001 GGTGCAGCTG CTGCAGCGGT CTAGAACTCG AGTCGAGACC ATGGCGATGG

2051 ATGTCACAAG GAGCCAGGCC CAGACAGCCT TGACTCTGGT AGAGCAGATC

2901 CTGGCAGAGT TCCAGCTGCA GGAGGAGGAC CTGAAGAAGG TGATGAGACG

2951 GATGCAGAAG GAGATGGACC GCGGCCTGAG GCTGGAGACC CATGAAGAGG

3001 CCAGTGTGAA GATGCTGCCC ACCTACGTGC GCTCCACCCC AGAAGGCTCA

3051 GAAGTCGGGG ACTTCCTCTC CCTGGACCTG GGTGGCACTA ACTTCAGGGT

3101 GATGCTGGTG AAGGTGGGAG AAGGTGAGGA GGGGCAGTGG AGCGTGAAGA

3131 CCAAACACCA GATGTACTCC ATCCCCGAGG ACGCCATGAC CGGCACTGCT

3201 GAGATGCTCT TCGACTACAT CTCTGAGTGC ATCTCCGAQT TCCTGGACAA

3251 GCATCAGATG AAACACAAGA AGCTGCCCCT GGGCTTCACC TTCTCCTTTC

3301 CTGTGAGGCA CGAAGACATC GATAAGGGCA TCCTTCTCAA CTGGACCAAG

3351 GGCTTCAAGG CCTCAGGAGC AGAAGGGAAC AATGTCGTGG GGCTTCTGCG

3401 AGACGCTATC AAACGGAGAG GGACTTTGA ATGGATGTG GTGGCAATGG

3451 TGAATGACAC GGTGGCCACG ATGATCTCCT GCTACTACGA AGACCATCAG

3501 TGCGAGGTCG GCATGATCGT GGGCACGGGC TGCAATGCCT GCTACATGGA

3551 GGAGATGCAG AATGTGGAGC TGGTGGAGGG GGACGAGGGC CGCATGTGCG

3501 TCAATACCGA GTGGGGCGCC TTCGGGGACT CCGGCGAGCT GGACGAGTTC

3651 CTGCTGGAGT ATGACCGCCT GGTGGACGAG AGCTCTGCAA ACCCCGGTCA

3701 GCAGCTGTAT GAGAAGCTCA TAGGTGGCAA GTACATGGGC GAGQTGGTGC

3751 GGCTTGTGCT GCTCAGGCTC GTGGAdGAAA ACCTGCTCTT CCACGGGGAG

3801 GCCTCCGAGC AGCTGCGCAC ACGCGGAGCC TTCGAGACGC GCTTCGTGTC

3851 GCAGGTGGAG AGCGACACGG GCGACCGCAA GCAGATCTAC AACATCCTGA

3901 GCACGCTGGG GCTGCGACCC TCGACCACCG ACTGCGACAT CGTGCGCCGC

3951 GCCTGCGAGA GCGTGTCTAC GCGCGCTGCG CACATGTGCT CGGCGGGGCT

4001 GGCGGGCGTC ATCAACCGCA TGCGCGAGAG CCGCAGCGAG GACGTAATGC

4051 GCATCACTGT GGGCGTGGAT GGCTCCGTGT ACAAGCTGCA CCCCAGCTTC

4101 AAGGAGCGGT TCCATGCCAG CGTGCGCAGG CTGACGCCCA GCTGCGAGAT

4151 CACCTTCATC GAGTCGGAGG AGGGCAGTGG CCGGGGCGCG GCCCTGGTCT

4201 CGGCGGTGGC CTGTAAGAAG GCCTGTATGC TGGGCCAGTG ACTCGAGCAC

4251 GTGGAGCTCG CTGATCAGCC TCGACTGTGC CTTCTAGTTG CCAGCCATCT
```

```
4301 GTTGTTTGCC CCTCCCCCGT GCCTTCCTTG ACCCTGGAAG GTGCCACTCC
4351 CACTGTCCTT TCCTAATAAA ATGAGGAAAT TGCATCGCAT TGTCTGAGTA
4401 GGTGTCATTC TATTCTGGGG GGTGGGGTGG GGCAGGACAG CAAGGGGGAG
4451 GATTGGGAAG ACAATAGCAG GCATGCTGGG GATGCGGTGG GCTCTATGGC
4501 CACGTGATTT AAATGCGGCC GCAGGAACCC CTAGTGATGG AGTTGGCCAC
4551 TCCCTCTCTG CGCGCTCGCT CGCTCACTGA GGCCGGGCGA CCAAAGGTCG
4501 CCCGACGCCC GGGCTTTGCC CGGGCGGCCT CAGTGAGCGA GCGAGCGCGC
4651 AGCTGCCTGC AGGGGCGCCT GATGCGGTAT TTTCTCCTTA CGCATCTGTG
4701 CGGTATTTCA CACCGCATAC GTCAAAGCAA CCATAGTACG CGCCCTGTAG
4751 CGGCGCATTA AGCGCGGCGG GTGTGGTGGT TACGCGCAGC GTGACCGCTA
4001 CACTTGCCAG CGCCCTAGCG CCCGCTCCTT TCGCTTTCTT CCCTTCCTTT
4051 CTCGCCACGT TCGCCGGCTT TCCCCGTCAA GCTCTAAATC GGGGGCTCCC
4901 TTTAGGGTTC CGATTTAGTG CTTTACGGCA CdTCGACCCC AAAAAACTTG
4951 ATTTGGGTGA TGGTTCACGT AGTGGGCCAT CGCCCTGATA GACGGTTTTT
5001 CGCCCTTTGA CGTTGGAGTC CACGTTCTTT AATAGTGGAC TCTTGTTCCA
5051 AACTGGAACA ACACTCAACC CTATCTCGGG CTATTCTTTT GATTTATAAG
5101 GGATTTTGCC GATTTCGGCC TATTGGTTAA AAAATGAGCT GATTTAACAA
5151 AAATTTAACG CGAATTTTAA CAAAATATTA ACGTTTACAA TTTTATGGTG
5201 CACTCTCAGT ACAATCTGCT CTGATGCCGC ATAGTTAAGC CAGCCCCGAC
5251 ACCCGCCAAC ACCCGCTGAC GCGCCCTGAC GGGCTTGTCT GCTCCCGGCA
5301 TCCGCTTACA GACAAGCTGT GACCGTCTCC GGGAGCTGCA TGTGTCAGAG
5351 GTTTTCACCG TCATCACCGA AACGCGCGAG ACGAAAGGGC CTCGTGATAC
5401 GCCTATTTTT ATAGGTTAAT GTCATGATAA TAATGGTTTC TTAGACGTCA
5451 GGTGGCACTT TTCGGGGAAA TGTGCGCGGA ACCCCTATTT GTTTATTTTT
5501 CTAAATACAT TCAAATATGT ATCCGCTCAT GAGACAATAA CCCTGATAAA
5551 TGCTTCAATA ATATTGAAAA AGGAAGAGTA TGAGTATTCA ACATTTCCGT
5501 GTCGCCCTTA TTCCCTTTTT TGCGGCATTT TGCCTTCCTG TTTTTGCTCA
5651 CCCAGAAACG CTGGTGAAAG TAAAAGATGC TGAAGATCAG TTGGGTGCAC
5701 GAGTGGGTTA CATCGAACTG GATCTCAACA GCGGTAAGAT CCTTGAGAGT
5751 TTTCGCCCCG AAGAACGTTT TCCAATGATG AGCACTTTTA AAGTTCTGCT
5801 ATGTGGCGCG GTATTATCCC GTATTGACGC CGGGCAAGAG CAACTCGGTC
5851 GCCGCATACA CTATTCTCAG AATGACTTGG TTGAGTACTC ACCAGTCACA
5901 GAAAAGCATC TTACGGATGG CATGACAGTA AGAGAATTAT GCAGTGCTGC
5951 CATAACCATG AGTGATAACA CTGCGGCCAA CTTACTTCTG ACAACGATCG
6001 GAGGACCGAA GGAGCTAACC GCTTTTTTGC ACAACATGGG GGATCATGTA
6051 ACTCGCCTTG ATCGTTGGGA ACCGGAGCTG AATGAAGCCA TACCAAACGA
6101 CGAGCGTGAC ACCACGATGC CTGTAGCAAT GGCAACAACG TTGCGCAAAC
6151 TATTAACTGG CGAACTACTT ACTCTAGCTT CCCGGCAACA ATTAATAGAC
6201 TGGATGGAGG CGGATAAAGT TGCAGGACCA CTTCTGCGCT CGGCCCTTCC
6251 GGCTGGCTGG TTTATTGCTG ATAAATCTGG AGCCGGTGAG CGTGGGTCTC
```

```
6301 GCGGTATCAT TGCAGCACTG GGGCCAGATG GTAAGCCCTC CCGTATCGTA

6351 GTTATCTACA CGACGGGAG TCAGGCAACT ATGGATGAAC GAAATAGACA

6401 GATCGCTGAG ATAGGTGCCT CACTGATTAA GCATTGGTAA CTGTCAGACC

5451 AAGTTTACTC ATATATACTT TAGATTGATT TAAAACTTCA TTTTTAATTT

6501 AAAAGGATCT AGGTGAAGAT CCTTTTTGAT AATCTCATGA CCAAAATCCC

6551 TTAACGTGAG TTTTCGTTCC ACTGAGCGTC AGACCCCGTA GAAAAGATCA

6601 AAGGATCTTC TTGAGATCCT TTTTTTCTGC GCGTAATCTG CTGCTTGCAA

6651 ACAAAAAAAC CACCGCTACC AGCGGTGGTT TGTTTGCCGG ATCAAGAGCT

6701 ACCAACTCTT TTTCCGAAGG TAACTGGCTT CAGCAGAGCG CAGATACCAA

6751 ATACTGTCCT TCTAGTGTAG CCGTAGTTAG GCCACCACTT CAAGAACTCT

6801 GTAGCACCGC CTACATACCT CGCTCTGCTA ATCCTGTTAC CAGTGGCTGC

6851 TGCCAGTGGC GATAAGTCGT GTCTTACCGG GTTGGACTCA AGACGATAGT

6901 TACCGGATAA GGCGCAGCGG TCGGGCTGAA CGGGGGGTTC GTGCACACAG

6951 CCCAGCTTGG AGCGAACGAC CTACACCGAA CTGAGATACC TACAGCGTGA

7001 GCTATGAGAA AGCGCCACGC TTCCCGAAGG GAGAAAGGCG GACAGGTATC

7051 CGGTAAGCGG CAGGGTCGGA ACAGGAGAGC GCACGAGGGA GCTTCCAGGG

7101 GGAAACGCCT GGTATCTTTA TAGTCCTGTC GGGTTTCGCC ACCTCTGACT

7151 TGAGCGTCGA TTTTTGTGAT GCTCGTCAGG GGGCGGAGC CTATGGAAAA

7201 ACGCCAGCAA CGCGGCCTTT TTACGGTTCC TGGCCTTTTG CTGGCCTTTT

7251 GCTCACATGT
```

ITR 5': 1-141 bp
CMV promoter: 193-1310 bp
hIns: 1318-1664 bp
SV40 polyA: 1678-1976 bp
RSV promoter: 2092-2801 bp hGck: 2826-4240 bp
bGH polyA: 4248-4506 bp
ITR 3': 4523-4663 bp E: RSV-hGck-CMV-hIns (SEQ ID NO:10; FIG. 4)

```
pAAV-RSV-hGck-CMV-hIns plasmid sequence
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCGCG

151 ATATCCATGT TGACAGCTT ATCATCGCAG ATCCGTATGG TGCACTCTCA

201 GTACAATCTG CTCTGATGCC GCATAGTTAA GCCAGTATCT GCTCCCTGCT

251 TGTGTGTTGG AGGTCGCTGA GTAGTGCGCG AGCAAAATTT AAGCTACAAC

301 AAGGCAAGGC TTGACCGACA ATTGCATGAA GAATCTGCTT AGGGTTAGGC

351 GTTTTGCGCT GCTTCGCGAT GTACGGGCCA GATATTCGCG TATCTGAGGG

401 GACTAGGGTG TGTTTAGGCG AAAAGCGGGG CTTCGGTTGT ACGCGGTTAG

451 GAGTCCCCTC AGGATATAGT AGTTTCGCTT TTGCATAGGG AGGGGGAAAT

501 GTAGTCTTAT GCAATACTCT TGTAGTCTTG CAACATGGTA ACGATGAGTT

551 AGCAACATGC CTTACAAGGA GAGAAAAAGC ACCGTGCATG CCGATTGGTG

601 GAAGTAAGGT GGTACGATCG TGCCTTATTA GGAAGGCAAC AGACGGGTCT

651 GACATGGATT GGACGAACCA CTAAATTCCG CATTGCAGAG ATATTGTATT

701 TAAGTGCCTA GCTCGATACA ATAAACGCCA TTTGACCATT CACCACATTG

751 GTGTGCACCT CCAAGCTGGG TACCAGCTTC TAGAGAGATC TGCTTCAGCT
```

```
 801 GGAGGCACTG GGCAGGTAAG TATCAAGGTT ACAAGACAGG TTTAAGGAGA
 851 CCAATAGAAA CTGGGCTTGT CGAGACAGAG AAGACTCTTG CGTTTCTGAT
 901 AGGCACCTAT TGGTCTTACT GACATCCACT TTGCCTTTCT CTCCACAGGT
 951 GCAGCTGCTG CAGCGGTCTA GAACTCGAGT CGAGACCATG GCGATGGATG
1001 TCACAAGGAG CCAGGCCCAG ACAGCCTTGA CTCTGGTAGA GCAGATCCTG
1051 GCAGAGTTCC AGCTGCAGGA GGAGGACCTG AAGAAGGTGA TGAGACGGAT
1101 GCAGAAGGAG ATGGACCGCG GCCTGAGGCT GGAGACCCAT GAAGAGGCCA
1151 GTGTGAAGAT GCTGCCCACC TACGTGCGCT CCACCCCAGA AGGCTCAGAA
1201 GTCGGGGACT TCCTCTCCCT GGACCTGGGT GGCACTAACT TCAGGGTGAT
1251 GCTGGTGAAG GTGGGAGAAG GTGAGGAGGG GCAGTGGAGC GTGAAGACCA
1301 AACACCAGAT GTACTCCATC CCCGAGGACG CCATGACCGG CACTGCTOAG
1351 ATGCTCTTCG ACTACATCTC TGAGTGCATC TCCGACTTCC TGGACAAGCA
1401 TCAGATGAAA CACAAGAAGC TGCCCCTGGG CTTCACCTTC TCCTTTCCTG
1451 TGAGGCACGA AGACATCGAT AAGGGCATCC TTCTCAACTG GACCAAGGGC
1501 TTCAAGGCCT CAGGAGCAGA AGGGAACAAT GTCGTGGGGC TTCTGCGAGA
1551 CGCTATCAAA CGGAGAGGGG ACTTTGAAAT GGATGTGGTG GCAATGGTGA
1601 ATGACACGGT GGCCACGATG ATCTCCTGCT ACTACGAAGA CCATCAGTGC
1651 GAGGTCGGCA TGATCGTGGG CACGGGCTGC AATGCCTGCT ACATGGAGGA
1701 GATGCAGAAT GTGGAGCTGG TGGAGGGGGA CGAGGGCCGC ATGTGCGTCA
1751 ATACCGAGTG GGGCGCCTTC GGGGACTCCG GCGAGCTGGA CGAGTTCCTG
1801 CTGGAGTATG ACCGCCTGGT GGACGAGAGC TCTGCAAACC CCGGTCAGCA
1851 GCTGTATGAG AAGCTCATAG GTGGCAAGTA CATGGGCGAG CTGGTGCGGC
1901 TTGTGCTGCT CAGGCTCGTG GACGAAAACC TGCTCTTCCA CGGGGAGGCC
1951 TCCGAGCAGC TGCGCACACG CGGAGCCTTC GAGACGCGCT TCGTGTCGCA
2001 GGTGGAGAGC GACACGGGCG ACCGCAAGCA GATCTACAAC ATCCTGAGCA
2051 CGCTGGGGCT GCGACCCTCG ACCACCGACT GCGACATCGT GCGCCGCGCC
2101 TGCGAGAGCG TGTCTACGCG CGCTGCGCAC ATGTGCTCGG CGGGGCTGGC
2151 GGGCGTCATC AACCGCATGC GCGAGAGCCG CAGCGAGGAC GTAATGCGCA
2201 TCACTGTGGG CGTGGATGGC TCCGTGTACA AGCTGCACCC CAGCTTCAAG
2251 GAGCGGTTCC ATGCCAGCGT GCGCAGGCTG ACGCCCAGCT GCGAGATCAC
2301 CTTCATCGAG TCGGAGGAGG GCAGTGGCCG GGGCGCGGCC CTGGTCTCGG
2351 CGGTGGCCTG TAAGAAGGCC TGTATGCTGG GCCAGTGACT CGAGCACGTG
2401 GAGCTCGCTG ATCAGCCTCG ACTGTGCCTT CTAGTTGCCA GCCATCTGTT
2451 GTTTGCCCCT CCCCCGTGCC TTCCTTGACC CTGGAAGGTG CCACTCCCAC
2501 TGTCCTTTCC TAATAAAATG AGGAAATTGC ATCGCATTGT CTGAGTAGGT
2551 GTCATTCTAT TCTGGGGGGT GGGGTGGGGC AGGACAGCAA GGGGGAGGAT
2601 TGGGAAGACA ATAGCAGGCA TGCTGGGGAT GCGGTGGGCT CTATGGCCAC
2651 GTGATTTATC TGTAGTTAAT GATTAACCCG CCATGCTACT TATCTACAGA
2701 TCTCAATATT GGCCATTAGC CATATTATTC ATTGGTTATA TAGCATAAAT
2751 CAATATTGGC TATTGGCCAT TGCATACGTT GTATCTATAT CATAATATGT
```

```
2801 ACATTTATAT TGGCTCATGT CCAATATGAC CGCCATGTTG CATTGATTA
2851 TTGACTAGTT ATTAATAGTA ATCAATTACG GGGTCATTAG TTCATAGCCC
2901 ATATATGGAG TTCCGCGTTA CATAACTTAC GGTAAATGGC CCGCCTGGCT
2951 GACCGCCCAA CGACCCCGC CCATTGACGT CAATAATGAC GTATGTTCCC
3001 ATAGTAACGC CAATAGGGAC TTTCCATTGA CGTCAATGGG TGGAGTATTT
3051 ACGGTAAACT GCCCACTTGG CAGTACATCA AGTGTATCAT ATGCCAAGTC
3101 CGCCCCCTAT TGACGTCAAT GACGGTAAAT GGCCCGCCTG GCATTATGCC
3151 CAGTACATGA CCTTACGGGA CTTTCCTACT TGGCAGTACA TCTACGTATT
3201 AGTCATCGCT ATTACCATGG TGATGCGGTT TTGGCAGTAC ACCAATGGGC
3251 GTGGATAGCG GTTTGACTCA CGGGGATTTC CAAGTCTCCA CCCCATTGAC
3301 GTCAATGGGA GTTTGTTTTG GCACCAAAAT CAACGGGACT TTCCAAAATG
3351 TCGTAACAAC TGCGATCGCC CGCCCCGTTG ACGCAAATGG GCGGTAGGCG
3401 TGTACGGTGG GAGGTCTATA TAAGCAGAGC TCGTTTAGTG AACCGTCAGA
3451 TCACTAGGCT AGCTATTGCG GTAGTTTATC ACAGTTAAAT TGCTAACGCA
3501 GTCAGTGCTT CTGACACAAC AGTCTCGAAC TTAAGCTGCA GTGACTCTCT
3551 TAAGGTAGCC TTGCAGAAGT TGGTCOTGAG GCACTGGGCA GGTAAGTATC
3601 AAGGTTACAA GACAGGTTTA AGGAGACCAA TAGAAACTGG GCTTGTCGAG
3651 ACAGAGAAGA CTCTTGCGTT TCTGATAGGC ACCTATTGGT CTTACTGACA
3701 TCCACTTTGC CTTTCTCTCC ACAGGTGTCC ACTCCCAGTT CAATTACAGC
3751 TCTTAAGGCT AGAGTACTTA ATACGACTCA CTATAGAATA CGACTCACTA
3801 TAGGGAGACG CTAGCGTCGA CCTTCTGCCA TGGCCCTGTG GATGCGCCTC
3851 CTGCCCCTGC TGGCGCTGCT GGCCCTCTGG GGACCTGACC CAGCCGCAGC
3901 CTTTGTGAAC CAACACCTGT GCGGCTCAGA TCTGGTGGAA GCTCTCTACC
3951 TAGTGTGCGG GGAACGAGGC TTCTTCTACA CACC6AGGAC CAAGCGGGAG
4001 GCAGAGGACC TGCAGGTGGG GCAGGTGGAG CTGGGCGOGG GCCCTGGTGC
4051 AGGCAGCCTG CAGCCCTTGG CCCTGGAGGG GTCGCGACAG AAGCGTGGCA
4101 TTGTGGAACA ATGCTGTACC AGCATCTGCT CCCTCTACCA GCTGGAGAAC
4151 TACTGCAACT AGACGCAGCC GTCGACGGTA CCAGCGCTGT CGAGGCCGCT
4201 TCGAGCAGAC ATGATAAGAT ACATTGATGA GTTTGGACAA ACCACAACTA
4251 GAATGCAGTG AAAAAAATGC TTTATTTGTG AAATTTGTGA TGCTATTGCT
4301 TTATTTGTAA CCATTATAAG CTGCAATAAA CAAGTTAACA ACAACAATTG
4351 CATTCATTTT ATGTTTCAGG TTCAGGGGGA GATGTGGGAG GTTTTTTAAA
4401 GCAAGTAAAA CCTCTACAAA TGTGGTAAAA TCGATTAGGA TCTTCCTAGA
4451 GCATGGCTAC CTAGACATGG CTCGACAGAT CAGCGCTCAT GCTCTGGAAG
4501 ATCTCGATTT AAATGCGGCC GCAGGAACCC CTAGTGATGG AGTTGGCCAC
4551 TCCCTCTCTG CGCGCTCGCT CGCTCACTGA GGCCGGGCGA CCAAAGGTCG
4601 CCCGACGCCC GGGCTTTGCC CGGGCGGCCT CAGTGAGCGA GCGAGCGCGC
4651 AGCTGCCTGC AGGGGCGCCT GATGCGGTAT TTTCTCCTTA CGCATCTGTG
4701 CGGTATTTCA CACCGCATAC GTCAAAGCAA CCATAGTACG CGCCCTGTAG
4751 CGGCGCATTA AGCGCGGCGG GTGTGGTGGT TACGCGCAGC GTGACCGCTA
4801 CACTTGCCAG CGCCCTAGCG CCCGCTCCTT TCGCTTTCTT CCCTTCCTTT
```

-continued

```
4851 CTCGCCACGT TCGCCGGCTT TCCCCGTCAA GCTCTAAATC GGGGGCTCCC

4901 TTTAGGGTTC CGATTTAGTG CTTTACGGCA CCTCGACCCC AAAAAACTTG

4951 ATTTGGGTGA TGGTTCACGT AGTGGGCCAT CGCCCTGATA GACGGTTTTT

5001 CGCCCTTTGA CGTTGGAGTC CACGTTCTTT AATAGTGGAC TCTTGTTCCA

5051 AACTGGAACA ACACTCAACC CTATCTCGGG CTATTCTTTT GATTTATAAG

5101 GGATTTTGCC GATTTCGGCC TATTGGTTAA AAAATGAGCT GATTTAACAA

5151 AAATTTAACG CGAATTTTAA CAAAATATTA ACGTTTACAA TTTTATGGTG

5201 CACTCTCAGT ACAATCTGCT CTGATGCCGC ATAGTTAAGC CAGCCCCGAC

5251 ACCCGCCAAC ACCCGCTGAC GCGCCCTGAC GGGCTTGTCT GCTCCCGGCA

5301 TCCGCTTACA GACAAGCTGT GACCGTCTCC GGGAGCTGCA TGTGTCAGAG

5351 GTTTTCACCG TCATCACCGA AACGCGCGAG ACGAAAGGGC CTCGTGATAC

5401 GCCTATTTTT ATAGGTTAAT GTCATGATAA TAATGGTTTC TTAGACGTCA

5451 GGTGGCACTT TTCGGGGAAA TGTGCGCGGA ACCCCTATTT GTTTATTTTT

5501 CTAAATACAT TCAAATATGT ATCCGCTCAT GAGACAATAA CCCTGATAAA

5551 TGCTTCAATA ATATTGAAAA AGGAAGAGTA TGAGTATTCA ACATTTCCGT

5601 GTCGCCCTTA TTCCCTTTTT TGCGGCATTT TGCCTTCCTG TTTTTGCTCA

5651 CCCAGAAACG CTGGTGAAAG TAAAAGATGC TGAAGATCAG TTGGGTGCAC

5701 GAGTGGGTTA CATCGAACTG GATCTCAACA GCGGTAAGAT CCTTGAGAGT

5751 TTTCGCCCCG AAGAACGTTT TCCAATGATG AGCACTTTTA AAGTTCTGCT

5801 ATGTGGCGCG GTATTATCCC GTATTGACGC CGGGCAAGAG CAACTCGGTC

5851 GCCGCATACA CTATTCTCAG AATGACTTGG TTGAGTACTC ACCAGTCACA

5901 GAAAAGCATC TTACGGATGG CATGACAGTA AGAGAATTAT GCAGTGCTGC

5951 CATAACCATG AGTGATAACA CTGCGGCCAA CTTACTTCTG ACAACGATCG

6001 GAGGACCGAA GGAGCTAACC GCTTTTTTGC ACAACATGGG GGATCATGTA

6051 ACTCGCCTTG ATCGTTGGGA ACCGGAGCTG AATGAAGCCA TACCAAACGA

6101 CGAGCGTGAC ACCACGATGC CTGTAGCAAT GGCAACAACG TTOCGCAAAC

6151 TATTAACTGG CGAACTACTT ACTCTAGCTT CCCGGCAACA ATTAATAGAC

6201 TGGATGGAGG CGGATAAAGT TGCAGGACCA CTTCTGCGCT CGGCCCTTCC

6251 GGCTGGCTGG TTTATTGCTG ATAAATCTGG AGCCGGTGAG CGTGGGTCTC

6301 GCGGTATCAT TGCAGCACTG GGGCCAGATG GTAAGCCCTC CCGTATCGTA

6351 GTTATCTACA CGACGGGGAG TCAGGCAACT ATGGATGAAC GAAATAGACA

6401 GATCGCTGAG ATAGGTGCCT CACTGATTAA GCATTGGTAA CTGTCAGACC

6451 AAGTTTACTC ATATATACTT TAGATTGATT TAAAACTTCA TTTTTAATTT

6501 AAAAGGATCT AGGTGAAGAT CCTTTTTGAT AATCTCATGA CCAAAATCCC

6551 TTAACGTGAG TTTTCGTTCC ACTGAGCGTC AGACCCCGTA GAAAAGATCA

6601 AAGGATCTTC TTGAGATCCT TTTTTTCTGC GCGTAATCTG CTGCTTGCAA

6651 ACAAAAAAAC CACCGCTACC AGCGGTGGTT TGTTTGCCGG ATCAAGAGCT

6701 A6CAACTCTT TTTCCGAAGG TAACTGGCTT CAGCAGAGCG CAGATACCAA

6751 ATACTGTCCT TCTAGTGTAG CCGTAGTTAG GCCACCACTT CAAGAACTCT

6801 GTAGCACCGC CTACATACCT CGCTCTGCTA ATCCTGTTAC CAGTGGCTGC
```

```
6651 TGCCAGTGGC GATAAGTCGT GTCTTACCGG GTTGGACTCA AGACGATAGT

6701 TACCGGATAA GGCGCAGCGG TCGGGCTGAA CGGGGGGTTC GTGCACACAG

6951 CCCAGCTTGG AGCGAACGAC CTACACCGAA CTGAGATACC TACAGCGTGA

7001 GCTATGAGAA AGCGCCACGC TTCCCGAAGG GAGAAAGGCG GACAGGTATC

7051 CGGTAAGCGG CAGGGTCGGA ACAGGAGAGC GCACGAGGGA GCTTCCAGGG

7101 GGAAACGCCT GGTATCTTTA TAGTCdTGTC GGGTTTCGCC ACCTCTGACT

7151 TGAGCGTCGA TTTTTGTGAT GCTCGTCAGG GGGCGGAGC CTATGGAAAA

7201 ACGCCAGCAA CGCGGCCTTT TTACGGTTCC TGGCCTTTTG CTGGCCTTTT

7251 GCTCACATGT
```

ITR 5': 1-141 bp
RSV promoter: 239-948 bp
hGck: 973-2387 bp
bGH polyA: 2395-2653 bp
CMV promoter: 2698-3815 bp hIns: 3823-4169 bp
SV40 polyA: 4183-4481 bp
ITR 3': 4523-4663 bp
F: CMV-hIns(rev)-RSV-hGck (SEQ ID NO: 11; FIG. 4)

```
pAAV-CMV-hIns(rev)-RSV-hGck plasmid sequence
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCGCG

151 ATAAATCGAG ATCTTCCAGA GCATGAGCGC TGATCTGTCG AGCCATGTCT

201 AGGTAGCCAT GCTCTAGGAA GATCCTAATC GATTTTACCA CATTTGTAGA

251 GGTTTTACTT GCTTTAAAAA ACCTCCCACA TCTCCCCCTG AACCTGAAAC

301 ATAAAATGAA TGCAATTGTT GTTGTTAACT TGTTTATTGC AGCTTATAAT

351 GGTTACAAAT AAAGCAATAG CATCACAAAT TTCACAAATA AAGCATTTTT

401 TTCACTGCAT TCTAGTTGTG GTTTGTCCAA ACTCATCAAT GTATCTTATC

451 ATGTCTGCTC GAAGCGGCCT CGACAGCGCT GGTACCGTCG ACGGCTGCGT

501 CTAGTTGCAG TAGTTCTCCA GCTGGTAGAG GGAGCAGATG CTGGTACAGC

551 ATTGTTCCAC AATGCCACGC TTCTGTCGCG ACCCCTCCAG GGCCAAGGGC

601 TGCAGGCTGC CTGCACCAGG GCCCCCGCCC AGCTCCACCT GCCCCACCTG

651 CAGGTCCTCT GCCTCCCGCT TGGTCCTGGG TGTGTAGAAG AAGCCTCGTT

701 CCCCGCACAC TAGGTAGAGA GCTTCCACCA GATCTGAGCC GCACAGGTGT

751 TGGTTCACAA AGGCTGCGGC TGGGTCAGGT CCCCAGAGGG CCAGCAGCGC

801 CAGCAGGGGC AGGAGGCGCA TCCACAGGGC CATGGCAGAA GGTCGACGCT

851 AGCGTCTCCC TATAGTGAGT CGTATTCTAT AGTGAGTCGT ATTAAGTACT

901 CTAGCCTTAA GAGCTGTAAT TGAACTGGGA GTGGACACCT GTGGAGAGAA

951 AGGCAAAGTG GATGTCAGTA AGACCAATAG GTGCCTATCA GAAACGCAAG

1001 AGTCTTCTCT GTCTCGACAA GCCCAGTTTC TATTGGTCTC CTTAAACCTG

1051 TCTTGTAACC TTGATACTTA CCTGCCCAGT GCCTCACGAC CAACTTCTGC

1101 AAGGCTACCT TAAGAGAGTC ACTGCAGCTT AAGTTCGAGA CTGTTGTGTC

1151 AGAAGCACTG ACTGCGTTAG CAATTTAACT GTGATAAACT ACCGCAATAG

1201 CTAGCCTAGT GATCTGACGG TTCACTAAAC GAGCTCTGCT TATATAGACC

1251 TCCCACCGTA CACGCCTACC GCCCATTTGC GTCAACGGGG CGGGCGATCG

1301 CAGTTGTTAC GACATTTTGG AAAGTCCCGT TGATTTTGGT GCCAAAACAA
```

-continued

```
1351 ACTCCCATTG ACGTCAATGG GGTGGAGACT TGGAAATCCC CGTGAGTCAA
1401 ACCGCTATCC ACGCCCATTG GTGTACTGCC AAAACCGCAT CACCATGGTA
1451 ATAGCGATGA CTAATACGTA GATGTACTGC CAAGTAGGAA AGTCCCGTAA
1501 GGTCATGTAC TGGGCATAAT GCCAGGCGGG CCATTTACCG TCATTGACGT
1551 CAATAGGGGG CGGACTTGGC ATATGATACA CTTGATGTAC TGCCAAGTGG
1601 GCAGTTTACC GTAAATACTC CACCCATTGA CGTCAATGGA AAGTCCCTAT
1651 TGGCGTTACT ATGGGAACAT ACGTOATTAT TGACGTCAAT GGGCGGGGGT
1701 CGTTGGGCGG TCAGCCAGGC GGGCCATTTA CCGTAAGTTA TGTAACGCGG
1751 AACTCCATAT ATGGGCTATG AACTAATGAC CCCGTAATTG ATTACTATTA
1801 ATAACTAGTC AATAATCAAT GCCAACATGG CGGTCATATT GGACATGAGC
1861 CAATATAAAT GTACATATTA TGATATAGAT ACAACGTATG CAATGGCCAA
1901 TAGoCAATAT TGATTTATGC TATATAACCA ATGAATAATA TGGCTAATGO
1951 CCAATATTGA GATCTGTAGA TAAGTAGCAT GGCGGGTTAA TCATTAACTA
2001 CAGATATCCA TGTTTGACAG CTTATCATCG CAGATCCGTA TGGTGCACTC
2051 TCAGTACAAT CTGCTCTGAT GCCGCAMAGT TAAGCCAGTA TCTGCTCCCT
2101 GCTTGTGTGT TGGAGGTCGC TGAGTAGTGC GCGAGCAAAA TTTAAGCTAC
2151 AACAAGGCAA GGCTTGACCG ACAATTGCAT GAAGAATCTG CTTAGGGTTA
2201 GGCGTTTTGC GCTGCTTCGC GATGTACGGG CCAGATATTC GCGTATCTGA
2251 GGGGACTAGG GTGTGTTTAG GCGAAAAGCG GGGCTTCGGT TGTACGCGGT
2301 TAGGAGTCCC CTCAGGATAT AGTAGTTTCG CTTTTGCATA GGGAGGGGGA
2351 AATGTAGTCT TATGCAATAC TCTTGTAGTC TTGCAACATG GTAACGATGA
2401 GTMAGCAACA TGCCTTACAA GGAGAGAAAA AGCACCGTGC ATGCCGATTG
2451 GTGGAAGTAA GGTGGTACGA TCGTGCCTTA TTAGGAAGGC AACAGACGGG
2501 TCTGACATGG ATTGGACGAA CCACTAAATT CCGCATTGCA GAGATATTGT
2551 ATTTAAGTGC CTAGCTCGAT ACAATAAACG CCATTTGACC ATTCACCACA
2601 TTGGTGTGCA CCTCCAAGCT GGGTACCAGC TTCTAGAGAG ATCTGCTTCA
2651 GCTGGAGGCA CTGGGCAGGT AAGTATCAAG GTTACAAGAC AGGTTTAAGG
2701 AGACCAATAG AAACTGGGCT TGTCGAGACA GAGAAGACTC TTGCGTTTCT
2751 GATAGGCACC TATTGGTCTT ACTGACATCC ACTTTGCCTT TCTCTCCACA
2801 GGTGCAGCTG CTGCAGCGGT CTAGAACTCG AGTCGAGACC ATGGCGATGG
2e51 ATGTCACAAG GAGCCAGGCC CAGACAGCCT TGACTCTGGT AGAGCAGATC
2901 CTGGCAGAGT TCCAGCTGCA GGAGGAGGAC CTGAAGAAGG TGATGAGACG
2951 GATGCAGAAG GAGATGGACC GCGGCCTGAG GCTGGAGACC CATGAAGAGG
3001 CCAGTGTGAA GATGCTGCCC ACCTACGTGC GCTCCACCCC AGAAGGCTCA
3051 GAAGTCGGGG ACTTCCTCTC CCTGGACCTG GGTGGCACTA ACTTCAGGGT
3101 GATGCTGGTG AAGGTGGGAG AAGGTGAGGA GGGGCAGTGG AGCGTGAAGA
3151 CCAAACACCA GATGTACTCC ATCCCCGAGG ACGCCATGAC CGGCACTGCT
3201 GAGATGCTCT TCGACTACAT CTCTGAGTGC ATCTCCGACT TCCTGGACAA
3251 GCATCAGATG AAACACAAGA AGCTGCCCCT GGGCTTCACC TTCTCCTTTC
3301 CTGTGAGGCA CGAAGACATC GATAAGGGCA TCCTTCTCAA CTGGACCAAG
```

-continued

```
3351 GGCTTCAAGG CCTCAGGAGC AGAAGGGAAC AATGTCGTGG GGCTTCTGCG

3401 AGACGCTATC AAACGGAGAG GGGACTTTGA AATGGATGTG GTGGCAATGG

3451 TGAATGACAC GGTGGCCACG ATGATCTCCT GCTACTACGA AGACCATCAG

3501 TGCGAGGTCG GCATGATCGT GGGCACGGGC TGCAATGCCT GCTACATGGA

3551 GGAGATGCAG AATGTGGAGC TGGTGGAGGG GGACGAGGGC CGCATGTGCG

3601 TCAATACCGA GTGGGCGCC TTCGGGGACT CCGGCGAGCT GGACGAGTTC

3651 CTGCTGGAGT ATGACCGCCT GGTGGACGAG AGCTCTGCAA ACCCCGGTCA

3701 GCAGCTGTAT GAGAAGCTCA TAGGTGGCAA GTACATGGGC GAGCTGGTGC

3751 GGCTTGTGCT GCTCAGGCTC GTGGACGAAA ACCTGCTCTT CCACGGGGAG

3801 GCCTCCGAGC AGCTGCGCAC ACGCGGAGCC TTCGAGACGC GCTTCGTGTC

3851 GCAGGTGGAG AGCGACACGG GCGACCGCAA GCAGATCTAC AACATCCTGA

3901 GCACGCTGGG GCTGCGACCC TCGACCACCG ACTGCGACAT CGTGCGCCGC

3951 GCCTGCGAGA GCGTGTCTAC GCGCGCTGCG CACATGTGCT CGGCGGGGCT

4001 GGCGGGCGTC ATCAACCGCA TGCGCGAGAG CCGCAGCGAG GACGTAATGC

4051 GCATCACTGT GGGCGTGGAT GGCTCCGTGT ACAAGCTGCA CCCCAGCTTC

4101 AAGGAGCGGT TCCATGCCAG CGTGCGCAGG CTGACGCCCA GCTGCGAGAT

4151 CACCTTCATC GAGTCGGAGG AGGGCAGTGG CCGGGGCGCG GCCCTGGTCT

4201 CGGCGGTGGC CTGTAAGAAG GCCTGTATGC TGGGCCAGTS ACTCGAGCAC

4251 GTGGAGCTCG CTGATCAGCC TCGACTGTGC CTTCTAGTTG CCAGCCATCT

4301 GTTGTTTGCC CCTCCCCCGT GCCTTCCTTG ACCCTGGAAG GTGCCACTCC

4351 CACTGTCCTT TCCTAATAAA ATGAGGAAAT TGCATCGCAT TGTCTGAGTA

4401 GGTGTCATTC TATTCTGGGG GGTGGdGTGG GGCAGGACAG CAAGGGGGAG 4451 dATTGGGAAG ACAATAGCAG GCATGCTGGG GATGCGGTG6 GCTCTATGGC

4501 CACGTGATTT AAATGCGGCC GCAGGAACCCCTAGTGATGG AGTTGGCCAC

4551 TCCCTCTCTG CGCGCTCGCT CGCTCACTGA GGCCGGGCGA CCAAAGGTCG

4601 CdCGACGCCC GGGCTTTGCC CGGGCGGCCT CAGTGAGCGA GCGAGCGCGC

4651 AGCTGCCTGC AGGGGCGCCT GATGCGGTAT TTTCTCCTTA CGCATCTGTG

4701 CGGTATTTCA CACCGCATAC GTCAAAGCAA CCATAGTACG CGCCCTGTAG

4751 CGGCGCATTA AGCGCGGCGG GTGTGGTGGT TACGCGCAGC GTGACCGCTA

4901 CACTTGCCAG CGCCCTAGCG CCCGCTCCTT TCGCTTTCTT CCCTTCCTTT

4051 CTCGCCACGT TCGCCGGCTT TCCCCGTCAA GCTCTAAATC GGGGGCTCCC

4901 TTTAGGGTTC CGATTTAGTG CTTTACGGCA CCTCGACCCC AAAAAACTTG

4951 ATTTGGGTGA TGGTTCACGT AGTGGGCCAT CGCCCTGATA GACGGTTTTT

5001 CGCCCTTTGA CGTTGGAGTC CACGTTCTTT AATAGTGGAC TCTTGTTCCA

5051 AACTGGAACA ACACTCAACC CTATCTCGGG CTATTCTTTT GATTTATAAG

5101 GGATTTTGCC GATTTCGGCC TATTGGTTAA AAAATGAGCT GATTTAACAA

5151 AAATTTAACG CGAATTTTAA CAAAATATTA ACGTTTACAA TTTTATGGTG

5201 CACTCTCAGT ACAATCTGCT CTGATGCCGC ATAGTTAAGC CAGCCCCGAC

5251 ACCCGCCAAC ACCCGCTGAC GCGCCCTGAC GGGCTTGTCT GCTCCCGGCA

5301 TCCGCTTACA GACAAGCTGT GACCGTCTCC GGGAGCTGCA TGTGTCAGAG

5351 GTTTTCACCG TCATCACCGA AACGCGCGAG ACGAAAGGGC CTCGTGATAC
```

```
5401 GTCATGATAA TAATGGTTTC TTAGACGTCA GCCTATTTTT ATAGGTTAAT

5451 GGTGGCACTT TTCGGGGAAA TGTGCGCGGA ACCCCTATTT GT7TATTTTT

5501 CTAAATACAT TCAAATATGT ATCCGCTCAT GAGACAATAA CCCTGATAAA

5551 TGCTTCAATA ATATTGAAAA AGGAAGAGTA TGAGTATTCA ACATTTCCGT

5601 GTCGCCCTTA TTCCCTTTTT TGCGGCATTT TGCCTTCCTG TTTTTGCTCA

5651 CCCAGAAACG CTGGTGAAAG TAAAAGATGC TGAAGATCAG TTGGGTGCAC

5701 GAGTGGGTTA CATCGAACTG GATCTCAACA GCGGTAAGAT CCTTGAGAGT

5751 TTTCGCCCCG AAGAACGTTT TCCAATGATG AGCACTTTTA AAGTTCTGCT

5801 ATGTGGCGCG GTATTATCCC GTATTGACGC CGGGCAAGAG CAACTCGGTC

5851 GCCGCATACA CTATTCTCAG AATGACTTGG TTGAGTACTC ACCAGTCACA

5901 GAAAAGCATC TTACGGATGG CATGACAGTA AGAGAATTAT GCAGTGCTGC

5951 CATAACCATG AGTGATAACA CTGCGGCCAA CTTACTTCTG ACAACGATCG

6001 GAGGACCGAA GGAGCTAACC GCTTTTTTGC ACAACATGGG GATCATGTA

6051 ACTCGCCTTG ATCGTTGGGA ACCGGAGCTG AATGAAGCCA TACCAAACGA

6101 CGAGCGTGAC ACCACGATGC CTGTAOCAAT GGCAACAACG TTGCGCAAAC

6151 TATTAACTGG CGAACTACTT ACTCTAGCTT CCCGGCAACA ATTAATAGAC

6201 TGGATGGAGG CGGATAAAGT TGCAGGACCA CTTCTGCGCT CGGCCCTTCC

6251 GGCTGGCTQG TTTATTGCTG ATAAATCTGG AGCCGGTGAG CGTGGGTCTC

6301 GCGGTATCAT TGCAGCACTG GGGCCAGATG GTAAGCCCTC CCGTATCGTA

6351 GTTATCTACA CGACGGGGAG TCAGGCAACT ATGGATGAAC GAAATAGACA

6401 GATCGCTGAG ATAGGTGCCT CACTGATTAA GCATTGGTAA CTGTCAGACC

6451 AAGTTTACTC ATATATACTT TAGATTGATT TAAAACTTCA TTTTTAATTT

6501 AAAAGGATCT AGGTGAAGAT CCTTTTTGAT AATCTCATGA CCAAAATCCC

6551 TTAACGTGAG TTTTCGTTCC ACTGAGCGTC AGACCCCGTA GAAAAGATCA

6601 AAGGATCTTC TTGAGATCCT TTTTTTCTGC GCGTAATCTG CTGCTTGCAA

6651 ACAAAAAAAC CACCGCTACC AGCGGTGGTT TGTTTGCCGG ATCAAGAGCT

6701 ACCAACTCTT TTTCCGAAGG TAACTGGCTT CAGCAGAGCG CAGATACCAA

6751 ATACTGTCCT TCTAGTGTAG CCGTAGTTAG GCCACCACTT CAAGAACTCT

6801 GTAGCACCGC CTACATACCT CGCTCTGCTA ATCCTGTTAC CAGTGGCTGC

6851 TGCCAGTGGC GATAAGTCGT GTCTTACCGG GTTGGACTCA AGACGATAGT

6901 TACCGGATAA GGCGCAGCGG TCGGGCTGAA CGGGGGGTTC GTGCACACAG

6951 CCCAGCTTGG AGCGAACGAC CTACACCGAA CTGAGATACC TACAGCGTGA

7001 GCTATGAGAA AGCGCCACGC TTCCCGAAGG GAGAAAGGCG ACAGGTATC

7051 CGGTAAGCGG CAGGGTCGGA ACAGGAGAGC GCACGAGGGA GCTTCCAGGG

7101 GGAAACGCCT GGTATCTTTA TAGTCCTGTC GGGTTTCGCC ACCTCTGACT

7151 TGAGCGTCGA TTTTTGTGAT GCTCGTCAGG GGGCGGAGC CTATGGAAAA

7201 ACGCCAGCAA CGCGGCCTTT TTACGGTTCC TGGCCTTTTG CTGGCCTTTT

7251 GCTCACATGT
```

ITR 5': 1-141 bp
SV40 polyA: 182-480 bp
hIns: 494-840 bp
CMV promoter: 4248-1965 bp
RSV promoter: 2092-2801 bp hGck: 2826-4240 bp
bGH polyA: 4248-4506 bp
ITR 3': 4523-4663 bp
G; RSV-hGck-CMV-hIns(rev) (SEQ ID NO:12; FIG. 4)

```
pAAV-RSV-hGck-CMV-hIns(rev) plasmid sequence
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCGCG
 151 ATATCCATGT TTGACAGCTT ATCATCGCAG ATCCGTATGG TGCACTCTCA
 201 GTACAATCTG CTCTGATGCC GCATAGTTAA GCCAGTATCT GCTCCCTGCT
 251 TGTGTGTTGG AGGTCGCTGA GTAGTGCGCG AGCAAAATTT AAGCTACAAC
 301 AAGGCAAGGC TTGACCGACA ATTGCATGAA GAATCTGCTT AGGGTTAGGC
 351 GTTTTGCGCT GCTTCGCGAT GTACGGGCCA GATATTCGCG TATCTGAGGG
 401 GACTAGGGTG TGTTTAGGCG AAAAGCGGGG CTTCGGTTGT ACGCGGTTAG
 451 GAGTCCCCTC AGGATATAGT AGTTTCGCTT TTGCATAGGG AGGGGGAAAT
 501 GTAGTCTTAT GCAATACTCT TGTAGTCTTG CAACATGGTA ACGATGAGTT
 551 AGCAACATGC CTTACAAGGA GAGAAAAAGC ACCGTGCATG CCGATTGGTG
 601 GAAGTAAGGT GGTACGATCG TGCCTTATTA GGAAGGCAAC AGACGGGTCT
 651 GACATGGATT GGACGAACCA CTAAATTCCG CATTGCAGAG ATATTGTATT
 701 TAAGTGCCTA GCTCGATACA ATAAACGCCA TTTGACCATT CACCACATTG
 751 GTGTGCACCT CCAAGCTGGG TACCAGCTTC TAGAGAGATC TGCTTCAGCT
 801 GGAGGCACTG GCAGGTAAG TATCAAGGTT ACAAGACAGG TTTAAGGAGA
 851 CCAATAGAAA CTGGGCTTGT CGAGACAGAG AAGACTCTTG CGTTTCTGAT
 901 AGGCACCTAT TGGTCTTACT GACATCCACT TTGCCTTTCT CTCCACAGGT
 951 GCAGCTGCTG CAGCGGTCTA GAACTCGAGT CGAGACCATG GCGATGGATG
1001 TCACAAGGAG CCAGGCCCAG ACAGCCTTGA CTCTGGTAGA GCAGATCCTG
1051 GCAGAGTTCC AGCTGCAGGA GGAGGACCTG AAGAAGGTGA TGAGACGGAT
1101 GCAGAAGGAG ATGGACCGCG GCCTGAGGCT GGAGACCCAT GAAGAGGCCA
1151 GTGTGAAGAT GCTGCCCACC TACGTGCGCT CCACCCCAGA AGGCTCAGAA
1201 GTCGGGGACT TCCTCTCCCT GGACCTGGGT GGCACTAACT TCAGGGTGAT
1251 GCTGGTGAAG GTGGGAGAAG GTGAGGAGGG GCAGTGGAGC GTGAAGACCA
1301 AACACCAGAT GTACTCCATC CCCGAGGACG CCATGACCGG CACTGCTGAG
1351 ATGCTCTTCG ACTACATCTC TGAGTGCATC TCCGACTTCC TGGACAAGCA
1401 TCAGATGAAA CACAAGAAGC TGCCCCTGGG CTTCACCTTC TCCTTTCCTG
1451 TGAGGCACGA AGACATCGAT AAGGGCATCC TTCTCAACTG GACCAAGGGC
1501 TTCAAGGCCT CAGGAGCAGA AGGGAACAAT GTCGTGGGGC TTCTGCGAGA
1551 CGCTATCAAA CGGAGAGGGG ACTTTGAAAT GGATGTGGTG GCAATGGTGA
1601 ATGACACGGT GGCCACGATG ATCTCCTGCT ACTACGAAGA CCATCAGTGC
1651 GAGGTCGGCA TGATCGTGGG CACGGGCTGC AATGCCTGCT ACATGGAGGA
1701 GATGCAGAAT GTGGAGCTGG TGGAGGGGGA CGAGGGCCGC ATGTGCGTCA
1751 ATACCGAGTG GGGCGCCTTC GGGGACTCCG GCGAGCTGGA CGAGTTCCTG
1801 CTGGAGTATG ACCGCCTGGT GGACGAGAGC TCTGCAAACC CCGGTCAGCA
```

```
1851 GCTGTATGAG AAGCTCATAG GTGGCAAGTA CATGGGCGAG CTGGTGCGGC

1901 TTGTGCTGCT CAGGCTCGTG GACGAAAACC TGCTCTTCCA CGGGGAGGCC

1951 TCCGAGCAGC TGCGCACACG CGGAGCCTTC GAGACGCGCT TCGTGTCGCA

2001 GGTGGAGAGC GACACGGGCG ACCGCAAGCA GATCTACAAC ATCCTGAGCA

2051 CGCTGGGGCT GCGACCCTCG ACCACCGACT GCGACATCGT GCGCCGCGCC

2101 TGCGAGAGCG TGTCTACGCG CGCTGCGCAC ATGTGCTCGG CGGGGCTGGC

2151 GGGCGTCATC AACCGCATGC GCGAGAGCCG CAGCGAGGAC GTAATGCGCA

2201 TCACTGTGGG CGTGGATGGC TCCGTGTACA AGCTGCACCC CAGCTTCAAG

2251 GAGCGGTTCC ATGCCAGCGT GCGCAGGCTG ACGCCCAGCT GCGAGATCAC

2301 CTTCATCGAG TCGAGGAGG GCAGTGGCCG GGGCGCGGCC CTGGTCTCGG

2351 CGGTGGCCTG TAAGAAGGCC TGTATGCTGG GCCAGTGACT CGAGCACGTG

2401 GAGCTCGCTG ATCAGCCTCG ACTGTGCCTT CTAGTTGCCA GCCATCTGTT

2451 GTTTGCCCCT CCCCCGTGCC TTCCTTGACC CTGGAAGGTG CCACTCCCAC

2501 TGTCCTTTCC TAATAAAATG AGGAAATTGC ATCGCATTGT CTGAGTAGGT

2551 GTCATTCTAT TCTGGGGGGT GGGGTGGGGC AGGACAGCAA GGGGGAGGAT

2601 TGGGAAGACA ATAGCAGGCA TGCTGGGGAT GCGGTGGGCT CTATGGCCAC

2651 GTGATTTAAA TCGAGATCTT CCAGAGCATG AGCGCTGATC TGTCGAGCCA

2701 TGTCTAGGTA GCCATGCTCT AGGAAGATCC TAATCGATTT TACCACATTT

2751 GTAGAGGTTT TACTTGCTTT AAAAAACCTC CCACATCTCC CCCTGAACCT

2801 GAAACATAAA ATGAATGCAA TTGTTGTTGT TAACTTGTTT ATTGCAGCTT

2851 ATAATGGTTA CAAATAAAGC AATAGCATCA CAAATTTCAC AAATAAAGCA

2901 TTTTTTTCAC TGCATTCTAG TTGTGGTTTG TCCAAACTCA TCAATGTATC

2951 TTATCATGTC TGCTCGAAGC GGCCTCGACA GCGCTGGTAC CGTCGACGGC

3001 TGCGTCTAGT TGCAGTAGTT CTCCAGCTGG TAGAGGGAGC AGATGCTGGT

3051 ACAGCATTGT TCCACAATGC CACGCTTCTG TCGCGACCCC TCCAGGGCCA

3101 AGGGCTGCAG GCTGCCTGCA CCAGGGCCCC CGCCCAGCTC CACCTGCCCC

3151 ACCTGCAGGT CCTCTGCCTC CCGCTTGGTC CTGGGTGTGT AGAAGAAGCC

3201 TCGTTCCCCG CACACTAGGT AGAGAGCTTC CACCAGATCT GAGCCGCACA

3251 GGTGTTGGTT CACAAAGGCT GCGGCTGGGT CAGGTCCCCA GAGGGCCAGC

3301 AGCGCCAGCA GGGGCAGGAG GCGCATCCAC AGGGCCATGG CAGAAGGTCG

3351 ACGCTAGCGT CTCCCTATAG TGAGTCGTAT TCTATAGTGA GTCGTATTAA

3401 GTACTCTAGC CTTAAGAGCT GTAATTGAAC TGGGAGTGGA CACCTGTGGA

3451 GAGAAAGGCA AAGTGGATGT CAGTAAGACC AATAGGTGCC TATCAGAAAC

3501 GCAAGAGTCT TCTCTGTCTC GACAAGCCCA GTTTCTATTG GTCTCCTTAA

3551 ACCTGTCTTG TAACCTTGAT ACTTACCTGC CCAGTGCCTC ACGACCAACT

3601 TCTGCAAGGC TACCTTAAGA GAGTCACTGC AGCTTAAGTT CGAGACTGTT

3651 GTGTCAGAAG CACTGACTGC GTTAGCAATT TAACTGTGAT AAACTACCGC

3701 AATAGCTAGC CTAGTGATCT GACGGTTCAC TAAACGAGCT CTGCTTATAT

3751 AGACCTCCCA CCGTACACGC CTACCGCCCA TTTGCGTCAA CGGGGCGGGC

3801 GATCGCAGTT GTTACGACAT TTTGGAAAGT CCCGTTGATT TTGGTGCCAA
```

-continued

```
3851 AACAAACTCC CATTGACGTC AATGGGGTGG AGACTTGGAA ATCCCCGTGA

3901 GTCAAACCGC TATCCACGCC CATTGGTGTA CTGCCAAAAC CGCATCACCA

3951 TGGTAATAGC GATGACTAAT ACGTAGATGT ACTGCCAAGT AGGAAAGTCC

4001 CGTAAGGTCA TGTACTGGGC ATAATGCCAG GCGGGCCATT TACCGTCATT

4051 GACGTCAATA GGGGGCGGAC TTGGCATATG ATACACTTGA TGTACTGCCA

4101 AGTGGGCAGT TTACCGTAAA TACTCCACCC ATTGACGTCA ATGGAAAGTC

4151 CCTATTGGCG TTACTATGGG AACATACGTC ATTATTGACG TCAATGGGCG

4201 GGGGTCGTTG GGCGGTCAGC CAGGCGGGCC ATTTACCGTA AGTTATGTAA

4251 CGCGGAACTC CATATATGGG CTATGAACTA ATGACCCCGT AATTGATTAC

4301 TATTAATAAC TAGTCAATAA TCAATGCCAA CATGGCGGTC ATATTGGACA

4351 TGAGCCAATA TAAATGTACA TATTATGATA TAGATACAAC GTATGCAATG

4401 GCCAATAGCC AATATTGATT TATGCTATAT AACCAATGAA TAATATGGCT

4451 AATGGCCAAT ATTGAGATCT GTAGATAAGT AGCATGGCGG GTTAATCATT

4501 AACTACAGAT AAATGCGGCC GCAGGAACCC CTAGTGATOG AGTTGGCCAC

4551 TCCCTCTCTG CGCGCTCGCT CGCTCACTGA GGCCGGGCGA CCAAAGGTCG

4601 CCCGACGCCC GGGCTTTGCC CGGGCGGCCT CAGTGAGCGA GCGAGCGCGC

4651 AGCTGCCTGC AGGGGCGCCT GATGCGGTAT TTTCTCCTTA CGCATCTGTG

4701 CGGTATTTCA CACCGCATAC GTCAAAGCAA CCATAGTACG CGCCCTGTAG

4751 CGGCGCATTA AGCGCGGCGG GTGTGGTGGT TACGCGCAGC GTGACCGCTA

4801 CACTTGCCAG CGCCCTAGCG CCCGCTCCTT TCGCTTTCTT CCCTTCCTTT

4851 CTCGCCACGT TCGCCGGCTT TCCCCGTCAA GCTCTAAATC GGGGGCTCCC

4901 TTTAGGGTTC CGATTTAGTG CTTTACGGCA CdTCGACCCC AAAAAACTTG

4951 ATTTGGGTGA TGGTTCACGT AGTGGGCCAT CGCCCTGATA GACGGTTTTT

5001 CGCCCTTTGA CGTTGGAGTC CACGTTCTTT AATAGTGGAC TCTTGTTCCA

5051 AACTGGAACA ACACTCAACC CTATCTCGGG CTATTCTTTT GATTTATAAG

5101 GGATTTTGCC GATTTCGGCC TATTGGTTAA AAAATGAGCT GATTTAACAA

5151 AAATTTAACG CGAATTTTAA CAAAATATTA ACGTTTACAA TTTTATGGTG

5201 CACTCTCAGT ACAATCTGCT CTGATGCCGC ATAGTTAAGC CAGCCCCGAC

5251 ACCCGCCAAC ACCCGCTGAC GCGCCCTGAC GGGCTTGTCT GCTCCCGGCA

5301 TCCGCTTACA GACAAGCTGT GACCGTCTCC GGGAGCTGCA TGTGTCAGAG

5351 GTTTTCACCG TCATCACCGA AACGCGCGAG ACGAAAGGGC CTCGTGATAC

5401 GCCTATTTTT ATAGGTTAAT GTCATGATAA TAATGGTTTC TTAGACGTCA

5451 GGTGGCACTT TTCGGGGAAA TGTGCGCGGA ACCCCTATTT GTTTATTTTT

5501 CTAAATACAT TCAAATATGT ATCCGCTCAT GAGACAATAA CCCTGATAAA

5551 TGCTTCAATA ATATTGAAAA AGGAAGAGTA TGAGTATTCA ACATTTCCGT

5601 GTCGCCCTTA TTCCCTTTTT TGCGGCATTT TGCCTTCCTG TTTTTGCTCA

5651 CCCAGAAACG CTGGTGAAAG TAAAAGATGC TGAAGATCAG TTGGGTGCAC

5701 GAGTGGGTTA CATCGAACTG GATCTCAACA GCGGTAAGAT CCTTGAGAGT

5751 TTTCGCCCCG AAGAACGTTT TCCAATGATG AGCACTTTTA AAGTTCTGCT

5801 ATGTGGCGCG GTATTATCCC GTATTGACGC CGGGCAAGAG CAACTCGGTC

5851 GCCGCATACA CTATTCTCAG AATGACTTGG TTGAGTACTC ACCAGTCACA
```

-continued

```
5901 GAAAAGCATC TTACGGATGG CATGACAGTA AGAGAATTAT GCAGTGCTGC

5951 CATAACCATG AGTGATAACA CTGCGGCCAA CTTACTTCTG ACAACGATCG

6001 GAGGACCGAA GGAGCTAACC GCTTTTTTGC ACAACATGGG GGATCATGTA

6051 ACTCGCCTTG ATCGTTGGGA ACCGGAGCTG AATGAAGCCA TACCAAACGA

6101 CGAGCGTGAC ACCACGATGC CTGTAGCAAT GGCAACAACG TTGCGCAAAC

6151 TATTAACTGG CGAACTACTT ACTCTAGCTT CCCGGCAACA ATTAATAGAC

6201 TGGATGGAGG CGGATAAAGT TGCAGGACCA CTTCTGCGCT CGGCCCTTCC

6251 GGCTGGCTGG TTTATTGCTG ATAAATCTGG AGCCGGTGAG CGTGGGTCTC

6301 GCGGTATCAT TGCAGCACTG GGGCCAGATG GTAAGCCCTC CCGTATCGTA

6351 GTTATCTACA CGACGGGGAG TCAGGCAACT ATGGATGAAC GAAATAGACA

6401 GATCGCTGAG ATAGGTGCCT CACTGATTAA GCATTGGTAA CTGTCAGACC

6451 AAGTTTACTC ATATATACTT TAGATTGATT TAAAACTTCA TTTTTAATTT

6501 AAAAGGATCT AGGTGAAGAT CCTTTTTGAT AATCTCATGA CCAAAATCCC

6551 TTAACGTGAG TTTTCGTTCC ACTGAGCGTC AGACCCCGTA GAAAAGATCA

6601 AAGGATCTTC TTGAGATCCT TTTTTTCTGC GCGTAATCTG CTGCTTGCAA

6651 ACAAAAAAAC CACCGCTACC AGCGGTGGTT TGTTTGCCGG ATCAAGAGCT

6701 ACCAACTCTT TTTCCGAAGG TAACTGGCTT CAGCAGAGCG CAGATACCAA

6751 ATACTGTCCT TCTAGTGTAG CCGTAGTTAG GCCACCACTT CAAGAACTCT

6801 GTAGCACCGC CTACATACCT CGCTCTGCTA ATCCTGTTAC CAGTGGCTGC

6851 TGCCAGTGGC GATAAGTCGT GTCTTACCGG GTTGGACTCA AGACGATAGT

6901 TACCGGATAA GGCGCAGCGG TCGGGCTGAA CGGGGGGTTC GTGCACACAG

6951 CCCAGCTTGG AGCGAACGAC CTACACCGAA CTGAGATACC TACAGCGTGA

7001 GCTATGAGAA AGCGCCACGC TTCCCGAAGG GAGAAAGGCG GACAGGTATC

7051 CGGTAAGCGG CAGGGTCGGA ACAGGAGAGC GCACGAGGGA GCTTCCAGGG

7101 GGAAACGCCT GGTATCTTTA TAGTCCTGTC GGGTTTCGCC ACCTCTGACT

7151 TGAGCGTCGA TTTTTGTGAT GCTCGTCAGG GGGGCGGAGC CTATGGAAAA

7201 ACGCCAGCAA CGCGGCCTTT TTACGGTTCC TGGCCTTTTG CTGGCCTTTT

7251 GCTCACATGT
```

ITR 5': 1-141 bp
RSV promoter: 239-948 bp
hGck: 973-2387 bp
bGH polyA: 2395-2653 bp
SV40 polya: 2687-2985 bp hIns: 2999-3345 bp
CMV promoter: 3353-4470 bp
ITR 3': 4523-4663 bp
H: CMV-hIns (SEQ ID NO: 19; FIG. 5)

```
pAAV-CMV-hIns plasmid sequence
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCGCG

151 ATATCTGTAG TTAATGATTA ACCCGCCATG CTACTTATCT ACAGATCTCA

201 ATATTGGCCA TTAGCCATAT TATTCATTGG TTATATAGCA TAAATCAATA

251 TTGGCTATTG GCCATTGCAT ACGTTGTATC TATATCATAA TATGTACATT

301 TATATTGGCT CATGTCCAAT ATGACCGCCA TGTTGGCATT GATTATTGAC

351 TAGTTATTAA TAGTAATCAA TTACGGGGTC ATTAGTTCAT AGCCCATATA
```

```
 401 TGGAGTTCCG CGTTACATAA CTTACGGTAA ATGGCCCGCC TGGCTGACCG
 451 CCCAACGACC CCCGCCCATT GACGTCAATA ATGACGTATG TTCCCATAGT
 501 AACGCCAATA GGGACTTTCC ATTGACGTCA ATGGGTGGAG TATTTACGGT
 551 AAACTGCCCA CTTGGCAGTA CATCAAGTGT ATCATATGCC AAGTCCGCCC
 601 CCTATTGACG TCAATGACGG TAAATGGCCC GCCTGGCATT ATGCCCAGTA
 651 CATGACCTTA CGGGACTTTC CTACTTGGCA GTACATCTAC GTATTAGTCA
 701 TCGCTATTAC CATGGTGATG CGGTTTTGGC AGTACACCAA TGGGCGTGGA
 751 TAGCGGTTTG ACTCACGGGG ATTTCCAAGT CTCCACCCCA TTGACGTCAA
 801 TGGGAGTTTG TTTTGGCACC AAAATCAACG GGACTTTCCA AAATGTCGTA
 851 ACAACTGCGA TCGCCCGCCC CGTTGACGCA AATGGGCGGT AGGCGTGTAC
 901 GGTGGGAGGT CTATATAAGC AGAGCTCGTT TAGTGAACCG TCAGATCACT
 951 AGGCTAGCTA TTGCGGTAGT TTATCACAGT TAAATTGCTA ACGCAGTCAG
1001 TGCTTCTGAC ACAACAGTCT CGAACTTAAG CTGCAGTGAC TCTCTTAAGG
1051 TAGCCTTGCA GAAGTTGGTC GTGAGGCACT GGGCAGGTAA GTATCAAGGT
1101 TACAAGACAG GTTTAAGGAG ACCAATAGAA ACTGGGCTTG TCGAGACAGA
1151 GAAGACTCTT GCGTTTCTGA TAGGCACCTA TTGGTCTTAC TGACATCCAC
1201 TTTGCCTTTC TCTCCACAGG TGTCCACTCC CAGTTCAATT ACAGCTCTTA
1251 AGGCTAGAGT ACTTAATACG ACTCACTATA GAATACGACT CACTATAGGG
1301 AGACGCTAGC GTCGACCTTC TGCCATGGCC CTGTGGATGC GCCTCCTGCC
1351 CCTGCTGGCG CTGCTGGCCC TCTGGGGACC TGACCCAGCC GCAGCCTTTG
1401 TGAACCAACA CCTGTGCGGC TCAGATCTGG TGGAAGCTCT CTACCTAGTG
1451 TGCGGGGAAC GAGGCTTCTT CTACACACCC AGGACCAAGC GGGAGGCAGA
1501 GGACCTGCAG GTGGGGCAGG TGGAGCTGGG CGGGGGCCCT GGTGCAGGCA
1551 GCCTGCAGCC CTTGGCCCTG GAGGGGTCGC GACAGAAGCG TGGCATTGTG
1601 GAACAATGCT GTACCAGCAT CTGCTCCCTC TACCAGCTGG AGAACTACTG
1651 CAACTAGACG CAGCCGTCGA CGGTACCAGC GCTGTCGAGG CCGCTTCGAG
1701 CAGACATGAT AAGATACATT GATGAGTTTG GACAAACCAC AACTAGAATG
1751 CAGTGAAAAA AATGCTTTAT TTGTGAAATT TGTGATGCTA TTGCTTTATT
1801 TGTAACCATT ATAAGCTGCA ATAAACAAGT TAACAACAAC AATTGCATTC
1851 ATTTTATGTT TCAGGTTCAG GGGGAGATGT GGGAGGTTTT TTAAAGCAAG
1901 TAAAACCTCT ACAAATGTGG TAAAATCGAT TAGGATCTTC CTAGAGCATG
1951 GCTACCTAGA CATGGCTCGA CAGATCAGCG CTCATGCTCT GGAAGATCTC
2001 GATTTAAATG CGGCCGCAGG AACCCCTAGT GATGGAGTTG GCCACTCCCT
2051 CTCTGCGCGC TCGCTCGCTC ACTGAGGCCG GGCGACCAAA GGTCGCCCGA
2101 CGCCCGGGCT TTGCCCGGGC GGCCTCAGTG AGCGAGCGAG CGCGCAGCTG
2152 CCTGCAGGGG CGCCTGATGC GGTATTTTCT CCTTACGCAT CTGTGCGGTA
2201 TTTCACACCG CATACGTCAA AGCAACCATA GTACGCGCCC TGTAGCGGCG
2251 CATTAAGCGC GGCGGGTGTG GTGGTTACGC GCAGCGTGAC CGCTACACTT
2301 GCCAGCGCCC TAGCGCCCGC TCCTTTCGCT TTCTTCCCTT CCTTTCTCGC
2351 CACGTTCGCC GGCTTTCCCC GTCAAGCTCT AAATCGGGGG CTCCCTTTAG
```

-continued

```
2401 GGTTCCGATT TAGTGCTTTA CGGCACCTCG ACCCCAAAAA ACTTGATTTG

2451 GGTGATGGTT CACGTAGTGG GCCATCGCCC TGATAGACGG TTTTTCGCCC

2501 TTTGACGTTG GAGTCCACGT TCTTTAATAG TGGACTCTTG TTCCAAACTG

2551 GAACAACACT CAACCCTATC TCGGGCTATT CTTTTGATTT ATAAGGGATT

2601 TTGCCGATTT CGGCCTATTG GTTAAAAAAT GAGCTGATTT AACAAAAATT

2651 TAACGCGAAT TTTAACAAAA TATTAACGTT TACAATTTTA TGGTGCACTC

2701 TCAGTACAAT CTGCTCTGAT GCCGCATAGT TAAGCCAGCC CCGACACCCG

2751 CCAACACCCG CTGACGCGCC CTGACGGGCT TGTCTGCTCC CGGCATCCGC

2801 TTACAGACAA GCTGTGACCG TCTCCGGGAG CTGCATGTGT CAGAGGTTTT

2851 CACCGTCATC ACCGAAACGC GCGAGACGAA AGGGCCTCGT GATACGCCTA

2901 TTTTTATAGG TTAATGTCAT GATAATAATG GTTTCTTAGA CGTCAGGTGG

2951 CACTTTTCGG GGAAATGTGC GCGGAACCCC TATTTGTTTA TTTTTCTAAA

3001 TACATTCAAA TATGTATCCG CTCATGAGAC AATAACCCTG ATAAATGCTT

3051 CAATAATATT GAAAAAGGAA GAGTATGAGT ATTCAACATT TCCGTGTCGC

3101 CCTTATTCCC TTTTTTGCGG CATTTTGCCT TCCTGTTTTT GCTCACCCAG

3151 AAACGCTGGT GAAAGTAAAA GATGCTGAAG ATCAGTTGGG TGCACGAGTG

3201 GGTTACATCG AACTGGATCT CAACAGCGGT AAGATCCTTG AGAGTTTTCG

3251 CCCCGAAGAA CGTTTTCCAA TGATGAGCAC TTTTAAAGTT CTGCTATGTG

3301 GCGCGGTATT ATCCCGTATT GACGCCGGGC AAGAGCAACT CGGTCGCCGC

3351 ATACACTATT CTCAGAATGA CTTGGTTGAG TACTCACCAG TCACAGAAAA

3401 GCATCTTACG GATGGCATGA CAGTAAGAGA ATTATGCAGT GCTGCCATAA

3451 CCATGAGTGA TAACACTGCG GCCAACTTAC TTCTGACAAC GATCGGAGGA

3501 CCGAAGGAGC TAACCGCTTT TTTGCACAAC ATGGGGGATC ATGTAACTCG

3551 CCTTGATCGT TGGGAACCGG AGCTGAATGA AGCCATACCA AACGACGAGC

3601 GTGACACCAC GATGCCTGTA GCAATGGCAA CAACGTTGCG CAAACTATTA

3651 ACTGGCGAAC TACTTACTCT AGCTTCCCGG CAACAATTAA TAGACTGGAT

3701 GGAGGCGGAT AAAGTTGCAG GACCACTTCT GCGCTCGGCC CTTCCGGCTG

3751 GCTGGTTTAT TGCTGATAAA TCTGGAGCCG GTGAGCGTGG GTCTCGCGGT

3801 ATCATTGCAG CACTGGGGCC AGATGGTAAG CCCTCCCGTA TCGTAGTTAT

3851 CTACACGACG GGGAGTCAGG CAACTATGGA TGAACGAAAT AGACAGATCG

3901 CTGAGATAGG TGCCTCACTG ATTAAGCATT GGTAACTGTC AGACCAAGTT

3951 TACTCATATA TACTTTAGAT TGATTTAAAA CTTCATTTTT AATTTAAAAG

4001 GATCTAGGTG AAGATCCTTT TTGATAATCT CATGACCAAA ATCCCTTAAC

4051 GTGAGTTTTC GTTCCACTGA GCGTCAGACC CCGTAGAAAA GATCAAAGGA

4101 TCTTCTTGAG ATCCTTTTTT TCTGCGCGTA ATCTGCTGCT TGCAAACAAA

4151 AAAACCACCG CTACCAGCGG TGGTTTGTTT GCCGGATCAA GAGCTACCAA

4201 CTCTTTTTCC GAAGGTAACT GGCTTCAGCA GAGCGCAGAT ACCAAATACT

4251 GTCCTTCTAG TGTAGCCGTA GTTAGGCCAC CACTTCAAGA ACTCTGTAGC

4301 ACCGCCTACA TACCTCGCTC TGCTAATCCT GTTACCAGTG GCTGCTGCCA

4351 GTGGCGATAA GTCGTGTCTT ACCGGGTTGG ACTCAAGACG ATAGTTACCG

4401 GATAAGGCGC AGCGGTCGGG CTGAACGGGG GGTTCGTGCA CACAGCCCAG
```

-continued

```
4451 CTTGGAGCGA ACGACCTACA CCGAACTGAG ATACCTACAG CGTGAGCTAT
4501 GAGAAAGCGC CACGCTTCCC GAAGGGAGAA AGGCGGACAG GTATCCGGTA
4551 AGCGGCAGGG TCGGAACAGG AGAGCGCACG AGGGAGCTTC CAGGGGGAAA
4601 CGCCTGGTAT CTTTATAGTC CTGTCGGGTT TCGCCACCTC TGACTTGAGC
4651 GTCGATTTTT GTGATGCTCG TCAGGGGGGC GGAGCCTATG GAAAAACGCC
4701 AGCAACGCGG CCTTTTTACG GTTCCTGGCC TTTTGCTGGC CTTTTGCTCA
4751 CATGT
```

ITR 5': 1-141 bp
CMV promoter: 193-1310 bp
hIns: 1318-1664 bp
SV40 polyA: 1678-1976 bp
ITR 3': 2018-2158 bp
I: RSV-hGck (SEQ ID NO: 20; FIGS. 5 and 8)

```
pAAV-RSV-hGck plasmid sequence
   1 CCTGCAGGCA GCTGCGCGCT CGCTCGCTCA CTGAGGCCGC CCGGGCAAAG
  51 CCCGGGCGTC GGGCGACCTT TGGTCGCCCO GCCTCAGTGA GCGAGCGAGC
 101 GCGCAGAGAG GGAGTGGCCA ACTCCATCAC TAGGGGTTaC TGCGGCCGCG
 151 ATATCCATGT TTGACAGCTT ATCATCGCAG ATCCGTATGG TGCACTCTCA
 201 GTACAATCTG CTCTGATGCC GCATAGTTAA GCCAGTATCT GCTCCCTGCT
 251 TGTGTGTTGG AGGTCGCTGA GTAGTGCGCG AGCAAAATTT AAGCTACAAC
 301 AAGGCAAGGC TTGACCGACA ATTGCATGAA GAATCTGCTT AGGGTTAGGC
 351 GTTTTGCGCT GCTTCGCGAT GTACGGGCCA GATATTGCGC TATCTGAGGG
 401 GACTAGGGTG TGTTTAGGCG AAAAGCGGGG CTTCGGTTGT ACGCGGTTAG
 451 GAGTCCCCTC AGGATATAGT AGTTTCGCTT TTGCATAGGG AGGGGGAAAT
 501 GTAGTCTTAT GCAATACTCT TGTAGTCTTG CAACATGGTA ACGATGAGTT
 551 AGCAACATGC CTTACAAGGA GAGAAAAAGC ACCGTGCATG CCGATTGGTG
 601 GAAGTAAGGT GGTACGATCG TGCCTTATTA GGAAGGCAAC AGACGGGTCT
 651 GACATGGATT GGACGAACCA CTAAATTCCG CATTGCAGAG ATATTGTATT
 701 TAAGTGCCTA GCTCGATACA ATAAACGCCA TTTGACCATT CACCACATTG
 751 GTGTGCACCT CCAAGCTGGG TACCAGCTTC TAGAGAGATC TGCTTCAGCT
 801 GGAGGCACTG GCAGGTAAG TATCAAGGTT ACAAGACAGG TTTAAGGAGA
 851 CCAATAGAAA CTGGGCTTGT CGAGACAGAG AAGACTCTTG CGTTTCTGAT
 901 AGGCACCTAT TGGTCTTACT GACATCCACT TTGCCTTTCT CTCCACAGGT
 951 GCAGCTGCTG CAGCGGTCTA GAACTCGAGT CGAGACCATG GCGATGGATG
1001 TCACAAGGAG CCAGGCCCAG ACAGCCTTGA CTCTGGTAGA GCAGATCCTG
1051 GCAGAGTTCC AGCTGGAGGA GGAGGACCTG AAGAAGGTGA TGAGACGGAT
1101 GCAGAAGGAG ATGGACCGCG GCCTGAGGCT GGAGACCCAT GAAGAGGCCA
1151 GTGTGAAGAT GCTGCCCACC TACGTGCGCT CCACCCCAGA AGGCTCAGAA
1201 GTCGGGGACT TCCTCTCCCT GGACCTGGGT GGCACTAACT TCAGGGTGAT
1251 GCTGGTGAAG GTGGGAGAAG GTGAGGAGGG GCAGTGGAGC GTGAAGACCA
1301 AACACCAGAT GTACTCCATC CCCGAGGACG CCATGACCGG CACTGCTGAG
1351 ATGCTCTTCG ACTACATCTC TGAGTGCATC TCCGACTTCC TGGACAAGCA
1401 TCAGATGAAA CACAAGAAGC TGCCCCTGGG CTTCACCTTC TCCTTTCCTG
```

```
1451 TGAGGCACGA AGACATCGAT AAGGGCATCC TTCTCAACTG GACCAAGGGC

1501 TTCAAGGCCT CAGGAGCAGA AGGGAACAAT GTCGTGGGGC TTCTGCGAGA

1551 CGCTATCAAA CGGAGAGGGG ACTTTGAAAT GGATGTGGTG GCAATGGTGA

1601 ATGACACGGT GGCCACGATG ATCTCCTGCT ACTACGAAGA CCATCAGTGC

1651 GAGGTCGGCA TGATCGTGGG CACGGGCTGC AATGCCTGCT ACATGGAGGA

1701 GATGCAGAAT GTGGAGCTGG TGGAGGGGGA CGAGGGCCGC ATGTGCGTCA

1751 ATACCGAGTG GGGCGCCTTC GGGGACTCCG GCGAGCTGGA CGAGTTCCTG

1801 CTGGAGTATG ACCGCCTGGT GGACGAGAGC TCTGCAAACC CCGGTCAGCA

1851 GCTGTATGAG AAGCTCATAG GTGGCAAGTA CATGGGCOAG CTGGTGCGGC

1901 TTGTGCTGCT CAGGCTCGTG GACGAAAACC TGCTCTTCCA CGGGGAGGCC

1951 TCCGAGCAGC TGCGCACACG CGGAGCCTTC GAGACGCGCT TCGTGTCGCA

2001 GGTGGAGAGC GACACGGGCG ACCGCAAGCA GATCTACAAC ATCCTGAGCA

2051 CGCTGGGGCT GCGACCCTCG ACCACCGACT GCGACATCGT GCGCCGCGCC

2101 TGCGAGAGCG TGTCTACGCG CGCTGCGCAC ATGTGCTCGG CGGGGCTGGC

2151 GGGCGTCATC AACCGCATGC GCGAGAGCCG CAGCGAGGAC GTAATGCGCA

2201 TCACTGTGGG CGTGGATGGC TCCGTGTACA AGCTGCACCC CAGCTTCAAG

2251 GAGCGGTTCC ATGCCAGCGT GCGCAGGCTG ACGCCCAGCT GCGAGATCAC

2301 CTTCATCGAG TCGGAGGAGG GCAGTGGCCG GGGCGCGOCC CTGGTCTCGG

2351 CGGTGGCCTG TAAGAAGGCC TGTATGCTGG CCAGTGACT CGAGCACGTG

2401 GAGCTCGCTG ATCAGCCTCG ACTGTGCCTT CTAGTTGCCA GCCATCTGTT

2451 GTTTGCCCCT CCCCCGTGCC TTCCTTGACC CTGGAAGGTG CCACTCCCAC

2501 TGTCCTTTCC TAATAAAATG AGGAAATTGC ATCGCATTGT CTGAGTAGGT

2551 GTCATTCTAT TCTGGGGGGT GGGGTGGGGC AGGACAGCAA GGGGGAGGAT

2601 TGGGAAGACA ATAGCAGGCA TGCTGGGGAT GCGGTGGGCT CTATGGCCAC

2651 GTGATTTAAA TGCGGCCGCA GGAACCCCTA GTGATGGAGT TGGCCACTCC

2701 CTCTCTGCGC GCTCGCTCGC TCACTGAGGC CGGGCGACCA AAGGTCGCCC

2751 GACGCCCGGG CTTTGCCCGG GCGGCCTCAG TGAGCGAGCG AGCGCGCAGC

2801 TGCCTGCAGG GGCGCCTGAT GCGGTATTTT CTCCTTACGC ATCTGTOCGG

2851 TATTTCACAC CGCATACGTC AAAGCAACCA TAGTACGCGC CCTGTAGCGG

2901 CGCATTAAGC GCGGCGGGTG TGGTGGTTAC GCGCAGCGTG ACCGCTACAC

2951 TTGCCAGCGC CCTAGCGCCC GCTCCTTTCG CTTTCTTCCC TTCCTTTCTC

3001 GCCACGTTCG CCGGCTTTCC CCGTCAAGCT CTAAATCGGG GGCTCCCTTT

3051 AGGGTTCCGA TTTAGTGCTT TACGGCACCT CGACCCCAAA AAACTTGATT

3101 TGGGTGATGG TTCACGTAGT GGGOCATCGC CCTGATAGAC GGTTTTTCGC

3151 CCTTTGACGT TGGAGTCCAC GTTCTTTAAT AGTGGACTCT TGTTCCAAAC

3201 TGGAACAACA CTCAACCCTA TCTCGGGCTA TTCTTTTGAT TTATAAGGGA

3251 TTTTGCCGAT TTCGGCCTAT TGGTTAAAAA ATGAGCTGAT TTAACAAAAA

3301 TTTAACGCGA ATTTTAACAA AATATTAACG TTTACAATTT TATGGTGCAC

3351 TCTCAGTACA ATCTGCTCTG ATGCCGCATA GTTAAGCCAG CCCCGACACC

3401 CGCCAACACC CGCTGACGCG CCCTGACGGG CTTGTCTGCT CCCGGCATCC

3451 GCTTACAGAC AAGCTGTGAC CGTCTCCGGG AGCTGCATGT GTCAGAGGTT
```

```
3501 TTCACCGTCA TCACCGAAAC GCGCGAGACG AAAGGGCCTC GTGATACGCC
3551 TATTTTTATA GGTTAATGTC ATGATAATAA TGGTTTCTTA GACGTCAGGT
3601 GGCACTTTTC GGGGAAATGT GCGCGGAACC CCTATTTGTT TATTTTTCTA
3651 AATACATTCA AATATGTATC CGCTCATGAG ACAATAACCC TGATAAATGC
3701 TTCAATAATA TTGAAAAAGG AAGAGTATGA GTATTCAACA TTTCCGTGTC
3751 GCCCTTATTC CCTTTTTTGC GGCATTTTGC CTTCCTGTTT TTGCTCACCC
3801 AGAAACGCTG GTGAAAGTAA AAGATGCTGA AGATCAGTTG GGTGCACGAG
3851 TGGGTTACAT CGAACTGGAT CTCAACAGCG GTAAGATCCT TGAGAGTTTT
3901 CGCCCCGAAG AACGTTTTCC AATGATGAGC ACTTTTAAAG TTCTGCTATG
3951 TGGCGCGGTA TTATCCCGTA TTGACGCCGG GCAAGAGCAA CTCGGTCGCC
4001 GCATACACTA TTCTCAGAAT GACTTGGTTG AGTACTCACC AGTCACAGAA
4051 AAGCATCTTA CGGATGGCAT GACAGTAAGA GAATTATGCA GTGCTGCCAT
4101 AACCATGAGT GATAACACTG CGGCCAACTT ACTTCTGACA ACGATCGGAG
4151 GACCGAAGGA GCTAACCGCT TTTTTGCACA ACATGGGGGA TCATGTAACT
4201 CGCCTTGATC GTTGGGAACC GGAGCTGAAT GAAGCCATAC CAAACGACGA
4251 GCGTGACACC ACGATGCCTG TAGCAATGGC AACAACGTTG CGCAAACTAT
4301 TAACTGGCGA ACTACTTACT CTAGCTTCCC GGCAACAATT AATAGACTGG
4351 ATGGAGGCGG ATAAAGTTGC AGGACCACTT CTGCGCTCGG CCCTTCCGGC
4401 TGGCTGGTTT ATTGCTGATA AATCTGGAGC CGGTGAGCGT GGGTCTCGCG
4451 GTATCATTGC AGCACTGGGG CCAGATGGTA AGCCCTCCCG TATCGTAGTT
4501 ATCTACACGA CGGGGAGTCA GGCAACTATG GATGAACGAA ATAGACAGAT
4551 CGCTGAGATA GGTGCCTCAC TGATTAAGCA TTGGTAACTG TCAGACCAAG
4601 TTTACTCATA TATACTTTAG ATTGATTTAA AACTTCATTT TTAATTTAAA
4651 AGGATCTAGG TGAAGATCCT TTTTGATAAT CTCATGACCA AAATCCCTTA
4701 ACGTGAGTTT TCGTTCCACT GAGCGTCAGA CCCCGTAGAA AAGATCAAAG
4751 GATCTTCTTG AGATCCTTTT TTTCTGCGCG TAATCTGCTG CTTGCAAACA
4801 AAAAAACCAC CGCTACCAGC GGTGGTTTGT TTGCCGGATC AAGAGCTACC
4851 AACTCTTTTT CCGAAGGTAA CTGGCTTCAG CAGAGCGCAG ATACCAAATA
4901 CTGTCCTTCT AGTGTAGCCG TAGTTAGGCC ACCACTTCAA GAACTCTGTA
4951 GCACCGCCTA CATACCTCGC TCTGCTAATC CTGTTACCAG TGGCTGCTGC
5001 CAGTGGCGAT AAGTCGTGTC TTACCGGGTT GGACTCAAGA CGATAGTTAC
5051 CGGATAAGGC GCAGCGGTCG GGCTGAACGG GGGGTTCGTG CACACAGCCC
5101 AGCTTGGAGC GAACGACCTA CACCGAACTG AGATACCTAC AGCGTGAGCT
5151 ATGAGAAAGC GCCACGCTTC CCGAAGGGAG AAAGGCGGAC AGGTATCCGG
5201 TAAGCGGCAG GGTCGGAACA GGAGAGCGCA CGAGGGAGCT TCCAGGGGGA
5251 AACGCCTGGT ATCTTTATAG TCCTGTCGGG TTTCGCCACC TCTGACTTGA
5301 GCGTCGATTT TTGTGATGCT CGTCAGGGGG GCGGAGCCTA TGGAAAAACG
5351 CCAGCAACGC GGCCTTTTTA CGGTTCCTGG CCTTTTGCTG GCCTTTTGCT
5401 CACATGT
```

ITR 5': 1-141 bp
RSV promoter: 239-948 bp
hGck: 973-2387 bp
bGH polyA: 2395-2653 bp
ITR 3': 2670-2810 bp
J: miniCMV-hIns-RSV-hGck (SEQ ID NO: 13; FIG. 7)

```
pAAV-miniCMV-hIns-RSV-hGck plasmid sequence
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCGCG

151 ATATCTATGC CAAGTACGCC CCTATTGAC GTCAATGACG GTAAATGGCC

201 CGCCTGGCAT TATGCCCAGT ACATGACCTT ATGGGACTTT CCTACTTGGC

251 AGTACATCTA CGTATTAGTC ATCGCTATTA CCATGGTGAT GCGGTTTTGG

301 CAGTACATCA ATGGGCGTGG ATAGCGGTTT GACTCACGGG GATTTCCAAG

351 TCTCCACCCC ATTGACGTCA ATGGGAGTTT GTTTTGGCAC CAAAATCAAC

401 GGGACTTTCC AAAATGTCGT AACAACTCCG CCCCATTGAC GCAAATGGGC

451 GGTAGGCGTG TACGGTGGGA GGTCTATATA AGCAGAGCTC TCTGGCTAAC

501 TAGAGAACCC ACTGCTTAAC TGGCTTATCG AAATTAATAC GACTCACTAT

551 AGGGAGACCC AAGCTTGCTA GCGTCGACCT TCTGCCATGG CCCTGTGGAT

601 GCGCCTCCTG CCCCTGCTGG CGCTGCTGGC CCTCTGGGGA CCTGACCCAG

651 CCGCAGCCTT TGTGAACCAA CACCTGTGCG GCTCAGATCT GGTGGAAGCT

701 CTCTACCTAG TGTGCGGGGA ACGAGGCTTC TTCTACACAC CCAGGACCAA

751 GCGGGAGGCA GAGGACCTGC AGGTGGGGCA GGTGGAGCTG GGCGGGGGCC

801 CTGGTGCAGG CAGCCTGCAG CCCTTGGCCC TGGAGGGGTC GCGACAGAAG

851 CGTGGCATTG TGGAACAATG CTGTACCAGC ATCTGCTCCC TCTACCAGCT

901 GGAGAACTAC TGCAACTAGA CGCAGCCGTC GACGGTACCA GCGCTGTCGA

951 GGCCGCTTCG AGCAGACATG ATAAGATACA TTGATGAGTT TGGACAAACC

1001 ACAACTAGAA TGCAGTGAAA AAAATGCTTT ATTTGTGAAA TTTGTGATGC

1051 TATTGCTTTA TTTGTAACCA TTATAAGCTG CAATAAACAA GTTAACAACA

1101 ACAATTGCAT TCATTTTATG TTTCAGGTTC AGGGGGAGAT GTGGGAGGTT

1151 TTTTAAAGCA AGTAAAACCT CTACAAATGT GGTAAAATCG ATTAGGATCT

1201 TCCTAGAGCA TGGCTACCTA GACATGGCTC GACAGATCAG CGCTCATGCT

1261 CTGGAAGATC TCGATTTATC CATGTTTGAC AGCTTATCAT CGCAGATCCG

1301 TATGGTGCAC TCTCAGTACA ATCTGCTCTG ATGCCGCATA GTTAAGCCAG

1391 TATCTGCTCC CTGCTTGTGT GTTGGAGGTC GCTGAGTAGT GCGCGAGCAA

1401 AATTTAAGCT ACAACAAGGC AAGGCTTGAC CGACAATTGC ATGAAGAATC

1451 TGCTTAGGGT TAGGCGTTTT GCGCTGCTTC GCGATGTACG GGCCAGATAT

1501 TCGCGTATCT GAGGGGACTA GGGTGTGTTT AGGCGAAAAG CGGGGCTTCG

1551 GTTGTACGCG GTTAGGAGTC CCCTCAGGAT ATAGTAGTTT CGCTTTTGCA

1601 TAGGGAGGGG GAAATGTAGT CTTATGCAAT ACTCTTGTAG TCTTGCAACA

1651 TGGTAACGAT GAGTTAGCAA CATGCCTTAC AAGGAGAGAA AAAGCACCGT

1701 GCATGCCGAT TGGTGGAAGT AAGGTGGTAC GATCGTGCCT TATTAGGAAG

1751 GCAACAGACG GGTCTGACAT GGATTGGACG AACCACTAAA TTQCGCATTG
```

```
1801 CAGAGATATT GTATTTAAGT GCCTAGCTCG ATAQAATAAA CGCCATTTGA

1851 CCATTCACCA CATTGGTGTG CACCTCCAAG CTGGGTACCA GCTTCTAGAG

1901 AGATCTGCTT CAGCTGGAGG CACTGGGCAG GTAAGTATCA AGGTTACAAG

1951 ACAGGTTTAA GGAGACCAAT AGAAACTGGG CTTGTCGAGA CAGAGAAGAC

2001 TCTTGCGTTT CTGATAGGCA CCTATTGGTC TTACTGACAT CCACTTTGCC

2051 TTTCTCTCCA CAGGTGCAGC TGCTGCAGCG GTCTAGAACT CGAGTCGAGA

2101 CCATGGCGAT GGATGTCACA AGGAGCCAGG CCCAGACAGC CTTGACTCTG

2151 GTAGAGCAGA TCCTGGCAGA GTTCCAGCTG CAGGAGGAGG ACCTGAAGAA

2201 GGTGATGAGA CGGATGCAGA AGGAGATGGA CCGCGGCCTG AGGCTGGAGA

2251 CCCATGAAGA GGCCAGTGTG AAGATGCTGC CCACCTACGT GCGCTCCACC

2301 CCAGAAGGCT CAGAAGTCGG GGACTTCCTC TCCCTGGACC TGGGTGGCAC

2351 TAACTTCAGG GTGATGCTGG TGAAGGTGGG AGAAGGTGAG GAGGGGCAGT

2401 GGAGCGTGAA GACCAAACAC CAGATGTACT CCATCCCCGA GGACGCCATG

2451 ACCGGCACTG CTGAGATGCT CTTCGACTAC ATCTCTGAGT GCATCTCCGA

2501 CTTCCTGGAC AAGCATCAGA TGAAACACAA GAAGCTGCCC CTGGGCTTCA

2551 CCTTCTCCTT TCCTGTGAGG CACGAAGACA TCGATAAGGG CATCCTTCTC

2601 AACTGGACCA AGGGCTTCAA GGCCTCAGGA GCAGAAGGGA ACAATGTCGT

2651 GGGGCTTCTG CGAGACGCTA TCAAACGGAG AGGGGACTTT GAAATGGATG

2701 TGGTGGCAAT GGTGAATGAC AdGGTGGCCA CGATGATCTC CTGCTACTAC

2751 GAAGACCATC AGTGCGAGGT CGGCATGATC GTGGGCACGG GCTGCAATGC

2801 CTGCTACATG GAGGAGATGC AGAATGTGGA OCTGGTGGAG GGGACGAGG

2851 GCCGCATGTG CGTCAATACC GAGTGGGGCG CCTTCGGGGA CTCCGGCGAG

2901 CTGGACGAGT TCCTGCTGGA GTATGACCGC TGGTGGACG AGAGCTCTGC

2951 AAACCCCGGT CAGCAGCTGT ATGAGAAGCT CATAGGTGGC AAGTACATGG

3001 GCGAGCTGGT GCGGCTTGTG CTGCTCAGGC TCGTGGACGA AAACCTGCTC

3051 TTCCACGGGG AGGCCTCCGA GCAGCTGCGC ACACGCGGAG CCTTCGAGAC

3101 GCGCTTCGTG TCGCAGGTGG AGAGCGACAC GGGCGACCGC AAGCAGATCT

3151 ACAACATCCT GAGCACGCTG GGGCTGCGAC CCTCGACCAC CGACTGCGAC

3201 ATCGTGCGCC GCGCCTGCGA GAGCGTGTCT ACGCGCGCTG CGCACATGTG

3251 CTCGGCGGGG CTGGCGGGCG TCATCAACCG CATGCGCGAG AGCCGCAGCG

3301 AGGACGTAAT GCGCATCACT GTGGGCGTGG ATGGCTCCGT GTACAAGCTG

3351 CACCCCAGCT TCAAGGAGCG GTTCCATGCC AGCGTGCGCA GGCTGACGCC

3401 CAGCTGCGAG ATCACCTTCA TCGAGTCGGA GGAGGGCAGT GGCCGGGGCG

3451 CGGCCCTGGT CTCGGCGGTG GCCTGTAAGA AGGCCTGTAT GCTGGGCCAG

3501 TGACTCGAGC ACGTGGAGCT CGCTGATCAG CCTCGACTGT GCCTTCTAGT

3551 TGCCAGCCAT CTGTTGTTTG CCCCTCCCCC GTGCCTTCCT TGACCCTGGA

3601 AGGTGCCACT CCCACTGTCC TTTCCTAATA AAATGAGGAA ATTGCATCGC

3651 ATTGTCTGAG TAGGTGTCAT TCTATTCTGG GGGTGGGGT GGGGCAGGAC

3701 AGCAAGGGGG AGGATTGGGA AGACAATAGC AGGCATGCTG GGGATGCGGT

3751 GGGCTCTATG GCCACGTGAT TTAAATGCGG CCGCAGGAAC CCCTAGTGAT

3801 GGAGTTGGCC ACTCCCTCTC TGCGCGCTCG CTCGCTCACT GAGGCCGGGC
```

```
3851 GACCAAAGGT CGCCCGACGC CCGGGCTTTG CCQGGGCGGC CTCAGTGAGC
3901 GAGCGAGCGC GCAGCTGCCT GCAGGGGCGC CTGATGCGOT ATTTTCTCCT
3951 TACGCATCTG TGCGGTATTT CACACCGCAT ACGTCAAAGC AACCATAGMA
4001 CGCGCCCTGT AGCGGCGCAT TAAGCGCGGC GGGTGTGGTG GTTACGCGCA
4051 GCGTGACCGC TACACTTGCC AGCGCCCTAG CGCCCGCTCC TTTCGCTTTC
4101 TTCCCTTCCT TTCTCGCCAC GTTCGCCGGC TTTCCCCGTC AAGCTCTAAA
4151 TCGGGGCTC CCTTTAGGGT TCCGATTTAG TGCTTTACGG CACCTCGACC
4201 CCAAAAAACT TGATTTGGGT GATGGTTCAC GTAGTGGGCC ATCGCCCTGA
4251 TAGACGGTTT TTCGCCCTTT GACGTTGGAG TCCACGTTCT TTAAMAGTGG
4301 ACTCTTGTTC CAAACTGGAA CAACACTCAA CCCTATCTCG GGCTATTCTT
4351 TTGATTTATA AGGGATTTTG CCGATTTCGG CCTATTGGTM AAAAAATGAG
4401 CTGATTTAAC AAAAATTTAA CGCGAATTTT AACAAAATAT TAACGTTTAC
4451 AATTTTATGG TGCACTCTCA GTACAATCTG CTCTGATGCC GCATAGTTAA
4501 GCCAGCCCCG ACACCCGCCA ACACCCGCTG ACGCGCCCTG ACGGGCTTGT
4551 CTGCTCCCGG CATCCGCTTA CAGACAAGCT GTGACCGTCT CCGGGAGCTG
4601 CATGTGTCAG AGGTTTTCAC CGTCATCACC GAAACGCGCG AGACGAAAGG
4651 GCCTCGTGAT ACGCCTATTT TTATAGGTTA ATGTCATGAT AATAATGGTT
4701 TCTTAGACGT CAGGTGGCAC TTTTCGGGGA AATGTGCGCG GAACCCCTAT
4751 TTGTTTATTT TTCTAAATAC ATTCAAATAT GTATCCGCTC ATGAGACAAT
4801 AACCCTGATA AATGCTTCAA TAATATTGAA AAAGGAAGAG TATGAGTATT
4851 CAACATTTCC GTGTCGCCCT TATTCCCTTT TTTGCGGCAT TTTGCCTTCC
4901 TGTTTTTGCT CACCCAGAAA CGCTGGTGAA AGTAAAAGAT GCTGAAGATC
4951 AGTTGGGTGC ACGAGTGGGT TACATCGAAC TGGATCTCAA CAGCGGTAAG
5001 ATCCTTGAGA GTTTTCGCCC CGAAGAACGT TTTCCAATGA TGAGCACTTT
5051 TAAAGTTCTG CTATGTGGCG CGGTATTATC CCGTATTGAC GCCGGGCAAG
5101 AGCAACTCGG TCGCCGCATA CACTATTCTC AGAATGACTT GGTTGAGTAC
5151 TCACCAGTCA CAGAAAAGCA TCTTACGGAT GGCATGACAG TAAGAGAATT
5201 ATGCAGTGCT GCCATAACCA TGAGTGATAA CACTGCGGCC AACTTACTTC
5251 TGACAACGAT CGGAGGACCG AAGGAGCTAA CCGCTTTTTT GCACAACATG
5301 GGGGATCATG TAACTCGCCT TGATCGTTGG GAACCGGAGC TGAATGAAGC
5351 CATACCAAAC GACGAGCGTG ACACCACGAT GCCTGTAGCA ATGGCAACAA
5401 CGTTGCGCAA ACTATTAACT GGCGAACTAC TTACTCTAGC TTCCCGGCAA
5451 CAATTAATAG ACTGGATGGA GGCGGATAAA GTTGCAGGAC CACTTCTGCG
5501 CTCGGCCCTT CCGGCTGGCT GGTTTATTGC TGATAAATCT GGAGCCGGTG
5551 AGCGTGGGTC TCGCGGTATC ATTGCAGCAC TGGGGCCAGA TGGTAAGCCC
5601 TCCCGTATCG TAGTTATCTA CACGACGGGG AGTCAGGCAA CTATGGATGA
5651 ACGAAATAGA CAGATCGCTG AGATAGGTGC CTCACTGATT AAGCATTGGT
5701 AACTGTCAGA CCAAGTTTAC TCATATATAC TTTAGATTGA TTTAAAACTT
5751 CATTTTTAAT TTAAAAGGAT CTAGGTGAAG ATCCTTTTTG ATAATCTCAT
5801 GACCAAAATC CCTTAACGTG AGTTTTCGTT CCACTGAGCG TCAGACCCCG
```

```
5851 TAGAAAAGAT CAAAGGATCT TCTTGAGATC CTTTTTTTCT GCGCGTAATC

5901 TGCTGCTTGC AAACAAAAAA ACCACCGCTA CCAGCGGTGG TTTGTTTGCC

5951 GGATCAAGAG CTACCAACTC TTTTTCCGAA GGTAACTGGC TTCAGCAGAG

6001 CGCAGATACC AAATACTGTC CTTCTAGTGT AGCCGTAGTT AGGCCACCAC

6051 TTCAAGAACT CTGTAPCACC GCCTACATAC CTCGCTCTGC TAATCCTGTT

6101 ACCAGTGGCT GCTGCCAGTG GCGATAAGTC GTGTCTTACC GGGTTGGACT

6151 CAAGACGATA GTTACCGGAT AAGGCGCAGC GGTCGGGCTG AACGGGGGGT

6201 TCGTGCACAC AGCCCAGCTT GGAGCGAACG ACCTACACCG AACTGAGATA

6251 CCTACAGCGT GAGCTATGAG AAAGCGCCAC GCTTCCCGAA GGGAGAAAGG

6301 CGGACAGGTA TCCGGTAAGC GGCAGGGTCG GAACAGGAGA GCGCACGAGG

6351 GAGCTTCCAG GGGGAAACGC CTGGTATCTT TATAGTCCTG TCGGGTTTCG

6401 CCACCTCTGA CTTGAGCGTC GATTTTTGTG ATGCTCGTCA GGGGGGCGGA

6451 GCCTATGGAA AAACGCCAGC AACGCGGCCT TTTTACGGTT CCTGGCCTTT

6501 TGCTGGCCTT TGCTCACAT GT
```
ITR 5': 1-141 bp  
miniCMV promoter: 156-566 bp  
hIns: 580-926 bp  
SV40 polyA: 940-1238 bp  
RSV promoter: 1354-2063 bp  
hGck: 2088-3502 bp  
bGH polyA: 3510-3768 bp  
ITR 3': 3785-3925 bp K: RSV-hGck-miniCMV-hIns (SEQ ID NO: 14; FIG. 7)

| pAAV-RSV-hGck-miniCMV-hIns plasmid sequence |
| --- |
| 1 CCTGCAGGCA GCTGCGCGCT CGCTCGCTCA CTGAGGCCGC CCGGGCAAAG |
| 51 CCCGGGCGTC GGGCGACCTT TGGTCGCCCG GCCTCAGTGA GCGAGCGAGC |
| 101 GCGCAGAGAG GGAGTGGCCA ACTCCATCAC TAGGGGTTCC TGCGGCCGCG |
| 151 ATATCCATGT TTGACAGCTT ATCATCGCAG ATCCGTATGG TGCACTCTCA |
| 201 GTACAATCTG CTCTGATGCC GCATAGTTAA GCCAGTATCT GCTCCCTGCT |
| 251 TGTGTGTTGG AGGTCGCTGA GTAGTGCGCG AGCAAAATTT AAGCTACAAC |
| 301 AAGGCAAGGC TTGACCGACA ATTGCATGAA GAATCTGCTT AGGGTTAGGC |
| 351 GTTTTGCGCT GCTTCGCGAT GTACGGGCCA GATATTGCG TATCTGAGGG |
| 401 GACTAGGGTG TGTTTAGGCG AAAAGCGGGG CTTCGGTTGT ACGCGGTTAG |
| 451 GAGTCCCCTC AGGATATAGT AGTTTCGCTT TTGCATAGGG AGGGGGAAAT |
| 501 GTAGTCTTAT GCAATACTCT TGTAGTCTTG CAACATGGTA ACGATGAGTT |
| 551 AGCAACATGC CTTACAAGGA GAGAAAAAGC ACCGTGCATG CCGATTGGTG |
| 601 GAAGTAAGGT GGTACGATCG TGCCTTATTA GGAAGGCAAC AGACGGGTCT |
| 651 GACATGGATT GGACGAACCA CTAAATTCCG CATTGCAGAG ATATTGTATT |
| 701 TAAGTGCCTA GCTCGATACA ATAAACGCCA TTTGACCATT CACCACATTG |
| 751 GTGTGCACCT CCAAGCTGGG TACCAGCTTC TAGAGAGATC TGCTTCAGCT |
| 801 GGAGGCACTG GCAGGTAAG TATCAAGGTT ACAAGACAGG TTTAAGGAGA |
| 851 CCAATAGAAA CTGGGCTTGT CGAGACAGAG AAGACTCTTG CGTTTCTGAT |
| 901 AGGCACCTAT TGGTCTTACT GACATCCACT TTGCCTTTCT CTCCACAGGT |
| 951 GCAGCTGCTG CAGCGGTCTA GAACTCGAGT CGAGACCATG GCGATGGATG |

| pAAV-RSV-hGck-miniCMV-hIns plasmid sequence |
|---|
| 1001 TCACAAGGAG CCAGGCCCAG ACAGCCTTGA CTCTGGTAGA GCAGATCCTG |
| 1051 GCAGAGTTCC AGCTGCAGGA GGAGGACCTG AAGAAGGTGA TGAGACGGAT |
| 1101 GCAGAAGGAG ATGGACCGCG GCCTGAGGCT GGAGACCCAT GAAGAGGCCA |
| 1151 GTGTGAAGAT GCTGCCCACC TACGTGCGCT CCACCCCAGA AGGCTCAGAA |
| 1201 GTCGGGGACT TCCTCTCCCT GGACCTGGGT GGCACTAACT TCAGGGTGAT |
| 1251 GCTGGTGAAG GTGGGAGAAG GTGAGGAGGG GCAGTGGAGC GTGAAGACCA |
| 1301 AACACCAGAT GTACTCCATC CCCGAGGACG CCATGACCGG CACTGCTGAG |
| 1351 ATGCTCTTCG ACTACATCTC TGAGTGCATC TCCGACTTCC TGGACAAGCA |
| 1401 TCAGATGAAA CACAAGAAGC TGCCCCTGGG CTTCACCTTC TCCTTTCCTG |
| 1451 TGAGGCACGA AGACATCGAT AAGGGCATCC TTCTCAACTG GACCAAGGGC |
| 1501 TTCAAGGCCT CAGGAGCAGA AGGGAACAAT GTCGTGGGGC TTCTGCGAGA |
| 1551 CGCTATCAAA CGGAGAGGGG ACTTTGAAAT GGATGTGGTG GCAATGGTGA |
| 1601 ATGACACGGT GGCCACGATG ATCTCCTGCT ACTACGAAGA CCATCAGTGC |
| 1651 GAGGTCGGCA TGATCGTGGG CACGGGCTGC AATGCCTGCT ACATGGAGGA |
| 1701 GATGCAGAAT GTGGAGCTGG TGGAGGGGGA CGAGGGCCGC ATGTGCGTCA |
| 1751 ATACCGAGTG GGGCGCCTTC GGGGACTCCG GCGAGCTGGA CGAGTTCCTG |
| 1801 CTGGAGTATG ACCGCCTGGT GGACGAGAGC TCTGCAAACC CCGGTCAGCA |
| 1851 GCTGTATGAG AAGCTCATAG GTGGCAAGTA CATGGGCGAG CTGGTGCGGC |
| 1901 TTGTGCTGCT CAGGCTCGTG GACGAAAACC TGCTCTTCCA CGGGGAGGCC |
| 1951 TCCGAGCAGC TGCGCACACG CGGAGCCTTC GAGACGCGCT TCGTGTCGCA |
| 2001 GGTGGAGAGC GACACGGGCG ACCGCAAGCA GATCTACAAC ATCCTGAGCA |
| 2051 CGCTGGGGCT GCGACCCTCG ACCACCGACT GCGACATCGT GCGCCGCGCC |
| 2101 TGCGAGAGCG TGTCTACGCG CGCTGCGCAC ATGTGCTCGG CGGGGCTGGC |
| 2151 GGGCGTCATC AACCGCATGC GCGAGAGCCG CAGCGAGGAC GTAATGCGCA |
| 2201 TCACTGTGGG CGTGGATGGC TCCGTGTACA AGCTGCACCC CAGCTTCAAG |
| 2251 GAGCGGTTCC ATGCCAGCGT GCGCAGGCTG ACGCCCAGCT GCGAGATCAC |
| 2301 CTTCATCGAG TCGGAGGAGG GCAGTGGCCG GGGCGCGGCC CTGGTCTCGG |
| 2351 CGGTGGCCTG TAAGAAGGCC TGTATGCTGG GCCAGTGACT CGAGCACGTG |
| 2401 GAGCTCGCTG ATCAGCCTCG ACTGTGCCTT CTAGTTGCCA GCCATCTGTT |
| 2451 GTTTGCCCCT CCCCCGTGCC TTCCTTGACC CTGGAAGGTG CCACTCCCAC |
| 2501 TGTCCTTTCC TAATAAAATG AGGAAATTGC ATCGCATTGT CTGAGTAGGT |
| 2551 GTCATTCTAT TCTGGGGGGT GGGGTGGGGC AGGACAGCAA GGGGGAGGAT |
| 2601 TGGGAAGACA ATAGCAGGCA TGCTGGGGAT GCGGTGGGCT CTATGGCCAC |
| 2651 GTGATTTATC TATGCCAAGT ACGCCCCCTA TTGACGTCAA TGACGGTAAA |
| 2701 TGGCCCGCCT GGCATTATGC CCAGTACATG ACCTTATGGG ACTTTCCTAC |
| 2751 TTGGCAGTAC ATCTACGTAT TAGTCATCGC TATTACCATG GTGATGCGGT |
| 2801 TTTGGCAGTA CATCAATGGG CGTGGATAGC GGTTTGACTC ACGGGGATTT |
| 2851 CCAAGTCTCC ACCCCATTGA CGTCAATGGG AGTTTGTTTT GGCACCAAAA |

-continued

| pAAV-RSV-hGck-miniCMV-hIns plasmid sequence |
| --- |
| 2901 TCAACGGGAC TTTCCAAAAT GTCGTAACAA CTCCGCCCCA TTGACGCAAA |
| 2951 TGGGCGGTAG GCGTGTACGG TGGGAGGTCT ATATAAGCAG AGCTCTCTGG |
| 3001 CTAACTAGAG AACCCACTGC TTAACTGGCT TATCGAAATT AATACGACTC |
| 3051 ACTATAGGGA GACCCAAGCT TGCTAGCGTC GACCTTCTGC CATGGCCCTG |
| 3101 TGGATGCGCC TCCTGCCCCT GCTGGCGCTG CTGGCCCTCT GGGGACCTGA |
| 3151 CCCAGCCGCA GCCTTTGTGA ACCAACACCT GTGCGGCTCA GATCTGGTGG |
| 3201 AAGCTCTCTA CCTAGTGTGC GGGGAACGAG GCTTCTTCTA CACACCCAGG |
| 3251 ACCAAGCGGG AGGCAGAGGA CCTGCAGGTG GGGCAGGTGG AGCTGGGCGG |
| 3301 GGGCCCTGGT GCAGGCAGCC TGCAGCCCTT GGCCCTGGAG GGGTCGCGAC |
| 3351 AGAAGCGTGG CATTGTGGAA CAATGCTGTA CCAGCATCTG CTCCCTCTAC |
| 3401 CAGCTGGAGA ACTACTGCAA CTAGACGCAG CCGTCGACGG TACCAGCGCT |
| 3451 GTCGAGGCCG CTTCGAGCAG ACATGATAAG ATACATTGAT GAGTTTGGAC |
| 3501 AAACCACAAC TAGAATGCAG TGAAAAAAAT GCTTTATTTG TGAAATTTGT |
| 3551 GATGCTATTG CTTTATTTGT AACCATTATA AGCTGCAATA AACAAGTTAA |
| 3601 CAACAACAAT TGCATTCATT TTATGTTTCA GGTTCAGGGG GAGATGTGGG |
| 3651 AGGTTTTTTA AAGCAAGTAA AACCTCTACA AATGTGGTAA AATCGATTAG |
| 3701 GATCTTCCTA GAGCATGGCT ACCTAGACAT GGCTCGACAG ATCAGCGCTC |
| 3751 ATGCTCTGGA AGATCTCGAT TTAAATGCGG CCGCAGGAAC CCCTAGTGAT |
| 3801 GGAGTTGGCC ACTCCCTCTC TGCGCGCTCG CTCGCTCACT GAGGCCGGGC |
| 3851 GACCAAAGGT CGCCCGACGC CCGGGCTTTG CCCGGGCGGC CTCAGTGAGC |
| 3901 GAGCGAGCGC GCAGCTGCCT GCAGGGGCGC CTGATGCGGT ATTTTCTCCT |
| 3951 TACGCATCTG TGCGGTATTT CACACCGCAT ACGTCAAAGC AACCATAGTA |
| 4001 CGCGCCCTGT AGCGGCGCAT TAAGCGCGGC GGGTGTGGTG GTTACGCGCA |
| 4051 GCGTGACCGC TACACTTGCC AGCGCCCTAG CGCCCGCTCC TTTCGCTTTC |
| 4101 TTCCCTTCCT TTCTCGCCAC GTTCGCCGGC TTTCCCCGTC AAGCTCTAAA |
| 4151 TCGGGGGCTC CCTTTAGGGT TCCGATTTAG TGCTTTACGG CACCTCGACC |
| 4201 CCAAAAAACT TGATTTGGGT GATGGTTCAC GTAGTGGGCC ATCGCCCTGA |
| 4251 TAGACGGTTT TTCGCCCTTT GACGTTGGAG TCCACGTTCT TTAATAGTGG |
| 4301 ACTCTTGTTC CAAACTGGAA CAACACTCAA CCCTATCTCG GCTATTCTT |
| 4351 TTGATTTATA AGGGATTTTG CCGATTTCGG CCTATTGGTT AAAAAATGAG |
| 4401 CTGATTTAAC AAAAATTTAA CGCGAATTTT AACAAAATAT TAACGTTTAC |
| 4451 AATTTTATGG TGCACTCTCA GTACAATCTG CTCTGATGCC GCATAGTTAA |
| 4501 GCCAGCCCCG ACACCCGCCA ACACCCGCTG ACGCGCCCTG ACGGGCTTGT |
| 4551 CTGCTCCCGG CATCCGCTTA CAGACAAGCT GTGACCGTCT CCGGGAGCTG |
| 4601 CATGTGTCAG AGGTTTTCAC CGTCATCACC GAAACGCGCG AGACGAAAGG |
| 4651 GCCTCGTGAT ACGCCTATTT TTATAGGTTA ATGTCATGAT AATAATGGTT |
| 4701 TCTTAGACGT CAGGTGGCAC TTTTCGGGGA AATGTGCGCG GAACCCCTAT |
| 4751 TTGTTTATTT TTCTAAATAC ATTCAAATAT GTATCCGCTC ATGAGACAAT |
| 4801 AACCCTGATA AATGCTTCAA TAATATTGAA AAAGGAAGAG TATGAGTATT | pAAV-RSV-hGck-miniCMV-hIns plasmid sequence

```
4851 CAACATTTCC GTGTCGCCCT TATTCCCTTT TTTGCGGCAT TTTGCCTTCC
4901 TGTTTTTGCT CACCCAGAAA CGCTGGTGAA AGTAAAAGAT GCTGAAGATC
4951 AGTTGGGTGC ACGAGTGGGT TACATCGAAC TGGATCTCAA CAGCGGTAAG
5001 ATCCTTGAGA GTTTTCGCCC CGAAGAACGT TTTCCAATGA TGAGCACTTT
5051 TAAAGTTCTG CTATGTGGCG CGGTATTATC CCGTATTGAC GCCGGGCAAG
5101 AGCAACTCGG TCGCCGCATA CACTATTCTC AGAATGACTT GGTTGAGTAC
5151 TCACCAGTCA CAGAAAAGCA TCTTACGGAT GGCATGACAG TAAGAGAATT
5201 ATGCAGTGCT GCCATAACCA TGAGTGATAA CACTGCGGCC AACTTACTCC
5251 TGACAACGAT CGGAGGACCG AAGGAGCTAA CCGCTTTTTT GCACAACATG
5301 GGGGATCATG TAACTCGCCT TGATCGTTGG GAACCGGAGC TGAATGAAGC
5351 CATACCAAAC GACGAGCGTG ACACCACGAT GCCTGTAGCA ATGGCAACAA
5401 CGTTGCGCAA ACTATTAACT GGCGAACTAC TTACTCTAGC TTCCCGGCAA
5451 CAATTAATAG ACTGGATGAA GGCGGATAAA GTTGCAGGAC CACTTCTGCG
5501 CTCGGCCCTT CCGGCTGGCT GGTTTATTGC TGATAAATCT GGAGCCGGTG
5551 AGCGTGGGTC TCGCGGTATC ATTGCAGCAC TGGGGCCAGA TGGTAAGCCC
5301 TCCCGTATCG TAGTTATCTA CACGACGGGG AGTCAGGCAA CTATGGATGA
5651 ACGAAATAGA CAGATCGCTG AGATAGGTGC CTCACTGATT AAGCATTGGT
5701 AACTGTCAGA CCAAGTTTAC TCATATATAC TTTAGATTGA TTTAAAACTT
5751 CATTTTTAAT TTAAAAGGAT CTAGGTGAAG ATCCTTTTTG ATAATCTCAT
5801 GACCAAAATC CCTTAACGTG AGTTTTCGTT CCACTGAGCG TCAGACCCCG
5851 TAGAAAAGAT CAAAGGATCT TCTTGAGATC CTTTTTTTCT GCGCGTAATC
5901 TGCTGCTTGC AAACAAAAAA ACCACCGCTA CCAGCGGTGG TTTGTTTGCC
5951 GGATCAAGAG CTACCAACTC TTTTTCCGAA GGTAACTGGC TTCAGCAGAG
6001 CGCAGATACC AAATACTGTC CTTCTAGTGT AGCCGTAGTT AGGCCACCAC
6051 TTCAAGAACT CTGTAGCACC GCCTACATAC CTCGCTGTGC TAATCCTGTT
6101 ACCAGTGGCT GCTGCCAGTG GCGATAAGTC GTGTCTTACC GGGTTGGACT
6151 CAAGACGATA GTTACCGGAT AAGGCGCAGC GGTCGGGCTG AACGGGGGGT
6201 TCGTGCACAC AGCCCAGCTT GGAGCGAACG AdCTACACCG AACTGAGATA
6251 CCTACAGCGT GAGCTATGAG AAAGCGCCAC GCTTCCCGAA GGGAGAAAGG
6301 CGGACAGGTA TCCGGTAAGC GGCAGGGTCG GAACAGGAGA GCGCACGAGG
6351 GAGCTTCCAG GGGGAAACGC CTGGTATCTT TATAGTCCTG TCGGGTTTCG
6401 CCACCTCTGA CTTGAGCGTC GATTTTTGTG ATGCTCGTCA GGGGGGCGGA
6451 GCCTATGGAA AAACGCCAGC AACGCGGCCT TTTTACGGTT CCTGGCCTTT
6501 TGCTGGCCTT TTGCTCACAT GT
```

ITR 5': 1-141 bp
RSV promoter: 239-948 bp
hGck: 973-2387 bp
bGH polyA: 2395-2653 bp
miniCMV promoter: 2661-3071 bp
hIns: 3085-3431 bp
SV40 polyA: 3445-3743 bp
ITR 3': 3785-3925 bp
L: miniCMV-hIns(rev)-RSV-hGck (SEQ ID NO: 15; FIG. 7)

| pAAV-miniCMV-hIns(rev)-RSV-hGCk plasmid sequence |
| --- |
| 1 CCTGCAGGCA GCTGCGCGCT CGCTCGCTCA CTGAGGCCGC CCGGGCAAAG |
| 51 CCCGGGCGTC GGGCGACCTT TGGTCGCCCG GCCTCAGTGA GCGAGCGAGC |
| 101 GCGCAGAGAG GGAGTGGCCA ACTCCATCAC TAGGGGTTCC TGCGGCCGCG |
| 151 ATAAATCGAG ATCTTCCAGA GCATGAGCGC TGATCTGTCG AGCCATGTCT |
| 201 AGGTAGCCAT GCTCTAGGAA GATCCTAATC GATTTTACCA CATTTGTAGA |
| 251 GGTTTTACTT GCTTTAAAAA ACCTCCCACA TCTCCCCCTG AACCTGAAAC |
| 301 ATAAAATGAA TGCAATTGTT GTTGTTAACT TGTTTATTGC AGCTTATAAT |
| 351 GGTTACAAAT AAAGCAATAG CATCACAAAT TTCACAAATA AAGCATTTTT |
| 401 TTCACTGCAT TCTAGTTGTG GTTTGTCCAA ACTCATCAAT GTATCTTATC |
| 451 ATGTCTGCTC GAAGCGGCCT CGACAGCGCT GGTACCGTCG ACGGCTGCGT |
| 501 CTAGTTGCAG TAGTTCTCCA GCTGGTAGAG GGAGCAGATG CTGGTACAGC |
| 551 ATTGTTCCAC AATGCCACGC TTCTGTCGCG ACCCCTCCAG GGCCAAGGGC |
| 601 TGCAGGCTGC CTGCACCAGG GCCCCCGCCC AGCTCCACCT GCCCCACCTG |
| 651 CAGGTCCTCT GCCTCCCGCT TGGTCCTGGG TGTGTAGAAG AAGCCTCGTT |
| 701 CCCCGCACAC TAGGTAGAGA GCTTCCACCA GATCTGAGCC GCACAGGTGT |
| 751 TGGTTCACAA AGGCTGCGGC TGGGTCAGGT CCCCAGAGGG CCAGCAGCGC |
| 801 CAGCAGGGGC AGGAGGCGCA TCCACAGGGC CATGGCAGAA GGTCGACGCT |
| 851 AGCAAGCTTG GTCTCCCTA TAGTGAGTCG TATTAATTTC GATAAGCCAG |
| 901 TTAAGCAGTG GGTTCTCTAG TTAGCCAGAG AGCTCTGCTT ATATAGACCT |
| 951 CCCACCGTAC ACGCCTACCG CCCATTTGCG TCAATGGGGC GGAGTTGTTA |
| 1001 CGACATTTTG GAAAGTCCCG TTGATTTTGG TGCCAAAACA AACTCCCATT |
| 1051 GACGTCAATG GGGTGGAGAC TTGGAAATCC CCGTGAGTCA AACCGCTATC |
| 1101 CACGCCCATT GATGTACTGC CAAAACCGCA TCACCATGGT AATAGCGATG |
| 1151 ACTAATACGT AGATGTACTG CCAAGTAGGA AAGTCCCATA AGGTCATGTA |
| 1201 CTGGGCATAA TGCCAGGCGG GCCATTTACC GTCATTGACG TCAATAGGGG |
| 1251 GCGTACTTGG CATAGATATC CATGTTTGAC AGCTTATCAT CGCAGATCCG |
| 1301 TATGGTGCAC TCTCAGTACA ATCTGCTCTG ATGCCGCATA GTTAAGCCAG |
| 1351 TATCTGCTCC CTGCTTGTGT GTTGGAGGTC GCTGAGTAGT GCGCGAGCAA |
| 1401 AATTTAAGCT ACAACAAGGC AAGGCTTGAC CGACAATTGC ATGAAGAATC |
| 1451 TGCTTAGGGT TAGGCGTTTT GCGCTGCTTC GCGATGTACG GGCCAGATAT |
| 1501 TCGCGTATCT GAGGGGACTA GGGTGTGTTT AGGCGAAAAG CGGGGCTTCG |
| 1551 GTTGTACGCG GTTAGGAGTC CCCTCAGGAT ATAGTAGTTT CGCTTTTGCA |
| 1601 TAGGGAGGGG GAAATGTAGT CTTATGCAAT ACTCTTGTAG TCTTGCAACA |

| pAAV-miniCMV-hIns(rev)-RSV-hGCk plasmid sequence |
|---|
| 1651 TGGTAACGAT GAGTTAGCAA CATGCCTTAC AAGGAGAGAA AAAGCACCGT |
| 1701 GCATGCCGAT TGGTGGAAGT AAGGTGGTAC GATCGTGCCT TATTAGGAAG |
| 1751 GCAACAGACG GGTCTGACAT GGATTGGACG AACCACTAAA TTCCGCATTG |
| 1801 CAGAGATATT GTATTTAAGT GCCTAGCTCG ATACAATAAA CGCCATTTGA |
| 1851 CCATTCACCA CATTGGTGTG CACCTCCAAG CTGGGTACCA GCTTCTAGAG |
| 1901 AGATCTGCTT CAGCTGGAGG CACTGGGCAG GTAAGTATCA AGGTTACAAG |
| 1951 ACAGGTTTAA GGAGACCAAT AGAAACTGGG CTTGTCGAGA CAGAGAAGAC |
| 2001 TCTTGCGTTT CTGATAGGCA CCTATTGGTC TTACTGACAT CCACTTTGCC |
| 2051 TTTCTCTCCA CAGGTGCAGC TGCTGCAGCG GTCTAGAACT CGAGTCGAGA |
| 2101 CCATGGCGAT GGATGTCACA AGGAGCCAGG CCCAGACAGC CTTGACTCTG |
| 2151 GTAGAGCAGA TCCTGGCAGA GTTCCAGCTG CAGGAGGAGG ACCTGAAGAA |
| 2201 GGTGATGAGA CGGATGCAGA AGGAGATGGA CCGCGGCCTG AGGCTGGAGA |
| 2251 CCCATGAAGA GGCCAGTGTG AAGATGCTGC CCACCTACGT GCGCTCCACC |
| 2301 CCAGAAGGCT CAGAAGTCGG GGACTTCCTC TCCCTGGACC TGGGTGGCAC |
| 2351 TAACTTCAGG GTGATGCTGG TGAAGGTGGG AGAAGGTGAG GAGGGGCAGT |
| 2401 GGAGCGTGAA GACCAAACAC CAGATGTACT CCATCCCCGA GGACGCCATG |
| 2451 ACCGGCACTG CTGAGATGCT CTTCGACTAC ATCTCTGAGT GCATCTCCGA |
| 2501 CTTCCTGGAC AAGCATCAGA TGAAACACAA GAAGCTGCCC CTGGGCTTCA |
| 2551 CCTTCTCCTT TCCTGTGAGG CACGAAGACA TCGATAAGGG CATCCTTCTC |
| 2601 AACTGGACCA AGGGCTTCAA GGCCTCAGGA GCAGAAGGGA ACAATGTCGT |
| 2651 GGGGCTTCTG CGAGACGCTA TCAAACGGAG AGGGGACTTT GAAATGGATG |
| 2701 TGGTGGCAAT GGTGAATGAC ACGGTGGCCA CGATGATCTC CTGCTACTAC |
| 2751 GAAGACCATC AGTGCGAGGT CGGCATGATC GTGGGCACGG GCTGCAATGC |
| 2801 CTGCTACATG GAGGAGATGC AGAATGTGGA GCTGGTGGAG GGGGACGAGG |
| 2851 GCCGCATGTG CGTCAATACC GAGTGGGGCG CCTTCGGGGA CTCCGGCGAG |
| 2901 CTGGACGAGT TCCTGCTGGA GTATGACCGC CTGGTGGACG AGAGCTCTGC |
| 2951 AAACCCCGGT CAGCAGCTGT ATGAGAAGCT CATAGGTGGC AAGTACATGG |
| 3001 GCGAGCTGGT GCGGCTTGTG CTGCTCAGGC TCGTGGACGA AAACCTGCTC |
| 3051 TTCCACGGGG AGGCCTCCGA GCAGCTGCGC ACACGCGGAG CCTTCGAGAC |
| 3101 GCGCTTCGTG TCGCAGGTGG AGAGCGACAC GGGCGACCGC AAGCAGATCT |
| 3151 ACAACATCCT GAGCACGCTG GGGCTGCGAC CCTCGACCAC CGACTGCGAC |
| 3201 ATCGTGCGCC GCGCCTGCGA GAGCGTGTCT ACGCGCGCTG CGCACATGTG |
| 3251 CTCGGCGGGG CTGGCGGGCG TCATCAACCG CATGCGCGAG AGCCGCAGCG |
| 3301 AGGACGTAAT GCGCATCACT GTGGGCGTGG ATGGCTCCGT GTACAAGCTG |
| 3351 CACCCCAGCT TCAAGGAGCG GTTCCATGCC AGCGTGCGCA GGCTGACGCC |
| 3401 CAGCTGCGAG ATCACCTTCA TCGAGTCGGA GGAGGGCAGT GGCCGGGGCG |
| 3451 CGGCCCTGGT CTCGGCGGTG GCCTGTAAGA AGGCCTGTAT GCTGGGCCAG |
| 3501 TGACTCGAGC ACGTGGAGCT CGCTGATCAG CCTCGACTGT GCCTTCTAGT |
| 3551 TGCCAGCCAT CTGTTGTTTG CCCCTCCCCC GTGCCTTCCT TGACCCTGGA |

| pAAV-miniCMV-hIns(rev)-RSV-hGCk plasmid sequence |
|---|
| 3601 AGGTGCCACT CCCACTGTCC TTTCCTAATA AAATGAGGAA ATTGCATCGC |
| 3651 ATTGTCTGAG TAGGTGTCAT TCTATTCTGG GGGGTGGGGT GGGGCAGGAC |
| 3701 AGCAAGGGGG AGGATTGGGA AGACAATAGC AGGCATGCTG GGGATGCGGT |
| 3751 GGGCTCTATG GCCACGTGAT TTAAATGCGG CCGCAGGAAC CCCTAGTGAT |
| 3801 GGAGTTGGCC ACTCCCTCTC TGCGCGCTCG CTCGCTCACT GAGGCCGGGC |
| 3851 GACCAAAGGT CGCCCGACGC CCGGGCTTTG CCCGGGCGGC CTCAGTGAGC |
| 3901 GAGCGAGCGC GCAGCTGCCT GCAGGGGCGC CTGATGCGGT ATTTTCTCCT |
| 3951 TACGCATCTG TGCGGTATTT CACACCGCAT ACGTCAAAGC AACCATAGTA |
| 4001 CGCGCCCTGT AGCGGCGCAT TAAGCGCGGC GGGTGTGGTG GTTACGCGCA |
| 4051 GCGTGACCGC TACACTTGCC AGCGCCCTAG CGCCCGCTCC TTTCGCTTTC |
| 4101 TTCCCTTCCT TTCTCGCCAC GTTCGCCGGC TTTCCCCGTC AAGCTCTAAA |
| 4151 TCGGGGCTC CCTTTAGGGT TCCGATTTAG TGCTTTACGG CACCTCGACC |
| 4201 CCAAAAAACT TGATTTGGGT GATGGTTCAC GTAGTGGGCC ATCGCCCTGA |
| 4251 TAGACGGTTT TTCGCCCTTT GACGTTGGAG TCCACGTTCT TTAATAGTGG |
| 4301 ACTCTTGTTC CAAACTGGAA CAACACTCAA CCCTATCTCG GCTATTCTT |
| 4351 TTGATTTATA AGGGATTTTG CCGATTTCGG CCTATTGGTT AAAAAATGAG |
| 4401 CTGATTTAAC AAAAATTTAA CGCGAATTTT AACAAAATAT TAACGTTTAC |
| 4451 AATTTTATGG TGCACTCTCA GTACAATCTG CTCTGATGCC GCATAGTTAA |
| 4501 GCCAGCCCCG ACACCCGCCA ACACCCGCTG ACGCGCCCTG ACGGGCTTdT |
| 4551 CTGCTCCCGG CATCCGCTTA CAGACAAGCT GTGACCGTCT CCGGGAGCTG |
| 4601 CATGTGTCAG AGGTTTTCAC CGTCATCACC GAAACGCGCG AGACGAAAGG |
| 4651 GCCTCGTGAT ACGCCTATTT TTATAGGTTA ATGTCATGAT AATAATGGTT |
| 4701 TCTTAGACGT CAGGTGGCAC TTTTCGGGGA AATGTGCGCG GAACCCCTAT |
| 4751 TTGTTTATTT TTCTAAATAC ATTCAAATAT GTATCCGCTC ATGAGACAAT |
| 4801 AACCCTGATA AATGCTTCAA TAATATTGAA AAAGGAAGAG TATGAGTATT |
| 4851 CAACATTTCC GTGTCGCCCT TATTCCCTTT TTTGCGGCAT TTTGCCTTCC |
| 4901 TGTTTTTGCT CACCCAGAAA CGCTGGTGAA AGTAAAAGAT GCTGAAGATC |
| 4951 AGTTGGGTGC ACGAGTGGGT TACATCGAAC TGGATCTCAA CAGCGGTAAG |
| 5001 ATCCTTGAGA GTTTTCGCCC CGAAGAACGT TTTCCAATGA TGAGCACTTT |
| 5051 TAAAGTTCTG CTATGTGGCG CGGTATTATC CCGTATTGAC GCCGGGCAAG |
| 5101 AGCAACTCGG TCGCCGCATA CACTATTCTC AGAATGACTT GGTTGAGTAC |
| 5151 TCACCAGTCA CAGAAAAGCA TCTTACGGAT GGCATGACAG TAAGAGAATT |
| 5201 ATGCAGTGCT GCCATAACCA TGAGTGATAA CACTGCGGCC AACTTACTTC |
| 5251 TGACAACGAT CGGAGGACCG AAGGAGCTAA CCGCTTTTTT GCACAACATG |
| 5301 GGGGATCATG TAACTCGCCT TGATCGTTGG GAACCGGAGC TGAATGAAGC |
| 5351 CATACCAAAC GACGAGCGTG ACACCACGAT GCCTGTAGCA ATGGCAACAA |
| 5401 CGTTGCGCAA ACTATTAACT GGCGAACTAC TTACTCTAGC TTCCCGGCAA |
| 5451 CAATTAATAG ACTGGATGGA GGCGGATAAA GTTGCAGGAC CACTTCTGCG |

| pAAV-miniCMV-hIns(rev)-RSV-hGCk plasmid sequence |
|---|
| 5501 CTCGGCCCTT CCGGCTGGCT GGTTTATTGC TGATAAATCT GGAGCCGGTG |
| 5551 AGCGTGGGTC TCGCGGTATC ATTGCAGCAC TGGGGCCAGA TGGTAAGCCC |
| 5601 TCCCGTATCG TAGTTATCTA CACGACGGGG AGTCAGGCAA CTATGGATGA |
| 5651 ACGAAATAGA CAGATCGCTG AGATAGGTGC CTCACTGATT AAGCATTGGT |
| 5701 AACTGTCAGA CCAAGTTTAC TCATATATAC TTTAGATTGA TTTAAAACTT |
| 5751 CATTTTTAAT TTAAAAGGAT CTAGGTGAAG ATCCTTTTTG ATAATCTCAT |
| 5801 GACCAAAATC CCTTAACGTG AGTTTTCGTT CCACTGAGCG TCAGACCCCG |
| 5851 TAGAAAAGAT CAAAGGATCT TCTTGAGATC CTTTTTTTCT GCGCGTAATC |
| 5901 TGCTGCTTGC AAACAAAAAA ACCACCGCTA CCAGCGGTGG TTTGTTTGCC |
| 5951 GGATCAAGAG CTACCAACTC TTTTTCCGAA GGTAACTGGC TTCAGCAGAG |
| 6001 CGCAGATACC AAATACTGTC CTTCTAGTGT AGCCGTAGTT AGGCCACCAC |
| 6051 TTCAAGAACT CTGTAGCACC GCCTACATAC CTCGCTCTGC TAATCCTGTT |
| 6101 ACCAGTGGCT GCTGCCAGTG GCGATAAGTC GTGTCTTACC GGGTTGGACT |
| 6151 CAAGACGATA GTTACCGGAT AAGGCGCAGC GGTCGGGCTG AACGGGGGGT |
| 6201 TCGTGCACAC AGCCCAGCTT GGAGCGAACG ACCTACACCG AACTGAGATA |
| 6231 CCTACAGCGT GAGCTATGAG AAAGCGCCAC GCTTCCCGAA GGGAGAAAGG |
| 6301 CGGACAGGTA TCCGGTAAGC GGCAGGGTCG GAACAGGAGA GCGCACGAGG |
| 6351 GAGCTTCCAG GGGGAAACGC CTGGTATCTT TATAGTCCTG TCGGGTTTCG |
| 6401 CCACCTCTGA CTTGAGCGTC GATTTTTGTG ATGCTCGTCA GGGGGGCGGA |
| 6451 GCCTATGGAA AAACGCCAGC AACGCOGCCT TTTTACGGTT CCTGGCCTTT |
| 6501 TGCTGGCCTT TTGCTCACAT GT |

ITR 5': 1-141 bp
SV40 polyA: 182-480 bp
hIns: 494-840 bp
miniCMV promoter: 854-1264 bp
RSV promoter: 1354-2063 bp
hGck: 2088-3502 bp
bGH polyA: 3510-3768 bp
ITR 3': 3785-3925 bp
M: RSV-hGck-miniCMV-hIns(rev) (SEQ ID NO: 16; FIG. 7)

| pAAV-RSV-hGck-miniCMV-hIns(rev) plasmid sequence |
|---|
| 1 CCTGCAGGCA GCTGCGCGCT CGCTCGCTCA CTGAGGCCGC CCGGGCAAAG |
| 51 CCCGGGCGTC GGGCGACCTT TGGTCGCCCG GCCTCAGTGA GCGAGCGAGC |
| 101 GCGCAGAGAG GGAGTGGCCA ACTCCATCAC TAGGGGTTCC TGCGGCCGCG |
| 151 ATATCCATGT TGACAGCTT ATCATCGCAG ATCCGTATGG TGCACTCTCA |
| 201 GTACAATCTG CTCTGATGCC GCATAGTTAA GCCAGTATCT GCTCCCTGCT |
| 251 TGTGTGTTGG AGGTCGCTGA GTAGTGCGCG AGCAAAATTT AAGCTACAAC |
| 301 AAGGCAAGGC TTGACCGACA ATTGCATGAA GAATCTGCTT AGGGTTAGGC |
| 351 GTTTTGCGCT GCTTCGCGAT GTACGGGCCA GATATTCGCG TATCTGAGGG |
| 401 GACTAGGGTG TGTTTAGGCG AAAAGCGGGG CTTCGGTTGT ACGCGGTTAG |
| 451 GAGTCCCCTC AGGATATAGT AGTTTCGCTT TTGCATAGGG AGGGGGAAAT |
| 501 GTAGTCTTAT GCAATACTCT TGTAGTCTTG CAACATGGTA ACGATGAGTT |
| 551 AGCAACATGC CTTACAAGGA GAGAAAAAGC ACCGTGCATG CCGATTGGTG |

-continued

| pAAV-RSV-hGck-miniCMV-hIns(rev) plasmid sequence |
|---|
| 601 GAAGTAAGGT GGTACGATCG TGCCTTATTA GGAAGGCAAC AGACGGGTCT |
| 651 GACATGGATT GGACGAACCA CTAAATTCCG CATTGCAGAG ATATTGTATT |
| 701 TAAGTGCCTA GCTCGATACA ATAAACGCCA TTTGACCATT CACCACATTG |
| 751 GTGTGCACCT CCAAGCTGGG TACCAGCTTC TAGAGAGATC TGCTTCAGCT |
| 801 GGAGGCACTG GCAGGTAAG TATCAAGGTT ACAAGACAGG TTTAAGGAGA |
| 851 CCAATAGAAA CTGGGCTTGT CGAGACAGAG AAGACTCTTG CGTTTCTGAT |
| 901 AGGCACCTAT TGGTCTTACT GACATCCACT TTGCCTTTCT CTCCACAGGT |
| 951 GCAGCTGCTG CAGCGGTCTA AACTCGAGT CGAGACCATG GCGATGGATG |
| 1001 TCACAAGGAG CCAGGCCCAG ACAGCCTTGA CTCTGGTAGA GCAGATCCTG |
| 1051 GCAGAGTTCC AGCTGCAGGA GGAGGACCTG AAGAAGGTGA TGAGACGGAT |
| 1101 GCAGAAGGAG ATGGACCGCG GCCTGAGGCT GGAGACCCAT GAAGAGGCCA |
| 1151 GTGTGAAGAT GCTGCCCACC TACGTGCGCT CCACCCCAGA AGGCTCAGAA |
| 1201 GTCGGGGACT TCCTCTCCCT GGACCTGGGT GGCACTAACT TCAGGGTGAT |
| 1251 GCTGGTGAAG GTGGGAGAAG GTGAGGAGGG GCAGTGGAGC GTGAAGACCA |
| 1301 AACACCAGAT GTACTCCATC CCCGAGGACG CCATGACCGG CACTGCTGAG |
| 1351 ATGCTCTTCG ACTACATCTC TGAGTGCATC TCCGACTTCC TGGACAAGCA |
| 1401 TCAGATGAAA CACAAGAAGC TGCCCCTGGG CTTCACCTTC TCCTTTCCTG |
| 1451 TGAGGCACGA AGACATCGAT AAGGGCATCC TTCTCAACTG GACCAAGGGC |
| 1501 TTCAAGGCCT CAGGAGCAGA AGGGAACAAT GTCGTGGGGC TTCTGCGAGA |
| 1551 CGCTATCAAA CGGAGAGGGG ACTTTGAAAT GGATGTGGTG GCAATGGTGA |
| 1601 ATGACACGGT GGCCACGATG ATCTCCTGCT ACTACGAAGA CCATCAGTGC |
| 1651 GAGGTCGGCA TGATCGTGGG CACGGGCTGC AATGCCTGCT ACATGGAGGA |
| 1701 GATGCAGAAT GTGGAGCTGG TGGAGGGGGA CGAGGGCCGC ATGTGCGTCA |
| 1751 ATACCGAGTG GGGCGCCTTC GGGGACTCCG GCGAGCTGGA CGAGTTCCTG |
| 1801 CTGGAGTATG ACCGCCTGGT GGACGAGAGC TCTGCAAACC CCGGTCAGCA |
| 1851 GCTGTATGAG AAGCTCATAG GTGGCAAGTA CATGGGCGAG CTGGTGCGGC |
| 1901 TTGTGCTGCT CAGGCTCGTG GACGAAAACC TGCTCTTCCA CGGGGAGGCC |
| 1951 TCCGAGCAGC TGCGCACACG CGGAGCCTTC GAGACGCGCT TCGTGTCGCA |
| 2001 GGTGGAGAGC GACACGGGCG ACCGCAAGCA GATCTACAAC ATCCTGAGCA |
| 2051 CGCTGGGGCT GCGACCCTCG ACCACCGACT GCGACATCGT GCGCCGCGCC |
| 2101 TGCGAGAGCG TGTCTACGCG CGCTGCGCAC ATGTGCTCGG CGGGGCTGGC |
| 2151 GGGCGTCATC AACCGCATGC GCGAGAGCCG CAGCGAGGAC GTAATGCGCA |
| 2201 TCACTGTGGG CGTGGATGGC TCCGTGTACA AGCTGCACCC CAGCTTCAAG |
| 2251 GAGCGGTTCC ATGCCAGCGT GCGCAGGCTG ACGCCCAGCT GCGAGATCAC |
| 2301 CTTCATCGAG TCGGAGGAGG GCAGTGGCCG GGGCGCGGCC CTGGTCTCGG |
| 2351 CGGTGGCCTG TAAGAAGGCC TGTATGCTGG GCCAGTGACT CGAGCACGTG |
| 2401 GAGCTCGCTG ATCAGCCTCG ACTGTGCCTT CTAGTTGCCA GCCATCTGTT |
| 2451 GTTTGCCCCT CCCCCGTGCC TTCCTTGACC CTGGAAGGTG CCACTCCCAC |

| pAAV-RSV-hGck-miniCMV-hIns(rev) plasmid sequence |
| --- |
| 2501 TGTCCTTTCC TAATAAAATG AGGAAATTGC ATCGCATTGT CTGAGTAGGT |
| 2551 GTCATTCTAT TCTGGGGGGT GGGGTGGGGC AGGACAGCAA GGGGGAGGAT |
| 2601 TGGGAAGACA ATAGCAGGCA TGCTGGGGAT GCGGTGGGCT CTATGGCCAC |
| 2651 GTGATTTAAA TCGAGATCTT CCAGAGCATG AGCGCTGATC TGTCGAGCCA |
| 2701 TGTCTAGGTA GCCATGQTCT AGGAAGATCC TAATCGATTT TACCACATTT |
| 2751 GTAGAGGTTT TACTTGCTTT AAAAAACCTC CCACATCTCC CCCTGAACCT |
| 2801 GAAACATAAA ATGAATGCAA TTGTTGTTGT TAACTTGTTT ATTGCAGCTT |
| 2851 ATAATGGTTA CAAATAAAGC AATAGCATCA CAAATTTCAC AAATAAAGCA |
| 2901 TTTTTTTCAC TGCATTCTAG TTGTGGTTTG TCCAAACTCA TCAATGTATC |
| 2951 TTATCATGTC TGCTCGAAGC GGCCTCGACA GCGCTGGTAC CGTCGACGGC |
| 3001 TGCGTCTAGT TGCAGTAGTT CTCCAGCTGG TAGAGGGAGC AGATGCTGGT |
| 3051 ACAGCATTGT TCCACAATGC CACGCTTCTG TCGCGACCCC TCCAGGGCCA |
| 3101 AGGGCTGCAG GCTGCCTGCA CCAGGGCCCC CGCCCAGCTC CACCTGCCCC |
| 3151 ACCTGCAGGT CCTCTGCCTC CCGCTTGGTC CTGGGTGTGT AGAAGAAGCC |
| 3201 TCGTTCCCCG CACACTAGGT AGAGAGCTTC CACCAGATCT GAGCCGCACA |
| 3251 GGTGTTGGTT CACAAAGGCT GCGGCTGGGT CAGGTCCCCA GAGGGCCAGC |
| 3301 AGCGCCAGCA GGGGCAGGAG GCGCATCCAC AGGGCCATGG CAGAAGGTCG |
| 3351 ACGCTAGCAA GCTTGGGTCT CCCTATAGTG AGTCGTATTA ATTTCGATAA |
| 3401 GCCAGTTAAG CAGTGGGTTC TCTAGTTAGC CAGAGAGCTC TGCTTATATA |
| 3451 GACCTCCCAC CGTACACGCC TACCGCCCAT TGCGTCAAT GGGGCGGAGT |
| 3501 TGTTACGACA TTTTGGAAAG TCCCGTTGAT TTTGGTGCCA AAACAAACTC |
| 3551 CCATTGACGT CAATGGGGTG GAGACTTGGA AATCCCCGTG AGTCAAACCG |
| 3601 CTATCCACGC CCATTGATGT ACTGCCAAAA CCGCATCACC ATGGTAATAG |
| 3651 CGATGACTAA TACGTAGATG TACTGCCAAG TAGGAAAGTC CCATAAGGTC |
| 3701 ATGTACTGGG CATAATGCCA GGCGGGCCAT TTACCGTCAT TGACGTCAAT |
| 3751 AGGGGGCGTA CTTGGCATAG ATAAATGCGG CCGCAGGAAC CCCTAGTGAT |
| 3801 GGAGTTGGCC ACTCCCTCTC TGCGCGCTCG CTCGCTCACT GAGGCCGGGC |
| 3851 GACCAAAGGT CGCCCGACGC CCGGGCTTTG CCCGGGCGGC CTCAGTGAGC |
| 3901 GAGCGAGCGC GCAGCTGCCT GCAGGGGCGC CTGATGCGGT ATTTTCTCCT |
| 3951 TACGCATCTG TGCGGTATTT CACACCGCAT ACGTCAAAGC AACCATAGTA |
| 4001 CGCGCCCTGT AGCGGCGCAT TAAGCGCGGC GGGTGTGGTG GTTACGCGCA |
| 4051 GCGTGACCGC TACACTTGCC AGCGCCCTAG CGCCCGCTCC TTTCGCTTTC |
| 4101 TTCCCTTCCT TTCTCGCCAC GTTCGCCGGC TTTCCCCGTC AAGCTCTAAA |
| 4151 TCGGGGGCTC CCTTTAGGGT TCCGATTTAG TGCTTTACGG CACCTCGACC |
| 4201 CCAAAAAACT TGATTTGGGT GATGGTTCAC GTAGTGGGCC ATCGCCCTGA |
| 4251 TAGACGGTTT TTCGCCCTTT GACGTTGGAG TCCACGTTCT TTAATAGTGG |
| 4301 ACTCTTGTTC CAAACTGGAA CAACACTCAA CCCTATCTCG GGCTATTCTT |
| 4351 TTGATTTATA AGGGATTTTG CCGATTTCGG CCTATTGGTT AAAAAATGAG |
| 4401 CTGATTTAAC AAAAATTTAA CGCGAATTTT AACAAAATAT TAACGTTTAC |

-continued

| pAAV-RSV-hGck-miniCMV-hIns(rev) plasmid sequence |
|---|

```
4451 AATTTTATGG TGCACTCTCA GTACAATCTG CTCTGATGCC GCATAGTTAA
4501 GCCAGCCCCG ACACCCGCCA ACACCCGCTG ACGCGCCCTG ACGGGCTTGT
4551 CTGCTCCCGG CATCCGCTTA CAGACAAGCT GTGACCGTCT CCGGGAGCTG
4601 CATGTGTCAG AGGTTTTCAC CGTCATCACC GAAACGCGCG AGACGAAAGG
4651 GCCTCGTGAT ACGCCTATTT TTATAGGTTA ATGTCATGAT AATAATGGTT
4701 TCTTAGACGT CAGGTGGCAC TTTTCGGGGA AATGTGCGCG GAACCCCTAT
4751 TTGTTTATTT TTCTAAATAC ATTCAAATAT GTATCCGCTC ATGAGACAAT
4801 AACCCTGATA AATGCTTCAA TAATATTGAA AAAGGAAGAG TATGAGTATT
4851 CAACATTTCC GTGTCGCCCT TATTCCCTTT TTTGCGGCAT TTTGCCTTCC
4901 TGTTTTTGCT CACCCAGAAA CGCTGGTGAA AGTAAAAGAT GCTGAAGATC
4951 AGTTGGGTGC ACGAGTGGGT TACATCGAAC TGGATCTCAA CAGCGGTAAG
5001 ATCCTTGAGA GTTTTCGCCC CGAAGAACGT TTTCCAATGA TGAGCACTTT
5051 TAAAGTTCTG CTATGTGGCG CGGTATTATC CCGTATTGAC GCCGGGCAAG
5101 AGCAACTCGG TCGCCGCATA CACTATTCTC AGAATGACTT GGTTGAGTAC
5151 TCACCAGTCA CAGAAAAGCA TCTTACGGAT GGCATGACAG TAAGAGAATT
5201 ATGCAGTGCT GCCATAACCA TGAGTGATAA CACTGCGGCC AACTTACTTC
5251 TGACAACGAT CGGAGGACCG AAGGAGCTAA CCGCTTTTTT GCACAACATG
5301 GGGGATCATG TAACTCGCCT TGATCGTTGG GAACCGGAGC TGAATGAAGC
5351 CATACCAAAC GACGAGCGTG ACACCACGAT GCCTGTAGCA ATGGCAACAA
5401 CGTTGCGCAA ACTATTAACT GGCGAACTAC TTACTCTAGC TTCCCOGCAA
5451 CAATTAATAG ACTGGATGGA GGCGGATAAA GTTGCAGGAC CACTTCTGCG
5501 CTCGGCCCTT CCGGCTGGCT GGTTTATTGC TGATAAATCT GGAGCCGGTG
5551 AGCGTGGGTC TCGCGGTATC ATTGCAGCAC TGGGGCCAGA TGGTAAGCCC
5601 TCCCGTATCG TAGTTATCTA CACGACGGGG AGTCAGGCAN CTATGGATGA
5651 ACGAAATAGA CAGATCGCTG AGATAGGTGC CTCACTGATT AAGCATTGGT
5701 AACTGTCAGA CCAAGTTTAC TCATATATAC TTTAGATTGA TTTAAAACTT
5751 CATTTTTAAT TTAAAAGGAT CTAGGTGAAG ATCCTTTTTG ATAATCTCAT
5801 GACCAAAATC CCTTAACGTG AGTTTTCGTT CCACTGAGCG TCAGACCCCG
5851 TAGAAAAGAT CAAAGGATCT TCTTGAGATC CTTTTTTTCT GCGCGTAATC
5901 TGCTGCTTGC AAACAAAAAA ACCACCGCTA CCAGCGGTGG TTTGTTTGCC
5951 GGATCAAGAG CTACCAACTC TTTTTCCGAA GGTAACTGGC TTCAGCAGAG
6001 CGCAGATACC AAATACTGTC CTTCTAGTGT AGCCGTAGTT AGGCCACCAC
6051 TTCAAGAACT CTGTAGCACC GCCTACATAC CTCGCTCTGC TAATCCTGTT
6101 ACCAGTGGCT GCTGCCAGTG GCGATAAGTC GTGTCTTACC GGGTTGGACT
6151 CAAGACGATA GTTACCGGAT AAGGCGCAGC GGTCGGGCTG AACGGGGGGT
6201 TCGTGCACAC AGCCCAGCTT GGAGCGAACG ACCTACACCG AACTGAGATA
6251 CCTACAGCGT GAGCTATGAG AAAGCGCCAC GCTTCCCGAA GGGAGAAAGG
6301 CGGACAGGTA TCCGGTAAGC GGCAGGGTCG GAACAGGAGA GCGCACGAGG
``` pAAV-RSV-hGck-miniCMV-hIns(rev) plasmid sequence

```
6351 GAGCTTCCAG GGGGAAACGC CTGGTATCTT TATAGTCCTG TCGGGTTTCG
6401 CCACCTCTGA CTTGAGCGTC GATTTTGTG ATGCTCGTCA GGGGGGCGGA
6451 GCCTATGGAA AAACGCCAGC AACGCGGCCT TTTTACGGTT CCTGGCCTTT
6501 TGCTGGCCTT TTGCTCACAT GT
```

ITR 5': 1-141 bp
RSV promoter: 239-948 bp
hGck: 973-2387 bp
bGH polyA: 2395-2653 bp
SV40 polyA: 2687-2985 bp hIns: 2999-3345 bp
miniCMV promoter: 3359-3769 pb
ITR 3': 3785-3925 bp
N: miniCMV-hIns (SEQ ID NO: 21; FIG. 8)

pAAV-miniCMV-hIns plasmid sequence

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCGCG
 151 ATATCTATGC CAAGTACGCC CCCTATTGAC GTCAATGACG GTAAATGGCC
 201 CGCCTGGCAT TATGCCCAGT ACATGACCTT ATGGGACTTT CCTACTTGGC
 251 AGTACATCTA CGTATTAGTC ATCGCTATTA CCATGGTGAT GCGGTTTTGG
 301 CAGTACATCA ATGGGCGTGG ATAGCGGTTT GACTCACGGG GATTTCCAAG
 351 TCTCCACCCC ATTGACGTCA ATGGGAGTTT GTTTTGGCAC CAAAATCAAC
 401 GGGACTTTCC AAAATGTCGT AACAACTCCG CCCCATTGAC GCAAATGGGC
 451 GGTAGGCGTG TACGGTGGGA GGTCTATATA AGCAGAGCTC TCTGGCTAAC
 501 TAGAGAACCC ACTGCTTAAC TGGCTTATCG AAATTAATAC GACTCACTAT
 551 AGGGAGACCC AAGCTTGCTA GCGTCGACCT TCTGCCATGG CCCTGTGGAT
 601 GCGCCTCCTG CCCCTGCTGG CGCTGCTGGC CCTCTGGGGA CCTGACCCAG
 651 CCGCAGCCTT TGTGAACCAA CACCTGTGCG GCTCAGATCT GGTGGAAGCT
 701 CTCTACCTAG TGTGCGGGGA ACGAGGCTTC TTCTACACAC CCAGGACCAA
 751 GCGGGAGGCA GAGGACCTGC AGGTGGGGCA GGTGGAGCTG GGCGGGGGCC
 801 CTGGTGCAGG CAGCCTGCAG CCCTTGGCCC TGGAGGGGTC GCGACAGAAG
 851 CGTGGCATTG TGGAACAATG CTGTACCAGC ATCTGCTCCC TCTACCAGCT
 901 GGAGAACTAC TGCAACTAGA CGCAGdCGTC GACGGTACCA GCGCTGTCGA
 951 GGCCGCTTCG AGCAGACATG ATAAGATACA TTGATGAGTT TGGACAAACC
1001 ACAACTAGAA TGCAGTGAAA AAAATGCTTT ATTTGTGAAA TTTGTGATGC
1051 TATTGCTTTA TTTGTAACCA TTATAAGCTG CAATAAACAA GTTAACAACA
1101 ACAATTGCAT TCATTTTATG TTTCAGGTTC AGGGGGAGAT GTGGGAGGTT
1151 TTTTAAAGCA AGTAAAACCT CTACAAATGT GGTAAAATCG ATTAGGATCT
1201 TCCTAGAGCA TGGCTACCTA GACATGGCTC GACAGATCAG CGCTCATGCT
1251 CTGGAAGATC TCGATTTAAA TGCGGCCGCA GGAACCCCTA GTGATGGAGT
1301 TGGCCACTCC CTCTCTGCGC GCTCGCTCGC TCACTGAGGC CGGGCGACCA
1351 AAGGTCGCCC GACGCCCGGG CTTTGCCCGG GCGGCCTCAG TGAGCGAGCG
1401 AGCGCGCAGC TGCCTGCAGG GGCGCCTGAT GCGGTATTTT CTCCTTACGC
```

| pAAV-miniCMV-hIns plasmid sequence |
|---|
| 1451 ATCTGTGCGG TATTTCACAC CGCATACGTC AAAGCAACCA TAGTACGCGC |
| 1501 CCTGTAGCGG CGCATTAAGC GCGGCGGGTG TGGTGGTTAC GCGCAGCGTG |
| 1551 ACCGCTACAC TTGCCAGCGC CCTAGCGCCC GCTCCTTTCG CTTTCTTCCC |
| 1601 TTCCTTTCTC GCCACGTTCG CCGGCITTCC CCGTCAAGCT CTAAATCGGG |
| 1651 GGCTCCCTTT AGGGTTCCGA TTTAGTGCTT TACGGCACCT CGACCCCAAA |
| 1701 AAACTTGATT TGGGTGATGG TTCACGTAGT GGGCCATCGC CCTGATAGAC |
| 1751 GGTTTTTCGC CCTTTGACGT TGGAGTCCAC GTTCTTTAAT AGTGGACTCT |
| 1801 TGTTCCAAAC TGGAACAACA CTCAACCCTA TCTCGGGCTA TTCTTTTGAT |
| 1851 TTATAAGGGA TTTTGCCGAT TTCGGCCTAT TGGTTAAAAA ATGAGCTGAT |
| 1901 TTAACAAAAA TTTAACGCGA ATTTTAACAA AATATTAACG TTTACAATTT |
| 1951 TATGGTGCAC TCTCAGTACA ATCTGCTCTG ATGCCGCATA GTTAAGCCAG |
| 2001 CCCCGACACC CGCCAACACC CGCTGACGCG CCCTGACGGG CTTGTCTGCT |
| 2051 CCCGGCATCC GCTTACAGAC AAGCTGTGAC CGTCTCCGGG AGCTGCATGT |
| 2101 GTCAGAGGTT TTCACCGTCA TCACCGAAAC GCGCGAGACG AAAGGGCCTC |
| 2151 GTGATACGCC TATTTTTATA GGTTAATGTC ATGATAATAA TGGTTTCTTA |
| 2201 GACGTCAGGT GGCACTTTTC GGGGAAATGT GCGCGGAACC CCTATTTGTT |
| 2251 TATTTTTCTA AATACATTCA AATATGTATC CGCTCATGAG ACAATAACCC |
| 2301 TGATAAATGC TTCAATAATA TTGAAAAAGG AAGAGTATGA GTATTCAACA |
| 2351 TTTCCGTGTC GCCCTTATTC CCTTTTTTGC GGCATTTTGC CTTCCTGTTT |
| 2401 TTGCTCACCC AGAAACGCTG GTGAAAGTAA AAGATGCTGA AGATCAGTTG |
| 2451 GGTGCACGAG TGGGTTACAT CGAACTGGAT CTCAACAGCG GTAAGATCCT |
| 2501 TGAGAGTTTT CGCCCCGAAG AACGTTTTCC AATGATGAGC ACTTTTAAAG |
| 2551 TTCTGCTATG TGGCGCGGTA TTATCCCGTA TTGACGCCGG GCAAGAGCAA |
| 2601 CTCGGTCGCC GCATACACTA TTCTCAGAAT GACTTGGTTG AGTACTCACC |
| 2651 AGTCACAGAA AAGCATCTTA COGATGGCAT GACAGTAAGA GAATTATGCA |
| 2701 GTGCTGCCAT AACCATGAGT GATAACACTG CGGCCAACTT ACTTCTGACA |
| 2751 ACGATCGGAG GACCGAAGGA GCTAACCGCT TTTTTGCACA ACATGGGGGA |
| 2801 TCATGTAACT CGCCTTGATC GTTGGGAACC GGAGCTGAAT GAAGCCATAC |
| 2851 CAAACGACGA GCGTGACACC ACGATGCCTG TAGCAATGGC AACAACGTTG |
| 2901 CGCAAACTAT TAACTGGCGA ACTACTTACT CTAGCTTCCC GGCAACAATT |
| 2951 AATAGACTGG ATGGAGGCGG ATAAAGTTGC AGGACCACTT CTGCGCTCGG |
| 3001 CCCTTCCGGC TGGCTGGTTT ATTGCTGATA AATCTGGAGC CGGTGAGCGT |
| 3051 GGGTCTCGCG GTATCATTGC AGCACTGGGG CCAGATGGTA AGCCCTCCCG |
| 3101 TATCGTAGTT ATCTACACGA CGGGGAGTCA GGCAACTATG GATGAACGAA |
| 3151 ATAGACAGAT CGCTGAGATA GGTGCCTCAC TGATTAAGCA TTGGTAACTG |
| 3201 TCAGACCAAG TTTACTCATA TATACTTTAG ATTGATTTAA AACTTCATTT |
| 3251 TTAATTTAAA AGGATCTAGG TGAAGATCCT TTTTGATAAT CTCATGACCA |
| 3301 AAATCCCTTA ACGTGAGTTT TCGTTCCACT GAGCGTCAGA CCCCGTAGAA |

| pAAV-miniCMV-hIns plasmid sequence |
|---|
| 3351 AAGATCAAAG GATCTTCTTG AGATCCTTTT TTTCTGCGCG TAATCTGCTG |
| 3401 CTTGCAAACA AAAAAACCAC CGCTACCAGC GGTGGTTTGT TTGCQGGATC |
| 3451 AAGAGCTACC AACTCTTTTT CCGAAGGTAA CTGGCTTCAG CAGAGCGCAG |
| 3501 ATACCAAATA CTGTCCTTCT AGTGTAGCCG TAGTTAGGCC ACCACTTCAA |
| 3551 GAACTCTGTA GCACCGCCTA CATACCTCGC TCTGCTAATC CTGTTACCAG |
| 3601 TGGCTGCTGC CAGTGGCGAT AAGTCGTGTC TTACCGGGTT GGACTCAAGA |
| 3651 CGATAGTTAC CGGATAAGGC GCAGCGGTCG GGCTGAACGG GGGGTTCGTG |
| 3701 CACACAGCCC AGCTTGGAGC GAACGACCTA CACCGAACTG AGATACCTAC |
| 3751 AGCGTGAGCT ATGAGAAAGC GCCACGCTTC CCGAAGGGAG AAAGGCGGAC |
| 3801 AGGTATCCGG TAAGCGGCAG GGTCGGAACA GGAGAGCGCA CGAGGGAGCT |
| 3851 TCCAGGGGGA AACGCCTGGT ATCTTTATAG TCCTGTCGGG TTTCGCCACC |
| 3901 TCTGACTTGA GCGTCGATTT TTGTGATGCT CGTCAGGGGG GCGGAGCCTA |
| 3951 TGGAAAAACG CCAGCAACGC GGCCTTTTTA CGGTTCCTGG CCTTTTGCTG |
| 4001 GCCTTTTGCT CACATGT |

ITR 5': 1-141 bp
miniCMV promoter: 156-566 bp
hIns: 580-926 bp
SV40 polyA: 940-1238 bp
ITR 3': 1280-1420 bp Equivalent mini CMV promoter    SEQ ID NO: 24
TAGGCGTGTACGGTGGGAGGTCTATATAAGCAGAGCTCTCTGGCTAACTA
GAGAACCCACTGCTTAACTGGCTTATCGAAATTAATACGACTCA O: miniCMV-hIns-bGH (SEQ ID NO: 25; FIG. 13)

| pAAV-miniCMV-hIns-bGH plasmid sequence |
|---|
| 1 GCTCATGCTC TGGAAGATCT CGATTTAAAT GCGGCCGCAG GAACCCCTAG |
| 51 TGATGGAGTT GGCCACTCCC TCTCTGCGCG CTCGCTCGCT CACTGAGGCC |
| 101 GGGCGACCAA AGGTCGCCCG ACGCCCGGGC TTTGCCCGGG CGGCCTCAGT |
| 151 GAGCGAGCGA GCGCGCAGCT GCCTGCAGGG GCGCCTGATG CGGTATTTTC |
| 201 TCCTTACGCA TCTGTGCGGT ATTTCACACC GCATACGTCA AGCAACCAT |
| 251 AGTACGCGCC CTGTAGCGGC GCATTAAGCG CGGCGGGTGT GGTGGTTACG |
| 301 CGCAGCGTGA CCGCTACACT TGCCAGCGCC CTAGCGCCCG CTCCTTTCGC |
| 351 TTTCTTCCCT TCCTTTCTCG CCACGTTCGC CGGCTTTCCC CGTCAAGCTC |
| 401 TAAATCGGGG GCTCCCTTTA GGGTTCCGAT TTAGTGCTTT ACGGCACCTC |
| 451 GACCCCAAAA AACTTGATTT GGGTGATGGT TCACGTAGTG GCCATCGCC |
| 501 CTGATAGACG GTTTTTCGCC CTTTGACGTT GGAGTCCACG TTCTTTAATA |
| 551 GTGGACTCTT GTTCCAAACT GGAACAACAC TCAACCCMAT CTCGGGCTAT |
| 601 TCTTTTGATT TATAAGGGAT TTTGCCGATT TCGGCCTATT GGTTAAAAAA |
| 651 TGAGCTGATT TAACAAAAAT TTAACGCGAA TTTTAACAAA ATATTAACGT |
| 701 TTACAATTTT ATGGTGCACT CTCAGTACAA TCTGCTCTGA TGCCGCATAG |
| 751 TTAAGCCAGC CCCGACACCC GCCAACACCC GCTGACGCGC CCTGACGGGC |
| 801 TTGTCTGCTC CCGGCATCCG CTTACAGACA AGCTGTGACC GTCTCCGGGA |
| 851 GCTGCATGTG TCAGAGGTTT TCACCGTCAT CACCGAAACG CGCGAGACGA |

| pAAV-miniCMV-hIns-bGH plasmid sequence |
| --- |
| 901 AAGGGCCTCG TGATACGCCT ATTTTTATAG GTTAATGTCA TGATAATAAT |
| 951 GGTTTCTTAG ACGTCAGGTG GCACTTTTCG GGGAAATGTG CGCGGAACCC |
| 1001 CTATTTGTTT ATTTTTCTAA ATACATTCAA ATATGTATCC GCTCATGAGA |
| 1051 CAATAACCCT GATAAATGCT TCAATAATAT TGAAAAAGGA AGAGTATGAG |
| 1101 TATTCAACAT TTCCGTGTCG CCCTTATTCC CTTTTTTGCG GCATTTTGCC |
| 1151 TTCCTGTTTT TGCTCACCCA GAAACGCTGG TGAAAGTAAA AGATGCTGAA |
| 1201 GATCAGTTGG GTGCACGAGT GGGTTACATC GAACTGGATC TCAACAGCGG |
| 1251 TAAGATCCTT GAGAGTTTTC GCCCCGAAGA ACGTTTTCCA ATGATGAGCA |
| 1301 CTTTTAAAGT TCTGCTATGT GGCGCGGTAT TATCCCGTAT TGACGCCGGG |
| 1351 CAAGAGCAAC TCGGTCGCCG CATACACTAT TCTCAGAATG ACTTGGTTGA |
| 1401 GTACTCACCA GTCACAGAAA AGCATCTTAC GGATGGCATG ACAGTAAGAG |
| 1451 AATTATGCAG TGCTGCCATA ACCATGAGTG ATAACACTGC GGCCAACTTA |
| 1501 CTTCTGACAA CGATCGGAGG ACCGAAGGAG CTAACCGCTT TTTTGCACAA |
| 1551 CATGGGGGAT CATGTAACTC GCCTTGATCG TTGGGAACCG GAGCTGAATG |
| 1601 AAGCCATACC AAACGACGAG CGTGACACCA CGATGCCTGT AGCAATGGCA |
| 1651 ACAACGTTGC GCAAACTATT AACTGGCGAA CTACTTACTC TAGCTTCCCG |
| 1701 GCAACAATTA ATAGACTGGA TGGAGGCGGA TAAAGTTGCA GGACCACTMC |
| 1751 TGCGCTCGGC CCTTCCGGCT GGCTGGTTTA TTGCTGATAA ATCTGGAGCC |
| 1801 GGTGAGCGTG GGTCTCGCGG TATCATTGCA GCACTGGGGC CAGATGGTAA |
| 1851 GCCCTCCCGT ATCGTAGTTA TCTACACGAC GGGGAGTCAG GCAACTATGG |
| 1901 ATGAACGAAA TAGACAGATC GCTGAGATAG GTGCCTCACT GATTAAGCAT |
| 1951 TGGTAACTGT CAGACCAAGT TTACTCATAT ATACTTTAGA TTGATTTAAA |
| 2001 ACTTCATTTT TAATTTAAAA GGATCTAGGT GAAGATCCTT TTTGATAATC |
| 2051 TCATGACCAA AATCCCTTAA CGTGAGTTTT CGTTCCACTG AGCGTCAGAC |
| 2101 CCCGTAGAAA AGATCAAAGG ATCTTCTTGA GATCCTTTTT TTCTGCGCGT |
| 2151 AATCTGCTGC TTGCAAACAA AAAAACCACC GCTACCAGCG GTGGTTTGTT |
| 2201 TGCCGGATCA AGAGCTACCA ACTCTTTTTC CGAAGGTAAC TGGCTTCAGC |
| 2251 AGAGCGCAGA TACCAAATAC TGTCCTTCTA GTGTAGCCGT AGTTAGGCCA |
| 2301 CCACTTCAAG AACTCTGTAG CACCGCCTAC ATACCTCGCT CTGCTAATCq |
| 2351 TGTTACCAGT GGCTGCTGCC AGTGGCGATA AGTCGTGTCT TACCGGGTTG |
| 2401 GACTCAAGAC GATAGTTACC GGATAAGGCG CAGCGGTCGG GCTGAACGGG |
| 2451 GGGTTCGTGC ACACAGCCCA GCTTGGAGCG AACGACCTAC ACCGAACTGA |
| 2501 GATACCTACA GCGTGAGCTA TGAGAAAGCG CCACGCTTCC CGAAGGGAGA |
| 2551 AAGGCGGACA GGTATCCGGT AAGCGGCAGG GTCGGAACAG GAGAGCGCAC |
| 2501 GAGGGAGCTT CCAGGGGGAA ACGCCTGGTA TCTTTATAGT CCTGTCGGGT |
| 2651 TTCGCCACCT CTGACTTGAG CGTCGATTTT TGTGATGCTC GTCAGGGGGG |
| 2701 CGGAGCCTAT GGAAAAACGC CAGCAACGCG GCCTTTTTAC GGTTCCTGGC |
| 2751 CTTTTGCTGG CCTTTTGCTC ACATGTCCTG CAGGCAGCTG CGCGCTCGCT |
| 2801 CGCTCACTGA GGCCGCCCGG GCAAAGCCCG GGCGTCGGGC GACCTTTGGT |

| pAAV-miniCMV-hIns-bGH plasmid sequence |
|---|
| 2851 CGCCCGGCCT CAGTGAGCGA GCGAGCGCGC AGAGAGGGAG TGGCCAACTC |
| 2901 CATCACTAGG GGTTCCTGCG GCCGCGATAT CTATGCCAAG TACGCCCCCT |
| 2951 ATTGACGTCA ATGACGGTAA ATGGCCCGCC TGGCATTATG CCCAGTACAT |
| 3001 GACCTTATGG GACTTTCCTA CTTGGCAGTA CATCTACGTA TTAGTCATCG |
| 3051 CTATTACCAT GGTGATGCGG TTTTGGCAGT ACATCAATGG GCGTGGATAG |
| 3101 CGGTTTGACT CACGGGGATT TCCAAGTCTC CACCCCATTG ACGTCAATGG |
| 3151 GAGTTTGTTT TGGCACCAAA ATCAACGGGA CTTTCCAAAA TGTCGTAACA |
| 3201 ACTCCGCCCC ATTGACGCAA ATGGGCGGTA GGCGTGTACG GTGGGAGGTC |
| 3251 TATATAAGCA GAGCTCTCTG GCTAACTAGA GAACCCACTG CTTAACTGGC |
| 3301 TTATCGAAAT TAATACGACT CACTATAGGG AGACCCAAGC TTGCTAGCGT |
| 3351 CGACCTTCTG CCATGGCCCT GTGGATGCGC CTCCTGCCCC TGCTGGCGCT |
| 3401 GCTGGCCCTC TGGGGACCTG ACCCAGCCGC AGCCTTTGTG AACCAACACC |
| 3451 TGTGCGGCTC AGATCTGGTG GAAGCTCTCT ACCTAGTGTG CGGGGAACGA |
| 3501 GGCTTCTTCT ACACACCCAG GACCAAGCGG GAGGCAGAGG ACCTGCAGGT |
| 3551 GGGGCAGGTG GAGCTGGGCG GGGGCCCTGG TGCAGGCAGC CTGCAGCCCT |
| 3601 TGGCCCTGGA GGGGTCGCGA CAGAAGCGTG GCATTGTGGA ACAATGCTGT |
| 3651 ACCAGCATCT GCTCCCTCTA CCAGCTGGAG AACTACTGCA ACTAGACGCA |
| 3701 GCCGTCGACG GTACCAGCGT GGAGCTCGCT GATCAGCCTC GACTGTGCCT |
| 3751 TCTAGTTGCC AGCCATCTGT TGTTTGCCCC TCCCCCGTGC CTTCCTTGAC |
| 3801 CCTGGAAGGT GCCACTCCCA CTGTCCTTTC CTAAMAAAAT GAGGAAATTG |
| 3851 CATCGCATTG TCTGAGMAGG TGTCATTCTA TTCTGGGGGG TGGGGTGGGG |
| 3901 CAGGACAGCA AGGGGGAGGA TTGGGAAGAC AATAGCAGGC ATGCTGGGGA |
| 3951 TGCGGTGGGC TCTATGGCCA C |

ITR 5': 2777-2917 bp
miniCMV promoter: 2932-3342 bp
hIns: 3356-3702 bp bGH polyA: 3719-3971 bp
ITR 3': 39-179 bp
P: RSV-hGck-SV40 (SEQ ID NO: 26; FIG. 13)

| pAAV-RS-hGck-SV40 plasmid sequence |
|---|
| 1 GTGATTTAAA TGCGGCCGCA GGAACCCCTA GTGATGGAGT TGGCCACTCC |
| 51 CTCTCTGCGC GCTCGCTCGC TCACTGAGGC CGGGCGACCA AAGGTCGCCC |
| 101 GACGCCCGGG CTTTGCCCGG GCGGCCTCAG TGAGCGAGCG AGCGCGCAGC |
| 151 TGCCTGCAGG GGCGCCTGAT GCGGTATTTT CTCCTTACGC ATCTGTGCGG |
| 201 TATTTCACAC CGCATACGTC AAAGCAACCA TAGTACGCGC CCTGTAGCGG |
| 251 CGCATTAAGC GCGGCGGGTG TGGTGGTTAC GCGCAGCGTG ACCGCTACAC |
| 301 TTGCCAGCGC CCTAGCGCCC GCTCCTTTCG CTTTCTTCCC TTCCTTTCTC |
| 351 GCCACGTTCG CCGGCTTTCC CCGTCAAGCT CTAAATCGGG GGCTCCCTTT |
| 401 AGGGTTCCGA TTTAGTGCTT TACGGCACCT CGACCCCAAA AAACTTGATT |
| 451 TGGGTGATGG TTCACGTAGT GGGCCATCGC CCTGATAGAC GGTTTTTCGC |
| 501 CCTTTGACGT TGGAGTCCAC GTTCTTTAAT AGTGGACTCT TGTTCCAAAC |

| pAAV-RS-hGck-SV40 plasmid sequence |
|---|
| 551 TGGAACAACA CTCAACCCTA TCTCGGGCTA TTCTTTTGAT TTATAAGGGA |
| 601 TTTTGCCGAT TTCGGCCTAT TGGTTAAAAA ATGAGCTGAT TTAACAAAAA |
| 651 TTTAACGCGA ATTTTAACAA AATATTAACG TTTACAATTT TATGGTGCAC |
| 701 TCTCAGTACA ATCTGCTCTG ATGCCGCATA GTTAAGCCAG CCCCGACACC |
| 751 CGCCAACACC CGCTGACGCG CCCTGACGGG CTTGTCTGCT CCCGGCATCC |
| 801 GCTTACAGAC AAGCTGTGAC CGTCTCCGGG AGCTGCATGT GTCAGAGGTT |
| 851 TTCACCGTCA TCACCGAAAC GCGCGAGACG AAAGGGCCTC GTGATACGCC |
| 901 TATTTTTATA GGTTAATGTC ATGATAATAA TGGTTTCTTA GACGTCAGGT |
| 951 GGCACTTTTC GGGGAAATGT GCGCGGAACC CCTATTTGTT TATTTTTCTA |
| 1001 AATACATTCA AATATGTATC CGCTCATGAG ACAATAACCC TGATAAATGC |
| 1051 TTCAATAATA TTGAAAAAGG AAGAGTATGA GTATTCAACA TTTCCGTGTC |
| 1101 GCCCTTATTC CCTTTTTTGC GGCATTTTGC CTTCCTGTTT TTGCTCACCC |
| 1151 AGAAACGCTG GTGAAAGTAA AAGATGCTGA AGATCAGTTG GGTGCACGAG |
| 1201 TGGGTTACAT CGAACTGGAT CTCAACAGCG GTAAGATCCT TGAGAGTTTT |
| 1251 CGCCCCGAAG AACGTTTTCC AATGATGAGC ACTTTTAAAG TTCTGCTATG |
| 1301 TGGCGCGGTA TTATCCCGTA TTGACGCCGG GCAAGAGCAA CTCGGTCGCC |
| 1351 GCATACACTA TTCTCAGAAT GACTTGGTTG AGTACTCACC AGTCACAGAA |
| 1401 AAGCATCTTA CGGATGGCAT GACAGTAAGA GAATTATGCA GTGCTGCCAT |
| 1451 AACCATGAGT GATAACACTG CGGCCAACTT ACTTCTGACA ACGATCGGAG |
| 1501 GACCGAAGGA GCTAACCGCT TTTTTGCACA ACATGGGGGA TCATGTAACT |
| 1551 CGCCTTGATC GTTGGGAACC GGAGCTGAAT GAAGCCATAC CAAACGACGA |
| 1601 GCGTGACACC ACGATGCCTG TAGCAATGGC AACAACGTTG CGCAAACTAT |
| 1651 TAACTGGCGA ACTACTTACT CTAGCTTCCC GGCAACAATT AATAGACTGG |
| 1701 ATGGAGGCGG ATAAAGTTGC AGGACCACTT CTGCGCTCGG CCCTTCCGGC |
| 1751 TGGCTGGTTT ATTGCTGATA AATCTGGAGC CGGTGAGCGT GGGTCTCGCG |
| 1801 GTATCATTGC AGCACTGGGG CCAGATGGTA AGCCCTCCCG TATCGTAGTT |
| 1851 ATCTACACGA CGGGGAGTCA GGCAACTATG GATGAACGAA ATAGACAGAT |
| 1901 CGCTGAGATA GGTGCCTCAC TGATTAAGCA TTGGTAACTG TCAGACCAAG |
| 1951 TTTACTCATA TATACTTTAG ATTGATTTAA AACTTCATTT TTAATTTAAA |
| 2001 AGGATCTAGG TGAAGATCCT TTTTGATAAT CTCATGACCA AAATCCCTTA |
| 2051 ACGTGAGTTT TCGTTCCACT GAGCGTCAGA CCCCGTAGAA AAGATCAAAG |
| 2101 GATCTTCTTG AGATCCTTTT TTTCTGCGCG TAATCTGCTG CTTGCAAACA |
| 2151 AAAAAACCAC CGCTACCAGC GGTGGTTTGT TTGCCGGATC AAGAGCTACC |
| 2201 AACTCTTTTT CCGAAGGTAA CTGGCTTCAG CAGAGCGCAG ATACCAAATA |
| 2251 CTGTCCTTCT AGTGTAGCCG TAGTTAGGCC ACCACTTCAA GAACTCTGTA |
| 2301 GCACCGCCTA CATACCTCGC TCTGCTAATC CTGTTACCAG TGGCTGCTGC |
| 2351 CAGTGGCGAT AAGTCGTGTC TTACCGGGTT GGACTCAAGA CGATAGTTAC |
| 2401 CGGATAAGGC GCAGCGGTCG GGCTGAACGG GGGGTTCGTG CACACAGCCC |

| pAAV-RS-hGck-SV40 plasmid sequence |
|---|
| 2451 AGCTTGGAGC GAACGACCTA CACCGAACTG AGATACCTAC AGCGTGAGCT |
| 2501 ATGAGAAAGC GCCACGCTTC CCGAAGGGAG AAAGGCGGAC AGGTATCCGG |
| 2551 TAAGCGGCAG GGTCGGAACA GGAGAGCGCA CGAGGGAGCT TCCAGGGGGA |
| 2601 AACGCCTGGT ATCTTTATAG TCCTGTCGGG TTTCGCCACC TCTGACTTGA |
| 2651 GCGTCGATTT TTGTGATGCT CGTCAGGGGG GCGGAGCCTA TGGAAAAACG |
| 2701 CCAGCAACGC GGCCTTTTTA CGGTTCCTGG CCTTTTGCTG GCCTTTTGCT |
| 2751 CACATGTCCT GCAGGCAGCT GCGCGCTCGC TCGCTCACTG AGGCCGCCCG |
| 2801 GGCAAAGCCC GGGCGTCGGG CGACCTTTGG TCGCCCGGCC TCAGTGAGCG |
| 2851 AGCGAGCGCG CAGAGAGGGA GTGGCCAACT CCATCACTAG GGGTTCCTGC |
| 2901 GGCCGCGATA TCCATGTTTG ACAGCTTATC ATCGCAGATC CGTATGGTGC |
| 2951 ACTCTCAGTA CAATCTGCTC TGATGCCGCA TAGTTAAGCC AGTATCTGCT |
| 3001 CCCTGCTTGT GTGTTGGAGG TCGCTGAGTA GTGCGCGAGC AAAATTTAAG |
| 3051 CTACAACAAG GCAAGGCTTG ACCGACAATT GCATGAAGAA TCTGCTTAGG |
| 3101 GTTAGGCGTT TTGCGCTGCT TCGCGATGTA CGGGCCAGAT ATTCGCGTAT |
| 3131 CTGAGGGGAC TAGGGTGTGT TTAGGCGAAA AGCGGGGCTT CGGTTGTACG |
| 3201 CGGTTAGGAG TCCCCTCAGG ATATAGTAGT TTCGCTTTTG CATAGGGAGG |
| 3251 GGGAAATGTA GTCTTATGCA ATACTCTTGT AGTCTTGCAA CATGGTAACG |
| 3301 ATGAGTTAGC AACATGCCTT ACAAGGAGAG AAAAAGCACC GTGCATGCCG |
| 3351 ATTGGTGGAA GTAAGGTGGT ACGATCGTGC CTTATTAGGA AGGCAACAGA |
| 3401 CGGGTCTGAC ATGGATTGGA CGAACCACTA AATTCCGCAT TGCAGAGATA |
| 3451 TTGTATTTAA GTGCCTAGCT CGATACAATA AACGCCATTT GACCATTCAC |
| 3501 CACATTGGTG TGCACCTCCA AGCTGGGTAC CAGCTTCTAG AGAGATCTGC |
| 3551 TTCAGCTGGA GGCACTGGGC AGGTAAGTAT CAAGGTTACA AGACAGGTTT |
| 3601 AAGGAGACCA ATAGAAACTG GGCTTGTCGA GACAGAGAAG ACTCTTGCGT |
| 3651 TTCTGATAGG CACCTATTGG TCTTACTGAC ATCCACTTTG CCTTTCTCTC |
| 3701 CACAGGTGCA GCTGCTGCAG CGGTCTAGAA CTCGAGTCGA CCATGGCG |
| 3751 ATGGATGTCA CAAGGAGCCA GGCCCAGACA GCCTTGACTC TGGTAGAGCA |
| 3801 GATCCTGGCA GAGTTCCAGC TGCAGGAGGA GGACCTGAAG AAGGTGATGA |
| 3851 GACGGATGCA GAAGGAGATG GACCGCGGCC TGAGGCTGGA GACCCATGAA |
| 3901 GAGGCCAGTG TGAAGATGCT GCCCACCTAC GTGCGCTCCA CCCCAGAAGG |
| 3951 CTCAGAAGTC GGGGACTTCC TCTCCCTGGA CCTGGGTGGC ACTAACTTCA |
| 4001 GGGTGATGCT GGTGAAGGTG GGAGAAGGTG AGGAGGGGCA GTGGAGCGTG |
| 4051 AAGACCAAAC ACCAGATGTA CTCCATCCCC GAGGACGCCA TGACCGGCAC |
| 4101 TGCTGAGATG CTCTTCGACT ACATCTCTGA GTGCATCTCC GACTTCCTGG |
| 4151 ACAAGCATCA GATGAAACAC AAGAAGCTGC CCCTGGGCTT CACCTTCTCC |
| 4201 TTTCCTGTGA GGCACGAAGA CATCGATAAG GGCATCCTTC TCAACTGGAC |
| 4251 CAAGGGCTTC AAGGCCTCAG GAGCAGAAGG GAACAATGTC GTGGGGCTTC |
| 4301 TGCGAGACGC TATCAAACGG AGAGGGGACT TTGAAATGGA TGTGGTGGCA |
| 4351 ATGGTGAATG ACACGGTGGC CACGATGATC TCCTGCTACT ACGAAGACCA |

| pAAV-RS-hGck-SV40 plasmid sequence |
|---|
| 4401 TCAGTGCGAG GTCGGCATGA TCGTGGGCAC GGGCTGCAAT GCCTGCTACA |
| 4451 TGGAGGAGAT GCAGAATGTG GAGCTGGTGG AGGGGGACGA GGGCCGCATG |
| 4501 TGCGTCAATA CCGAGTGGGG CGCCTTCGGG GACTCCGGCG AGCTGGACGA |
| 4551 GTTCCTGCTG GAGTATGACC GCCTGGTGGA CGAGAGCTCT GCAAACCCCG |
| 4601 GTCAGCAGCT GTATGAGAAG CTCATAGGTG GCAAGTACAT GGGCGAGCTG |
| 4651 GTGCGGCTTG TGCTGCTCAG GCTCGTGGAC GAAAACCTGC TCTTCCACGG |
| 4701 GGAGGCCTCC GAGCAGCTGC GCACACGCGG AGCCTTCGAG ACGCGCTTCG |
| 4751 TGTCGCAGGT GGAGAGCGAC ACGGGCGACC GCAAGCAGAT CTACAACATC |
| 4801 CTGAGCACGC TGGGGCTGCG ACCCTCGACC ACCGAQTGCG ACATCGTGCG |
| 4851 CCGCGCCTGC GAGAGCGTGT CTACGCGCGC TGCGCACATG TGCTCGGCGG |
| 4901 GGCTGGCGGG CGTCATCAAC CGCATGCGCG AGAGCCGCAG CGAGGACGTA |
| 4951 ATGCGCATCA CTGTGGGCGT GGATGGCTCC GTGTACAAGC TGCACCCCAG |
| 5001 CTTCAAGGAG CGGTTCCATG CCAGCGTGCG CAGGCTGACG CCCAGCTGCG |
| 5051 AGATCACCTT CATCGAGTCG GAGGAGGGCA GTGGCCGGGO CGCGGCCCTG |
| 5101 GTCTCGGCGG TGGCCTGTAA GAAGGCCTGT ATGCTGGGCC AGTGACTCGA |
| 5151 GCACGCTGTC GAGGCCGCTT CGAGCAGACA TGATAAGATA CATTGATGAG |
| 5201 TTTGGACAAA CCACAACTAG AATGCAGTGA AAAAAATGCT TTATTTGTGA |
| 5251 AATTTGTGAT GCTATTGCTT TATTTGTAAC CATTATAAGC TGCAATAAAC |
| 5301 AAGTTAACAA CAACAATTGC ATTCATTTTA TGTTTCAGGT TCAGGGGGAG |
| 5351 ATGTGGGAGG TTTTTTAAAG CAAGTAAAAC CTCTACAAAT GTGGTAAAAT |
| 5401 CGATTAGGAT CTTCCTAGAG CATGGCTACC TAGACATGGC TCGACAGATC |
| 5451 AGC |

ITR 5': 2758-2898 bp
RSV promoter: 2996-3705 bp
hGck: 3730-5144 bp
SV40 polyA: 5155-5450 bp ITR 3': 20-160 bp Q: miniCMV-hIns-bGH(rev)-RSV-hGck-SV40 (SEQ ID NO: 27; FIG. 13)

| AAV-miniCMV-hIns-bGH(rev)-RSV-hGck-SV40 plasmid sequence |
|---|
| 1 ATCCATGTTT GACAGCTTAT CATCGCAGAT CCGTATGGTG CACTCTCAGT |
| 51 ACAATCTGCT CTGATGCCGC ATAGTTAAGC CAGTATCTGC TCCCTGCTTG |
| 101 TGTGTTGGAG GTCGCTGAGT AGTGCGCGAG CAAAATTTAA GCTACAACAA |
| 151 GGCAAGGCTT GACCGACAAT TGCATGAAGA ATCTGCTTAG GGTTAGGCGT |
| 201 TTTGCGCTGC TTCGCGATGT ACGGGCCAGA TATTCGCGTA TCTGAGGGGA |
| 251 CTAGGGTGTG TTTAGGCGAA AGCGGGGCT TCGGTTGTAC GCGGTTAGGA |
| 301 GTCCCCTCAG GATATAGTAG TTTCGCTTTT GCATAGGGAG GGGGAAATGT |
| 351 AGTCTTATGC AATACTCTTG TAGTCTTGCA ACATGGTAAC GATGAGTTAG |
| 401 CAACATGCCT TACAAGGAGA GAAAAAGCAC CGTGCATGCC GATTGGTGGA |
| 451 AGTAAGGTGG TACGATCGTG CCTTATTAGG AAGGCAACAG ACGGGTCTGA |
| 501 CATGGATTGG ACGAACCACT AAATTCCGCA TTGCAGAGAT ATTGTATTTA |

-continued

| AAV-miniCMV-hIns-bGH(rev)-RSV-hGck-SV40 plasmid sequence |
|---|

```
 551 AGTGCCTAGC TCGATACAAT AAACGCCATT TGACCATTCA CCACATTGGT
 601 GTGCACCTCC AAGCTGGGTA CCAGCTTCTA GAGAGATCTG CTTCAGCTGG
 651 AGGCACTGGG CAGGTAAGTA TCAAGGTTAC AAGACAGGTT TAAGGAGACC
 701 AATAGAAACT GGGCTTGTCG AGACAGAGAA GACTCTTGCG TTTCTGATAG
 751 GCACCTATTG GTCTTACTGA CATCCACTTT GCCTTTCTCT CCACAGGTGC
 801 AGCTGCTGCA GCGGTCTAGA ACTCGAGTCG AGACCATGGC GATGGATGTC
 851 ACAAGGAGCC AGGCCCAGAC AGCCTTGACT CTGGTAGAGC AGATCCTGGC
 901 AGAGTTCCAG CTGCAGGAGG AGGACCTGAA GAAGGTGATG AGACGGATGC
 951 AGAAGGAGAT GGACCGCGGC CTGAGGCTGG AGACCCATGA AGAGGCCAGT
1001 GTGAAGATGC TGCCCACCTA CGTGCGCTCC ACCCCAGAAG CTCAGAAGT
1051 CGGGGACTTC CTCTCCCTGG ACCTGGGTGG CACTAACTTC AGGGTGATGC
1101 TGGTGAAGGT GGGAGAAGGT GAGGAGGGGC AGTGGAGCGT GAAGACCAAA
1151 CACCAGATGT ACTCCATCCC CGAGGACGCC ATGACCGGCA CTGCTGAGAT
1201 GCTCTTCGAC TACATCTCTG AGTGCATCTC CGACTTCCTG GACAAGCATC
1251 AGATGAAACA CAAGAAGCTG CCCCTGGGCT TCACCTTCTC CTTTCCTGTG
1301 AGGCACGAAG ACATCGATAA GGGCATCCTT CTCAACTGGA CCAAGGGCTT
1351 CAAGGCCTCA GGAGCAGAAG GGAACAATGT CGTGGGCTT CTGCGAGACG
1401 CTATCAAACG GAGAGGGGAC TTTGAAATGG ATGTGGTGGC AATGGTGAAT
1451 GACACGGTGG CCACGATGAT CTCCTGCTAC TACGAAGACC ATCAGTGCGA
1501 GGTCGGCATG ATCGTGGGCA CGGGCTGCAA TGCCTGCTAC ATGGAGGAGA
1551 TGCAGAATGT GGAGCTGGTG GAGGGGGACG AGGGCCGCAT GTGCGTCAAT
1601 ACCGAGTGGG GCGCCTTCGG GGACTCCGGC GAGCTGGACG AGTTCCTGCT
1651 GGAGTATGAC CGCCTGGTGG ACGAGAGCTC TGCAAACCCC GGTCAGCAGC
1701 TGTATGAGAA GCTCATAGGT GGCAAGTACA TGGGCGAGCT GGTGCGGCTT
1751 GTGCTGCTCA GGCTCGTGGA CGAAAACCTG CTCTTCCACG GGGAGGCCTC
1801 CGAGCAGCTG CGCACACGCG GAGCCTTCGA GACGCGCTTC GTGTCGCAGG
1851 TGGAGAGCGA CACGGGCGAC CGCAAGCAGA TCTACAACAT CCTGAGCACG
1901 CTGGGGCTGC GACCCTCGAC CACCGACTGC GACATCGTGC GCCGCGCCTG
1951 CGAGAGCGTG TCTACGCGCG CTGCGCACAT GTGCTCGGCG GGGCTGGCGG
2001 GCGTCATCAA CCGCATGCGC GAGAGCCGCA GCGAGGACGT AATGCGCATC
2051 ACTGTGGGCG TGGATGGCTC CGTGTACAAG CTGCACCCCA GCTTCAAGGA
2101 GCGGTTCCAT GCCAGCGTGC GCAGGCTGAC GCCCAGCTGC GAGATCACCT
2151 TCATCGAGTC GGAGGAGGGC AGTGGCCGGG GCGCGGCCCT GGTCTCGGCG
2201 GTGGCCTGTA AGAAGGCCTG TATGCTGGGC CAGTGACTCG AGCACGCTGT
2251 CGAGGCCGCT TCGAGCAGAC ATGATAAGAT ACATTGATGA GTTTGGACAA
2301 ACCACAACTA GAATGCAGTG AAAAAAATGC TTTATTTGTG AAATTTGTGA
2351 TGCTATTGCZ TTATTTGTAA CCATTATAAG CTGCAATAAA CAAGTTAACA
2401 ACAACAATTG CATTCATTTT ATGTTTCAGG TTCAGGGGGA GATGTGGGAG
2451 GTTTTTTAAA GCAAGTAAAA CCTCTACAAA TGTGGTAAAA TCGATTAGGA
```

| AAV-miniCMV-hIns-bGH(rev)-RSV-hGck-SV40 plasmid sequence |
|---|
| 2501 TCTTCCTAGA GCATGGCTAC CTAGACATGG CTCGACAGAT CAGCGTGATT |
| 2551 TAAATGCGGC CGCAGGAACC CCTAGTGATG GAGTTGGCCA CTCCCTCTCT |
| 2601 GCGCGCTCGC TCGCTCACTG AGGCCGGGCG ACCAAAGGTC GCCCGACGCC |
| 2651 CGGGCTTTGC CCGGGCGGCC TCAGTGAGCG AGCGAGCGCG CAGCTGCCTG |
| 2701 CAGGGGCGCC TGATGCGGTA TTTTCTCCTT ACGCATCTGT GCGGTATTTC |
| 2751 ACACCGCATA CGTCAAAGCA ACCATAGTAC GCGCCCTGTA GCGGCGCATT |
| 2801 AAGCGCGGCG GGTGTGGTGG TTACGCGCAG CGTGACCGCT ACACTTGCCA |
| 2851 GCGCCCTAGC GCCCGCTCCT TTCGCTTTCT TCCCTTCCTT TCTCGCCACG |
| 2901 TTCGCCGGCT TTCCCCGTCA AGCTCTAAAT CGGGGGCTCC CTTTAGGGTT |
| 2951 CCGATTTAGT GCTTTACGGC ACCTCGACCC CAAAAAACTT GATTTGGGTG |
| 3001 ATGGTTCACG TAGTGGGCCA TCGCCCTGAT AGACGGTTTT TCGCCCTTTG |
| 3051 ACGTTGGAGT CCACGTTCTT TAATAGTGGA CTCTTGTTCC AAACTGGAAC |
| 3101 AACACTCAAC CCTATCTCGG GCTATTCTTT TGATTTATAA GGGATTTTGC |
| 3151 CGATTTCGGC CTATTGGTTA AAAAATGAGC TGATTTAACA AAAATTTAAC |
| 3201 GCGAATTTTA ACAAAATATT AACGTTTACA ATTTTATGGT GCACTCTCAG |
| 3251 TACAATCTGC TCTGATGCCG CATAGTTAAG CCAGCCCCGA CACCCGCCAA |
| 3301 CACCCGCTGA CGCGCCCTGA CGGGCTTGTC TGCTCCCGGC ATCCGCTTAC |
| 3351 AGACAAGCTG TGACCGTCTC CGGGAGCTGC ATGTGTCAGA GGTTTTCACC |
| 3401 GTCATCACCG AAACGCGCGA GACGAAAGGG CCTCGTGATA CGCCTATTTT |
| 3451 TATAGGTTAA TGTCATGATA ATAATGGTTT CTTAGACGTC AGGTGGCACT |
| 3501 TTTCGGGGAA ATGTGCGCGG AACCCCTATT TGTTTATTTT TCTAAATACA |
| 3551 TTCAAATATG TATCCGCTCA TGAGACAATA ACCCTGATAA ATGCTTCAAT |
| 3601 AATATTGAAA AAGGAAGAGT ATGAGTATTC AACATTTCCG TGTCGCCCTT |
| 3651 ATTCCCTTTT TTGCGGCATT TTGCCTTCCT GTTTTTGCTC ACCCAGAAAC |
| 3701 GCTGGTGAAA GTAAAAGATG CTGAAGATCA GTTGGGTGCA CGAGTGGGTT |
| 3751 ACATCGAACT GGATCTCAAC AGCGGTAAGA TCCTTGAGAG TTTTCGCCCC |
| 3801 GAAGAACGTT TTCCAATGAT GAGCACTTTT AAAGTTCTGC TATGTGGCGC |
| 3851 GGTATTATCC CGTATTGACG CCGGGCAAGA GCAACTCGGT CGCCGCATAC |
| 3901 ACTATTCTCA GAATGACTTG GTTGAGTACT CACCAGTCAC AGAAAAGCAT |
| 3951 CTTACGGATG GCATGACAGT AAGAGAATTA TGCAGTGCTG CCATAACCAT |
| 4001 GAGTGATAAC ACTGCGGCCA ACTTACTTCT GACAACGATC GGAGGACCGA |
| 4051 AGGAGCTAAC CGCTTTTTTG CACAACATGG GGATCATGT AACTCGCCTT |
| 4101 GATCGTTGGG AACCGGAGCT GAATGAAGCC ATACCAAACG ACGAGCGTGA |
| 4151 CACCACGATG CCTGTAGCAA TGGCAACAAC GTTGCGCAAA CTATTAACTG |
| 4201 GCGAACTACT TACTCTAGCT TCCCGGCAAC AATTAATAGA CTGGATGGAG |
| 4251 GCGGATAAAG TTGCAGGACC ACTTCTGCGC TCGGCCCTTC CGGCTGGCTG |
| 4301 GTTTATTGCT GATAAATCTG GAGCCGGTGA GCGTGGGTCT CGCGGTATCA |
| 4351 TTGCAGCACT GGGGCCAGAT GGTAAGCCCT CCCGTATCGT AGTTATCTAC |

| AAV-miniCMV-hIns-bGH(rev)-RSV-hGck-SV40 plasmid sequence |
|---|
| 4401 ACGACGGGGA GTCAGGCAAC TATGGATGAA CGAAATAGAC AGATCGCTGA |
| 4451 GATAGGTGCC TCACTGATTA AGCATTGGTA ACTGTCAGAC CAAGTTTACT |
| 4501 CATATATACT TTAGATTGAT TTAAAACTTC ATTTTTAATT TAAAAGGATC |
| 4551 TAGGTGAAGA TCCTTTTTGA TAATCTCATG ACCAAAATCC CTTAACGTGA |
| 4601 GTTTTCGTTC CACTGAGCGT CAGACCCCGT AGAAAAGATC AAAGGATCTT |
| 4651 CTTGAGATCC TTTTTTTCTG CGCGTAATCT GCTGCTTGCA AACAAAAAAA |
| 4701 CCACCGCTAC CAGCGGTGGT TTGTTTGCCG GATCAAGAGC TACCAACTCT |
| 4751 TTTTCCGAAG GTAACTGGCT TCAGCAGAGC GCAGATACCA AATACTGTCC |
| 4801 TTCTAGTGTA GCCGTAGTTA GGCCACCACT TCAAGAACTC TGTAGCACCG |
| 4851 CCTACATACC TCGCTCTGCT AATCCTGTTA CCAGTGGCTG CTGCCAGTGG |
| 4901 CGATAAGTCG TGTCTTACCG GGTTGGACTC AAGACGATAG TTACCGGATA |
| 4951 AGGCGCAGCG GTCGGGCTGA ACGGGGGGTT CGTGCACACA GCCCAGCTTG |
| 5001 GAGCGAACGA CCTACACCGA ACTGAGATAC CTACAGCGTG AGCTATGAGA |
| 5051 AAGCGCCACG CTTCCCGAAG GGAGAAAGGC GGACAGGTAT CCGGTAAGCG |
| 5101 GCAGGGTCGG AACAGGAGAG CGCACGAGGG AGCTTCCAGG GGGAAACGCC |
| 5151 TGGTATCTTT ATAGTCCTGT CGGGTTTCGC CACCTCTGAC TTGAGCGTCG |
| 5201 ATTTTTGTGA TGCTCGTCAG GGGGCGGAG CCTATGGAAA AACGCCAGCA |
| 5251 ACGQGGCCTT TTTACGGTTC CTGGCCTTTT GCTGGCCTTT TGCTCACATG |
| 5301 TCCTGCAGGC AGCTGCGCGC TCGCTCGCTC ACTGAGGCCG CCCGGGCAAA |
| 5351 GCCCGGGCGT CGGGCGACCT TTGGTCGCCC GGCCTCAGTG AGCGAGCGAG |
| 5401 CGCGCAGAGA GGGAGTGGCC AACTCCATCA CTAGGGGTTC CTGCGGCCGC |
| 5451 GATAAATCGA GATCTTCCAG AGCATGAGCG TGGCCATAGA GCCCACCGCA |
| 5501 TCCCCAGCAT GCCTGCTATT GTCTTCCCAA TCCTCCCCCT TGCTGTCCTG |
| 5551 CCCCACCCCA CCCCCCAGAA TAGAATGACA CCTACTCAGA CAATGCGATG |
| 5601 CAATTTCCTC ATTTTATTAG GAAAGGACAG TGGGAGTGGC ACCTTCCAGG |
| 5651 GTCAAGGAAG GCACGGGGGA GGGGCAAACA ACAGATGGCT GGCAACTAGA |
| 5701 AGGCACAGTC GAGGCTGATC AGCGAGCTCC ACGCTGGTAC CGTCGACGGC |
| 5751 TGCGTCTAGT TGCAGTAGTT CTCCAGCTGG TAGAGGGAGC AGATGCTGGT |
| 5801 ACAGCATTGT TCCACAATGC CACGCTTCTG TCGCGACCCC TCCAGGGCCA |
| 5851 AGGGCTGCAG GCTGCCTGCA CCAGGGCCCC CGCCCAGCTC CACCTGCCCC |
| 5901 ACCTGCAGGT CCTCTGCCTC CCGCTTGGTC CTGGGTGTGT AGAAGAAGCC |
| 5951 TCGTTCCCCG CACACTAGGT AGAGAGCTTC CACCAGATCT GAGCCGCACA |
| 6001 GGTGTTGGTT CACAAAGGCT GCGGCTGGGT CAGGTCCCCA GAGGGCCAGC |
| 6051 AGCGCCAGCA GGGGCAGGAG GCGCATCCAC AGGGCCATGG CAGAAGGTCG |
| 6101 ACGCTAGCAA GCTTGGGTCT CCCTATAGTG AGTCGTATTA ATTTCGATAA |
| 6151 GCCAGTTAAG CAGTGGGTTC TCTAGTTAGC CAGAGAGCTC TGCTTATATA |
| 6201 GACCTCCCAC CGTACACGCC TACCGCCCAT TTGCGTCAAT GGGGCGGAGT |
| 6251 TGTTACGACA TTTTGGAAAG TCCCGTTGAT TTTGGTGCCA AAACAAACTC |
| 6301 CCATTGACGT CAATGGGGTG GAGACTTGGA AATCCCCGTG AGTCAAACCG |

| AAV-miniCMV-hIns-bGH(rev)-RSV-hGck-SV40 plasmid sequence |
|---|
| 6351 CTATCCACGC CCATTGATGT ACTGCCAAAA CCGCATCACC ATGGTAATAG |
| 6401 CGATGACTAA TACGTAGATG TACTGCCAAG TAGGAAAGTC CCATAAGGTC |
| 6451 ATGTACTGGG CATAATGCCA GGCGGGCCAT TTACCGTCAT TGACGTCAAT |
| 6501 AGGGGGCGTA CTTGGCATAG AT |

ITR 5': 5302-5442 bp
miniCMV promoter: 6109-6519 bp
hIns: 5749-6095 bp
bGH polyA: 5480-5732 bp
RSV promoter: 87-796 bp hGck: 821-2235 bp
SV40 polyA: 2246-2541 bp
ITR 3': 2564-2704 bp
R: miniCMV-hIns-SV40enhancer (SEQ ID NO: 28; FIG. 16)

| pAAV-miniCMV-hIns-SV40enhancer plasmid sequence |
|---|
| 1 GCTCATGCTC TGGAAGATCT CGATTTAAAT GCGGCCGCAG GAACCCCTAG |
| 51 TGATGGAGTT GGCCACTCCC TCTCTGCGCG CTCGCTCGCT CACTGAGGCC |
| 101 GGGCGACCAA AGGTCGCCCG ACGCCCGGGC TTTGCCCGGG CGGCCTCAGT |
| 151 GAGCGAGCGA GCGCGCAGCT GCCTGCAGGG GCGCCTGATG CGGTATTTTC |
| 201 TCCTTACGCA TCTGTGCGGT ATTTCACACC GCATACGTCA AAGCAACCAT |
| 251 AGTACGCGCC CTGTAGCGGC GCATTAAGCG CGGCGGGTGT GGTGGTTACG |
| 301 CGCAGCGTGA CCGCTACACT TGCCAGCGCC CTAGCGCCCG CTCCTTTCGC |
| 351 TTTCTTCCCT TCCTTTCTCG CCACGTTCGC CGGCTTTCCC CGTCAAGCTC |
| 401 TAAATCGGGG GCTCCCTTTA GGGTTCCGAT TTAGTGCTTT ACGGCACCTC |
| 451 GACCCCAAAA AACTTGATTT GGGTGATGGT TCACGTAGTG GGCCATCGCC |
| 501 CTGATAGACG GTTTTTCGCC CTTTGACGTT GGAGTCCACG TTCTTTAATA |
| 551 GTGGACTCTT GTTCCAAACT GGAACAACAC TCAACCCTAT CTCGGGCTAT |
| 601 TCTTTTGATT TATAAGGGAT TTTGCCGATT TCGGCCTATT GGTTAAAAAA |
| 651 TGAGCTGATT TAACAAAAAT TTAACGCGAA TTTTAACAAA ATATTAACGT |
| 701 TTACAATTTT ATGGTGCACT CTCAGTACAA TCTGCTCTGA TGCCGCATAG |
| 751 TTAAGCCAGC CCCGACACCC GCCAACACCC GCTGACGCGC CCTGACGGGC |
| 801 TTGTCTGCTC CCGGCATCCG CTTACAGACA AGCTGTGACC GTCTCCGGGA |
| 851 GCTGCATGTG TCAGAGGTTT TCACCGTCAT CACCGAAACG CGCGAGACGA |
| 901 AAGGGCCTCG TGATACGCCT ATTTTTATAG GTTAATGTCA TGATAATAAT |
| 951 GGTTTCTTAG ACGTCAGGTG GCACTTTTCG GGGAAATGTG CGCGGAACCC |
| 1001 CTATTTGTTT ATTTTTCTAA ATACATTCAA ATATGTATCC GCTCATGAGA |
| 1051 CAATAACCCT GATAAATGCT TCAATAATAT TGAAAAAGGA AGAGTATGAG |
| 1101 TATTCAACAT TTCCGTGTCG CCCTTATTCC CTTTTTTGCG GCATTTTGCC |
| 1151 TTCCTGTTTT TGCTCACCCA GAAACGCTGG TGAAAGTAAA AGATGCTGAA |
| 1201 GATCAGTTGG GTGCACGAGT GGGTTACATC GAACTGGATC TCAACAGCGG |
| 1251 TAAGATCCTT GAGAGTTTTC GCCCCGAAGA ACGTTTTCCA ATGATGAGCA |
| 1301 CTTTTAAAGT TCTGCTATGT GGCGCGGTAT TATCCCGTAT TGACGCCGGG |
| 1351 CAAGAGCAAC TCGGTCGCCG CATACACTAT TCTCAGAATG ACTTGGTTGA |

| pAAV-miniCMV-hIns-SV40enhancer plasmid sequence |
|---|
| 1401 GTACTCACCA GTCACAGAAA AGCATCTTAC GGATGGCATG ACAGTAAGAG |
| 1451 AATTATGCAG TGCTGCCATA ACCATGAGTG ATAACACTGC GGCCAACTTA |
| 1501 CTTCTGACAA CGATCGGAGG ACCGAAGGAG CTAACCGCTT TTTTGCACAA |
| 1551 CATGGGGGAT CATGTAACTC GCCTTGATCG TTGGGAACCG GAGCTGAATG |
| 1601 AAGCCATACC AAACGACGAG CGTGACACCA CGATGCCTGT AGCAATGGCA |
| 1651 ACAACGTTGC GCAAACTATT AACTGGCGAA CTACTTACTC TAGCTTCCCG |
| 1701 GCAACAATTA ATAGACTGGA TGGAGGCGGA TAAAGTTGCA GGACCACTTC |
| 1751 TGCGCTCGGC CCTTCCGGCT GGCTGGTTTA TTGCTGATAA ATCTGGAGCC |
| 1801 GGTGAGCGTG GGTCTCGCGG TATCATTGCA GCACTGGGGC CAGATGGTAA |
| 1851 GCCCTCCCGT ATCGTAGTTA TCTACACGAC GGGGAGTCAG GCAACTATGG |
| 1901 ATGAACGAAA TAGACAGATC GCTGAGATAG GTGCCTCACT GATTAAGCAT |
| 1951 TGGTAACTGT CAGACCAAGT TTACTCATAT ATACTTTAGA TTGATTTAAA |
| 2001 ACTTCATTTT TAATTTAAAA GGATCTAGGT GAAGATCCTT TTTGATAATC |
| 2051 TCATGACCAA AATCCCTTAA CGTGAGTTTT CGTTCCACTG AGCGTCAGAC |
| 2101 CCCGTAGAAA AGATCAAAGG ATCTTCTTGA GATCCTTTTT TTCTGCGCGT |
| 2151 AATCTGCTGC TTGCAAACAA AAAAACCACC GCTACCAGCG GTGGTTTGTT |
| 2201 TGCCGGATCA AGAGCTACCA ACTCTTTTTC CGAAGGTAAC TGGCTTCAGC |
| 2251 AGAGCGCAGA TACCAAATAC TGTCCTTCTA GTGTAGCCGT AGTTAGGCCA |
| 2301 CCACTTCAAG AACTCTGTAG CACCGCCTAC ATACCTCGCT CTGCTAATCC |
| 2351 TGTTACCAGT GGCTGCTGCC AGTGGCGATA AGTCGTGTCT TACCGGGTTG |
| 2401 GACTCAAGAC GATAGTTACC GGATAAGGCG CAGCGGTCGG GCTGAACGGG |
| 2451 GGGTTCGTGC ACACAGCCCA GCTTGGAGCG AACGACCTAC ACCGAACTGA |
| 2501 GATACCTACA GCGTGAGCTA TGAGAAAGCG CCACGCTTCC CGAAGGGAGA |
| 2551 AAGGCGGACA GGTATCCGGT AAGCGGCAGG GTCGGAACAG GAGAGCGCAC |
| 2601 GAGGGAGCTT CCAGGGGGAA ACGCCTGGTA TCTTTATAGT CCTGTCGGGT |
| 2651 TTCGCCACCT CTGACTTGAG CGTCGATTTT TGTGATGCTC GTCAGGGGGG |
| 2701 CGGAGCCTAT GGAAAAACGC CAGCAACGCG GCCTTTTTAC GGTTCCTGGC |
| 2751 CTTTTGCTGG CCTTTTGCTC ACATGTCCTG CAGGCAGCTG CGCGCTCGCT |
| 2801 CGCTCACTGA GGCCGCCCGG GCAAAGCCCG GGCGTCGGGC GACCTTTGGT |
| 2851 CGCCCGGCCT CAGTGAGCGA GCGAGCGCGC AGAGAGGGAG TGGCCAACTC |
| 2901 CATCACTAGG GGTTCCTGCG GCCGCGATAT CTATGCCAAG TACGCCCCCT |
| 2951 ATTGACGTCA ATGACGGTAA ATGGCCCGCC TGGCATTATG CCCAGTACAT |
| 3001 GACCTTATGG GACTTTCCTA CTTGGCAGTA CATCTACGTA TTAGTCATCG |
| 3051 CTATTACCAT GGTGATGCGG TTTTGGCAGT ACATCAATGG GCGTGGATAG |
| 3101 CGGTTTGACT CACGGGGATT TCCAAGTCTC CACCCCATTG ACGTCAATGG |
| 3151 GAGTTTGTTT TGGCACCAAA ATCAACGGGA CTTTCCAAAA TGTCGTAACA |
| 3201 ACTCCGCCCC ATTGACGCAA ATGGGCGGTA GGCGTGTACG GTGGGAGGTC |
| 3251 TATATAAGCA GAGCTCTCTG GCTAACTAGA GAACCCACTG CTTAACTGGC |
| 3301 TTATCGAAAT TAATACGACT CACTATAGGG AGACCCAAGC TTGCTAGCGT |

| pAAV-miniCMV-hIns-SV40enhancer plasmid sequence |
|---|
| 3351 CGACCTTCTG CCATGGCCCT GTGGATGCGC CTCCTGCCCC TGCTGGCGCT |
| 3401 GCTGGCCCTC TGGGGACCTG ACCCAGCCGC AGCCTTTGTG AACCAACACC |
| 3451 TGTGCGGCTC AGATCTGGTG GAAGCTCTCT ACCTAGTGTG CGGGGAACGA |
| 3501 GGCTTCTTCT ACACACCCAG GACCAAGCGG GAGGCAGAGG ACCTGCAGGT |
| 3551 GGGGCAGGTG GAGCTGGGCG GGGGCCCTGG TGCAGGCAGC CTGCAGCCCT |
| 3601 TGGCCCTGGA GGGGTCGCGA CAGAAGCGTG GCATTGTGGA ACAATGCTGT |
| 3651 ACCAGCATCT GCTCCCTCTA CCAGCTGGAG AACTACTGCA ACTAGACGCA |
| 3701 GCCGTCGACG GTACCAGCGC TGAGTCGGGG CGGCCGGCCG CTTCGAGCAG |
| 3751 ACATGATAAG ATACATTGAT GAGTTTGGAC AAACCACAAC TAGAATGCAG |
| 3801 TGAAAAAAAT GCTTTATTTG TGAAATTTGT GATGCTATTG CTTTATTTGT |
| 3851 AACCATTATA AGCTGCAATA AACAAGTTAA CAACAACAAT TGCATTCATT |
| 3901 TTATGTTTCA GGTTCAGGGG GAGGTGTGGG AGGTTTTTTA AAGCAAGTAA |
| 3951 AACCTCTACA AATTTGGTAA AATCGATAAG GATCTGAACG ATGGAGCGGA |
| 4001 GAATGGGCGG AACTGGGCGG AGTTAGGGGC GGGATGGGCG GAGTTAGGGG |
| 4051 CGGGACTATG GTTGCTGACT AATTGAGATG CATGCTTTGC ATACTTCTGC |
| 4101 CTGCTGGGGA GCCTGGGGAC TTTCCACACC TGGTTGCTGA CTAATTGAGA |
| 4151 TGCATGCTTT GCATACTTCT GCCTGCTGGG GAGCCTGGGG ACTTTCCACA |
| 4201 CCCTAACTGA CACACATTCC ACAGCGGCAA ATTTGAGC |

ITR 5': 2777-2917 bp
miniCMV promoter: 2932-3342 bp
hIns: 3356-3702 bp
SV40 enhancer and SV40 polyA: 3719-4238 bp
ITR 3': 39-179 bp
S: miniCMV-hIns-SV40enhancer(rev)-RSV-hGck-bGH (SEQ ID NO: 29; FIG. 16)
pAAV-miniCMV-hIns-SV40enhancer(rev)-RSV-hGck-bGH Plasmid Sequence ITR 5': 5256-5396 bp
miniCMV promoter: 6330-6740 bp
hIns: 5970-6316 bp
SV40 enhancer and SV40 polyA: 5434-5953 bp
RSV promoter: 87-796 bp
hGck: 821-2235 bp
bGH polyA: 2243-2501 bp
ITR 3': 2518-2658 bp

```
  1 ATCCATGTTT GACAGCTTAT CATCGCAGAT CCGTATGGTG CACTCTCAGT
 51 ACAATCTGCT CTGATGCCGC ATAGTTAAGC CAGTATCTGC TCCCTGCTTG
101 TGTGTTGGAG GTCGCTGAGT AGTGCGCGAG CAAAATTTAA GCTACAACAA
151 GGCAAGGCTT GACCGACAAT TGCATGAAGA ATCTGCTTAG GGTTAGGCGT
201 TTTGCGCTGC TTCGCGATGT ACGGGCCAGA TATTCGCGTA TCTGAGGGGA
251 CTAGGGTGTG TTTAGGCGAA AAGCGGGGCT TCGGTTGTAC GCGGTTAGGA
301 GTCCCCTCAG GATATAGTAG TTTCGCTTTT GCATAGGGAG GGGGAAATGT
351 AGTCTTATGC AATACTCTTG TAGTCTTGCA ACATGGTAAC GATGAGTTAG
401 CAACATGCCT TACAAGGAGA GAAAAGCAC CGTGCATGCC GATTGGTGGA
451 AGTAAGGTGG TACGATCGTG CCTTATTAGG AAGCAACAG ACGGGTCTGA
501 CATGGATTGG ACGAACCACT AAATTCCGCA TTGCAGAGAT ATTGTATTTA
551 AGTGCCTAGC TCGATACAAT AAACGCCATT TGACCATTCA CCACATTGGT
601 GTGCACCTCC AAGCTGGGTA CCAGCTTCTA GAGAGATCTG CTTCAGCTGG
```

```
 651 AGGCACTGGG CAGGTAAGTA TCAAGGTTAC AAGACAGGTT TAAGGAGACC
 701 AATAGAAACT GGGCTTGTCG AGACAGAGAA GACTCTTGCG TTTCTGATAG
 751 GCACCTATTG GTCTTACTGA CATCCACTTT GCCTTTCTCT CCACAGGTGC
 801 AGCTGCTGCA GCGGTCTAGA ACTCGAGTCG AGACCATGGC GATGGATGTC
 851 ACAAGGAGCC AGGCCCAGAC AGCCTTGACT CTGGTAGAGC AGATCCTGGC
 901 AGAGTTCCAG CTGCAGGAGG AGGACCTGAA GAAGGTGATG AGACGGATGC
 951 AGAAGGAGAT GGACCGCGGC CTGAGGCTGG AGACCCATGA AGAGGCCAGT
1001 GTGAAGATGC TGCCCACCTA CGTGCGCTCC ACCCCAGAAG GCTCAGAAGT
1051 CGGGGACTTC CTCTCCCTGG ACCTGGGTGG CACTAACTTC AGGGTGATGC
1101 TGGTGAAGGT GGGAGAAGGT GAGGAGGGGC AGTGGAGCGT GAAGACCAAA
1151 CACCAGATGT ACTCCATCCC CGAGGACGCC ATGACCGGCA CTGCTGAGAT
1201 GCTCTTCGAC TACATCTCTG AGTCCATCTC CGACTTCCTG GACAAGCATC
1251 AGATGAAACA CAAGAAGCTG CCCCTGGGCT TCACCTTCTC CTTTCCTGTG
1301 AGGCACGAAG ACATCGATAA GGGCATCCTT CTCAACTGGA CCAAGGGCTT
1351 CAAGGCCTCA GGAGCAGAAG GAACAATGT CGTGGGGCTT CTGCGAGACG
1401 CTATCAAACG GAGAGGGAC TTTGAAATGG ATGTGGTGGC AATGGTGAAT
1451 GACACGGTGG CCACGATGAT CTCCTGCTAC TACGAAGACC ATCAGTGCGA
1501 GGTCGGCATG ATCGTGGGCA CGGGCTGCAA TGCCTGCTAC ATGGAGGAGA
1551 TGCAGAATGT GGAGCTGGTG GAGGGGACG AGGGCCGCAT GTGCGTCAAT
1601 ACCGAGTGGG GCGCCTTCGG GGACTCCGGC GAGCTGGACG AGTTCCTGCT
1651 GGAGTATGAC CGCCTGGTGG ACGAGAGCTC TGCAAACCCC GGTCAGCAGC
1701 TGTATGAGAA GCTCAMAGGT GGCAAGTACA TGGGCGAGCT GGTGCGGCTT
1751 GTGCTGCTCA GGCTCGTGGA CGAAAACCTG CTCTTCCACG GGAGGCCTC
1801 CGAGCAGCTG CGCACACGCG GAGCCTTCGA GACGCGCTTC GTGTCGCAGG
1851 TGGAGAGCGA CACGGGCGAC CGCAAGCAGA TCTACAACAT CQTGAGCACG
1901 CTGGGGCTGC GACCCTCGAC CACCGACTGC GACATCGTGC GCCGCGCCTG
1951 CGAGAGCGTG TCTACGCGCG CTGCGCACAT GTGCTCGGCG GGCTGGCGG
2001 GCGTCATCAA CCGCATGCGC GAGAGCCGCA GCGAGGACGT AATGCGCATC
2051 ACTGTGGGCG TGGATGGCTC CGTGTACAAG CTGCACCCCA GCTTCAAGGA
2101 GCGGTTCCAT GCCAGCGTGC GCAGGCTGAC GCCCAGCTGC GAGATCACCT
2151 TCATCGAGTC GGAGGAGGGC AGTGGCCGGG GCGCGGCCCT GGTCTCGGCG
2201 GTGGCCTGTA AGAAGGCCTG TATGCTGGGC CAGTGACTCG AGCACGTGGA
2251 GCTCGCTGAT CAOCCTCGAC TGTGCCTTCT AGTTGCCAGC CATCTGTTGT
2301 TTGCCCCTCC CCCGTGCCTT CCTTGACCCT GGAAGOTGCC ACTCCCACTG
2351 TCCTTTCCTA ATAAAATGAG GAAATTGCAT CGCATTGTCT GAGTAGGTGT
2401 CATTCTATTC TGGGGGGTGG GGTGGGCAG GACAGCAAGG GGGAGGATTG
2451 GGAAGACAAT AGCAGGCATG CTGGGGATGC GGTGGGCTCT ATGGCCACGT
2501 GATTTAAATG CGGCCGCAGG AACCCCTAGT GATGGAGTTG GCCACTCCCT
2551 CTCTGCGCGC TCGCTCGCTC ACTGAGGCCG GGCGACCAAA GGTCGCCCGA
2601 CGCCCGGGCT TTGCCCGGGC GGCCTCAGTG AGCGAGCGAG CGCGCAGCTG
2651 CCTGCAGGGG CGCCTGATGC GGTATTTTCT CCTTACGCAT CTGTGCGGTA
```

```
-continued
2701 TTTCACACCG CATACGTCAA AGCAACCATA GTACGCGCCC TGTAGCGGCG
2751 CATTAAGCGC GGCGGGTGTG GTGGTTACGC GCAGCGTGAC CGCTACACTT
2801 GCCAGCGCCC TAGCGCCCGC TCCTTTCGCT TTCTTCCCTT CCTTTCTCGC
2851 CACGTTCGCC GGCTTTCCCC GTCAAGCTCT AAATCGGGGG CTCCCTTTAG
2901 GGTTCCGATT TAGTGCTTTA CGGCACCTCG ACCCCAAAAA ACTTGATTTG
2951 GGTGATGGTT CACGTAGTGG GCCATCGCCC TGATAGACGG TTTTTCGCCC
3001 TTTGACGTTG GAGTCCACGT TCTTTAATAG TGGACTCTTG TTCCAAACTG
3051 GAACAACACT CAACCCTATC TCGGGCTATT CTTTTGATTT ATAAGGGATT
3101 TTGCCGATTT CGGCCTATTG GTTAAAAAAT GAGCTGATTT AACAAAAATT
3151 TAACGCGAAT TTTAACAAAA TATTAACGTT TACAATTTTA TGGTGCACTC
3201 TCAGTACAAT CTGCTCTGAT GCCGCATAGT TAAGCCAGCC CCGACACCCG
3251 CCAACACCCG CTGACGCGCC CTGACGGGCT TGTCTGCTCC CGGCATCCGC
3301 TTACAGACAA GCTGTGACCG TCTCCGGGAG CTGCATGTGT CAGAGGTTTT
3351 CACCGTCATC ACCGAAACGC GCGAGACGAA AGGGCCTCGT GATACGCCTA
3401 TTTTTATAGG TTAATGTCAT GATAATAATG GTTTCTTAGA CGTCAGGTGG
3451 CACTTTTCGG GGAAATGTGC GCGGAACCCC TATTTGTTTA TTTTTCTAAA
3501 TACATTCAAA TATGTATCCG CTCATGAGAC AATAACCCTG ATAAATGCTT
3551 CAATAATATT GAAAAAGGAA GAGTATGAGT ATTCAACATT TCCGTGTCGC
3601 CCTTATTCCC TTTTTTGCGG CATTTTGCCT TCCTGTTTTT GCTCACCCAG
3651 AAACGCTGGT GAAAGTAAAA GATGCTGAAG ATCAGTTGGG TGCACGAGTG
3701 GGTTACATCG AACTGGATCT CAACAGCGGT AAGATCCTTG AGAGTTTTCG
3751 CCCCGAAGAA CGTTTTCCAA TGATGAGCAC TTTTAAAGTT CTGCTATGTG
3801 GCGCGGTATT ATCCCGTATT GACGCCGGGC AAGAGCAACT CGGTCGCCGC
3851 ATACACTATT CTCAGAATGA CTTGGTTGAG TACTCACCAG TCACAGAAAA
3901 GCATCTTACG GATGGCATGA CAGTAAGAGA ATTATGCAGT GCTGCCATAA
3951 CCATGAGTGA TAACACTGCG GCCAACTTAC TTCTGACAAC GATCGGAGGA
4001 CCGAAGGAGC TAACCGCTTT TTTGCACAAC ATGGGGGATC ATGTAACTCG
4051 CCTTGATCGT TGGGAACCGG AGCTGAATGA AGCCATACCA AACGACGAGC
4101 GTGACACCAC GATGCCTGTA GCAATGGCAA CAACGTTGCG CAAACTATTA
4151 ACTGGCGAAC TACTTACTCT AGCTTCCCGG CAACAATTAA TAGACTGGAT
4201 GGAGGCGGAT AAAGTTGCAG GACCACTTCT GCGCTCGGCC CTTCCGGCTG
4251 GCTGGTTTAT TGCTGATAAA TCTGGAGCCG GTGAGCGTGG GTCTCGCGGT
4301 ATCATTGCAG CACTGGGGCC AGATGGTAAG CCCTCCCGTA TCGTAGTTAT
4351 CTACACGACG GGGAGTCAGG CAACTATGGA TGAACGAAAT AGACAGATCG
4401 CTGAGATAGG TGCCTCACTG ATTAAGCATT GGTAACTGTC AGACCAAGTT
4451 TACTCATATA TACTTTAGAT TGATTTAAAA CTTCATTTTT AATTTAAAAG
4501 GATCTAGGTG AAGATCCTTT TTGATAATCT CATGACCAAA ATCCCTTAAC
4551 GTGAGTTTTC GTTCCACTGA GCGTCAGACC CCGTAGAAAA GATCAAAGGA
4601 TCTTCTTGAG ATCCTTTTTT TCTGCGCGTA ATCTGCTGCT TGCAAACAAA
4651 AAAACCACCG CTACCAGCGG TGGTTTGTTT GCCGGATCAA GAGCTACCAA
```

-continued

```
4701 CTCTTTTTCC GAAGGTAACT GGCTTCAGCA GAGCGCAGAT ACCAAATACT
4751 GTCCTTCTAG TGTAGCCGTA GTTAGGCCAC CACTTCAAGA ACTCTGTAGC
4801 ACCGCCTACA TACCTCGCTC TGCTAATCCT GTTACCAGTG GCTGCTGCCA
4851 GTGGCGATAA GTCGTGTCTT ACCGGGTTGG ACTCAAGACG ATAGTTACCG
4901 GATAAGGCGC AGCGGTCGGG CTGAACGGGG GGTTCGTGCA CACAGCCCAG
4951 CTTGGAGCGA ACGACCTACA CCGAACTGAG ATACCTACAG CGTGAGCTAT
5001 GAGAAAGCGC CACGCTTCCC GAAGGGAGAA AGGCGGACAG GTATCCGGTA
5051 AGCGGCAGGG TCGGAACAGG AGAGCGCACG AGGGAGCTTC CAGGGGGAAA
5101 CGCCTGGTAT CTTTATAGTC CTGTCGGGTT TCGCCACCTC TGACTTGAGC
5151 GTCGATTTTT GTGATGCTCG TCAGGGGGGC GGAGCCTATG GAAAAACGCC
5201 AGCAACGCGG CCTTTTTACG GTTCCTGGCC TTTTGCTGGC CTTTTGCTCA
5251 CATGTCCTGC AGGCAGCTGC GCGCTCGCTC GCTCACTGAG GCCGCCCGGG
5301 CAAAGCCCGG GCGTCGGGCG ACCTTTGGTC GCCCGGCCTC AGTGAGCGAG
5351 CGAGCGCGCA GAGAGGGAGT GGCCAACTCC ATCACTAGGG GTTCCTGCGG
5401 CCGCGATAAA TCGAGATCTT CCAGAGCATG AGCGCTCAAA TTTGCCGCTG
5451 TGGAATGTGT GTCAGTTAGG GTGTGGAAAG TCCCCAGGCT CCCCAGCAGG
5501 CAGAAGTATG CAAAGCATGC ATCTCAATTA GTCAGCAACC AGGTGTGGAA
5551 AGTCCCCAGG CTCCCCAGCA GGCAGAAGTA TGCAAAGCAT GCATCTCAAT
5601 TAGTCAGCAA CCATAGTCCC GCCCCTAACT CCGCCCATCC CGCCCCTAAC
5651 TCCGCCCAGT TCCGCCCATT CTCCGCTCCA TCGTTCAGAT CCTTATCGAT
5701 TTTACCAAAT TTGTAGAGGT TTTACTTGCT TTAAAAAACC TCCCACACCT
5751 CCCCCTGAAC CTGAAACATA AAATGAATGC AATTGTTGTT GTTAACTTGT
5801 TTATTGCAGC TTATAATGGT TACAAATAAA GCAATAGCAT CACAAATTTC
5861 ACAAATAAAG CATTTTTTTC ACTGCATTCT AGTTGTGGTT TGTCCAAACT
5901 CATCAATGTA TCTTATCATG TCTGCTCGAA GCGGCCGGCC GCCCCGACTC
5951 AGCGCTGGTA CCGTCGACGG CTGCGTCTAG TTGCAGTAGT TCTCCAGCTG
6001 GTAGAGGGAG CAGATGCTGG TACAGCATTG TTCCACAATG CCACGCTTCT
6051 GTCGCGACCC CTCCAGGGCC AAGGGCTGCA GGCTGCCTGC ACCAGGGCCC
6101 CCGCCCAGCT CCACCTGCCC CACCTGCAGG TCCTCTGCCT CCCGCTTGGT
6151 CCTGGGTGTG TAGAAGAAGC CTCGTTCCCC GCACACTAGG TAGAGAGCTT
6201 CCACCAGATC TGAGCCGCAC AGGTGTTGGT TCACAAAGGC TGCGGCTGGG
6251 TCAGGTCCCC AGAGGGCCAG CAGCGCCAGC AGGGGCAGGA GGCGCATCCA
6301 CAGGGCCATG GCAGAAGGTC GACGCTAGCA AGCTTGGGTC TCCCTATAGT
6351 GAGTCGTATT AATTTCGATA AGCCAGTTAA GCAGTGGGTT CTCTAGTTAG
6401 CCAGAGAGCT CTGCTTATAT AGACCTCCCA CCGTACACGC CTACCGCCCA
6451 TTTGCGTCAA TGGGGCGGAG TTGTTACGAC ATTTTGGAAA GTCCCGTTGA
6501 TTTTGGTGCC AAAACAAACT CCCATTGACG TCAATGGGGT GGAGACTTGG
6551 AAATCCCCGT GAGTCAAACC GCTATCCACG CCCATTGATG TACTGCCAAA
6601 ACCGCATCAC CATGGTAATA GCGATGACTA ATACGTAGAT GTACTGCCAA
```

6651 GTAGGAAAGT CCCATAAGGT CATGTACTGG GCATAATGCC AGGCGGGCCA

6701 TTTACCGTCA TTGACGTCAA TAGGGGGCGT ACTTGGCATA GAT

The invention claimed is:

1. A viral expression construct comprising the following elements:
   a) a nucleotide sequence at least 80% identical to the sequence set forth as SEQ ID NO:1 encoding an insulin, operably linked to a cytomegalovirus (CMV) promoter,
   b) a nucleotide sequence at least 80% identical to the sequence set forth as SEQ ID NO:2 encoding a glucokinase, operably linked to a Rous Sarcoma Virus (RSV) promoter,
   c) elements selected from any one of:
      i) a SV40 polyadenylation signal or a SV40 polyadenylation signal and enhancer sequence at the 3' of the nucleotide sequence encoding an insulin, and a bovine growth hormone (bGH) polyadenylation signal at the 3' of the nucleotide sequence encoding a glucokinase; or
      ii) a bGH polyadenylation signal at the 3' of the nucleotide sequence encoding an insulin, and a SV40 polyadenylation signal or a SV40 polyadenylation signal and enhancer sequence at the 3' of the nucleotide sequence encoding a glucokinase,
   d) the CMV promoter and the RSV promoter are positioned in reverse orientation within the expression construct and are located adjacent to each other, and
   e) inverted terminal repeats (ITRs) flanking the expression cassette formed by elements a) to d), wherein the construct comprises a nucleotide sequence having at least 95% identity with the viral expression construct sequence of SEQ ID NO: 11, 15, 27 or 29.

2. A viral vector comprising the viral expression construct as defined in claim 1, wherein said viral vector is a recombinant adeno-associated virus vector.

3. A composition comprising the viral expression construct according to claim 1 or the viral vector according to claim 2.

4. The composition according to claim 3, wherein the composition is a pharmaceutical composition.

5. The viral vector according to claim 2, which is an AAV1 vector.

* * * * *